United States Patent
Qiu et al.

(10) Patent No.: US 9,127,021 B2
(45) Date of Patent: Sep. 8, 2015

(54) HEPATITIS C VIRUS INHIBITORS

(75) Inventors: Yao-Ling Qiu, Andover, MA (US); Ce Wang, Beijing (CN); Xiaowen Peng, Cambridge, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 168 days.

(21) Appl. No.: 13/082,621

(22) Filed: Apr. 8, 2011

(65) Prior Publication Data
US 2011/0250172 A1    Oct. 13, 2011

Related U.S. Application Data

(60) Provisional application No. 61/322,438, filed on Apr. 9, 2010.

(51) Int. Cl.
| C07D 498/18 | (2006.01) |
|---|---|
| A61K 38/21 | (2006.01) |
| C07D 519/00 | (2006.01) |
| A61K 45/06 | (2006.01) |
| A61K 38/55 | (2006.01) |
| A61K 31/4188 | (2006.01) |
| A61K 31/422 | (2006.01) |
| A61K 31/427 | (2006.01) |
| A61K 31/4439 | (2006.01) |
| A61K 31/454 | (2006.01) |
| A61K 31/496 | (2006.01) |
| A61K 31/5377 | (2006.01) |

(52) U.S. Cl.
CPC .......... *C07D 498/18* (2013.01); *A61K 31/4188* (2013.01); *A61K 31/422* (2013.01); *A61K 31/427* (2013.01); *A61K 31/4439* (2013.01); *A61K 31/454* (2013.01); *A61K 31/496* (2013.01); *A61K 31/5377* (2013.01); *A61K 38/21* (2013.01); *A61K 38/55* (2013.01); *A61K 45/06* (2013.01); *C07D 519/00* (2013.01); *C12N 2770/24211* (2013.01)

(58) Field of Classification Search
CPC .................................................... C07D 206/56
See application file for complete search history.

(56) References Cited

U.S. PATENT DOCUMENTS

| 5,935,982 | A | 8/1999 | Dykstra et al. |
|---|---|---|---|
| 7,141,574 | B2 | 11/2006 | Beaulieu et al. |
| 2004/0039043 | A1 | 2/2004 | Elbe et al. |
| 2005/0153877 | A1 | 7/2005 | Miao et al. |
| 2006/0003942 | A1 | 1/2006 | Tung et al. |
| 2006/0058317 | A1 | 3/2006 | Gravestock et al. |
| 2006/0178399 | A1 | 8/2006 | Nishizawa et al. |
| 2006/0276511 | A1 | 12/2006 | Serrano-Wu et al. |
| 2007/0244148 | A1 | 10/2007 | Bondy et al. |
| 2007/0299068 | A1 | 12/2007 | Karp et al. |
| 2008/0044379 | A1 | 2/2008 | Bachand et al. |
| 2008/0050336 | A1 | 2/2008 | Bachand et al. |
| 2008/0194803 | A1 | 8/2008 | Sinclair et al. |
| 2008/0299075 | A1 | 12/2008 | Bachand et al. |
| 2009/0004111 | A1 | 1/2009 | Rice et al. |
| 2009/0047247 | A1 | 2/2009 | Qiu et al. |
| 2009/0060874 | A1 | 3/2009 | Qiu et al. |
| 2009/0068140 | A1 | 3/2009 | Bachand et al. |
| 2009/0202478 | A1 | 8/2009 | Bachand et al. |
| 2009/0202483 | A1 | 8/2009 | Bachand et al. |
| 2009/0226398 | A1 | 9/2009 | Leivers et al. |
| 2009/0317360 | A1 | 12/2009 | Rai et al. |
| 2010/0003214 | A1 | 1/2010 | Gai et al. |
| 2010/0221214 | A1 | 9/2010 | Or et al. |

(Continued)

FOREIGN PATENT DOCUMENTS

| WO | 2011059887 A1 | 5/2001 |
|---|---|---|
| WO | 2006133326 A1 | 12/2006 |

(Continued)

OTHER PUBLICATIONS

Kayali et al. "Finally sofosbuvir: an oral anti-HCV drug with wide performance capability" Phamacogenomics and Personalized Medicine, 2014, vol. 2014:7, pp. 387-398.*
Bressanelli, et al., "Crystal Structure of the RNA-dependent RNA Polymerase of Hepatitis C Virus," PNAS, 96(23):13034-13039, 1999.
Love, R. A., et al., Crystal Structure of a Novel Dimeric Form of NS5A Domain I Protein from Hepatitis C Virus,: J. of Virology, 83(9):4395-4403 (2009).

*Primary Examiner* — Joseph Kosack
(74) *Attorney, Agent, or Firm* — Roy P. Issac; Carolyn S. Elmore; Elmore Patent Law Group, P.C.

(57) ABSTRACT

The present invention discloses compounds of Formula (I), or pharmaceutically acceptable salts, esters, or prodrugs thereof:

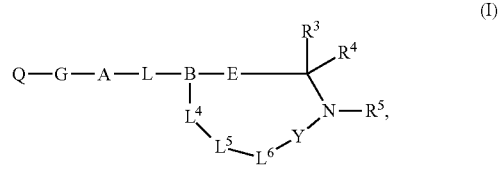

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

20 Claims, No Drawings

(56) References Cited

U.S. PATENT DOCUMENTS

| | | |
|---|---|---|
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Or et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0305117 A1 | 12/2010 | Herdewijn et al. |
| 2010/0310512 A1 | 12/2010 | Guo et al. |
| 2010/0316607 A1 | 12/2010 | Or et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |

FOREIGN PATENT DOCUMENTS

| | | |
|---|---|---|
| WO | 2007128086 A2 | 11/2007 |
| WO | 2008021927 A2 | 2/2008 |
| WO | 2008021928 A2 | 2/2008 |
| WO | 2008021936 A2 | 2/2008 |
| WO | 2008144380 A1 | 11/2008 |
| WO | 2009020825 A1 | 2/2009 |
| WO | 2009020828 A1 | 2/2009 |
| WO | 2009079353 A1 | 6/2009 |
| WO | 2009082701 A1 | 7/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2009117594 A1 | 9/2009 |
| WO | 2010014744 A1 | 2/2010 |
| WO | 2010017401 A1 | 2/2010 |
| WO | 2010039793 A1 | 4/2010 |
| WO | 2010065668 A1 | 6/2010 |
| WO | 2010065674 A1 | 6/2010 |
| WO | 2010065681 A1 | 6/2010 |
| WO | 2010096302 A1 | 8/2010 |
| WO | 2010096777 A1 | 8/2010 |
| WO | 2010111483 A1 | 9/2010 |
| WO | 2010111534 A1 | 9/2010 |
| WO | 2010111673 A1 | 9/2010 |
| WO | 2010117635 A1 | 10/2010 |
| WO | 2010117704 A1 | 10/2010 |
| WO | 2010117977 A1 | 10/2010 |
| WO | 2010120621 A1 | 10/2010 |
| WO | 2010120935 A1 | 10/2010 |
| WO | 2010122162 A1 | 10/2010 |
| WO | 2010132538 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2011004276 A1 | 1/2011 |
| WO | 2011009084 A1 | 1/2011 |
| WO | 2011015657 A1 | 2/2011 |
| WO | 2011015658 A1 | 2/2011 |
| WO | 2011026920 A1 | 3/2011 |
| WO | 2011028596 A1 | 3/2011 |
| WO | 2011031904 A1 | 3/2011 |
| WO | 2011031934 A1 | 3/2011 |
| WO | 2011046811 A1 | 4/2011 |
| WO | 2011050146 A1 | 4/2011 |
| WO | 2011054834 A1 | 5/2011 |

* cited by examiner

HEPATITIS C VIRUS INHIBITORS

RELATED APPLICATION

This application claims the benefit of U.S. Provisional Application Ser. No. 61/322,438 filed Apr. 9, 2010. The entire teachings of the above application are incorporated herein by reference.

TECHNICAL FIELD

The present invention relates to novel antiviral agents. More specifically, the present invention relates to compounds which can inhibit the function of the NS5A protein encoded by Hepatitis C Virus (HCV), compositions comprising such compounds, methods for inhibiting HCV viral replication, methods for treating or preventing HCV infection, and processes for making the compounds.

BACKGROUND OF THE INVENTION

Infection with HCV is a major cause of human liver disease throughout the world. In the U.S., an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the U.S. in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. Recently, with the introduction of pegylated interferon (Peg-IFN), both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al, 'An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several nonstructural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et at (1996) *EMBO J.* 151 2-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) *Journal of Virology*, 74(4): 2046-2051). Thus, inhibition of NS5B RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1; and in Rice, C. M. *Nature* 2005, 435, 374.

Based on the foregoing, there exists a significant need to identify compounds with the ability to inhibit HCV.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal aspect, the present invention provides a compound of Formula (I):

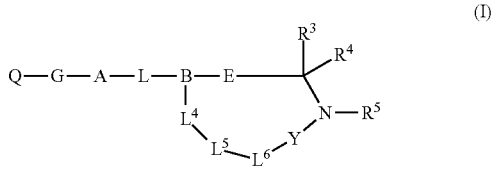

(I)

or a pharmaceutically acceptable salt thereof, wherein:

A is absent or a monocyclic or polycyclic group selected from the group consisting of aryl, heteroaryl, heterocyclic, $C_3$-$C_8$ cycloalkyl, and $C_3$-$C_8$ cycloalkenyl, each optionally substituted; preferably, A is optionally substituted aryl or optionally substituted heteroaryl;

B at each occurrence is independently a monocyclic or polycyclic group independently selected from the group consisting of aryl, heteroaryl, heterocyclic, $C_3$-$C_8$ cycloalkyl, and $C_3$-$C_8$ cycloalkenyl, each optionally substituted; preferably, B is optionally substituted aryl or optionally substituted heteroaryl;

E at each occurrence is independently —C(O)NH— or an optionally substituted 5-membered heteroaryl containing one or more nitrogen atoms; preferably, E is —C(O)NH— or optionally substituted imidazolyl;

L is absent or selected from the group consisting of O, optionally substituted $C_1$-$C_4$ alkyl, optionally substituted $C_2$-$C_4$ alkenyl, and optionally substituted $C_2$-$C_4$ alkynyl;

G is absent, —C(O)NH—, or an optionally substituted 5-membered heteroaryl containing one or more nitrogen atoms or optionally substituted 5/6-membered fused heteroaryl, wherein the 5-membered ring of said 5/6-membered fused heteroaryl contains one or more nitrogen atoms and is attached to group Q, and wherein the 6-membered ring of said 5/6-membered fused heteroaryl is attached to one of groups A, L and B and is aryl or heteroaryl; preferably, G is —C(O)NH—, optionally substituted imidazolyl, optionally substituted benzimidazolyl or optionally substituted imidazopyridyl;

Q is hydrogen or

Alternatively, G and Q can be taken together to form a group selected from:

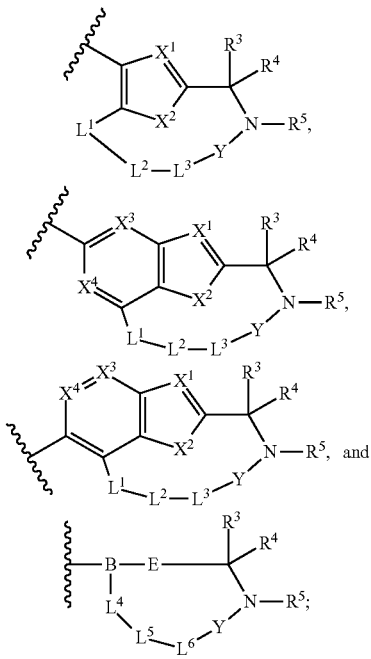

$X^1$ is N or $C(R^{11})$; preferably N;
$X^2$ is $N(R^1)$, O or S; preferably NH;
$X^3$ and $X^4$ are each independently selected from N or $C(R^{12})$; preferably CH;
$R^1$ is hydrogen or optionally substituted $C_1$-$C_4$ alkyl;
$R^{11}$ is hydrogen, halogen or optionally substituted $C_1$-$C_4$ alkyl; and
$R^{12}$ at each occurrence is independently hydrogen, halogen, hydroxy, optionally substituted $C_1$-$C_4$ alkyl, or optionally substituted $O(C_1$-$C_4$ alkyl).

$L^1$ and $L^3$ at each occurrence are each independently absent or an aliphatic group wherein at least one of $L^1$ and $L^3$ is present; preferably, $L^1$ and $L^3$ are each independently a linear aliphatic group;

$L^4$ and $L^6$ at each occurrence are each independently absent or an aliphatic group wherein at least one of $L^4$ and $L^6$ is present; preferably, $L^4$ and $L^6$ are each independently a linear aliphatic group;

$L^2$ and $L^5$ at each occurrence are each independently absent, or selected from the group consisting of aryl, heteroaryl, heterocyclic, $C_3$-$C_8$ cycloalkyl, and $C_3$-$C_8$ cycloalkenyl, each optionally substituted;

Y at each occurrence is independently C(O) or $S(O)_2$; preferably C(O);

wherein -$L^1$-$L^2$-$L^3$- together forms a linker; preferably, a linker of from 6 to 16 bond lengths;

wherein -$L^4$-$L^5$-$L^6$- together forms a linker; preferably, a linker of from 8 to 18 bond lengths;

$R^3$ and $R^4$ are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; preferably, hydrogen or optionally substituted $C_1$-$C_4$ alkyl; alternatively, $R^3$ and $R^4$ are taken together with the carbon atom to which they are attached to form optionally substituted $C_3$-$C_8$ cycloalkyl or optionally substituted heterocyclic;

$R^5$ is independently hydrogen, optionally substituted $C_1$-$C_8$ alkyl, or optionally substituted $C_3$-$C_8$ cycloalkyl; preferably hydrogen or optionally substituted $C_1$-$C_4$ alkyl;

Alternatively $R^3$, $R^4$ and $R^5$ are taken together with the carbon and nitrogen atom to which they are attached to form

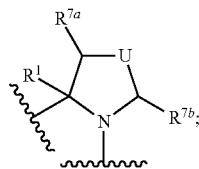

U is absent or independently selected from the group consisting of O, S, S(O), $SO_2$, NC(O)—($C_1$-$C_4$ alkyl), C(O), protected carbonyl, $OCH_2$, $OCH_2CH_2$, $SCH_2$, $SCH_2CH_2$, $C(R^7)_2$, $C(R^7)_2C(R^7)_2$, and $C=C(R^2)_2$; preferably, U is $CH_2$, C=N-OMe, or $C=CH_2$;

$R^2$ at each occurrence is independently hydrogen, halogen, optionally substituted $C_1$-$C_4$ alkyl, optionally substituted aryl, or optionally substituted heteroaryl;

$R^7$ at each occurrence is independently selected from the group consisting of hydrogen, halogen, cyano, hydroxy, $O(C_1$-$C_4$ alkyl), $S(C_1$-$C_4$ alkyl), amino optionally substituted with one or two $C_1$-$C_4$ alkyl, optionally substituted aryl, optionally substituted heteroaryl, optionally substituted $C_1$-$C_4$ alkyl, and optionally substituted $C_3$-$C_8$ cycloalkyl; preferably, $R^7$ is hydrogen, halogen, methyl, or cyclopropyl;

Alternatively two geminal $R^7$ groups are taken together with the carbon atom to which they are attached to form a spiro, optionally substituted 3- to 7-membered cyclic group selected from the group consisting of $C_3$-$C_7$ cycloalkyl, $C_3$-$C_7$ cycloalkenyl and 3- to 7-membered heterocyclic ring; preferably, spiro and optionally substituted cyclopropyl;

$R^{7a}$ and $R^{7b}$ at each occurrence are each independently selected from the group consisting of hydrogen, optionally substituted aryl, optionally substituted $C_1$-$C_4$ alkyl, and optionally substituted $C_3$-$C_8$ cycloalkyl; preferably, $R^{7a}$ and $R^{7b}$ at each occurrence are each independently hydrogen, cyclopropyl, or methyl;

Alternatively, $CHR^{7a}$—U or $CHR^{7b}$—U are taken together to form a group selected from CH=CH, fused and optionally substituted $C_3$-$C_8$ cycloalkyl, fused and optionally substituted aryl, or fused and optionally substituted heterocyclic; preferably, fused and optionally substituted cyclopropyl;

Yet alternatively, U, $R^{7a}$, and $R^{7b}$ are taken together with the carbon atoms to which they are attached to form a bridged, optionally substituted 4- to 7-membered cyclic group selected from the group consisting of $C_4$-$C_7$ cycloalkyl, $C_4$-$C_7$ cycloalkenyl and 4- to 7-membered heterocyclic; preferably, U, $R^{7a}$, and $R^{7b}$ are taken together with the carbon atoms to which they are attached to form a bridged cyclopentyl; and $R^6$ at each occurrence is independently selected from the group consisting of $O(C_1$-$C_8$ alkyl), amino, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably, $R^6$ at each occurrence is independently optionally substituted $C_1$-$C_8$ alkyl; more preferably, $R^6$ at each occurrence is independently $C_1$-$C_8$ alkyl optionally substituted with amino, hydroxy, protected amino or $O(C_1$-$C_4$ alkyl).

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with a therapeutically effective amount of a compound or a combination of compounds of the present invention, or a pharmaceutically acceptable salt thereof. Particularly, this invention is directed to methods of inhibiting the replication of HCV.

In still another aspect, the present invention provides a method of treating or preventing infection caused by an RNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HCV.

Yet another aspect of the present invention provides the use of a compound or combination of compounds of the present invention, or a pharmaceutically acceptable salt thereof, as defined hereinafter, in the preparation of a medicament for the treatment or prevention of infection caused by RNA-containing virus, specifically HCV.

DETAILED DESCRIPTION OF THE INVENTION

The present invention relates to compounds of Formula (I) as illustrated above, and pharmaceutically acceptable salts thereof.

The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. application Ser. No. 12/702,673 filed Feb. 9, 2010 entitled "Linked Dibenzimidiazole Derivatives"; U.S. application Ser. No. 12/702,692 filed Feb. 9, 2010 entitled "Linked Dibenzimidiazole Derivatives"; U.S. application Ser. No. 12/702,802 filed Feb. 9, 2010 entitled "Linked Dibenzimidiazole Derivatives"; U.S. application Ser. No. 12/707,190 filed Feb. 17, 2010 entitled "Linked Diimidazole Antivirals"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; U.S. application Ser. No. 12/714,583 filed Mar. 1, 2010 entitled "Novel Benzimidazole Derivatives"; and U.S. application Ser. No. 12/714,576 filed Mar. 1, 2010 entitled "Hepatitis C Virus Inhibitors"; U.S. application Ser. No. 12/816,148 filed Jun. 15, 2010 entitled "Hepatitis C Virus Inhibitors"; U.S. application Ser. No. 12/816,171 filed Jun. 15, 2010 entitled "Hepatitis C Virus Inhibitors"; U.S. application Ser. No. 12/879,025 filed Sep. 10, 2010 entitled "Hepatitis C Virus Inhibitors"; U.S. application Ser. No. 12/879,026 filed Sep. 10, 2010 entitled "Hepatitis C Virus Inhibitors"; U.S. application Ser. No. 12/879,027 filed Sep. 10, 2010 entitled "Hepatitis C Virus Inhibitors";

U.S. application Ser. No. 12/879,028 filed Sep. 10, 2010 entitled "Hepatitis C Virus Inhibitors"; U.S. application Ser. No. 12/879,029 filed Sep. 10, 2010 entitled "Hepatitis C Virus Inhibitors"; U.S. application Ser. No. 12/879,031 filed Sep. 10, 2010 entitled "Hepatitis C Virus Inhibitors"; U.S. application Ser. No. 12/967,486 filed Dec. 14, 2010 entitled "Hepatitis C Virus Inhibitors"; U.S. Provisional Application Ser. No. 61/322,438 filed Apr. 9, 2010 entitled "Hepatitis C Virus Inhibitors"; U.S. Provisional Application Ser. No. 61/351,327 filed Jun. 4, 2010 entitled "Hepatitis C Virus Inhibitors"; U.S. Provisional Application Ser. No. 61/372,999 filed Aug. 12, 2010 entitled "Hepatitis C Virus Inhibitors"; U.S. Provisional Application Ser. No. 61/415,447 filed Nov. 19, 2010 entitled "Hepatitis C Virus Inhibitors"; and U.S. patent application Ser. No. 13/013,213 filed Jan. 25, 2011; the contents of each of which are expressly incorporated by reference herein.

As discussed above, a general strategy for the development of antiviral agents is to inactivate virally encoded proteins, including NS5A, that are essential for the replication of the virus. The relevant patent disclosures describing the synthesis of HCV NS5A inhibitors are: US 2009/0202478; US 2009/0202483; US 2010/0233120; US 2010/0260708; WO 2004/014852; WO 2006/079833; WO 2006/133326; WO 2007/031791; WO 2007/070556; WO 2007/070600; WO 2007/082554; WO 2008/021927; WO 2008/021928; WO 2008/021936; WO 2008/048589; WO 2008/064218; WO 2008/070447; WO 2008/144380; WO 2008/154601; WO 2009/020825; WO 2009/020828; WO 2009/034390; WO 2009/102318; WO 2009/102325; WO 2009/102694; WO 2010/017401; WO 2010/039793; WO 2010/065668; WO 2010/065674; WO 2010/065681; WO 2010/091413; WO 2010/096777; WO 2010/096462; WO 2010/096302; WO2010/099527; WO 2010/111483; WO 2010/111534; WO 2010/117635; WO 2010/111673; WO 2010/117704; WO 2010/132538; WO 2010/132601; WO 2010/138488; WO 2010/138368; WO 2010/138790; WO 2010/138791; WO 2010/148006; US 2010/0215618; WO 2011/004276; WO 2011/009084; WO 2011/015657; WO 2011/015658; WO 2011/026920; WO 2011/028596; WO 2011/031904; and WO 2011/031934, the contents of each of which are expressly incorporated by reference herein.

In one embodiment, the present invention relates to compounds of Formula (I), and pharmaceutically acceptable salts thereof, wherein L is absent or selected from the group consisting of optionally substituted $C_1$-$C_4$ alkyl, optionally substituted $C_2$-$C_4$ alkenyl, and optionally substituted $C_2$-$C_4$ alkynyl.

In another embodiment, the present invention relates to compounds of Formula (I), and pharmaceutically acceptable salts thereof, wherein $L^4$ and $L^6$ at each occurrence are independently absent or an aliphatic group containing one or more of an optionally substituted alkyl, optionally substituted alkenyl, optionally substituted alkynyl, optionally substituted cycloalkyl, optionally substituted aryl, optionally substituted heteroaryl, optionally substituted heterocyclic, O, S, N($R^{11}$), C(O), and S(O)$_2$; wherein at least one of $L^4$ and $L^6$ is present. In yet another aspect, $L^4$ and $L^6$ at each occurrence are independently absent or a linear aliphatic group containing one or more of an optionally substituted alkyl, optionally substituted alkenyl, optionally substituted alkynyl, O, S, N($R^{11}$), C(O), and S(O)$_2$; wherein at least one of $L^4$ and $L^6$ is present.

In another embodiment, the present invention relates to compounds of Formula (I), and pharmaceutically acceptable salts thereof, wherein $L^1$ and $L^3$ at each occurrence are independently absent or a linear aliphatic group containing one or more of an optionally substituted alkyl, optionally substituted alkenyl, optionally substituted alkynyl, optionally substituted cycloalkyl, optionally substituted aryl, optionally substituted heteroaryl, optionally substituted heterocyclic, O, S, N($R^{11}$), C(O), and S(O)$_2$, wherein at least one of $L^1$ and $L^3$ is present. In yet another aspect, $L^1$ and $L^3$ at each occurrence are independently absent or a linear aliphatic group containing one or more of an optionally substituted alkyl, optionally substituted alkenyl, optionally substituted alkynyl, O, S, NR$^{11}$, C(O), and S(O)$_2$, wherein at least one of $L^1$ and $L^3$ is present.

In some embodiments, the present invention relates to compounds represented by Formula (Ia) and pharmaceutically acceptable salts thereof:

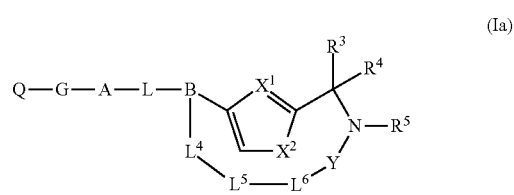

(Ia)

wherein A, B, G, L, Q, Y, $L^4$, $L^5$, $L^6$, $X^1$, $X^2$, $R^3$, $R^4$, and $R^5$ are as previously defined and wherein $X^1$ is N; or wherein $X^2$ is N($R^1$); or wherein $X^1$ is N and $X^2$ is N($R^1$).

In some embodiments, the present invention relates to compounds represented by Formula (Ib), and pharmaceutically acceptable salts thereof:

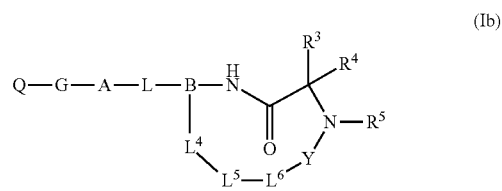

(Ib)

wherein A, B, G, L, Q, Y, $L^4$, $L^5$, $L^6$, $R^3$, $R^4$, and $R^5$ are as previously defined.

In one embodiment, the present invention relates to compounds of Formulae (Ia~Ib), and pharmaceutically acceptable salts thereof, wherein L is absent or selected from the group consisting of optionally substituted $C_1$-$C_4$ alkyl, optionally substituted $C_2$-$C_4$ alkenyl, and optionally substituted $C_2$-$C_4$ alkynyl.

In yet another embodiment, the present invention relates to compounds of Formula (Ia) and pharmaceutically acceptable salts thereof; wherein $X^1$ is N and $X^2$ is NH.

In yet another embodiment, the present invention relates to compounds of Formula (Ia) and pharmaceutically acceptable salts thereof; wherein $X^1$ is N and $X^2$ is O or S.

In yet another embodiment, the present invention relates to compounds of Formulae (Ia~Ib) and pharmaceutically acceptable salts thereof; wherein $L^4$ and $L^6$ at each occurrence are each independently absent or a linear aliphatic group, wherein at least one of $L^4$ and $L^6$ is present.

In yet another embodiment, the present invention relates to compounds of Formulae (Ia~Ib) and pharmaceutically acceptable salts thereof; wherein one of $L^4$ and $L^6$ is a linear aliphatic group and the other of $L^4$ and $L^6$ is an aliphatic group containing an optionally substituted cycloalkyl, heterocyclic or cycloalkenyl.

In yet another embodiment, the present invention relates to compounds of Formulae (Ia~Ib) and pharmaceutically acceptable salts thereof; wherein -L⁴-L⁵-L⁶- together forms a linker that is a linear aliphatic group and wherein said linker is from 8 to 18 bond lengths.

In yet another embodiment, the present invention relates to compounds of Formulae (Ia~Ib) and pharmaceutically acceptable salts thereof; wherein -L⁴-L⁵-L⁶- together forms a linker that is a combination of a linear aliphatic group(s) and a cyclic group and wherein said linker is from 8 to 18 bond lengths.

In another aspect of the invention, -L⁴-L⁵-L⁶- together forms a linker of from 8 to 14 bond lengths.

In still another embodiment, the present invention relates to compounds of Formulae (Ia~Ib) or a pharmaceutically acceptable salt thereof; wherein -L⁴-L⁵-L⁶- together forms a linker illustrated by one of the following groups:

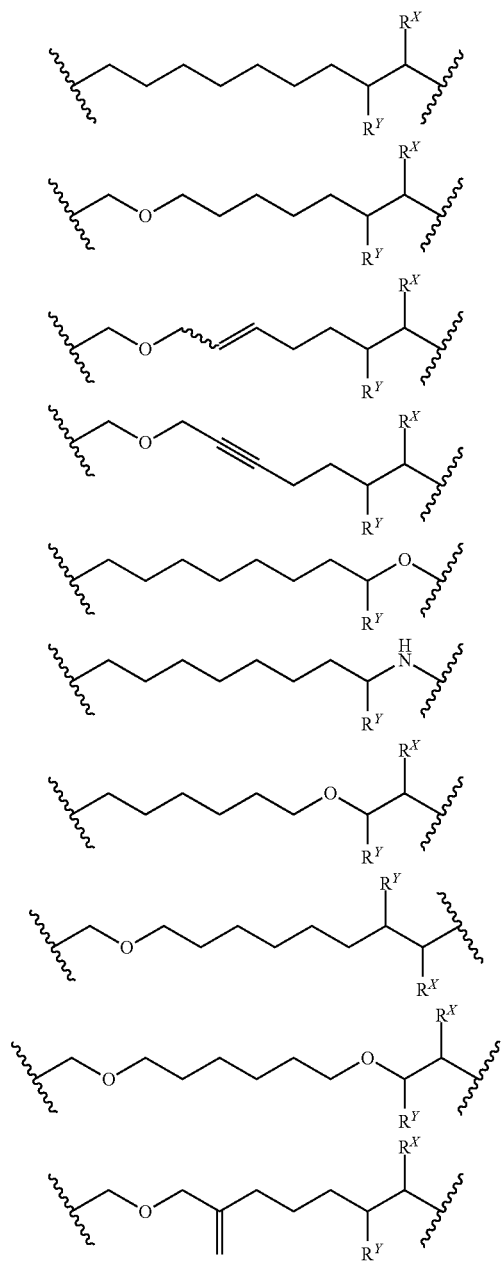
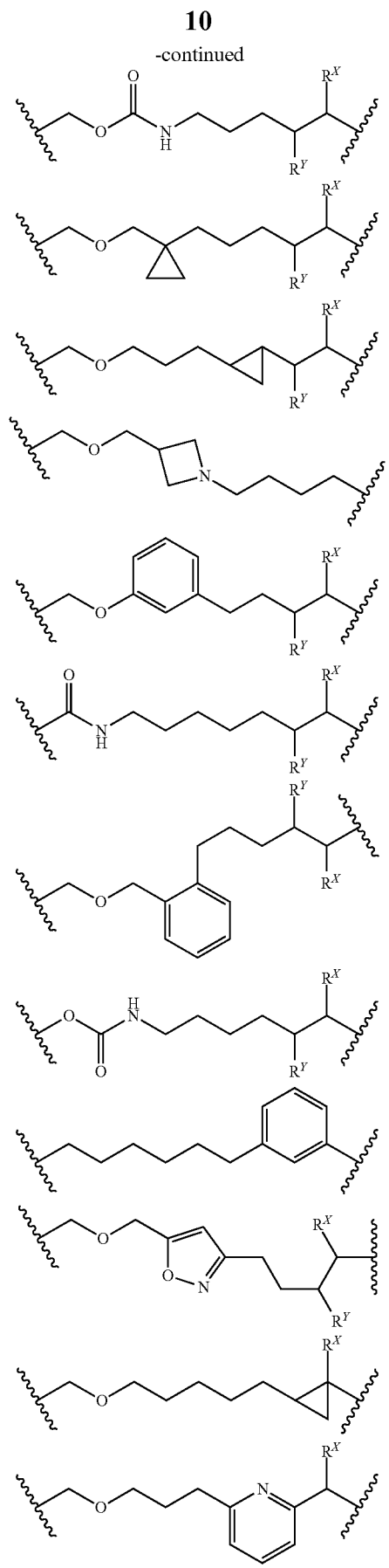

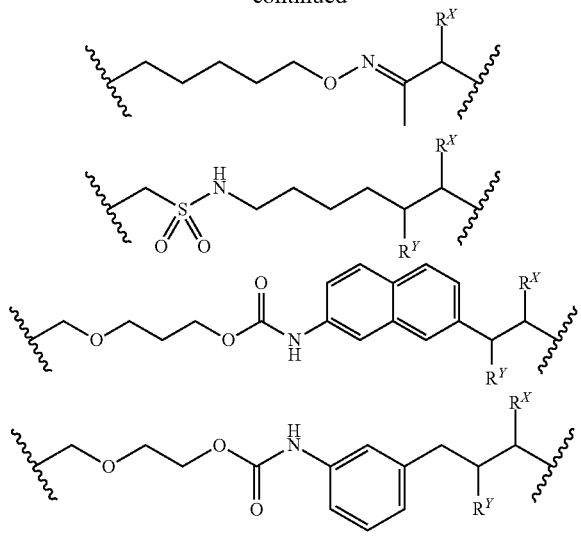

wherein $R^X$ is hydrogen, amino, hydroxy, protected amino or $O(C_1\text{-}C_4\text{ alkyl})$; $R^Y$ is hydrogen, $C_1\text{-}C_8$ alkyl, $C_2\text{-}C_8$ alkenyl, $C_2\text{-}C_8$ alkynyl, $C_3\text{-}C_8$ cycloalkyl, $C_3\text{-}C_8$ cycloalkenyl, heterocyclic, aryl, or heteroaryl, each optionally substituted; preferably, optionally substituted $C_1\text{-}C_8$ alkyl; and wherein each of the above shown groups is further optionally substituted.

In yet another embodiment, the present invention relates to compounds of Formula (Id), (Ie) or (If), and pharmaceutically acceptable salts thereof:

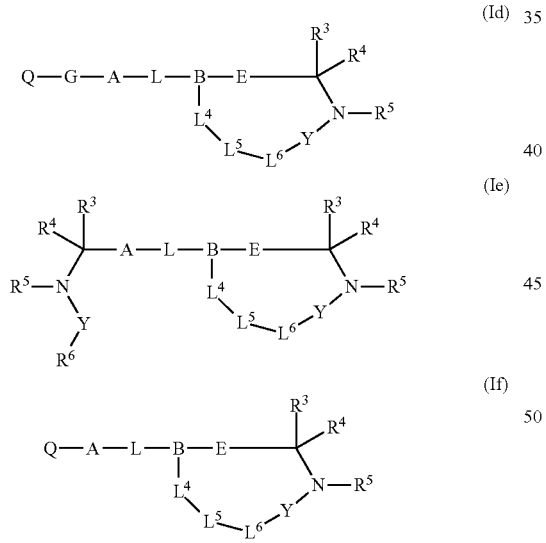

wherein A, B, E, L, Y, $R^3$, $R^4$, $R^5$, and $R^6$ are as previously defined; in Formula (Id), G is present and as previously defined.

In yet another embodiment, the present invention relates to compounds of Formula (If), and pharmaceutically acceptable salts thereof; wherein one of A and L is absent, and B is as previously defined.

In yet another embodiment, the present invention relates to compounds of Formula (If), and pharmaceutically acceptable salts thereof; wherein each of A and L are present and as previously defined.

In still another embodiment, the present invention relates to compounds of Formulae (I), (Ia), (Ib) and (Id), and pharmaceutically acceptable salts thereof; wherein G is optionally substituted five-membered heteroaryl containing one or more nitrogen atoms, and is C-attached to Q and to one of groups A, L and B.

In still another embodiment, the present invention relates to compounds of Formulae (I), (Ia), (Ib) and (Id), and pharmaceutically acceptable salts thereof; wherein G is optionally substituted 5/6-membered ring fused heteroaryl, wherein the 5-membered ring of said 5/6-membered fused heteroaryl is a heteroaryl containing one or more nitrogen atoms and wherein the 5-membered ring is C-attached to Q, and wherein the 6-membered ring of said 5/6-membered fused heteroaryl is aryl or heteroaryl and is C-attached to one of groups A, L and B.

In still another embodiment, the present invention relates to compounds of Formulae (I), (Ia), (Ib) and (Id~If), and pharmaceutically acceptable salts thereof; wherein L is absent, one of A and B is a $C_3\text{-}C_8$ cycloalkyl, and the other of A and B is an optionally substituted aryl or heteroaryl.

In still another embodiment, the present invention relates to compounds of Formulae (I), (Ia), (Ib) and (Id~If), and pharmaceutically acceptable salts thereof; wherein L is absent, one of A and B is a heterocyclic, and the other of A and B is an optionally substituted aryl or heteroaryl.

In still another embodiment, the present invention relates to compounds of Formulae (I), (Ia), (Ib) and (Id~If), and pharmaceutically acceptable salts thereof; wherein L is absent, A and B are taken together to form a cyclic group illustrated by one of the following groups:

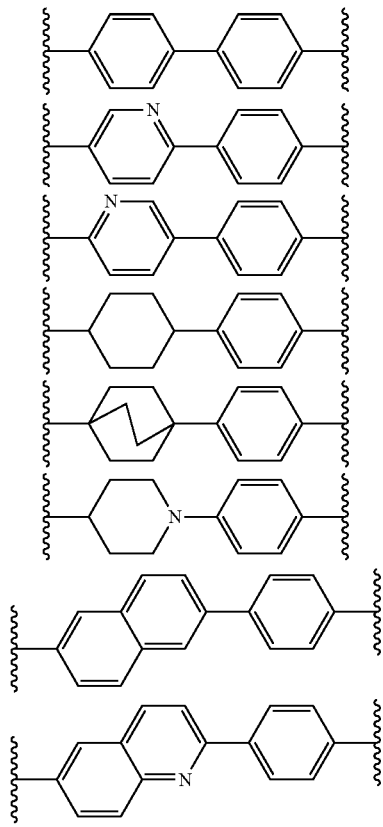

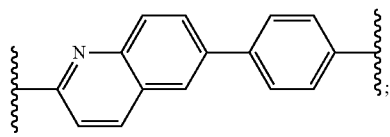

wherein each of the above shown cyclic groups is optionally substituted.

In still another embodiment, the present invention relates to compounds of Formulae (I), (Ia), (Ib) and (Id~If), and pharmaceutically acceptable salts thereof; wherein A, L and B are taken together to form a group as illustrated by the following:

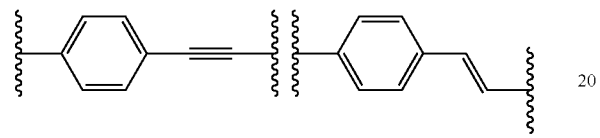

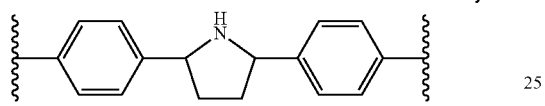

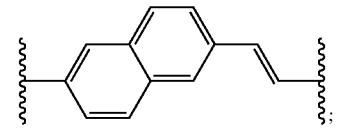

wherein each of the above shown groups is optionally substituted.

In still another embodiment, the present invention relates to compounds of Formula (I), Formulae (Ia~Ib) and (Id~It) and pharmaceutically acceptable salts thereof; wherein A and L are each absent, and B is a fused polycyclic aryl or heteroaryl selected from the following groups:

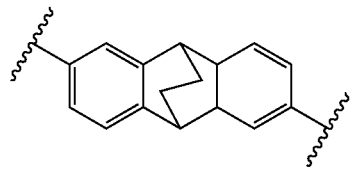

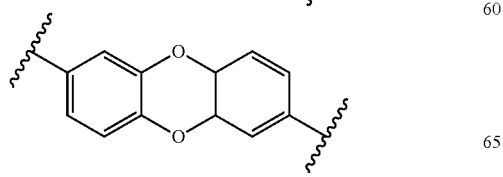

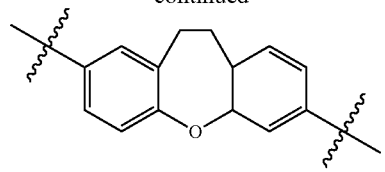

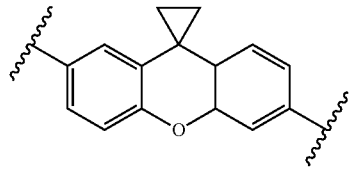

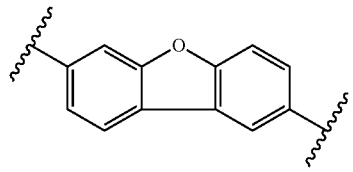

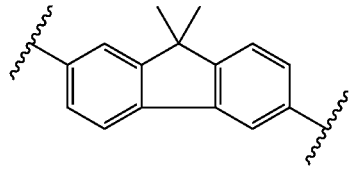

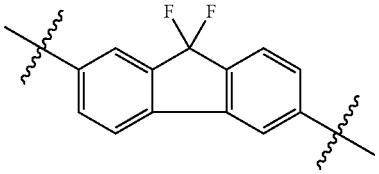

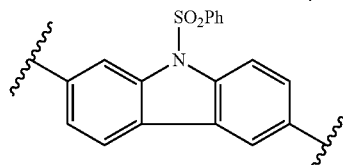

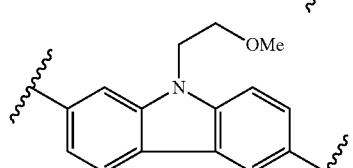

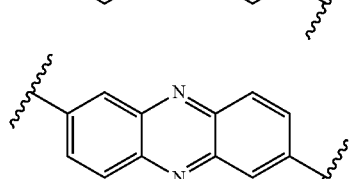

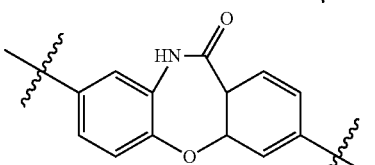

wherein each of the above shown cyclic groups is optionally substituted.

In still another embodiment, the present invention relates to compounds of Formulae (I), (Ia), (Ib) and (Id), and pharmaceutically acceptable salts thereof; wherein G is selected from the following heteroaryl groups:

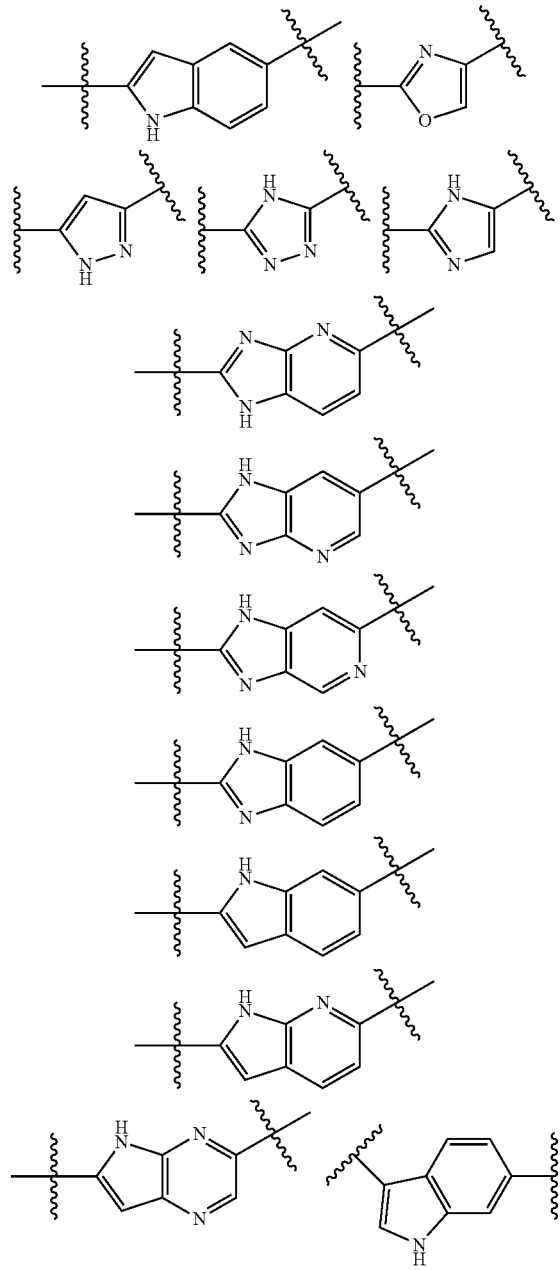

wherein each of the above shown heteroaryl groups is optionally substituted.

In still another embodiment, the present invention relates to compounds of Formula (I), (Ia), (Ib) and (Id), and pharmaceutically acceptable salts thereof; wherein G is optionally substituted imidazolyl, benzimidazolyl or imidazopyridyl.

In still another embodiment, the present invention relates to compounds of Formula (I), (Ia), (Ib) and (Id~If), and pharmaceutically acceptable salts thereof; wherein L is absent, A and B are each independently optionally substituted phenyl, monocyclic heteroaryl, naphthyl, or bicyclic heteroaryl.

In still another embodiment, the present invention relates to compounds of Formula (I), (Ia), (Ib) and (Id~If), and pharmaceutically acceptable salts thereof; wherein L is optionally substituted $C_2$-$C_4$ alkenyl or optionally substituted $C_2$-$C_4$ alkynyl; and wherein A is absent, and B is independently optionally substituted phenyl, monocyclic heteroaryl, naphthyl, or bicyclic heteroaryl.

In still another embodiment, the present invention relates to compounds of Formulae (IIa~IId), and pharmaceutically acceptable salts thereof:

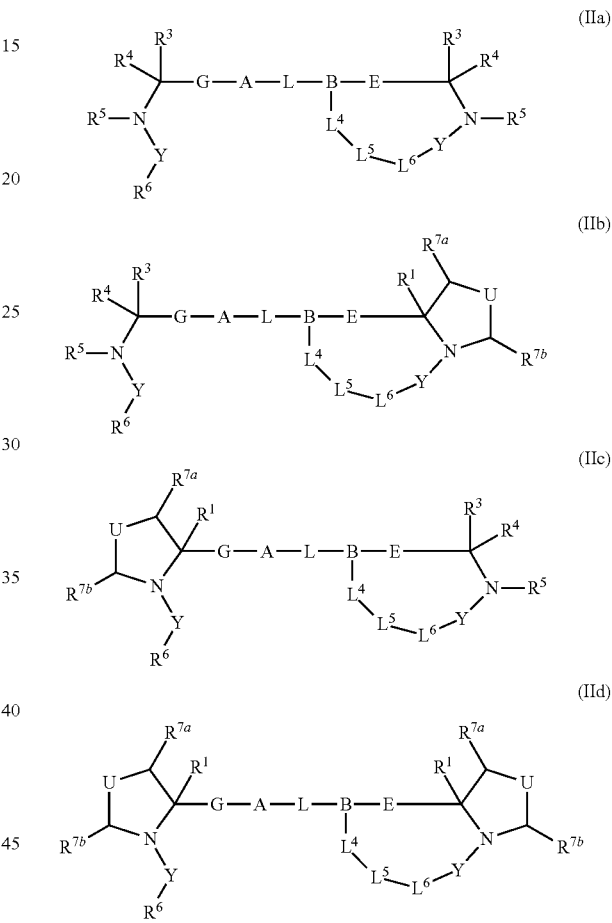

wherein A, B, E, G, L, U, Y, $R^1$, $R^3$, $R^4$, $R^5$, $R^6$, $R^{7a}$, and $R^{7b}$ are as previously defined.

In still another embodiment, the present invention relates to compounds of Formulae (IIa~IId), and pharmaceutically acceptable salts thereof; wherein Y is C(O); $R^6$ is $C_1$-$C_8$ alkyl optionally substituted with amino, halogen, hydroxy, protected amino or $O(C_1$-$C_4$ alkyl).

In still another embodiment, the present invention relates to compounds of Formulae (IIa~IId), and pharmaceutically acceptable salts thereof; wherein Y is C(O); $R^6$ is $C_1$-$C_8$ alkyl optionally substituted with amino, halogen, hydroxy, protected amino or $O(C_1$-$C_4$ alkyl); and E and G are each independently —C(O)NH— or optionally substituted imidazolyl.

In still another embodiment, the present invention relates to compounds of Formulae (IIe~IIh), and pharmaceutically acceptable salts thereof;

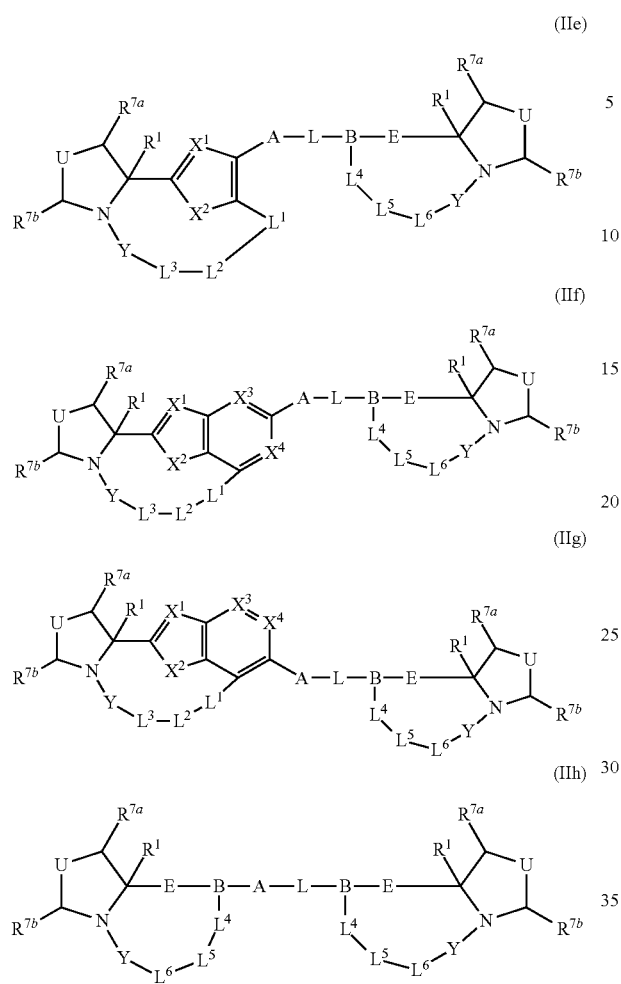

(IIe)
(IIf)
(IIg)
(IIh)

wherein A, B, E, L, U, Y, $L^1$, $L^2$, $L^3$, $L^4$, $L^5$, $L^6$, $X^1$, $X^2$, $X^3$, $X^4$, $R^1$, $R^{7a}$, and $R^{7b}$ are as previously defined.

In still another embodiment, the present invention relates to compounds of Formulae (IIe~IIh), and pharmaceutically acceptable salts thereof; wherein each E is independently —C(O)NH— or optionally substituted imidazolyl.

In still another embodiment, the present invention relates to compounds of Formulae (IIe~IIg), and pharmaceutically acceptable salts thereof; wherein -$L^1$-$L^2$-$L^3$- is taken together to form one of the following groups:

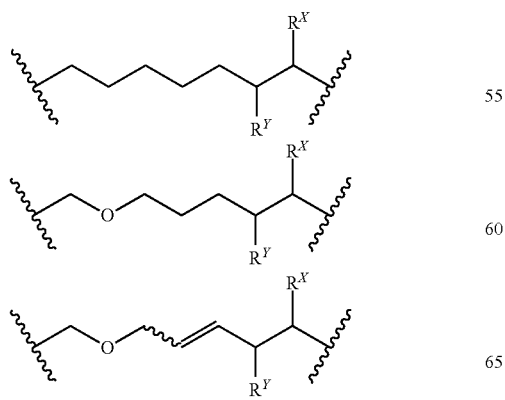

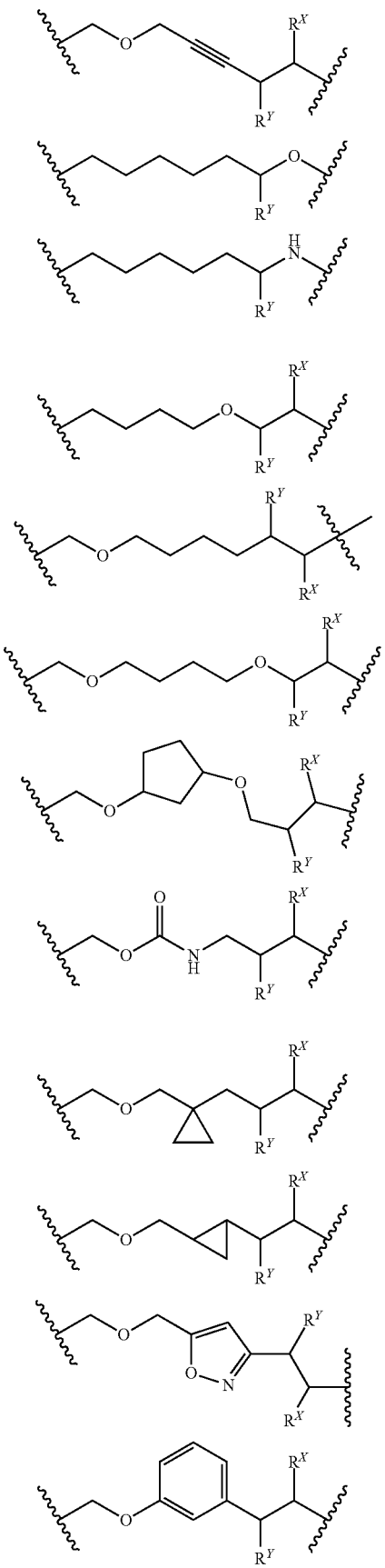

-continued

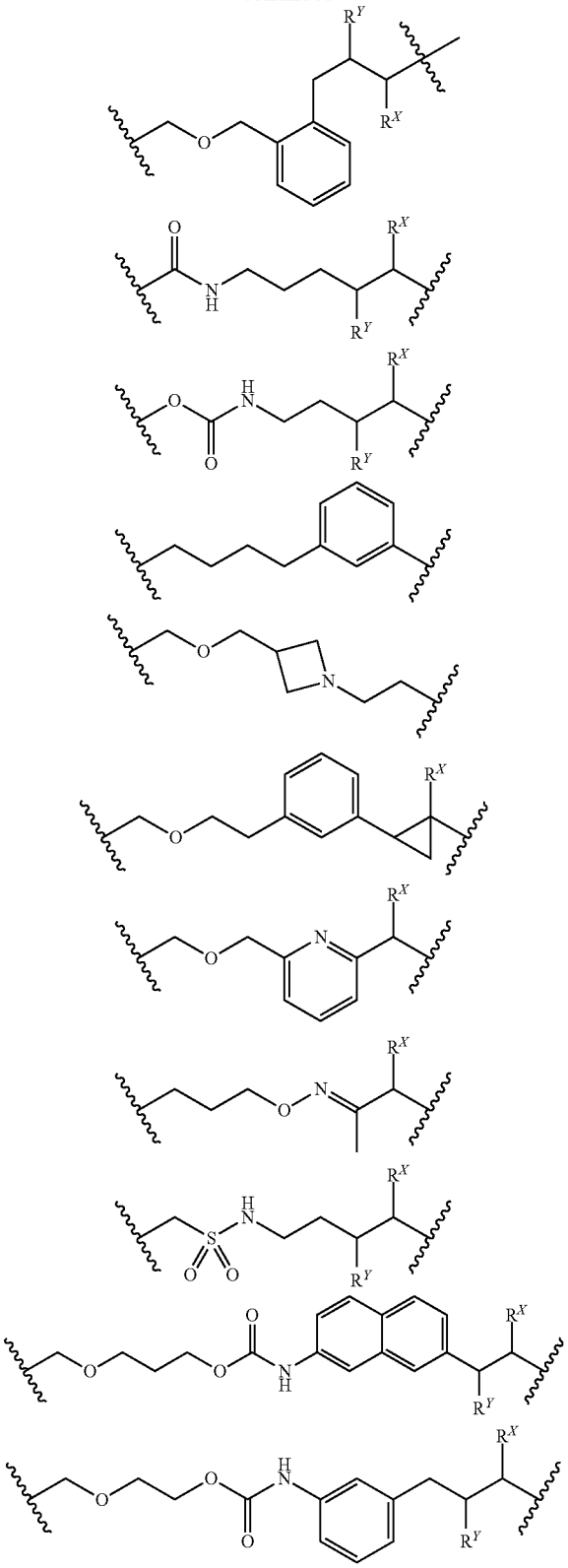

wherein $R^x$ and $R^y$ are as previously defined.

In still another embodiment, the present invention relates to compounds of Formulae (IIIa~IIIb), and pharmaceutically acceptable salts thereof:

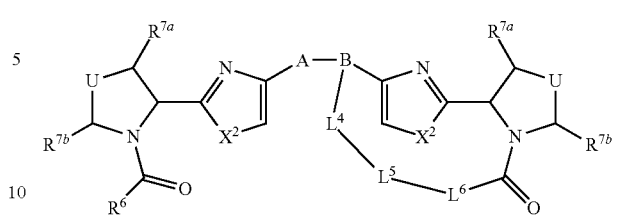
(IIIa)

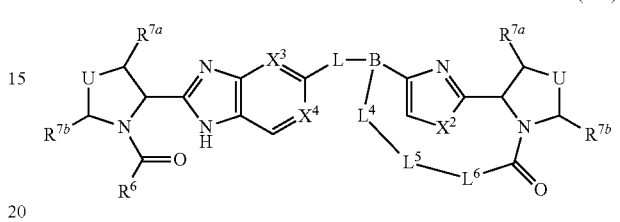
(IIIb)

wherein U, $X^2$, $X^3$, $X^4$, $R^{7a}$, and $R^{7b}$ are as previously defined; $R^6$ is $C_1$-$C_8$ alkyl optionally substituted with amino, hydroxy, protected amino, or $O(C_1$-$C_4$ alkyl); A and B are each independently phenyl, monocyclic heteroaryl, bicyclic aryl, or bicyclic heteroaryl, each optionally substituted; L is O, optionally substituted $C_2$-$C_4$ alkenyl, or optionally substituted $C_2$-$C_4$ alkynyl; the linker -$L^1$-$L^2$-$L^3$- is from 6 to 16 bond lengths and the linker -$L^4$-$L^5$-$L^6$- is from 8 to 18 bond lengths. In yet another aspect, L is optionally substituted $C_2$-$C_4$ alkenyl, or optionally substituted $C_2$-$C_4$ alkynyl; and the linker -$L^4$-$L^5$-$L^6$- is from 8 to 14 bond lengths.

In still another embodiment, the present invention relates to compounds of Formulae (IVa~IVd), and pharmaceutically acceptable salts thereof:

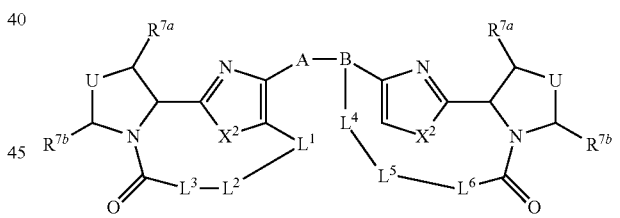
(IVa)

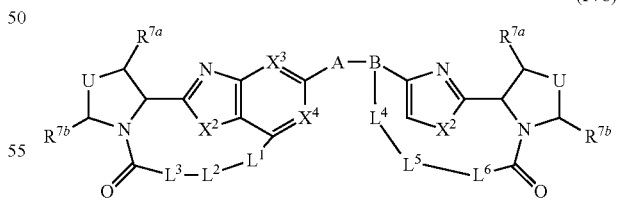
(IVb)

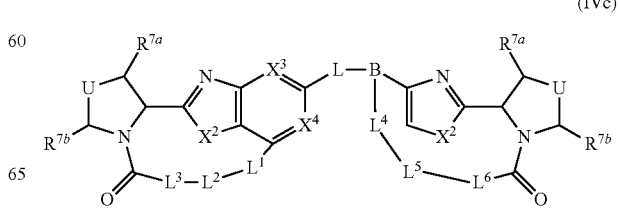
(IVc)

-continued (IVd)

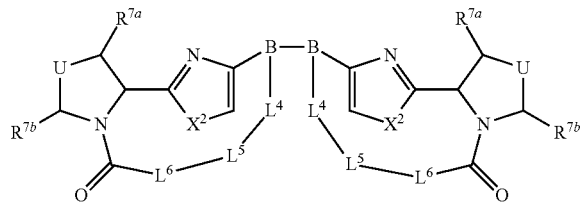

(Vb)

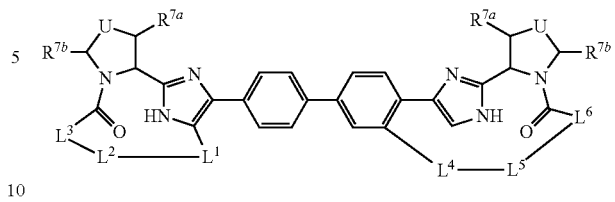

wherein U, $L^1$, $L^2$, $L^3$, $L^4$, $L^5$, $L^6$, $X^2$, $X^3$, $X^4$, $R^{7a}$, and $R^{7b}$ are as previously defined; A and B are each independently phenyl, monocyclic heteroaryl, bicyclic aryl, or bicyclic heteroaryl, each optionally substituted; the linker -$L^1$-$L^2$-$L^3$- is from 6 to 16 bond lengths; and -$L^4$-$L^5$-$L^6$- is from 8 to 18 bond lengths. In yet another aspect, L is optionally substituted $C_2$-$C_4$ alkenyl, or optionally substituted $C_2$-$C_4$ alkynyl; and the linker -$L^4$-$L^5$-$L^6$- is from 8 to 14 bond lengths. In another embodiment, the present invention relates to compounds of Formulae (IVa~IVd), and pharmaceutically acceptable salts thereof, wherein A and B are each independently phenyl, monocyclic heteroaryl, bicyclic aryl, or bicyclic heteroaryl, each optionally substituted; L is absent or O, optionally substituted $C_2$-$C_4$ alkenyl, or optionally substituted $C_2$-$C_4$ alkynyl; $L^4$ and $L^6$ at each occurrence are each independently absent or a linear aliphatic group wherein at least one of $L^4$ and $L^6$ is present; $X^3$ and $X^4$ at each occurrence is each independently N or C($R^{12}$); and $R^{12}$ at each occurrence is independently hydrogen, halogen, hydroxy, optionally substituted $C_1$-$C_4$ alkyl or O($C_1$-$C_4$ alkyl); or a pharmaceutically acceptable salt thereof.

In still another embodiment, the present invention relates to compounds of Formulae (Va~Vc), and pharmaceutically acceptable salts thereof:

(Vc)

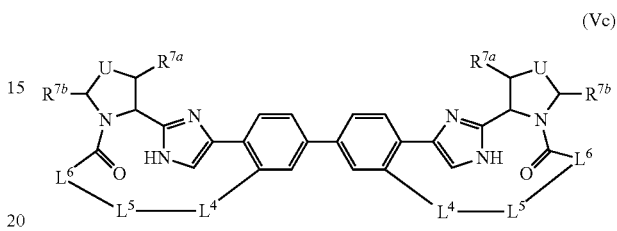

wherein $R^6$ is $C_1$-$C_8$ alkyl optionally substituted with amino, halogen, hydroxy, protected amino, or O($C_1$-$C_4$ alkyl); U at each occurrence is independently $CH_2$, CHF, CHMe, $CF_2$, C=$CH_2$, C=$CF_2$, or C($R^7$)$_2$, wherein $R^7$ is hydrogen, halogen, optionally substituted $C_1$-$C_4$ cycloalkyl, or optionally substituted $C_3$-$C_8$ cycloalkyl; alternatively, the two geminal $R^7$ groups are taken together with the carbon atom to which they are attached to form a spiro, optionally substituted $C_3$-$C_7$ cycloalkyl or optionally substituted 3- to 7-membered heterocyclic; $R^{7a}$ is hydrogen; and $R^{7b}$ is hydrogen, methyl, or optionally substituted $C_3$-$C_8$ cycloalkyl; or alternatively, $R^{7a}$ and U or U and $R^{7b}$ are taken together with the carbon atoms to which they are attached to form a fused, optionally substituted $C_3$-$C_8$ cycloalkyl, and the other of $R^{7b}$ or $R^{7a}$ is hydrogen; or yet alternatively U, $R^{7a}$ and $R^{7b}$ are taken together with the carbon atoms to which they are attached to form a bridged, optionally substituted $C_4$-$C_7$ cycloalkyl; the linker -$L^1$-$L^2$-$L^3$- is from 6 to 16 bond lengths; and -$L^4$-$L^5$-$L^6$- is from 8 to 18 bond lengths.

In still another embodiment, the present invention relates to compounds of Formulae (Vd~Vg), and pharmaceutically acceptable salts thereof:

(Va)

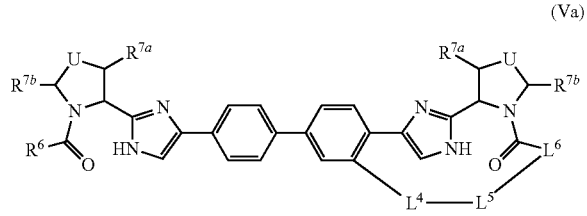

(Vd)

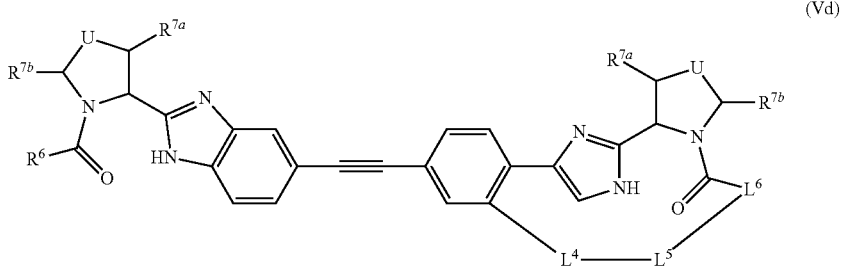

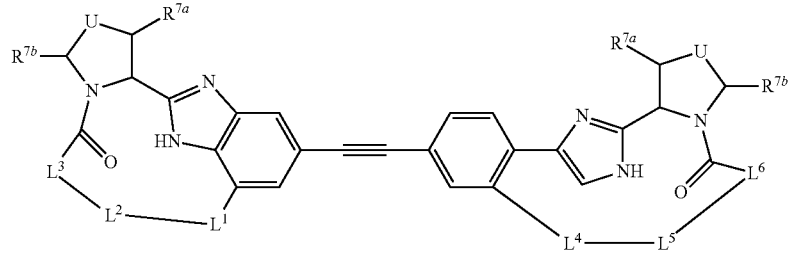

(Ve)

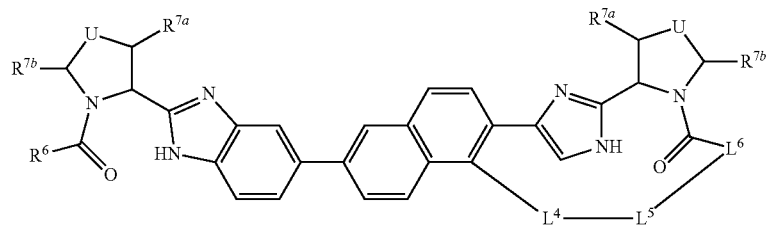

(Vf)

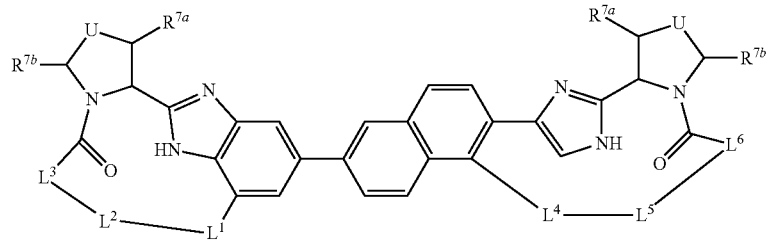

(Vg)

wherein R⁶ is $C_1$-$C_8$ alkyl optionally substituted with amino, halogen, hydroxy, protected amino, or $O(C_1-C_4$ alkyl); U at each occurrence is independently $CH_2$, CHF, CHMe, $CF_2$, $C=CH_2$, $C=CF_2$, or $C(R^7)_2$, wherein $R^7$ is hydrogen, halogen, optionally substituted $C_1$-$C_4$ cycloalkyl, or optionally substituted $C_3$-$C_8$ cycloalkyl; alternatively, the two geminal $R^7$ groups are taken together with the carbon atom to which they are attached to form a spiro, optionally substituted $C_3$-$C_7$ cycloalkyl or optionally substituted 3- to 7-membered heterocyclic; $R^{7a}$ is hydrogen; and $R^{7b}$ is hydrogen, methyl, or optionally substituted $C_3$-$C_8$ cycloalkyl; or alternatively, $R^{7a}$ and U or U and $R^{7b}$ are taken together with the carbon atoms to which they are attached to form a fused, optionally substituted $C_3$-$C_8$ cycloalkyl, and the other of $R^{7b}$ or $R^{7a}$ is hydrogen; or yet alternatively U, $R^{7a}$ and $R^{7b}$ are taken together with the carbon atoms to which they are attached to form a bridged, optionally substituted $C_4$-$C_7$ cycloalkyl; $L^1$, $L^3$, $L^4$ and $L^6$ at each occurrence are each independently absent or a linear aliphatic group wherein at least one of $L^1$ and $L^3$ is present and wherein at least one of $L^4$ and $L^6$ is present. In some embodiments, the invention is a compound of Formulae (Vd~Vg), and pharmaceutically acceptable salts thereof, wherein the linker -$L^1$-$L^2$-$L^3$- is from 6 to 16 bond lengths; and the linker -$L^4$-$L^2$-$L^6$- is from 8 to 18 bond lengths.

In another embodiment, the present invention relates to compounds of Formulae (VIa~VIb):

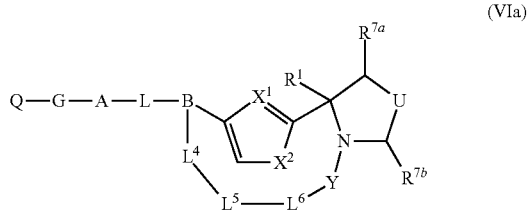

(VIa)

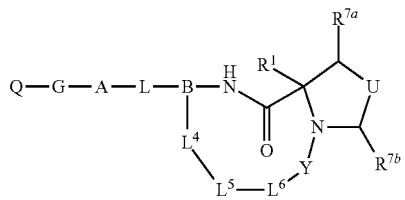

(VIb)

wherein Q, G, A, L, B, $L^4$, $L^6$, $L^8$, Y, $R^1$, $R^{7a}$, $R^{7b}$ and U are as defined above; and $X^1$ is N; or $X^2$ is $N(R^1)$; or $X^1$ is N and $X^2$ is $N(R^1)$; or a pharmaceutically acceptable salt thereof. In yet another aspect, the invention is a compound having the Formula (VIa) or (VIb), or a pharmaceutically acceptable salt thereof, wherein A is absent, optionally substituted aryl, or optionally substituted heteroaryl; B is optionally substituted aryl or optionally substituted heteroaryl; L is absent, O, optionally substituted $C_2$-$C_4$ alkenyl, or optionally substituted $C_2$-$C_4$ alkynyl; $X^1$ is N; $X^2$ is NH, O, S or NMe; Y is C(O); $R^1$ is hydrogen;

Q is hydrogen of

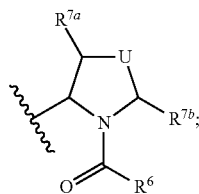

G is absent or selected from

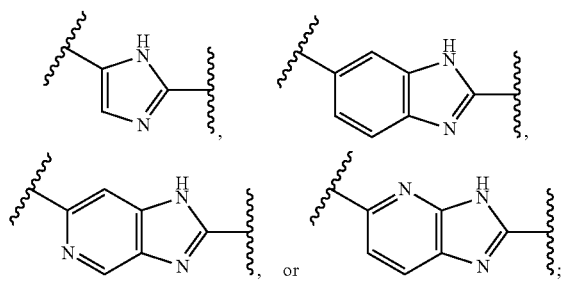

wherein each of said imidazolyl, benzimidazolyl or imidazopyridyl groups are each optionally substituted.

In a further embodiment, the present invention relates to compounds of Formulae (Id~If), (IIa~IIh), (IIIa~IIIb), (IVa~IVd), (Va~Vg), and (VIa~VIb), and pharmaceutically acceptable salts thereof; wherein -$L^4$-$L^5$-$L^6$- together forms a linker illustrated by one of the following groups:

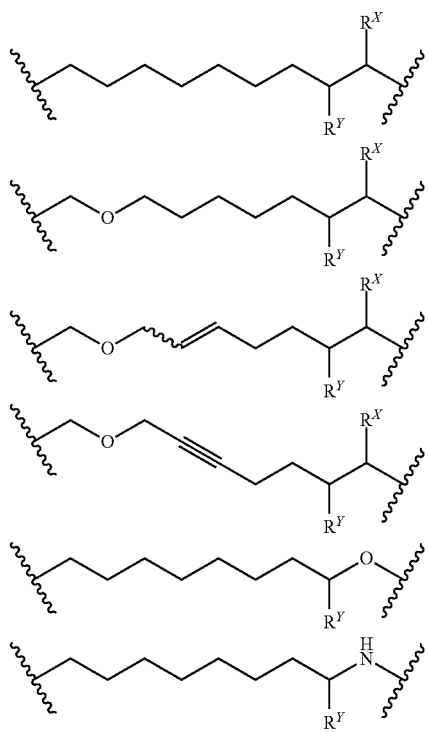

-continued

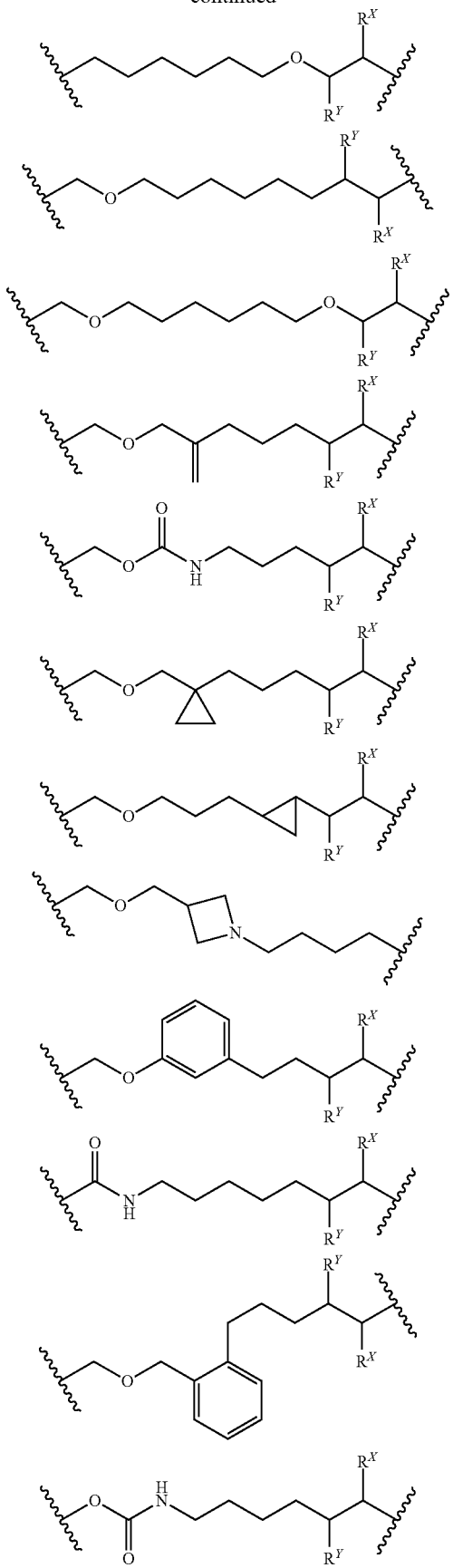

-continued

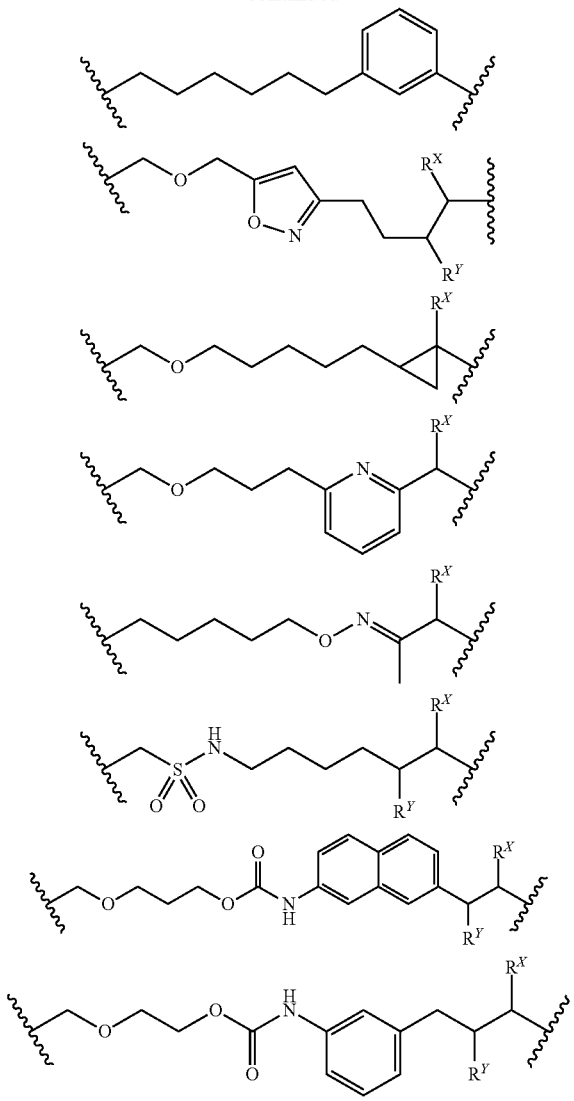

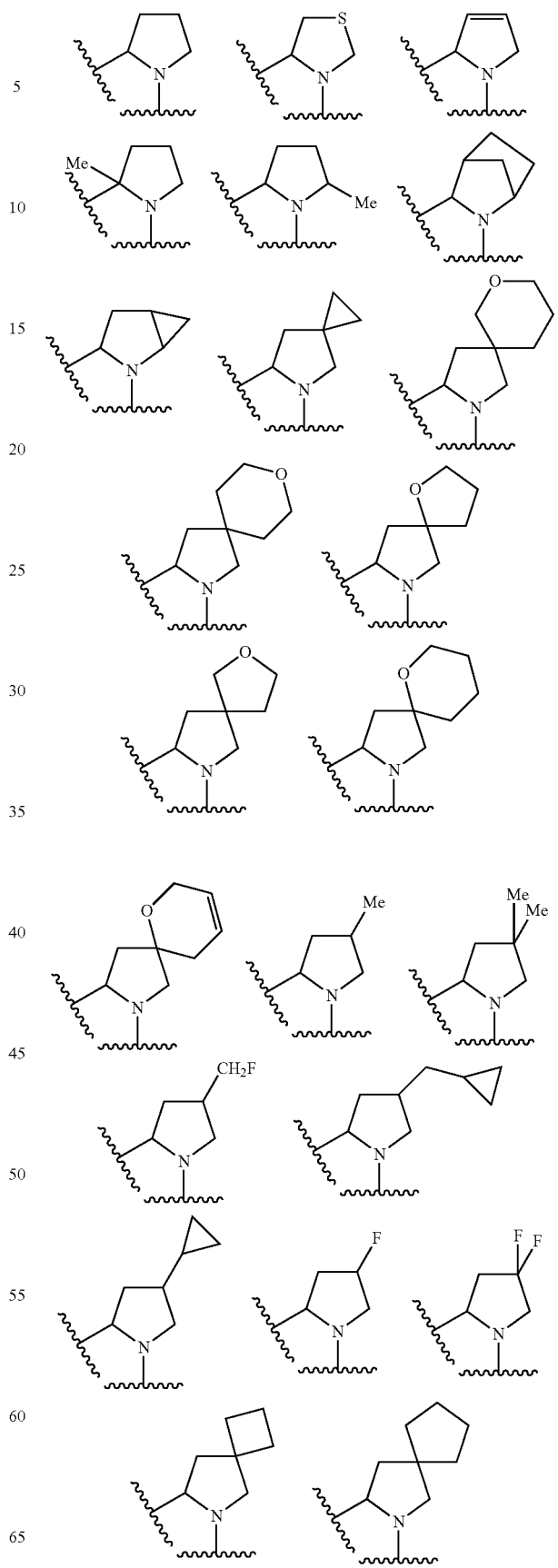

wherein $R^X$ is hydrogen, amino, hydroxy, protected amino or $O(C_1-C_4$ alkyl); $R^Y$ is hydrogen, $C_1-C_8$ alkyl, $C_2-C_8$ alkenyl, $C_2-C_8$ alkynyl, $C_3-C_8$ cycloalkyl, $C_3-C_8$ cycloalkenyl, heterocyclic, aryl, or heteroaryl, each optionally substituted; preferably, optionally substituted $C_1-C_8$ alkyl; and wherein each of the above shown groups is further optionally substituted.

In still another embodiment, the present invention relates to compounds of Formula (I), (Ia), (Ib), (Id~If), (IIb~IIh), (IIa~IIIb), (IVa~IVd), (Va~Vg), and (VIa~Vb), and pharmaceutically acceptable salts thereof; wherein

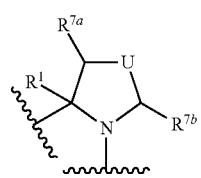

at each occurrence is independently illustrated by one of the following groups:

-continued

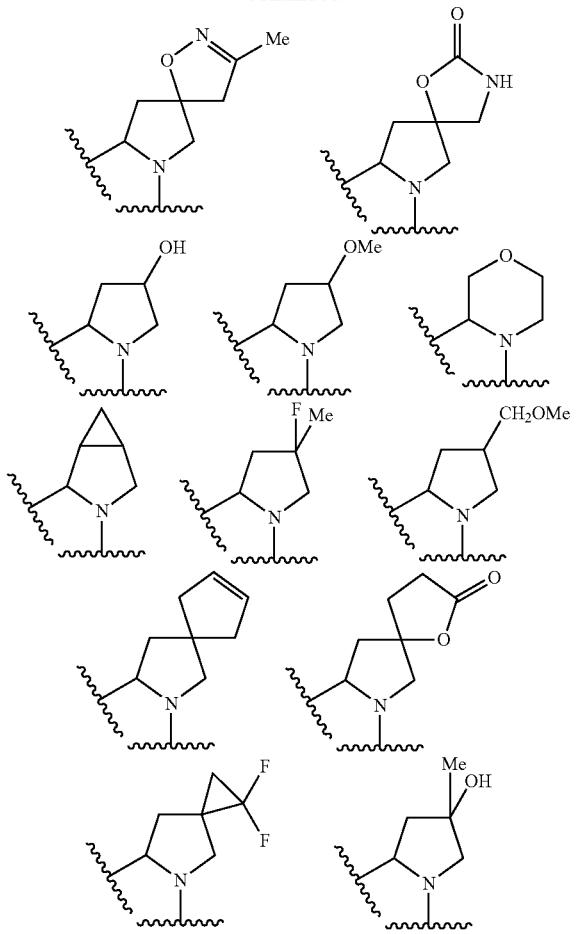

In an additional aspect, the invention relates to a compound of Formula (I), or a pharmaceutically acceptable salt thereof wherein E at each occurrence is independently an optionally substituted 5-membered heteroaryl containing one or more nitrogen atoms; preferably optionally substituted imidazolyl.

In yet an additional aspect, the invention relates to a compound of Formula (I), or a salt thereof wherein G is absent or an optionally substituted 5-membered heteroaryl containing one or more nitrogen atoms or optionally substituted 5/6-membered fused heteroaryl, wherein the 5-membered ring of said 5/6-membered fused heteroaryl contains one or more nitrogen atoms and is attached to group Q, and wherein the 6-membered ring of said 5/6-membered fused heteroaryl is attached to one of groups A, L and B and is aryl or heteroaryl. In an additional aspect, G is optionally substituted imidazolyl, optionally substituted benzimidazolyl or optionally substituted imidazopyridyl.

In an additional embodiment, the invention is directed to a compound of Formula (I), or a pharmaceutically acceptable salt thereof wherein $R^7$ at each occurrence is independently selected from the group consisting of hydrogen, halogen, cyano, hydroxy, $O(C_1\text{-}C_4$ alkyl), $S(C_1\text{-}C_4$ alkyl), amino optionally substituted with one or two $C_1\text{-}C_4$ alkyl, optionally substituted aryl, optionally substituted heteroaryl, and optionally substituted $C_1\text{-}C_4$ alkyl.

In yet another aspect, the invention relates to a compound of Formula (I), or a pharmaceutically acceptable salt thereof wherein:

A is absent or independently a monocyclic or polycyclic group independently selected from the group consisting of aryl, heteroaryl, heterocyclic, $C_3\text{-}C_8$ cycloalkyl, and $C_3\text{-}C_8$ cycloalkenyl, each optionally substituted; preferably optionally substituted aryl or optionally substituted heteroaryl;

B at each occurrence is independently a monocyclic or polycyclic group independently selected from the group consisting of aryl, heteroaryl, heterocyclic, $C_3\text{-}C_8$ cycloalkyl, and $C_3\text{-}C_8$ cycloalkenyl, each optionally substituted; preferably optionally substituted aryl or optionally substituted heteroaryl;

E at each occurrence is independently an optionally substituted 5-membered heteroaryl containing one or more nitrogen atoms; preferably optionally substituted imidazolyl;

L is absent or selected from the group consisting of O, optionally substituted $C_1\text{-}C_4$ alkyl, optionally substituted $C_2\text{-}C_4$ alkenyl, and optionally substituted $C_2\text{-}C_4$ alkynyl;

G is absent or an optionally substituted 5-membered heteroaryl containing one or more nitrogen atoms or optionally substituted 5/6-membered fused heteroaryl, wherein the 5-membered ring of said 5/6-membered fused heteroaryl contains one or more nitrogen atoms and is attached to group Q, and wherein the 6-membered ring of said 5/6-membered fused heteroaryl is attached to one of groups A, L and B and is aryl or heteroaryl; preferably, optionally substituted imidazolyl, optionally substituted benzimidazolyl or optionally substituted imidazopyridyl;

Q is hydrogen or

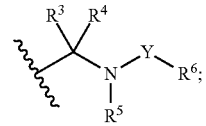

Alternatively, G and Q can be taken together to form a group selected from:

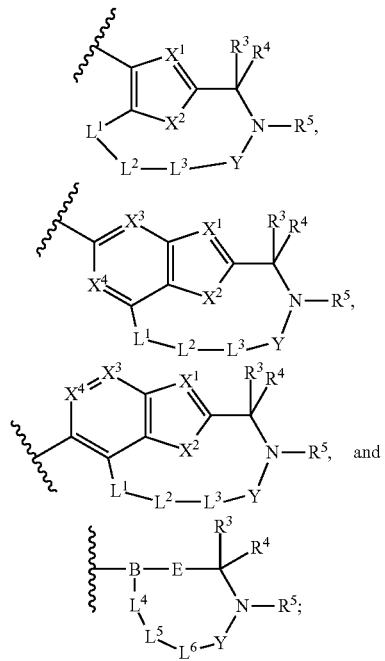

$X^1$ at each occurrence is independently N or $C(R^{11})$; preferably N;

$X^2$ at each occurrence is independently $N(R^1)$, O or S; preferably NH;

$X^3$ and $X^4$ are each independently selected from N or $C(R^{12})$; preferably CH;

$R^1$ at each occurrence is independently hydrogen or optionally substituted $C_1$-$C_4$ alkyl;

$R^{11}$ at each occurrence is independently hydrogen, halogen or optionally substituted $C_1$-$C_4$ alkyl; and $R^{12}$ at each occurrence is independently hydrogen, halogen, hydroxy, optionally substituted $C_1$-$C_4$ alkyl, or $O(C_1$-$C_4$ alkyl).

$L^1$ and $L^3$ at each occurrence are each independently absent or an aliphatic group wherein at least one of $L^1$ and $L^3$ is present; preferably, a linear aliphatic group;

$L^4$ and $L^6$ at each occurrence are each independently absent or an aliphatic group wherein at least one of $L^4$ and $L^6$ is present; preferably, a linear aliphatic group;

$L^2$ and $L^5$ at each occurrence are each independently absent, or selected from the group consisting of aryl, heteroaryl, heterocyclic, $C_3$-$C_8$ cycloalkyl, and $C_3$-$C_8$ cycloalkenyl, each optionally substituted;

Y at each occurrence is independently C(O) or $S(O)_2$; preferably C(O);

wherein -$L^1$-$L^2$-$L^3$- together forms a linker; preferably, a linker of from 6 to 16 bond lengths;

wherein -$L^4$-$L^5$-$L^6$- together forms a linker; preferably, a linker from 8 to 18 bond lengths;

$R^3$ and $R^4$ are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; preferably hydrogen or optionally substituted $C_1$-$C_4$ alkyl; alternatively, $R^3$ and $R^4$ are taken together with the carbon atom to which they are attached to form optionally substituted $C_3$-$C_8$ cycloalkyl or optionally substituted heterocyclic;

$R^5$ is independently hydrogen, optionally substituted $C_1$-$C_8$ alkyl, or optionally substituted $C_3$-$C_8$ cycloalkyl; preferably hydrogen or optionally substituted $C_1$-$C_4$ alkyl;

Alternatively $R^3$, $R^4$ and $R^5$ are taken together with the carbon and nitrogen atom to which they are attached to form

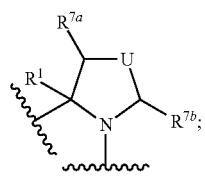

U is absent or independently selected from O, S, S(O), $SO_2$, NC(O)—($C_1$-$C_4$ alkyl), C(O), protected carbonyl, $OCH_2$, $OCH_2CH_2$, $SCH_2$, $SCH_2CH_2$, $C(R^7)_2$, $C(R^7)_2C(R^7)_2$, or C=$C(R^2)_2$; preferably $CH_2$, C=N—OMe, or C=$CH_2$;

$R^2$ at each occurrence is independently hydrogen, halogen, optionally substituted $C_1$-$C_4$ alkyl, optionally substituted aryl, or optionally substituted heteroaryl;

$R^7$ at each occurrence is independently selected from the group consisting of hydrogen, halogen, cyano, hydroxy, $O(C_1$-$C_4$ alkyl), $S(C_1$-$C_4$ alkyl), amino optionally substituted with one or two $C_1$-$C_4$ alkyl, optionally substituted aryl, optionally substituted heteroaryl, and optionally substituted $C_1$-$C_4$ alkyl; preferably hydrogen, halogen or hydroxy;

Alternatively two geminal $R^7$ groups are taken together with the carbon atom to which they are attached to form a spiro, optionally substituted 3- to 7-membered cycloalkyl, cycloalkenyl or heterocyclic ring; preferably, spiro and optionally substituted cyclopropyl;

$R^{7a}$ and $R^{7b}$ at each occurrence are each independently selected from the group consisting of hydrogen, optionally substituted aryl, and optionally substituted $C_1$-$C_4$ alkyl; preferably hydrogen or methyl;

Alternatively, $CHR^{7a}$—U or $CHR^{7b}$—U are taken together to form a group selected from CH=CH, fused and optionally substituted $C_3$-$C_8$ cycloalkyl, fused and optionally substituted aryl, or fused and optionally substituted heterocyclic; preferably, fused and optionally substituted cyclopropyl;

Yet alternatively, U, $R^{7a}$, and $R^{7b}$ are taken together with the carbon atoms to which they are attached to form a bridged, optionally substituted 4- to 7-membered ring including cycloalkyl, cycloalkenyl and heterocyclic; preferably bridged cyclopentyl; and $R^6$ at each occurrence is independently selected from the group consisting of $O(C_1$-$C_8$ alkyl), amino, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably, optionally substituted $C_1$-$C_8$ alkyl; more preferably $C_1$-$C_8$ alkyl optionally substituted with amino, hydroxy, protected amino or $O(C_1$-$C_4$ alkyl).

Representative compounds of the present invention include compounds 1-350 compiled in the following tables:

TABLE 1

Compounds 1-219.

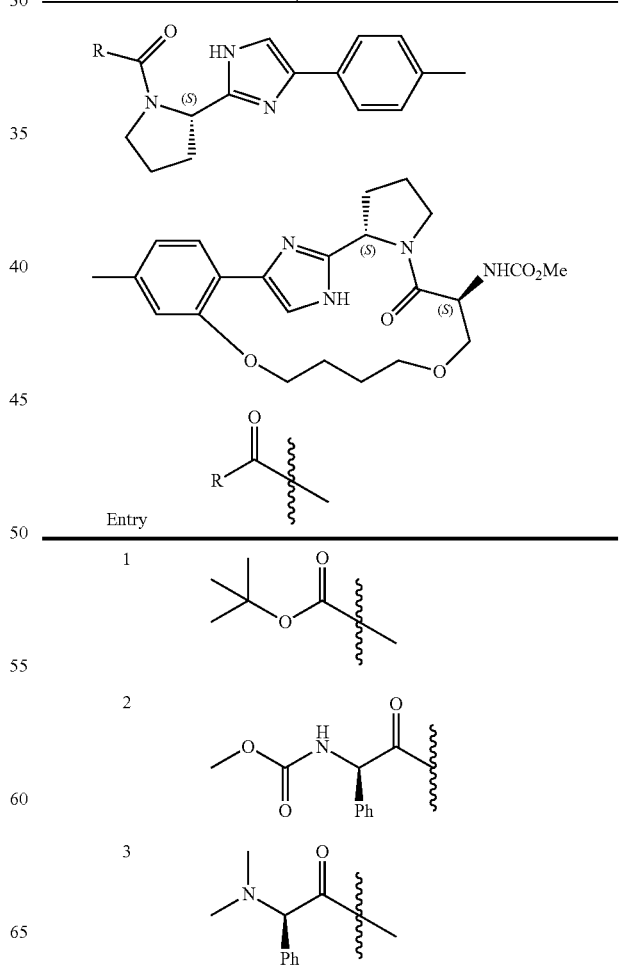

TABLE 1-continued

Compounds 1-219.

| Entry | R group |
|---|---|
| 4 | (S)-1-hydroxyethyl carbonyl |
| 5 | (S)-1-hydroxypropyl carbonyl |
| 6 | propanoyl |
| 7 | methoxyacetyl |
| 8 | N,N-dimethylaminoacetyl |
| 9 | methoxycarbonyl |
| 10 | 4-oxopentanoyl |
| 11 | (S)-1-hydroxy-2-methylpropyl carbonyl |
| 12 | pent-4-enoyl |
| 13 | cyclopropanecarbonyl |
| 14 | 1-(trifluoromethyl)cyclopropanecarbonyl |
| 15 | 1-hydroxycyclopropanecarbonyl |
| 16 | benzoyl |
| 17 | phenylacetyl |

TABLE 1-continued

Compounds 1-219.

| Entry | R group structure |
|---|---|
| 18 | cyclopropyl-CH2-C(=O)- |
| 19 | Ph-C(CH3)(OH)-C(=O)- |
| 20 | Ph-CH(OMe)-C(=O)- |
| 21 | Ph-CH(OH)-C(=O)- |
| 22 | (pyridin-3-yl)-CH2-C(=O)- |
| 23 | (pyridin-4-yl)-CH2-C(=O)- |
| 24 | Ph-CH2-CH(OH)-C(=O)- (S) |
| 25 | (tetrahydrofuran-2-yl)-C(=O)- |
| 26 | (tetrahydrofuran-2-yl)-C(=O)- |
| 27 | (tetrahydrofuran-3-yl)-C(=O)- |
| 28 | (1-methylpiperidin-4-yl)-C(=O)- |
| 29 | (tetrahydro-2H-pyran-4-yl)-C(=O)- |
| 30 | (morpholin-4-yl)-C(=O)- |
| 31 | (trans-4-(Boc-amino)cyclohexyl)-C(=O)- |

TABLE 1-continued

Compounds 1-219.

| Entry | R group |
|---|---|
| 32 | Boc-NH-cyclohexyl-C(O)- |
| 33 | Boc-N-piperidin-4-yl-C(O)- |
| 34 | (Et)₂N-cyclohexyl-C(O)- |
| 35 | MeO₂C-NH-cyclohexyl-C(O)- |
| 36 | 4-methylpiperazin-1-yl-C(O)- |
| 37 | 2-(piperidin-1-ylmethyl)phenyl-CH₂-C(O)- |
| 38 | 2-(pyrrolidin-1-ylmethyl)phenyl-CH₂-C(O)- |
| 39 | 2-((dimethylamino)methyl)phenyl-CH₂-C(O)- |
| 40 | 2-((4-methylpiperazin-1-yl)methyl)phenyl-CH₂-C(O)- |

TABLE 1-continued

Compounds 1-219.

| Entry | |
|---|---|
| 41 | 2-(morpholinomethyl)phenyl-CH2-C(=O)- |
| 42 | trans-4-(methoxycarbonylamino)cyclohexyl-C(=O)- |
| 43 | thiazol-4-yl-C(=O)- |
| 44 | oxazol-2-yl-C(=O)- |
| 45 | oxazol-5-yl-C(=O)- |
| 46 | 1H-imidazol-5-yl-CH2-C(=O)- |
| 47 | 1H-imidazol-5-yl-C(=O)- |
| 48 | 1-methyl-1H-imidazol-5-yl-C(=O)- |
| 49 | 1H-tetrazol-5-yl-CH2-C(=O)- |
| 50 | 2-fluorophenyl-C(=O)- |
| 51 | 4-(dimethylamino)phenyl-C(=O)- |
| 52 | pyridin-4-yl-C(=O)- |

TABLE 1-continued

Compounds 1-219.

| Entry | R group |
|---|---|
| 53 | 3-pyridyl-C(O)- |
| 54 | 2-pyridyl-C(O)- |
| 55 | Ph-CH(OMe)-C(O)- |
| 56 | Ph-C(OMe)(CF₃)-C(O)- |
| 57 | Ph₂CH-C(O)- |
| 58 | Ph-C(Me)₂-C(O)- |
| 59 | (2-F-C₆H₄)-C(OH)(Me)-C(O)- |
| 60 | 1-phenylcyclopropyl-C(O)- |
| 61 | MeO₂C-NH-CH(Me)-C(O)- (S) |
| 62 | MeO₂C-NH-CH(Me)-C(O)- (S) |
| 63 | EtO₂C-NH-CH(Me)-C(O)- |
| 64 | (tetrahydropyran-4-yl)-O-C(O)-NH-CH(Me)-C(O)- |
| 65 | (tetrahydropyran-4-yl)-O-C(O)-NH-CH(Me)-C(O)- (S) |

TABLE 1-continued

Compounds 1-219.

| Entry | |
|---|---|
| 66 | methyl carbamate-CH(CH2OMe)-C(O)- |
| 67 | methyl carbamate-CH(Et)-C(O)- |
| 68 | methyl carbamate-CH(Et)-C(O)- |
| 69 | methyl carbamate-CH(CH2CH2OMe)-C(O)- |
| 70 | methyl carbamate-CH(CH(OH)CH3)-C(O)- |
| 71 | methyl carbamate-CH(CH(OH)CH3)-C(O)- |
| 72 | methyl carbamate-CH(CH(OMe)CH3)-C(O)- |
| 73 | methyl carbamate-CH(CH2CH=CH2)-C(O)- |
| 74 | methyl carbamate-CH(n-Pr)-C(O)- |
| 75 | Boc-NH-CH(CH2CH2NMe2)-C(O)- |
| 76 | methyl carbamate-C(Me)2-C(O)- |
| 77 | methyl carbamate-CH(cyclopropyl)-C(O)- |

TABLE 1-continued
Compounds 1-219.
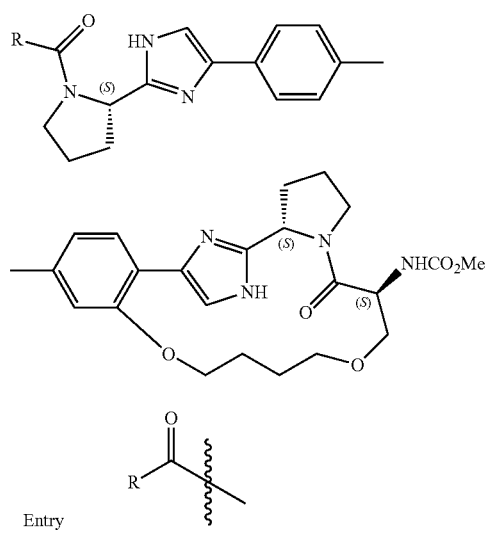
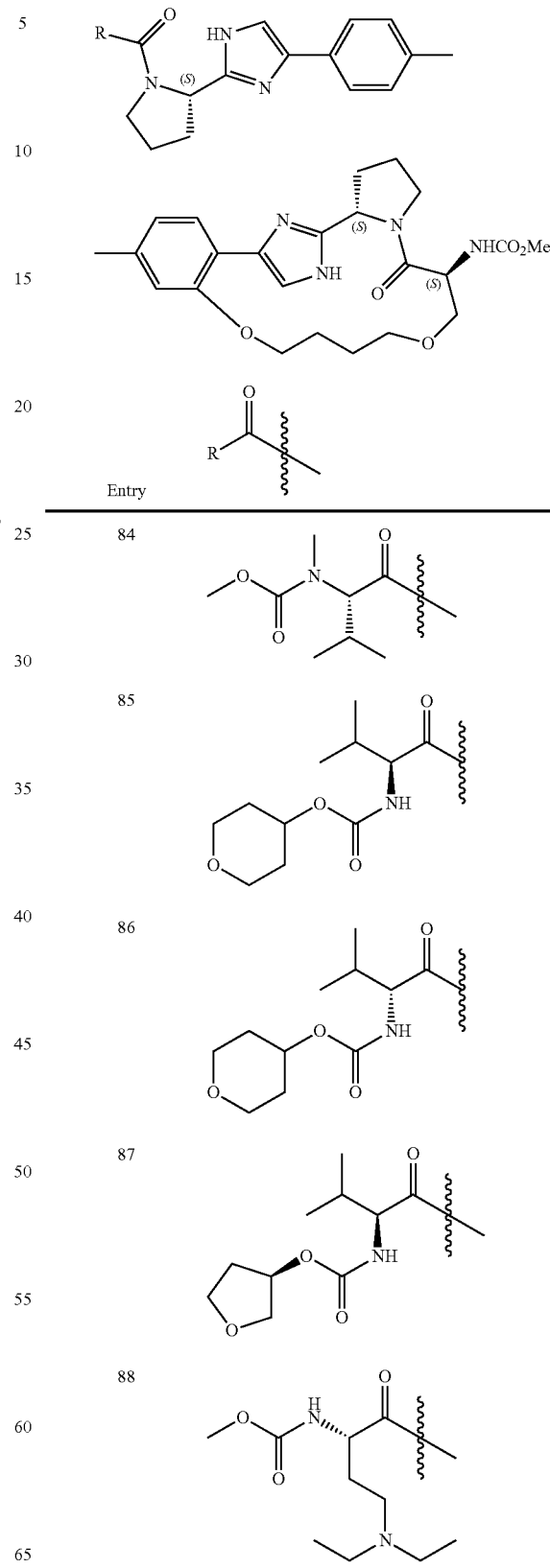

TABLE 1-continued
Compounds 1-219.
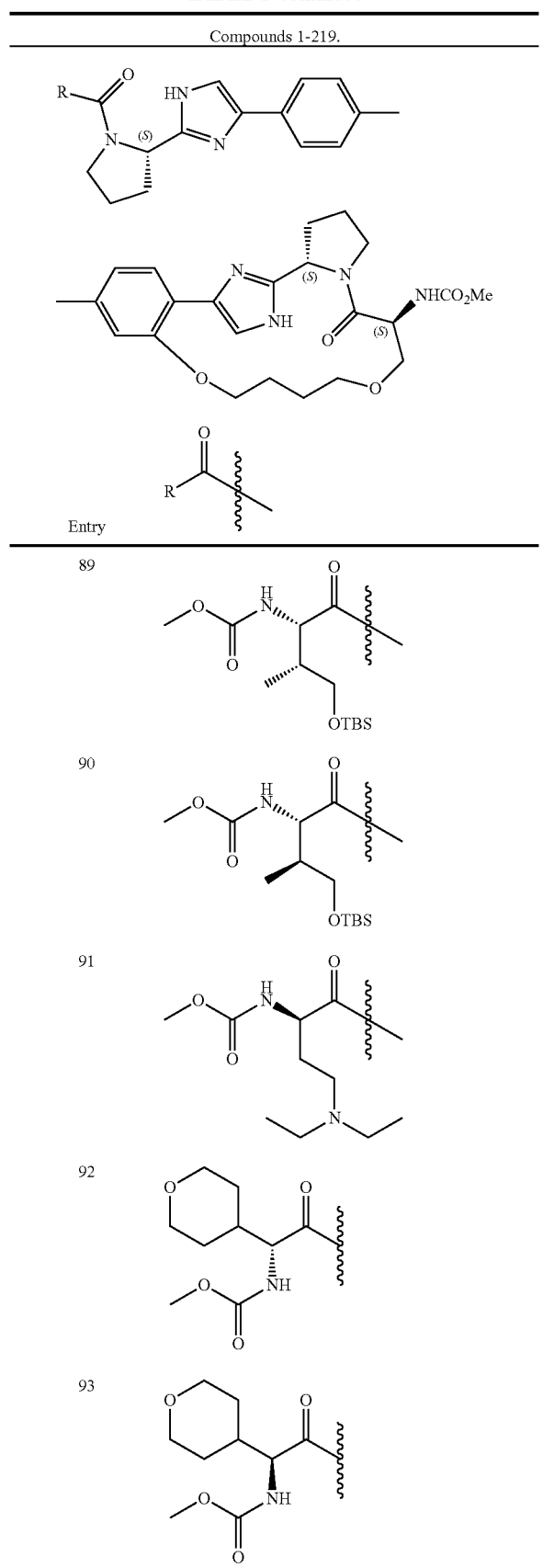
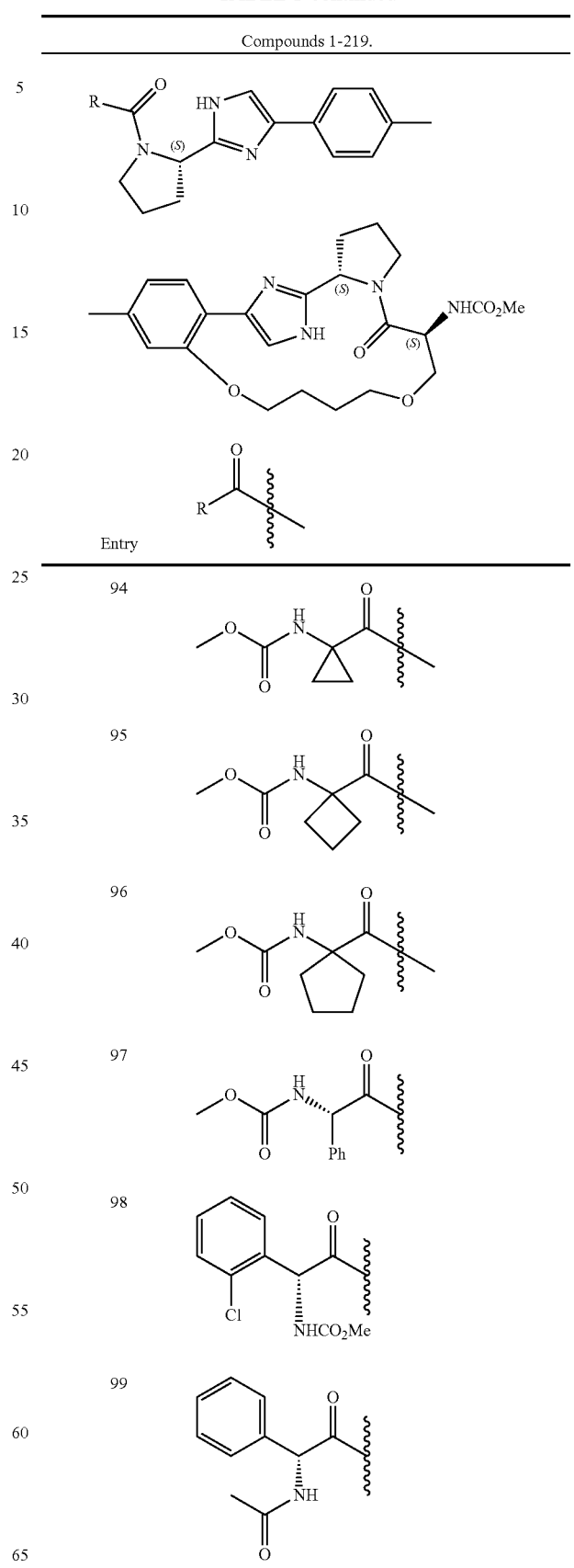

TABLE 1-continued
Compounds 1-219.
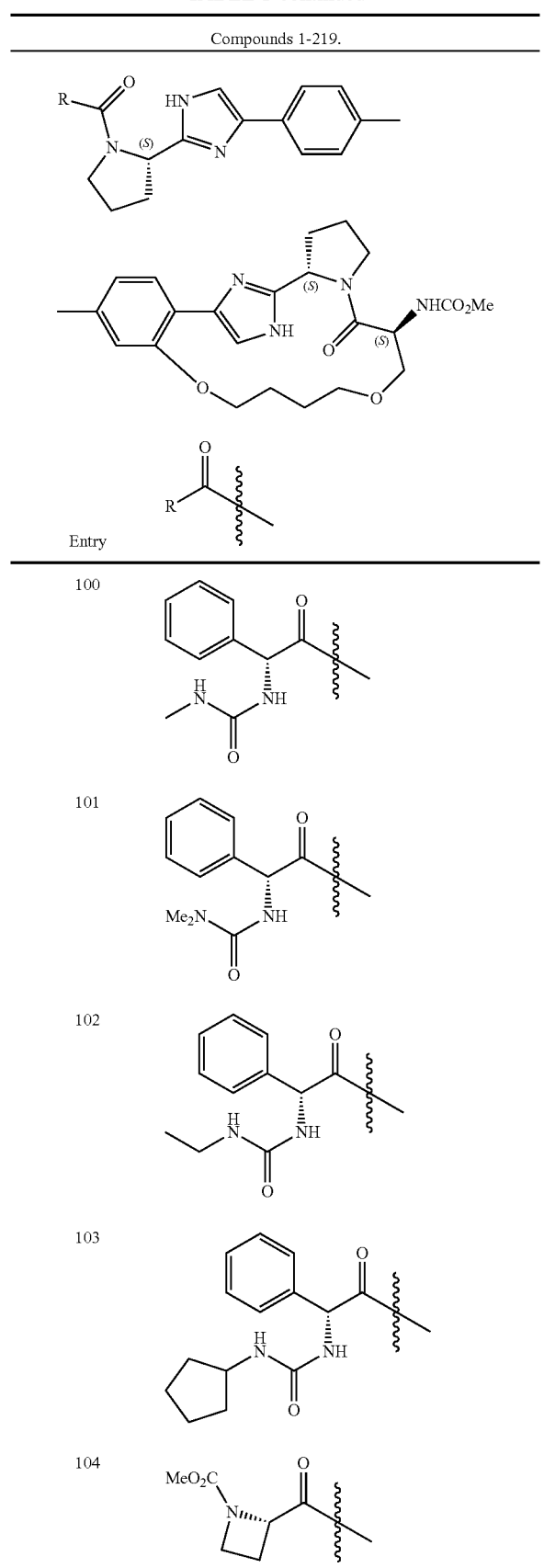
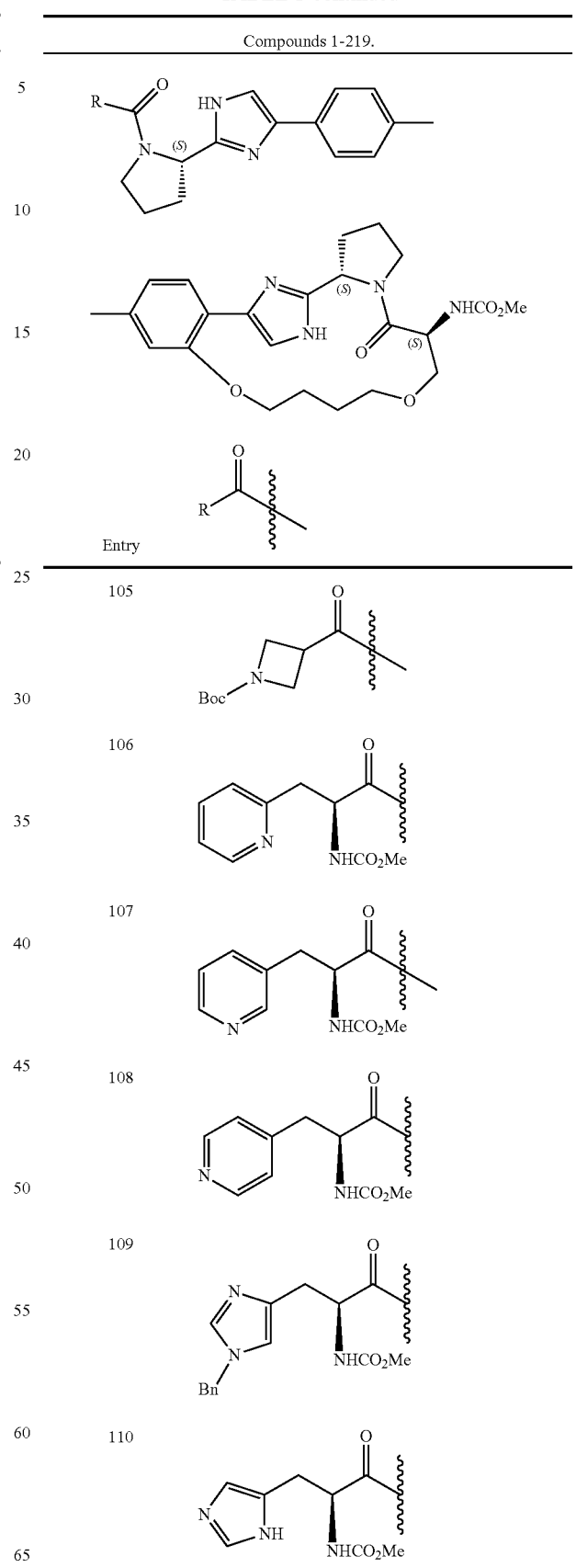

TABLE 1-continued

Compounds 1-219.

| Entry | |
|---|---|
| 111 | (thiazol-4-ylmethyl, NHCO2Me) |
| 112 | (thiophen-2-ylmethyl, MeO2CHN) |
| 113 | (thiophen-2-ylmethyl, MeO2CHN) |
| 114 | (pyrazol-1-ylmethyl, NHCO2Me) |
| 115 | (1H-1,2,3-triazol-4-ylmethyl, NHCO2Me) |
| 116 | (1-methylimidazol-2-ylmethyl, NHCO2Me) |
| 117 | (1-methylimidazol-4-ylmethyl, NHCO2Me) |
| 118 | (benzyl, NHCO2Me) |
| 119 | (benzyl, NHCO2Me) |

TABLE 1-continued

Compounds 1-219.

| Entry | |
|---|---|
| 120 | (4-(methyl phosphate)phenyl)-NHCO₂Me substituted acyl group |
| 121 | (indol-3-yl)-NHCO₂Me substituted acyl group |
| 122 | (4-OBn-phenyl)-NHCO₂Me substituted acyl group |
| 123 | (4-(Fmoc-NH-CH₂)phenyl)-NHCO₂Me substituted acyl group |
| 124 | oxazolidinone-acyl |
| 125 | oxazolidinone-acyl |
| 126 | 5-methyl-oxazolidinone-acyl |
| 127 | (2-(methoxycarbonylamino)cyclopentyl)-acyl |

TABLE 1-continued

Compounds 1-219.

| Entry | R group |
|---|---|
| 128 | (methyl carbamate)-NH-cyclopentyl-C(O)- (trans) |
| 129 | (methyl carbamate)-NH-cyclohexyl-C(O)- (trans) |
| 130 | (methyl carbamate)-NH-cyclopentyl-C(O)- (1,3-trans) |
| 131 | (methyl carbamate)-NH-cyclopentyl-C(O)- (1,3-cis) |
| 132 | (methyl carbamate)-NH-cyclohexyl-C(O)- (cis) |
| 133 | (S)-PhCH₂-CH(NHCO₂Me)-CH₂-C(O)- |
| 134 | (R)-PhCH₂-CH(NHCO₂Me)-CH₂-C(O)- |
| 135 | (2-F-C₆H₄)-CH₂-CH(NHCO₂Me)-CH₂-C(O)- |
| 136 | Ph-CH(NHCO₂Me)-CH₂-C(O)- |

TABLE 1-continued

Compounds 1-219.

| Entry | Structure |
|---|---|
| 137 | MeO-carbamate-NH-CH(Ph)-CH2-C(=O)- |
| 138 | MeO-carbamate-NH-CH(CH2CH2Ph)-CH2-C(=O)- |
| 139 | (Me)(Et)N-CH(Ph)-C(=O)- |
| 140 | (Et)2N-CH(Ph)-C(=O)- |
| 141 | (Et)(cyclopropyl)N-CH(Ph)-C(=O)- |
| 142 | 7-azabicyclo[2.2.1]heptane-N-CH(Ph)-C(=O)- |
| 143 | 7-azabicyclo[2.2.1]heptane-N-CH(Ph)-C(=O)- (other stereo) |
| 144 | 4-methylpiperazine-N-CH(Ph)-C(=O)- |
| 145 | pyrrolidine-N-CH(Ph)-C(=O)- |
| 146 | (4-F)-pyrrolidine-N-CH(Ph)-C(=O)- |
| 147 | (3-F)-pyrrolidine-N-CH(Ph)-C(=O)- |

TABLE 1-continued

Compounds 1-219.

| Entry | |
|---|---|
| 148 | 4-phenylpiperidine, α-Ph |
| 149 | 4-hydroxy-4-methylpiperidine, α-Ph |
| 150 | 4-hydroxypiperidine, α-Ph |
| 151 | 2-oxopiperazine, α-Ph |
| 152 | morpholine, α-Ph |
| 153 | piperidine, α-Ph |
| 154 | 4-Cbz-piperazine, α-Ph |
| 155 | 2-CF₃-phenyl, NMe₂ |
| 156 | 3-CF₃-phenyl, NMe₂ |
| 157 | pyridin-3-yl, NMe₂ |
| 158 | pyridin-2-yl, NMe₂ |
| 159 | pyridin-4-yl, NMe₂ |

TABLE 1-continued

Compounds 1-219.

| Entry | |
|---|---|
| 160 | 3-chlorophenyl, N(Me)₂ |
| 161 | 2-chlorophenyl, N(Me)₂ |
| 162 | 6-chloropyridin-3-yl, N(Me)₂ |
| 163 | 2-fluorophenyl (R), N(Me)₂ |
| 164 | 2-chlorophenyl, N(Me)₂ |
| 165 | 4-chlorophenyl, N(Me)₂ |
| 166 | 2-fluorophenyl (S), N(Me)₂ |
| 167 | 2-fluorophenyl, N(Me)₂ |
| 168 | 3-fluorophenyl, N(Me)₂ |
| 169 | 2-fluorophenyl, piperidin-1-yl |
| 170 | 4-nitrophenyl, N(Me)₂ |
| 171 | 2-methylthiazol-4-yl, N(Me)₂ |

TABLE 1-continued
Compounds 1-219.
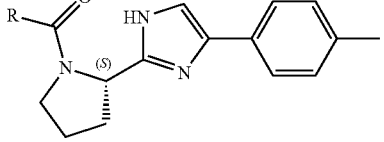
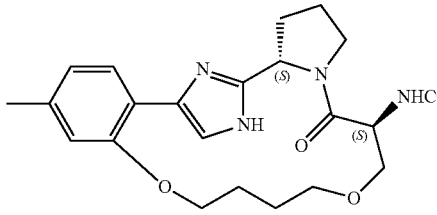
| Entry | |
|---|---|
| 172 | 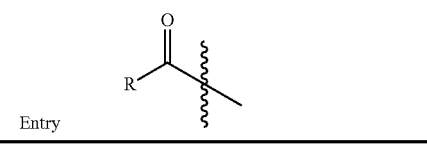 |
| 173 | 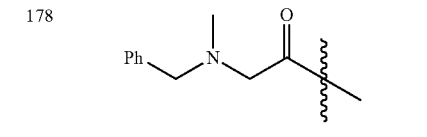 |
| 174 | 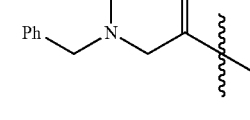 |
| 175 | 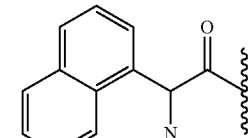 |
| 176 | 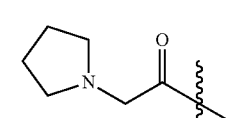 |
| 177 | 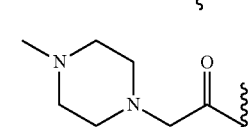 |
| 178 | 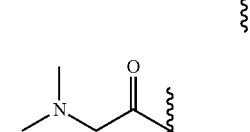 |
| 179 | 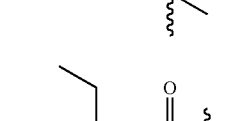 |
| 180 | 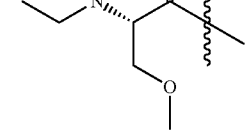 |
| 181 | |
| 182 | |
| 183 | |
| 184 | |

TABLE 1-continued
Compounds 1-219.
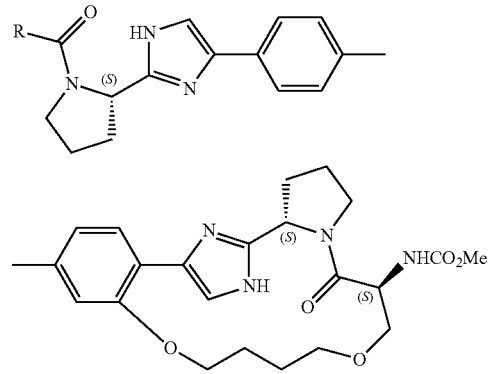
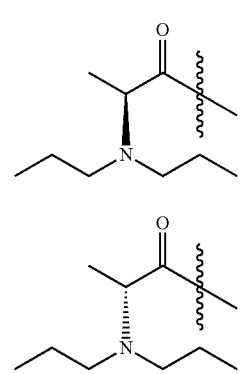
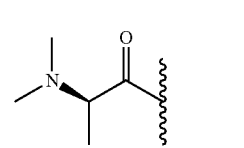 [SMILES: *C(=O)[C@@H](C)N(C)C]
| Entry | |
|---|---|
| 185 | 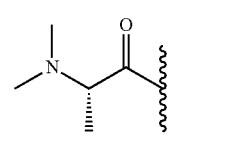 [SMILES: *C(=O)[C@H](C)N(C)C] |
| 186 | 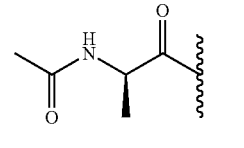 |
| 187 | 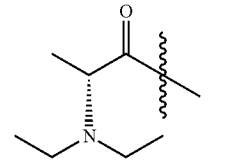 [SMILES: *C(=O)[C@@H](C)N(CC)CC] |
| 188 | 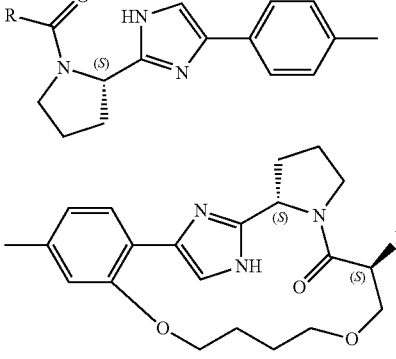 |
| 189 | 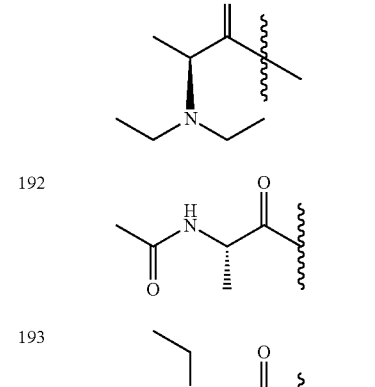 |
| 190 | 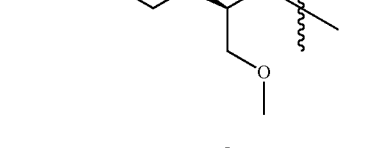 |
| 191 | 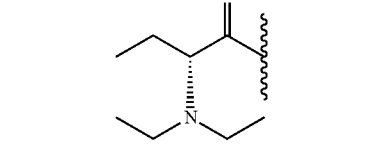 |
| 192 | 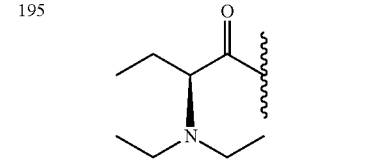 |
| 193 | 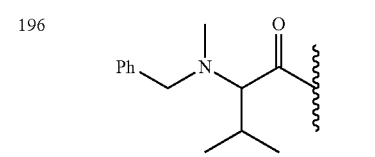 |
| 194 | 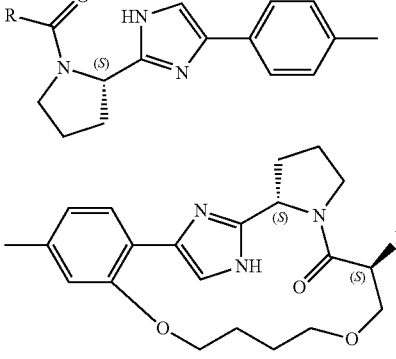 |
| 195 | 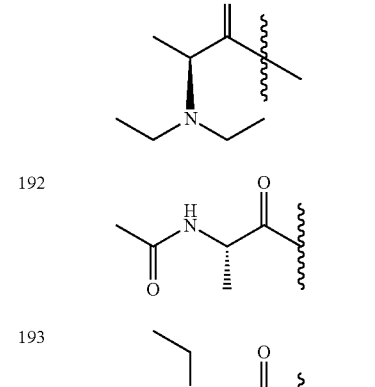 |
| 196 | 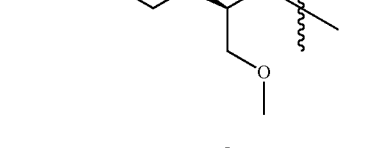 |

TABLE 1-continued

Compounds 1-219.

| Entry | |
|---|---|
| 197 | (dimethylamino-alanyl) |
| 198 | (diethylamino-asparaginyl) |
| 199 | (N,N-diethyl-valyl) |
| 200 | (4,5-dihydro-1H-imidazol-2-ylamino-valyl) |
| 201 | (4,5-dihydro-1H-imidazol-2-ylamino-valyl) |
| 202 | (1-methyl-4,5-dihydro-1H-imidazol-2-ylamino-valyl) |
| 203 | (3-amino-1-methyl-1H-1,2,4-triazol-5-ylamino-valyl) |
| 204 | (4,5-dihydrothiazol-2-ylamino-valyl) |
| 205 | (3-amino-1H-1,2,4-triazol-5-ylamino-valyl) |
| 206 | (pyridin-3-ylamino-valyl) |
| 207 | (pyrimidin-4-ylamino-valyl) |
| 208 | (5-amino-1,2,4-oxadiazol-3-ylamino-valyl) |

TABLE 1-continued

Compounds 1-219.

| Entry | |
|---|---|
| 209 | (diethylamino, tert-butyl) |
| 210 | (benzyl, dimethylamino) |
| 211 | pyrrolidine |
| 212 | 5-oxopyrrolidine |
| 213 | (pyrimidin-5-ylamino, isopropyl) |
| 214 | 4,4-difluoropyrrolidine |
| 215 | 4-fluoropyrrolidine |
| 216 | 3-azabicyclo[3.1.0]pyrrolidine |
| 217 | N-methylpyrrolidine |
| 218 | N-methyl-4-fluoropyrrolidine |
| 219 | 4-fluoropyrrolidine |

TABLE 2
Compounds 220-229.
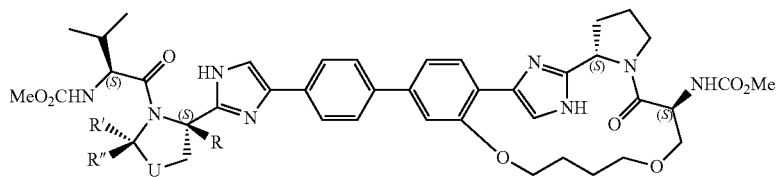
| Entry | R | R' | R" | U |
|---|---|---|---|---|
| 220 | Me | H | H | CH₂ |
| 221 | H | H | H | CF₂ |
| 222 | Me | H | H | S |
| 223 | H | H | H | CHF-CH (F up) |
| 224 | H | Me | H | CH₂ |
| 225 | H | H | H | CHF-CH (F down) |
| 226 | H | Ph | H | CH₂ |
| 227 | H | H | H | CH(OH) |
| 228 | H | H | Ph | CH₂ |
| 229 | H | H | H | CH(OH) epimer |
TABLE 3
Compounds 230-239.
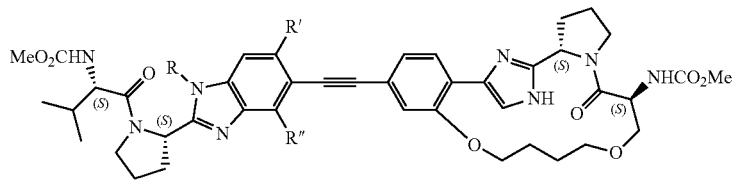
| Entry | R | R' | R" |
|---|---|---|---|
| 230 | Me | H | H |
| 231 | H | CO₂Me | H |
| 232 | H | F | H |
| 233 | H | H | CO₂Me |
| 234 | H | H | F |
| 235 | H | OMe | H |
| 236 | H | Cl | H |
| 237 | H | H | OMe |
| 238 | H | H | Cl |
| 239 | H | CF₃ | H |

TABLE 4
Compounds 240-249.
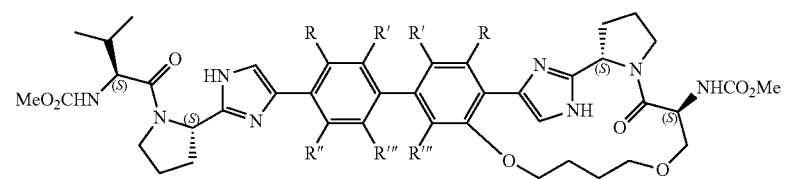
| Entry | R | R' | R'' | R''' |
|---|---|---|---|---|
| 240 | F | H | H | H |
| 241 | F | F | H | H |
| 242 | Me | H | H | H |
| 243 | Me | Me | H | H |
| 244 | H | H | Me | Me |
| 245 | H | H | Et | Et |
| 246 | CF$_3$ | H | H | H |
| 247 | CF$_3$ | H | CF$_3$ | H |
| 248 | Cl | H | H | H |
| 249 | Cl | H | Cl | H |
TABLE 5
Compounds 250-264.
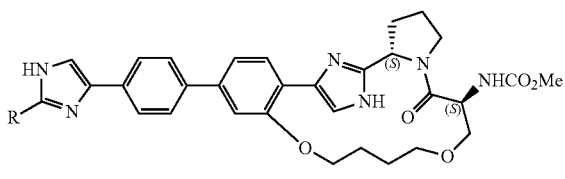
| Entry | R |
|---|---|
| 250 | |
| 251 | |
| 252 | |
| 253 | |
| 254 | |
TABLE 5-continued
Compounds 250-264.
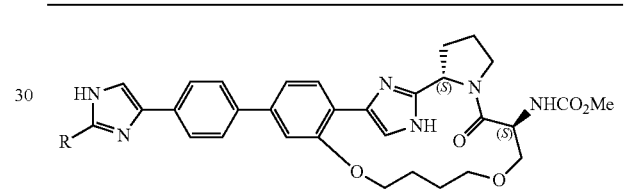
| Entry | R |
|---|---|
| 255 | |
| 256 | |
| 257 | |
| 258 | |

TABLE 5-continued

Compounds 250-264.

| Entry | R |
|---|---|
| 259 | (4-methylpyrrolidine with valine-NHCO₂Me) |
| 260 | (4-fluoropyrrolidine with valine-NHCO₂Me) |
| 261 | (4-difluoromethylenepyrrolidine with valine-NHCO₂Me) |
| 262 | (N-ethyl-N-sec-butyl valine-NHCO₂Me) |
| 263 | (N-methyl-N-(cyclopropylmethyl) valine-NHCO₂Me) |
| 264 | (pent-4-en-2-yl amide valine-NHCO₂Me) |

TABLE 6

Compounds 265-282.

| Entry | Aᵃ |
|---|---|
| 265 | naphthalene-2,6-diyl (linked at 1,6) |
| 266 | quinoline-2,3,6-triyl |
| 267 | anthracene-2,6-diyl |
| 268 | naphthalene-phenyl biaryl |
| 269 | styryl-phenyl |
| 270 | phenylacetylene |
| 271 | cyclohexyl-phenyl |

TABLE 6-continued
Compounds 265-282.
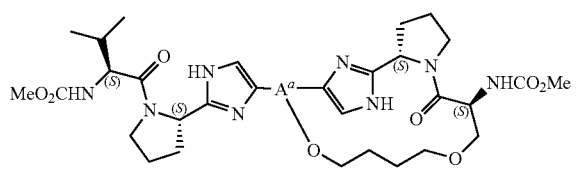
| Entry | A$^a$ |
|---|---|
| 272 | 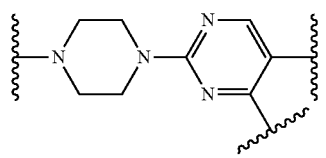 [SMILES: *c1cnc(N2CCN(*)CC2)nc1*] |
| 273 | 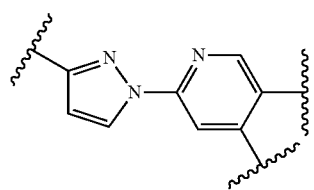 [SMILES: *c1ccn(-c2cc(*)c(*)cn2)n1] |
| 274 | 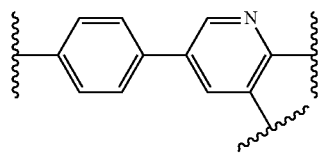 [SMILES: *c1ccc(-c2cnc(*)c(*)c2)cc1] |
| 275 | 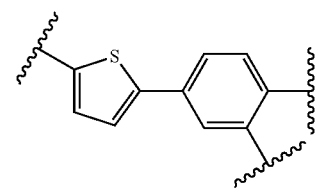 [SMILES: *c1ccc(-c2ccc(*)c(*)c2)s1] |
| 276 | 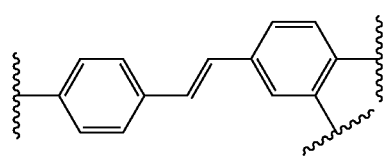 [SMILES: *c1ccc(/C=C/c2ccc(*)c(*)c2)cc1] |
| 277 | 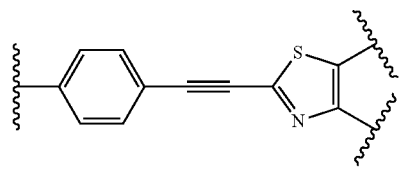 [SMILES: *c1ccc(C#Cc2nc(*)c(*)s2)cc1] |
TABLE 6-continued
Compounds 265-282.
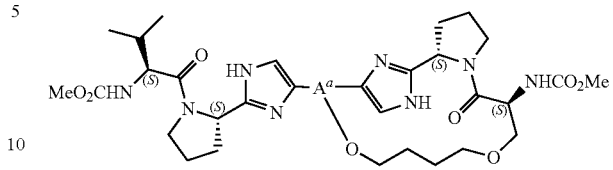
| Entry | A$^a$ |
|---|---|
| 278 | 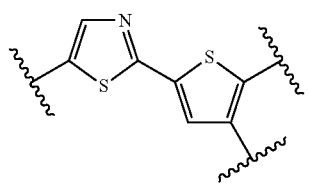 [SMILES: *c1cnc(-c2cc(*)c(*)s2)s1] |
| 279 | 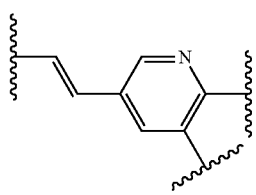 [SMILES: */C=C/c1cnc(*)c(*)c1] |
| 280 | 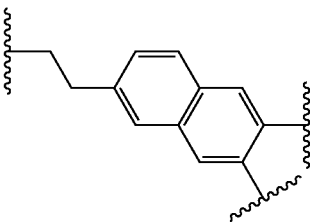 [SMILES: *CCc1ccc2cc(*)c(*)cc2c1] |
| 281 | 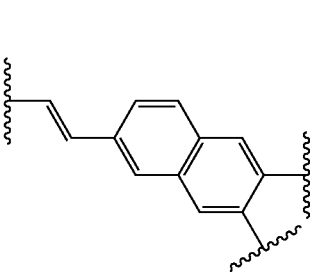 [SMILES: */C=C/c1ccc2cc(*)c(*)cc2c1] |
| 282 | 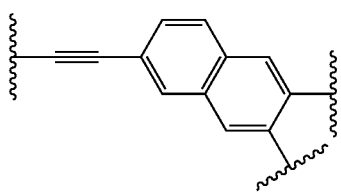 [SMILES: *C#Cc1ccc2cc(*)c(*)cc2c1] |

TABLE 7
Compounds 283-303.
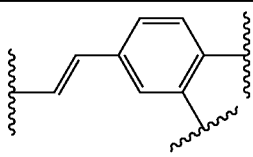
| Entry | $A^a$ |
|---|---|
| 283 | 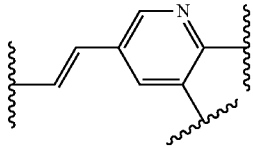 [SMILES: */C=C/c1cnc(*)c(*)c1] |
| 284 | 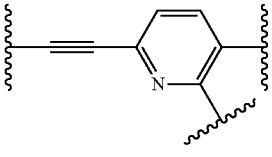 |
| 285 | 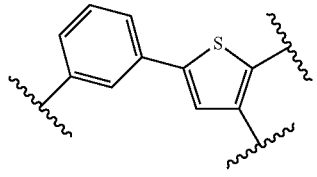 [SMILES: *c1cccc(-c2cc(*)c(*)s2)c1] |
| 286 | 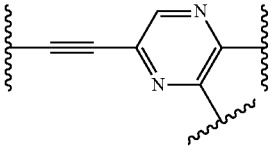 |
| 287 | 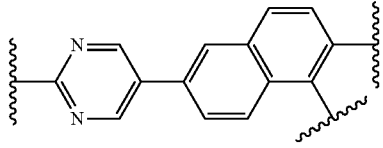 [SMILES: *c1ncc(-c2ccc3c(*)c(*)ccc3c2)cn1] |
| 288 | 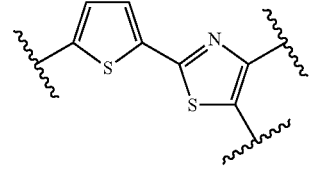 [SMILES: *c1ccc(-c2nc(*)c(*)s2)s1] |
| 289 | 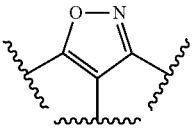 [SMILES: *c1noc(*)c1*] |
| 290 |  |

TABLE 7-continued

Compounds 283-303.

| Entry | $A^a$ |
|---|---|
| 291 | (pyrrolopyrrole fragment) |
| 292 | (vinyl-naphthalene fragment) |
| 293 | (ethynyl-quinoline fragment) |
| 294 | (quinoline fragment) |
| 295 | (quinazoline fragment) |
| 296 | (benzothiazole fragment) |

TABLE 7-continued

Compounds 283-303.

| Entry | $A^a$ |
|---|---|
| 297 | (benzimidazole) |
| 298 | (phenyl with ethylene linker) |
| 299 | (phenyl with vinyl linker) |
| 300 | (phenyl with alkyne linker) |
| 301 | (phenyl-pyridinone) |
| 302 | (pyrimidinone-thiophene) |
| 303 | (coumarin) |

TABLE 8
Compounds 304-315.
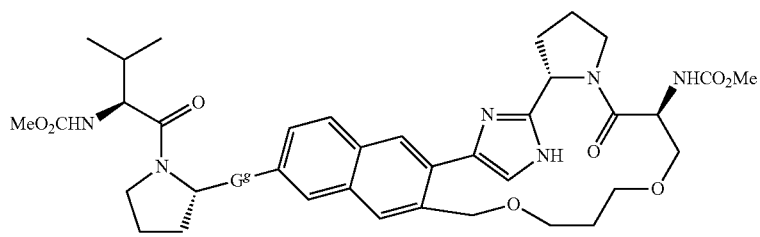
| Entry | G^g |
|---|---|
| 304 | 3,5-(1H-pyrazole)diyl |
| 305 | 3,5-(4H-1,2,4-triazole)diyl |
| 306 | 2,5-oxazolediyl |
| 307 | 2,5-(1H-benzimidazole)diyl |
| 308 | 2,6-(1H-indole)diyl |
| 309 | 2,6-(1H-pyrrolo[3,2-b]pyridine)diyl |
| 310 | 2,6-(5H-pyrrolo[3,2-d]pyrimidine)diyl |
| 311 | 2,5-(3H-imidazo[4,5-b]pyridine)diyl |
| 312 | 2,6-(1H-imidazo[4,5-c]pyridine)diyl |

TABLE 8-continued

Compounds 304-315.

| Entry | G^g |
|---|---|
| 313 | [imidazo-pyridine structure] |
| 314 | [imidazo-pyrimidine structure] |
| 315 | [indole structure] |

TABLE 9

Compounds 316-333.

| Entry | L^a—L^b—L^c |
|---|---|
| 316 | [branched alkyl chain structure] |
| 317 | [alkyl ether chain structure] |
| 318 | [alkyl ether chain with alkene structure] |
| 319 | [carbamate-containing linker structure] |

TABLE 9-continued
Compounds 316-333.
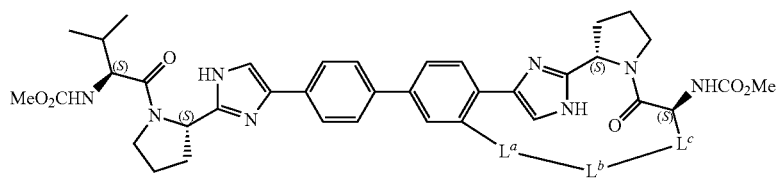
| Entry | $L^a$—$L^b$—$L^c$ |
|---|---|
| 320 | 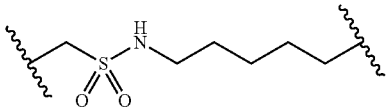 [SMILES: *CCCCCNS(=O)(=O)C*] |
| 321 | 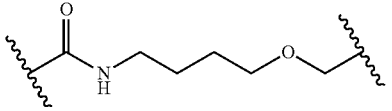 [SMILES: *COCCCCNC(*)=O] |
| 322 | 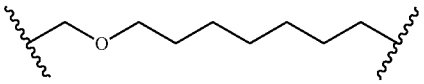 [SMILES: *CCCCCCCOC*] |
| 323 | 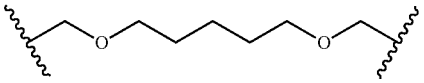 [SMILES: *COCCCCCOC*] |
| 324 | 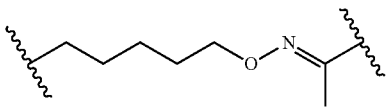 [SMILES: *CCCCCO/N=C(/*)C] |
| 325 | 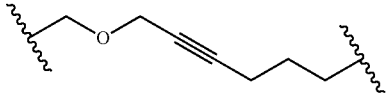 [SMILES: *CCCC#CCOC*] |
| 326 | 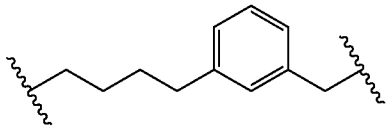 [SMILES: *CCCCc1cccc(C*)c1] |
| 327 | 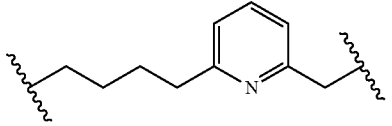 [SMILES: *CCCCc1cccc(C*)n1] |
| 328 | 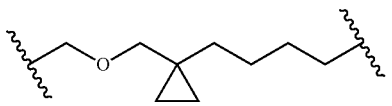 [SMILES: *CCCCC1(COC*)CC1] |
| 329 |  |
| 330 | 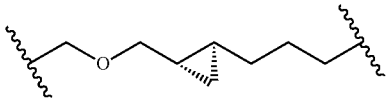 [SMILES: *CCC[C@H]1C[C@@H]1COC*] |

TABLE 9-continued
Compounds 316-333.
| Entry | $L^a$—$L^b$—$L^c$ |
|---|---|
| 331 | |
| 332 | |
| 333 | |
TABLE 10
Compounds 334-343.
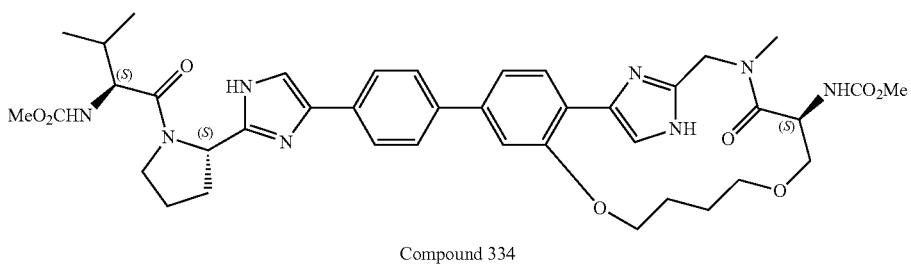
Compound 334
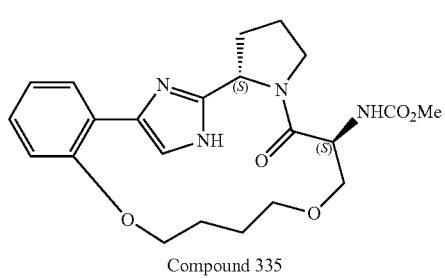
Compound 335

TABLE 10-continued
Compounds 334-343.
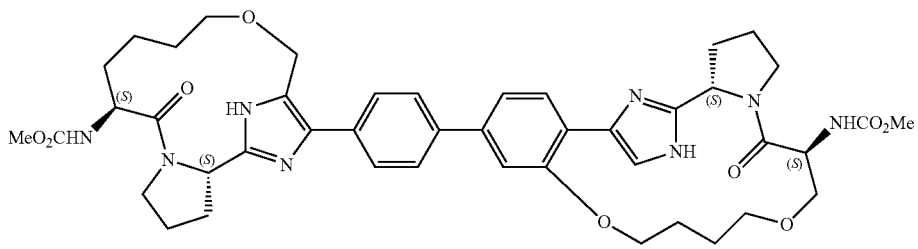
Compound 336
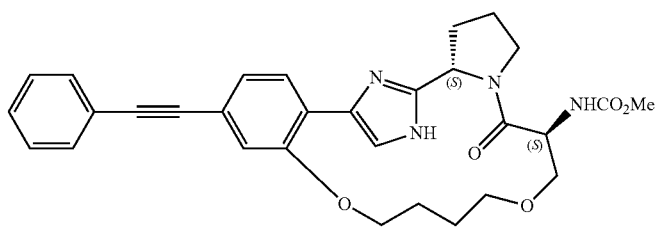
Compound 337
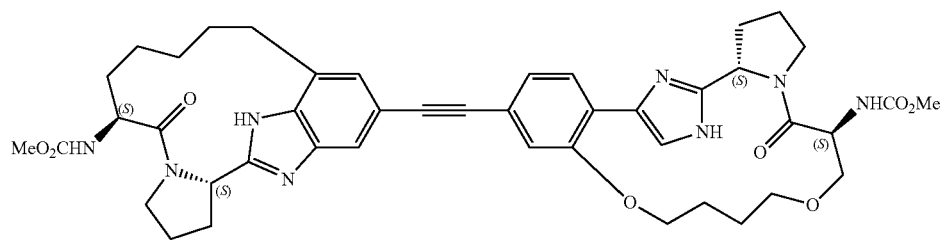
Compound 338
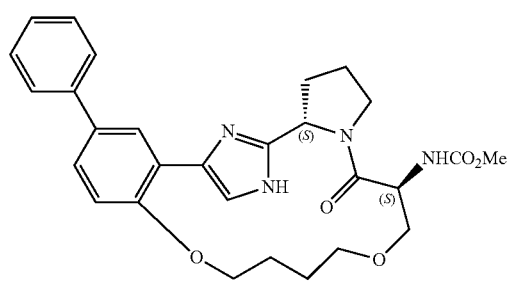
Compound 339
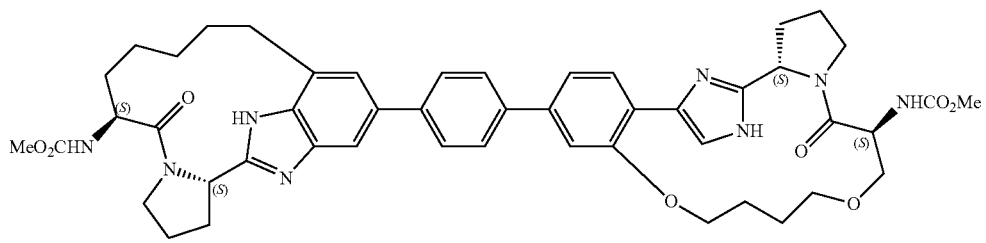
Compound 340

TABLE 10-continued
Compounds 334-343.
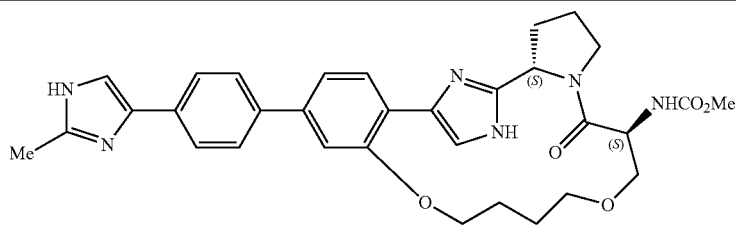
Compound 341
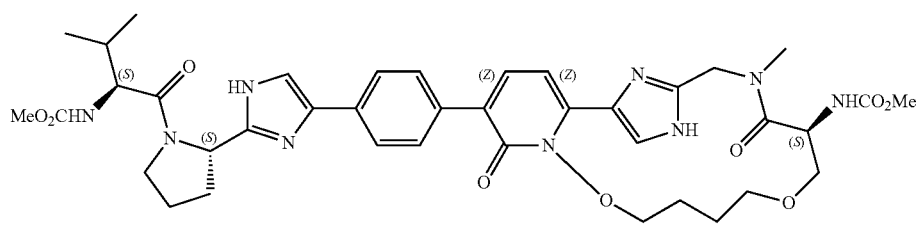
Compound 342
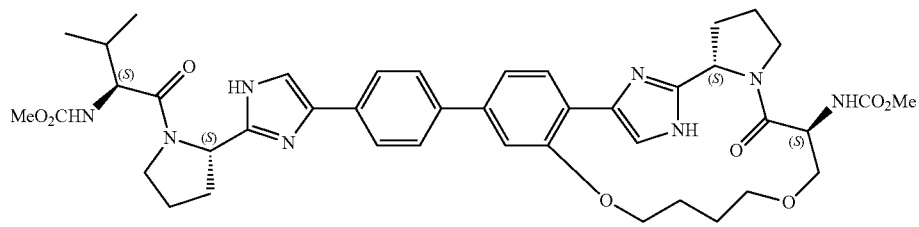
Compound 343
TABLE 11
Compounds 344-350.
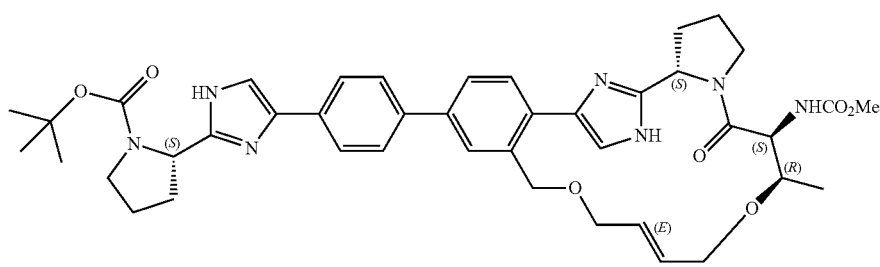
Compound 344
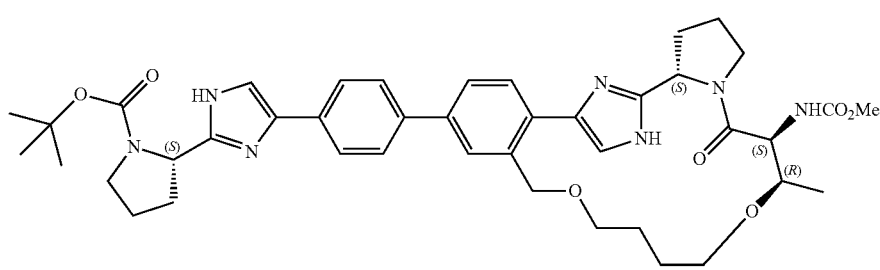
Compound 345

TABLE 11-continued

Compounds 344-350.

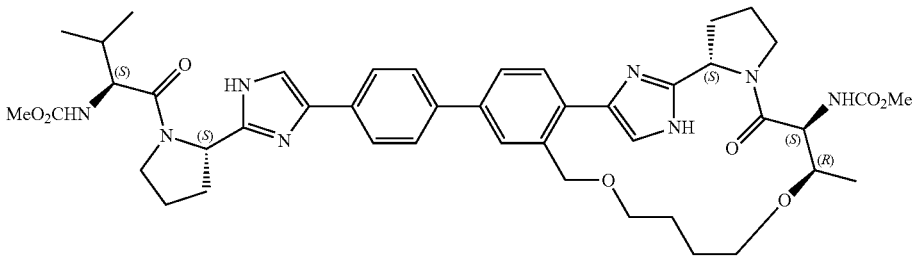

Compound 346

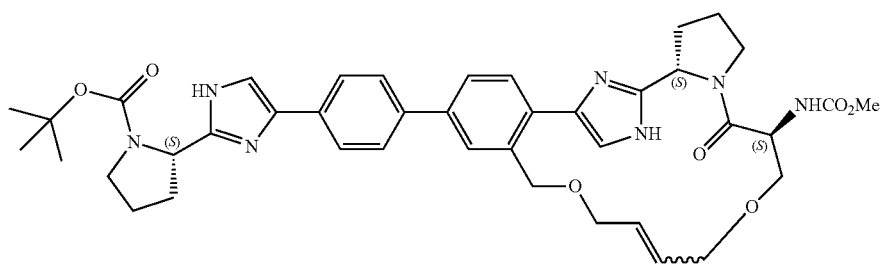

Compound 347

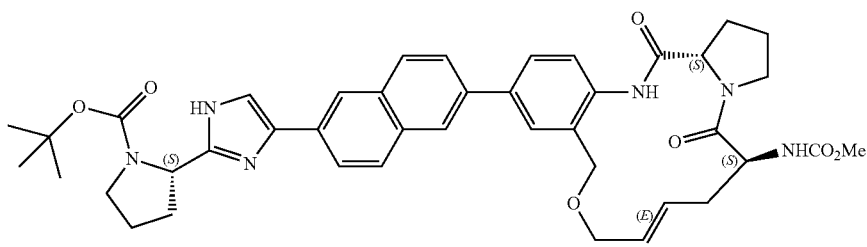

Compound 348

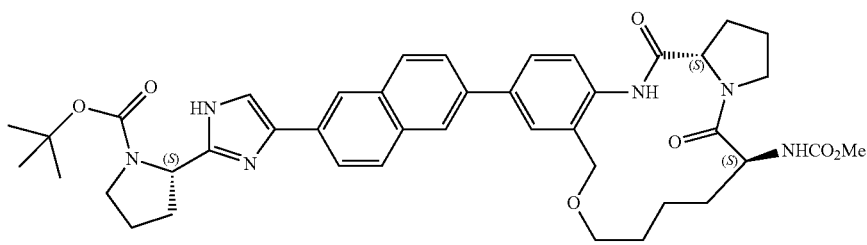

Compound 349

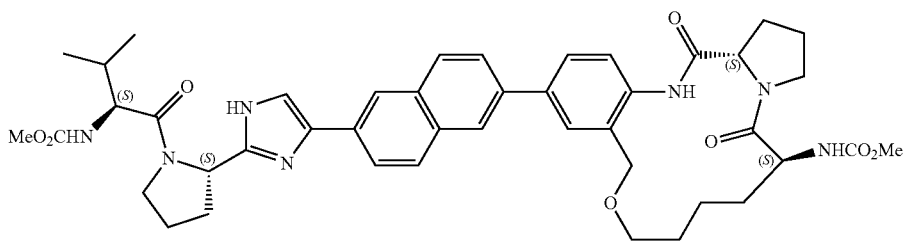

Compound 350

It will be appreciated that the description of the present invention herein should be construed in congruity with the laws and principals of chemical bonding. In some instances, it may be necessary to remove a hydrogen atom in order to accommodate a substituent at any given location.

It is intended that the definition of any substituent or variable (e.g., $R^1$, $R^2$, $X^1$, $X^2$, U, etc.) at a particular location in a molecule is independent of its definitions elsewhere in that molecule. For example, when U is $C(R^7)_2$, each of the two $R^7$ groups can be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and/or cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound or a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, and pharmaceutically acceptable salts thereof. Examples of the host immune modulator include, but are not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. A non-limiting example of the RNA-containing virus is hepatitis C virus (HCV).

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, and pharmaceutically acceptable salts thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, and pharmaceutically acceptable salts thereof. An agent that treats patients for disease caused by hepatitis B (HBV) infection may be for example, but not limited thereto, L-deoxythymidine, adefovir, lamivudine or tenfovir, or any combination thereof. A non-limiting example of the RNA-containing virus is hepatitis C virus (HCV).

A further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, and pharmaceutically acceptable salts thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of the RNA-containing virus is hepatitis C virus (HCV).

It can occur that a patient may be co-infected with hepatitis C virus and one or more other viruses, including, but not limited to, human immunodeficiency virus (HIV), hepatitis A virus (HAV) and hepatitis B virus (HBV). Thus also contemplated herein is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, and pharmaceutically acceptable salts thereof, and one or more agents selected from the group consisting of a host immune modulator and one or more additional antiviral agents, or a combination thereof, to prepare a medicament for the treatment of an infection caused by an RNA-containing virus in a patient, particularly hepatitis C virus. Non-limiting examples of the host immune modulator are interferon-alpha, pegylated-interferon-alpha, interferon-beta, interferon-gamma, a cytokine, a vaccine, and a vaccine comprising an antigen and an adjuvant. Preferably, said additional antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, or as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including, but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents that can be administered in combination with a compound of the present invention include a cytochrome P450 monooxygenase inhibitor (also referred to herein as a CYP inhibitor), which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount sufficient to improve one or more pharmacokinetic (PK) features including, but not limited to, plasma concentration, bioavailiablity, area under the plasma concentration time curve (AUC), elimination half-life, and systemic clearance, of a compound of the invention when one or more of its PK features of said compound is improved in comparison to that in the absence of the CYP inhibitor.

In one embodiment, the invention provides methods for improving the pharmacokinetics of compounds of the invention. The advantages of improving the pharmacokinetics of drugs are recognized in the art (see, for example, US Patent App. Nos. 2004/0091527; US 2004/0152625; and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, ditiazem, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect, the invention is a pack comprising at least a compound of the invention and a CYP inhibitor and an information insert containing directions on the use of the combination of the invention. In an alternative embodiment of this invention, the pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e.g. a composition of a compound of the invention and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_5$-$C_7$-cycloalkyl," as used herein, refers to a monocyclic or polycyclic saturated carbocyclic ring compound, and the carbon atoms may be optionally oxo-substituted. Examples of $C_3$-$C_8$-cycloalkyl include, but are not limited to, cyclopropyl, cyclobutyl, cyclopentyl, cyclohexyl, cyclopentyl and cyclooctyl; and examples of $C_5$-$C_7$-cycloalkyl include, but not limited to, cyclopentyl, cyclohexyl, bicyclo[2.2.1]heptyl, and the like.

The term "$C_3$-$C_8$ cycloalkenyl", or "$C_5$-$C_7$ cycloalkenyl" as used herein, refers to monocyclic or polycyclic carbocyclic ring compound having at least one carbon-carbon double bond, and the carbon atoms may be optionally oxo-substituted. Examples of $C_3$-$C_8$ cycloalkenyl include, but are not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but are not limited to, cyclopentenyl, cyclohexenyl, cycloheptenyl, and the like.

The term "arylalkyl", as used herein, refers to an aryl-substituted alkyl group. More preferred arylalkyl groups are aryl-$C_1$-$C_6$-alkyl groups.

The term "heteroarylalkyl", as used herein, refers to a heteroaryl-substituted alkyl group. More preferred heteroarylalkyl groups are heteroaryl-$C_1$-$C_6$-alkyl groups.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, OC(O)$NH_2$, $S(O)_2$NH, $S(O)_2$$NH_2$, NHC(O)$NH_2$, NHC(O)C(O)NH, NHS(O)$_2$NH, NHS(O)$_2$$NH_2$, C(O)NHS(O)$_2$, C(O)NHS(O)$_2$NH or C(O)NHS(O)$_2$$NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the aliphatic group can be selected from one or more of the specified functional groups or a combination thereof, or a group wherein one or more carbons of a non-aromatic hydrocarbon (optionally substituted) is replaced by a specified functional group. In some examples, the linear aliphatic group can be represented by the formula M-V-M', where M and M' are each independently absent or an alkyl, alkenyl or alkynyl, each optionally substituted, and V is a functional group. In some examples, V is selected from the group consisting of C(O), $S(O)_2$, C(O)O, C(O)N($R^{11}$), OC(O)O, OC(O)N($R^{11}$), $S(O)_2$N($R^{11}$), N($R^{11}$)C(O)N($R^{11}$), N($R^{11}$)C(O)C(O)N($R^{11}$), N($R^{11}$)S(O)$_2$N($R^{11}$), C(O)N($R^{11}$)S(O)$_2$ or C(O)N($R^{11}$)S(O)$_2$N($R^{11}$); wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCO$_2$—C$_1$-C$_{12}$ alkyl, —OCO$_2$—C$_2$-C$_8$ alkenyl, —CO$_2$—C$_2$-C$_8$ alkynyl, CO$_2$—C$_3$-C$_{12}$-cycloalkyl, —CO$_2$—aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH— heterocycloalkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$— heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH— heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

As described above, each of -L$^1$-L$^2$-L$^3$- taken together and -L$^4$-L$^5$-L$^6$-taken together is a linker group of preferably from 6 to 16 and 8 to 18 bond lengths, respectively. The preferred range of bond lengths in the linker group -L$^4$-L$^5$-L$^6$- (such as 8 to 18, 8 to 14, or the like) is inclusive of the bonds between the linker group and Y and between the linker group and the atom of a ring in group B (to which atom, the linker group is attached). The preferred range of bond lengths in the linker group -L$^1$-L$^2$-L$^3$- (such as 6 to 16 bond lengths) is inclusive of the bonds between the linker group and Y and between the linker group and the carbon of 6-membered or 5-membered ring of group G. It is to be understood that when a linker includes a cyclic group, the preferred bond length is the shortest possible distance, as measured in bond lengths, between Y and the atom of the ring of group B or between Y and the carbon of the 6-membered or 5-membered ring of group G.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenylmethoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject" as used herein refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs," Textbook of Drug Design and Development, Chapter 5, 113-191 (1991); Bundgaard, et al., *Journal of Drug Deliver Reviews,* 8:1-38 (1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include, but are not limited to, the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula (I) described herein and one or more additional therapeutic or prophylactic agents, both the compound and the additional agent should be present at dosage levels of between about 1 to about 100%, and more preferably between about 5 to about 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g., N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

A compound of the present invention can also be administered in combination or alternation with antiviral agent. Exemplary antiviral agents include ribavarin, interferon, interleukin or a stabilized prodrug of any of them. More broadly described, the compound of the present invention can be administered in combination or alternation with any of the anti-HCV drugs listed in Table 12 below.

TABLE 12

Table of anti-Hepatitis C Compounds in Current Clinical Development

| Drug name | Drug category | Pharmaceutical Company |
|---|---|---|
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HepX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |
| Narlaprevir (SCH 900518) | Protease inhibitor | Schering/Merck |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |

TABLE 12-continued

Table of anti-Hepatitis C Compounds in Current Clinical Development

| Drug name | Drug category | Pharmaceutical Company |
|---|---|---|
| R7128 (PSI6130) | Polymerase Inhibitor | Roche/Pharmasset |
| IDX184 | Polymerase Inhibitor | Idenix |
| INX-189 | Polymerase Inhibitor | Inhibitex |
| PSI-7977 | Polymerase Inhibitor | Pharmasset |
| PSI-938 | Polymerase Inhibitor | Pharmasset |
| R1626 | Polymerase inhibitor | Roche |
| MK-3281 | Polymerase Inhibitor | Merck |
| PSI-7851 | Polymerase Inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| VCH-759 | Polymerase Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| BMS-824393 | NS5A inhibitor | Bristol-Myers-Squibb |
| GS-5885 | NS5A inhibitor | Gilead |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-antimiR ™-122) | microRNA | Santaris Pharma |
| Debio 025 | Cyclophilin inhibitor | Debiopharm |
| SCY-635 | Cyclophilin inhibitor | Scynexis |

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $Boc_2O$ for di-tert-butyl-dicarbonate; Boc for t-butoxycarbonyl; Bpoc for 1-methyl-1-(4-biphenyl)ethyl carbonyl; BtOH for 1-hydroxybenzotriazole; Bz for benzoyl; Bn for benzyl; BocNHOH for tert-butyl N-hydroxycarbamate; t-BuOK for potassium tert-butoxide; $Bu_3SnH$ for tributyltin hydride; BOP for (benzotriazol-1-yloxy)tris(dimethylamino)phosphonium Hexafluorophosphate; Brine for sodium chloride solution in water; Cbz for carbobenzyloxy; CDI for carbonyldiimidazole; $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIBAL-H for diisobutylaluminium hydride; DIPEA or $(i-Pr)_2EtN$ for N,N-diisopropylethyl amine; Dess-Martin periodinane for 1,1,1-tris(acetyloxy)-1,1-dihydro-1,2-benziodoxol-3-(1H)-one; DMAP for 4-dimethylaminopyridine; DME for 1,2-dimethoxy-ethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; $Et_2O$ for diethyl ether; Fmoc for 9-fluorenylmethoxycarbonyl; Grubbs-1 catalyst for benzylidene-bis(tricyclohexylphosphine)dichlororuthenium; HATU for O-(7-azabenzotriazol-1-yl)-N,N,N',N'-tetramethyluronium hexafluorophosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or $-SO_2-CH_3$; $Ms_2O$ for methanesulfonic anhydride or mesyl-anhydride; $NaBH_4$ for sodium borohydride; $NaBH_3CN$ for sodium cyanoborohydride; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMMO for N-methylmorpholine N-oxide; $NaIO_4$ for sodium periodate; Ni for nickel; OH for hydroxyl; $OsO_4$ for osmium tetroxide; Pd for palladium; Ph for phenyl; PMB for p-methoxybenzyl; POPd for dihydrogen dichlorobis(di-tert-butylphosphinito-κP)palladate(II); $Pd_2(dba)_3$ for tris(dibenzylidene-acetone) dipalladium (0); $PdCl_2(dppf)$ for dichloro[1,1'-bis(diphenylphosphino)ferrocene]palladium (II) dichloromethane adduct; $Pd(PPh_3)_4$ for tetrakis(triphenylphosphine)palladium (0); $PdCl_2(PPh_3)_2$ for trans-dichlorobis(triphenyl-phosphine)palladium (II); Pt for platinum; Rh for rhodium; rt for room temperature; Ru for ruthenium; SEM for (trimethylsilyl)ethoxymethyl; TBAF for tetrabutylammonium fluoride; TBS for tert-butyl dimethylsilyl; TEA or $Et_3N$ for triethylamine; Teoc for 2-trimethylsilyl-ethoxycarbonyl; TFA for trifluoroacetic acid; THF for tetrahydrofuran; TMEDA for N,N,N',N'-tetramethylethylenediamine; TPP or $PPh_3$ for triphenyl-phosphine; Troc for 2,2,2-trichloroethyl carbonyl; Ts for tosyl or $-SO_2-C_6H_4CH_3$; $Ts_2O$ for tolylsulfonic anhydride or tosyl-anhydride; TsOH for p-tolylsulfonic acid; TMS for trimethylsilyl; TMSCl for trimethylsilyl chloride; or Zhan-1b catalyst for 1,3-bis(2,4,6-trimethylphenyl)-4,5-dihydroimidazol-2-ylidene[2-(iso-propoxy)-5-(N,N-dimethylaminosulfonyl)phenyl]methylene ruthenium(II) dichloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of 5/6-membered ring fused heteroaryl, 5-membered ring heteroaryl, and related intermediates. An exemplary method is shown in Schemes 1, 2, 3, and 4. A retro-synthesis of those title compounds include direct formation of a suitable heterocycle (5/6-membered ring fused heteroaryl or 5-membered ring heteroaryl) optionally with a suitable macrocyclic linkage, followed by attachment of a suitable capping group (such as —C(O)R⁶), plus some functional group manipulations in between and/or after. Various 5/6-membered ring fused heteroaryl or 5-membered ring heteroaryl intermediates are known to those skilled in the art, for example see the encyclopedic volumes edited by A. R. Katrizky, et al, "Comprehensive Heterocyclic Chemistry" 1984; "Comprehensive Heterocyclic Chemistry II" 1996; "Comprehensive Heterocyclic Chemistry III" 2008.

A general synthesis and further elaboration of some 6-membered ring fused with imidazole related intermediates are summarized in Scheme 1, in which Z is N or CH.

The synthesis starts from the construction of an optionally substituted imidazopyridine or benzimidazole 1-2, which may be obtained by condensation of an amino acid or its derivatives 1-1.1 or 1-1.2 with 2,3-diaminopyridine or 1,2-diaminobenzene 1-1 under the conditions to those skilled in the art. The imidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDCHCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat. Other imidazopyridines or benzimidazoles with more substitution may be prepared similarly using the procedures described hereinwith.

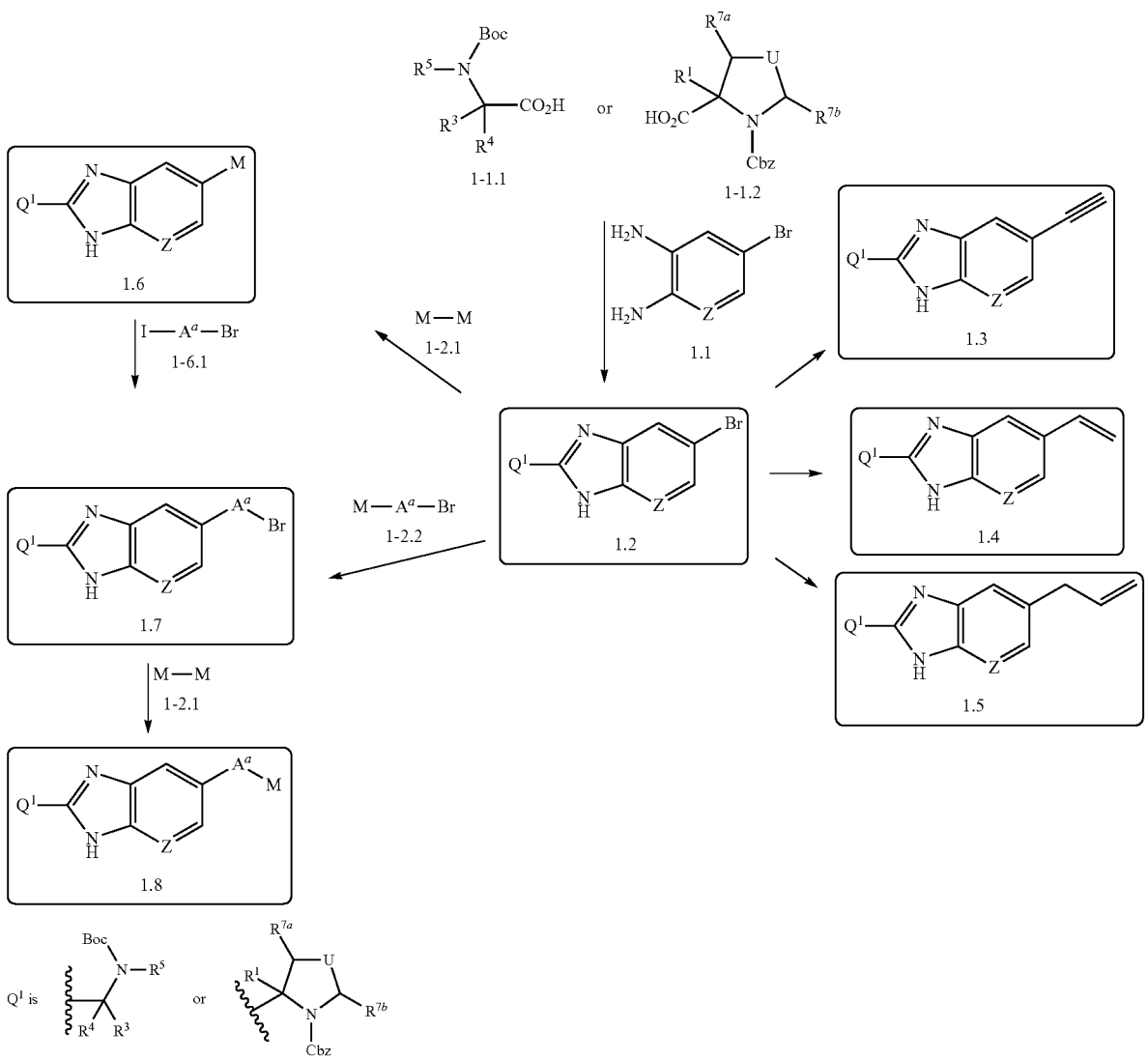

Scheme 1

The imidazopyridine or benzimidazole 1-2 may be subjected to Suzuki, Stille or related coupling conditions known to those skilled in the art (see reviews: A. Suzuki, *Pure Applied Chem.*, 1991, 63, 419; A. Suzuki, *Handbook of Organopalladium Chemistry for Organic Synthesis*, 2002, 1, 249; A. Anastasia, et al, *Handbook of Organopalladium Chemistry for Organic Synthesis*, 2002, 1, 311; F. Bellina, et al, *Synthesis*, 2004, 2419; M. G. Organ, et al, *Synthesis* 2008, 2776; A. T. Lindhardt, et al, *Chem.—A European J.*, 2008, 14, 8756; E. A. B. Kantchev, et al, *Angew. Chem. Int. Ed.*, 2007, 46, 2768; V. Farina, et al, *Advances in Metal-Organic Chem.*, 1996, 5:1) with different coupling partners to provide a variety of key intermediates. For example, Sonogashira coupling between bromide 1-2 and trimethylsilylacetylene can generate alkyne 1-3 after removal of TMS by $K_2CO_3$ in MeOH. Alternatively, bromide 1-2 may be coupled with tributylvinylstanne through Stille reaction conditions known to those skilled in the art to provide alkene 1-4. Analogously, a key allyl intermediate 1-5 may be prepared by Stille reaction from bromide 1-2 with an allylstanne such as allyltributylstanne.

Alternatively, bromide 1-2 may be converted to key intermediate 1-7 by selectively reacting with metallic reagent 1-2.2 under the Suzuki or Stille conditions which are known to those skilled in the art. Yet alternatively, intermediate 1-7 may be prepared by treating bromide 1-2 with dimetallic agent 1-2.1 to afford organometallic 1-6, followed by coupling with bromoiodoaryl compound 1-6.1, both may be under the previously described Suzuki or Stille reaction conditions. The bromide 1-7 may be further converted to organometallic 1-8 with dimetallic agent 1-2.1 using the conditions described above to prepare 1-6.

It should be noted that optionally the NH group of all the imidazopyridine or benzimidazole related intermediates listed above may be protected with an amino protecting group, such as SEM (i.e. SEM-Cl, NaH), Boc, Cbz, Teoc, Troc, or the like.

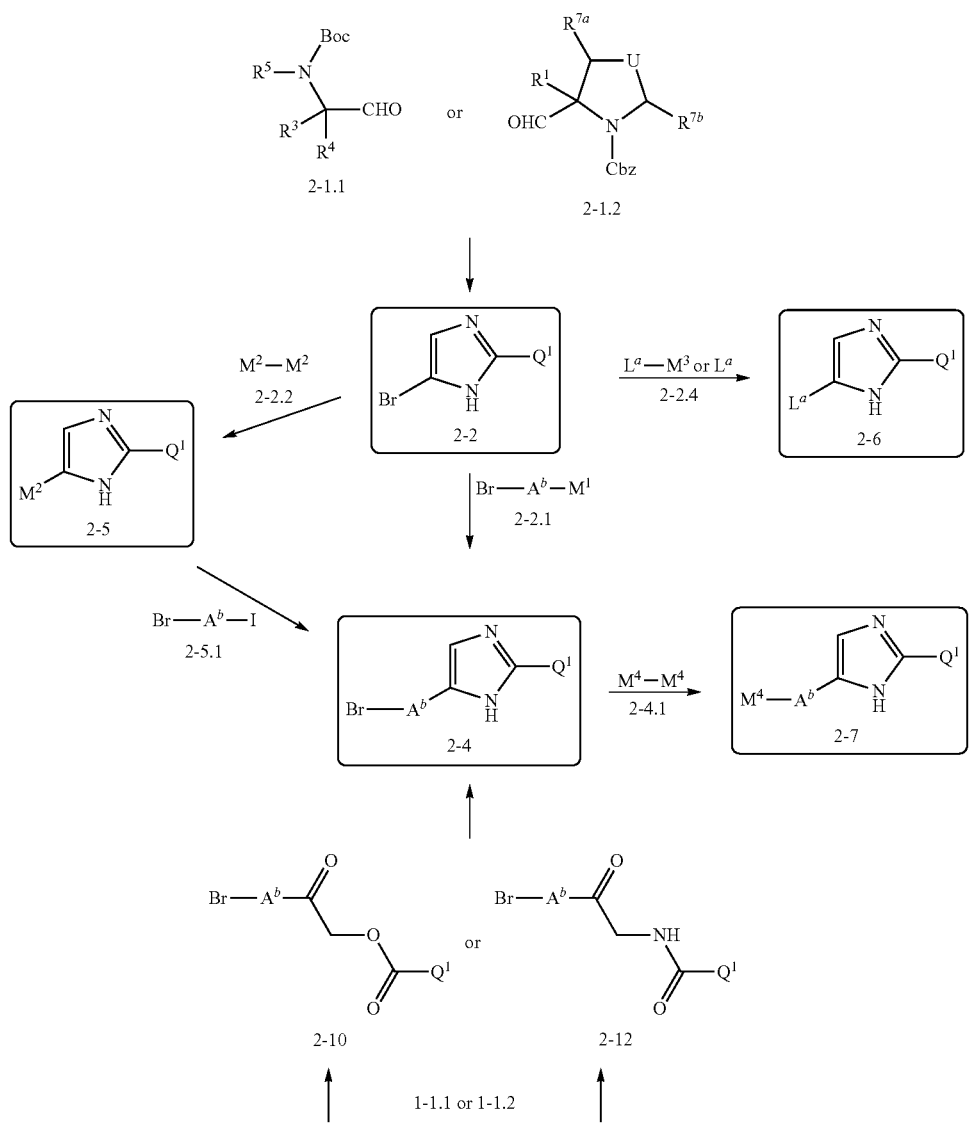

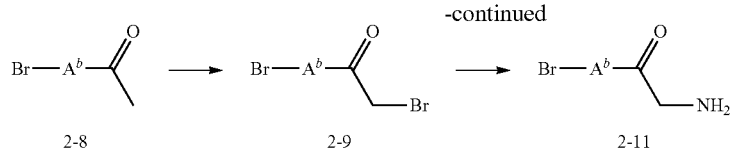

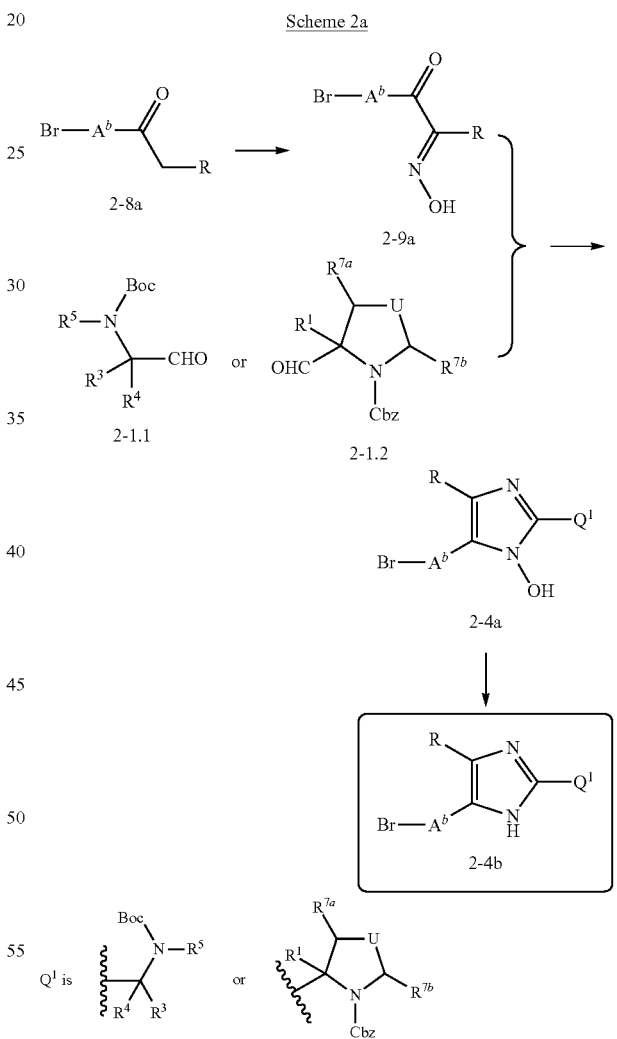

$A^b$ = aryl, hetroaryl
$L^a$ = allyl, vinyl, alkynyl
$M^1, M^2, M^3, M^4$ = tin or boron species A typical synthesis of imidazole related intermediates are analogous to that of the imidazopyridine or benzimidazole intermediates. As shown in Scheme 2, bromo-imidazole 2-2 can be synthesized by condensation of amino acid derived aldehyde 2-1.1 or 2-1.2 and glyoxal in the presence of methanolic ammonia; followed by bromination of the imidazole ring under the conditions which are known to those skilled in the art. The bromination of the imidazole ring may be realized either in one pot by NBS, bromine, 2,4,4,6-tetrabromo-2,5-cyclohexadienone, or the like; or in two steps: 1) dibromide formation in the presence of excess bromination reagent such as NBS, bromine, 2,4,4,6-tetrabromo-2,5-cyclohexadienone, or the like, optionally with heat; and 2) reduction of the dibromide to monobromide in the presence of a reducing reagent such as $NaHSO_3$, $Na_2S_2O_3$, $Na_2SO_3$, or the like. Bromide 2-2 then may be served as a common intermediate further elaborable to many other imidazole derivatives using the chemistry discussed in Scheme 1. For example, bromide 2-2 may be coupled with allytin or vinyltin or TMS-acetylene to provide intermediate 2-6. Also, bromide 2-2 may be converted to key intermediate 2-4 by selectively reacting with metallic reagent 2-2.1 under the Suzuki or Stille conditions to provide key intermediate 2-4. Yet alternatively, intermediate 2-4 may be prepared by treating bromide 2-2 with dimetallic agent 2-2.2 to afford organometallic 2-5, followed by coupling with bromoiodoaryl compound 2-5.1, both may be under the previously described Suzuki or Stille reaction conditions. The bromide 2-4 may be further converted to organometallic 2-7 with dimetallic agent 2-4.1 using the conditions described above for the preparation of intermediate 2-5.

Yet alternatively, aryl or heteroaryl bromide 2-4 may also be derived from bromoketone 2-9, which can be prepared from the corresponding ketone 2-8 in the presence of a bromination reagent such as NBS, bromine, or the like, optionally in the presence of an acid and/or with heating. Bromoketone 2-9 may be either converted to the corresponding amine 2-11 through azide substitution followed by reduction, or coupled with protected amino acid 1-1.1 or 1-1.2 in the presence of a base such as $Et_3N$ or DIPEA to afford keto-ester 2-10. Similarly, amine 2-11 may be converted to the corresponding keto-amide 2-12 via condensation with appropriate amino acid under standard amide formation conditions. Both 2-12 and 2-13 may be transformed to key intermediate 2-4 via heating with $NH_4OAc$ under thermal or microwave conditions.

The synthesis of 4,5-disubstituted imidazole related intermediates are analogous to that described in Scheme 2. Alternatively, these imidazole intermediates can be synthesized from ketone 2-8a (Scheme 2a) through nitrosation (sodium nitrite, HCl) to ketooxime 2-9a, which can be cyclized with aldehyde 2-1.1 or 2-1.2 to 1-hydroxyimidazole 2-4a in the presence of ammonia or ammonium hydroxide. Reduction of 2-4a with a suitable reducing reagent such as triethyl phosphite can lead to the requisite imidazole 2-4b.

Scheme 3

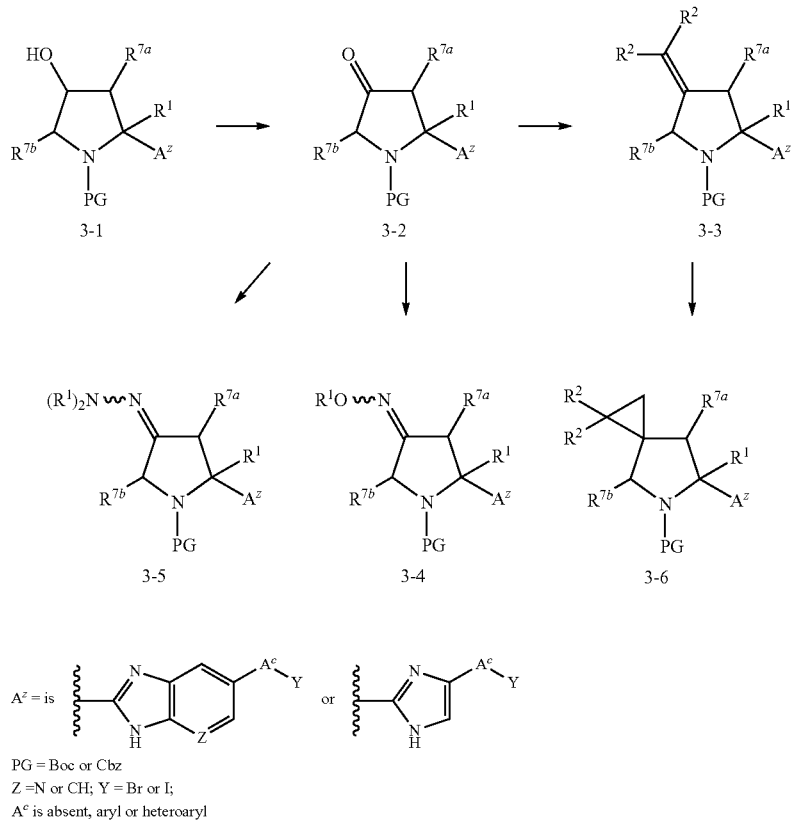

PG = Boc or Cbz
Z = N or CH; Y = Br or I;
$A^c$ is absent, aryl or heteroaryl

As shown in Scheme 3, a compound 3-1 containing a hydroxy group substituted at the C4-position of the pyrrolidine ring may be illustrated by intermediates 1-2, 1-3, 1-4, 1-5, 1-7, 2-2, 2-4, and 2-6 when U is CH(OH) as shown in Schemes 1-2. Oxidation of 3-1 by a variety of oxidation agents such as Dess-Martin periodinane optionally in the presence of an acid such as acetic acid or camphorsulfonic acid to afford the ketone 3-2. More reagents and conditions for the oxidation of an alcohol to a ketone can be found in *Comprehensive Organic transformations*, R. C. Larock Ed., Wiley-RCH, 1999, page 1236-1249. 3-2 may then serve as a universal intermediate for further derivatization to olefin 3-3, oxime 3-4 and hydrazone 3-5. The olefination of 3-2 may be realized by various types of Wittig Reaction or Peterson Reaction, a more detailed reagents and conditions can be found in *Comprehensive Organic transformations*, R. C. Larock Ed., Wiley-RCH, 1999, page 327-350. The olefin 3-3 may be converted to cyclopropane 3-6 through the well-known Simmons-Smith cyclopropanation, a more detailed reagents and conditions can be found in *Name Reactions and Reagents in Organic Synthesis* B. P. Munday, et al Ed., Wiley, 2005, page 600 and J. C. Lorenz, et al, *J. Org. Chem.*, 2004, 69, 327 and references cited therein.

Scheme 3a

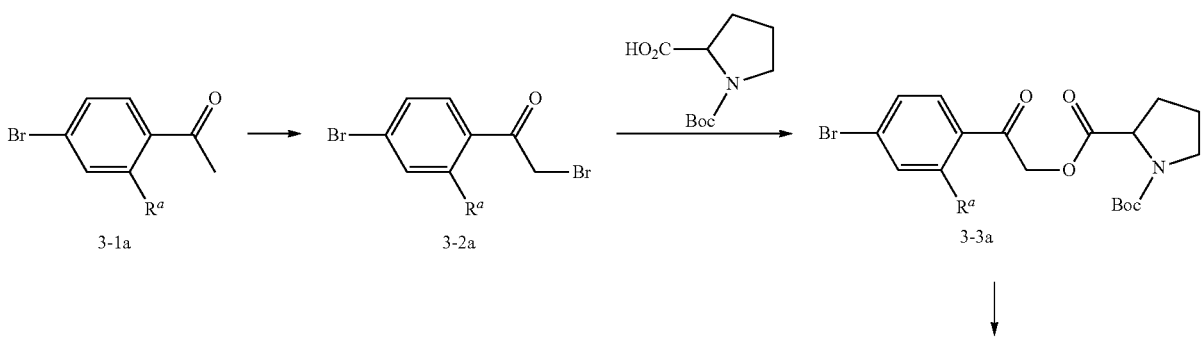

-continued

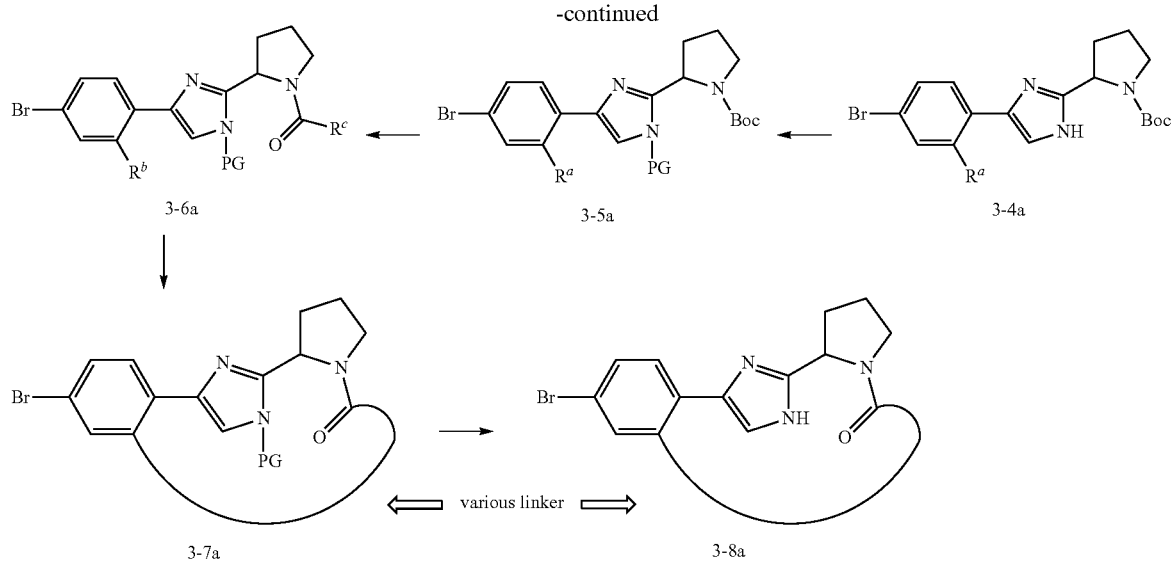

Suitably substituted analogs of intermediates 1-2, 2-4, 2-4b or the compounds in Scheme 3 may be used as precursors to make a macrocyclic derivative after suitable manipulations and transformations of functional groups or protection groups. As illustrated in Scheme 3a with phenyl-imidazole analogs. Bromination of ketone 3-1a (wherein $R^a$ is an optionally substituted alkyl, optionally substituted alkenyl, optionally substituted alkynyl, or alkoxycarbonyl), may lead to bromide 3-2a. The latter is then esterified with Boc-protected proline to afford ketoester 3-3a, which can be converted to imidazole 3-4a (wherein PG is an amino protecting group) using the chemistry described in Scheme 2. The imidazole moiety in 3-4a may be optionally protected to 3-5a, which can be converted to 3-6a in two steps: 1) deprotection of the Boc group and 2) the released amine functionality may be acylated with a carboxylic acid ($R^c$COOH, wherein $R^c$ is $R^6$ as previously defined) under standard acylation conditions, for example a coupling reagent such as HATU in combination with an organic base such as DIPEA can be used in this regard. Various carboxylic acids including amino acids in racemic or optical form are commercially available, and/or can be synthesized in racemic or optical form, see references cited in reviews by D. Seebach, et al, *Synthesis,* 2009, 1; C. Cativiela and M. D. Diaz-de-Villegas, *Tetrahedron: Asymmetry,* 2007, 18, 569; 2000, 11, 645; and 1998, 9, 3517; and experimental examples compiled in patent application WO 08/021,927 A2 by C. Bachand, et al, from Bristol-Myers Squibb (BMS), which is incorporated herein by reference. The conversion from 3-5a to 3-6a may optionally involve one or more steps of functional group manipulation, thus $R^b$ in 3-6a may be the same as or different from $R^a$ as in 3-5a depending on the interchange of functional groups. These transformation step(s) may include, but not limited to alkylation, etherification, esterification, amidation, reduction, oxidation, olefination, halogenation, oximation, and/or hydroxylation. Two reactive groups in $R^b$ and $R^c$ in 3-6a may undergo an intramolecular reaction to form a macrocyclic structure as seen in 3-7a under appropriate reaction conditions, optionally in the presence of catalyst(s) and/or promoter(s). The reaction that can be used to succeed this intramolecular cyclization may include, but not limited to etherification, ester formation, reductive amination, amide formation, carbamate formation, urea formation, ring-closure-metathesis, Pd-catalyzed selective cross-couplings, oximation, various types of Diels-Alder reaction, and/or radical cyclization. Then the imidazole protection group may be optionally removed to 3-8a.

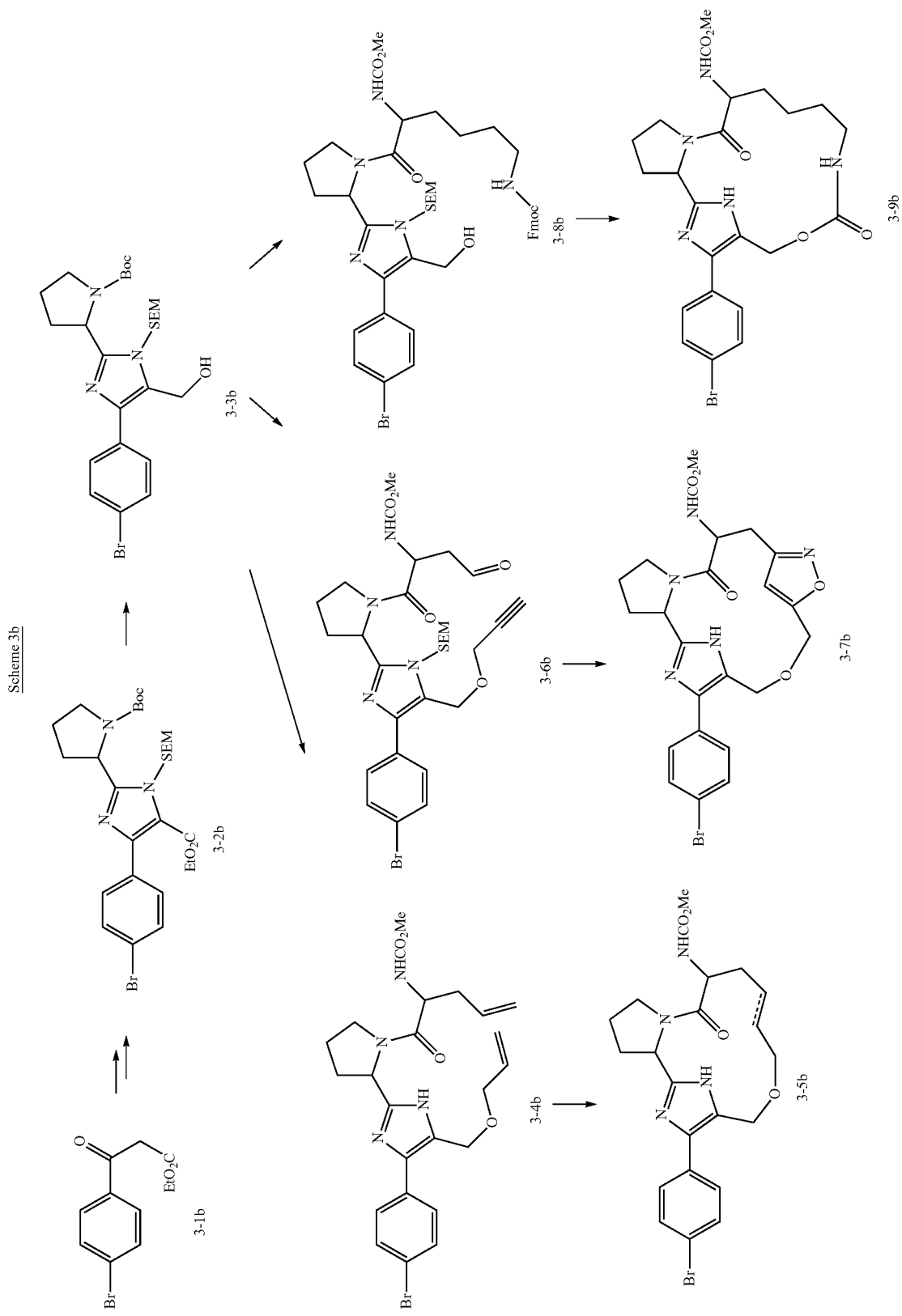

An example of strategies that may be used to form the macrocyclic structures are illustrated in Scheme 3b, wherein bromophenyl imidazole 3-2b can be obtained from ketone 3-1b using the procedures described above. 3-2b can be reduced by DIBAL-H to alcohol 3-3b, which is then served as a universal intermediate for further transformations. Thus, 3-4b may be obtained from 3-3b in three steps: 1) allylation with allyl bromide and sodium hydride in DMF; 2) simultaneously deprotection of boc and SEM with HCl under heat; and 3) capping the released pyrrolidine with methoxycarbonyl-protected allylglycine. The di-olefin 3-4b can be converted to macrocyclic olefin 3-5b (wherein the dotted bond may be nil or a single bond) through metal-catalyzed ring-closure-metathesis (RCM), which is well-known to those-in-the-art. Similarly 3-3b can be alkylated with propargyl bromide, followed by a) selective deprotection of Boc; b) capping with an appropriately substituted amino acid (wherein the aldehyde group may be protected as acetal); and c) deprotection of the acetal to release the aldehyde moiety, to afford 3-6b. The aldehyde in 3-6b may be converted to oxime by hydroxylamine, which can be converted in situ to its nitrile oxide by NCS type reagent, and the latter may react with the triple bond to fulfill the "click" reaction to afford the macrocyclic isoxazole derivative 3-7b after removal of SEM-protection. Alternatively 3-3b can be selectively deprotected and capped with a protected lysine derivative to compound 3-8b. After removal of Fmoc protection by piperidine, the free hydroxy and amino group may be united into a carbamate group by a reagent such as CDI, phosgene or the like to the macrocyclic carbamate 3-9b.

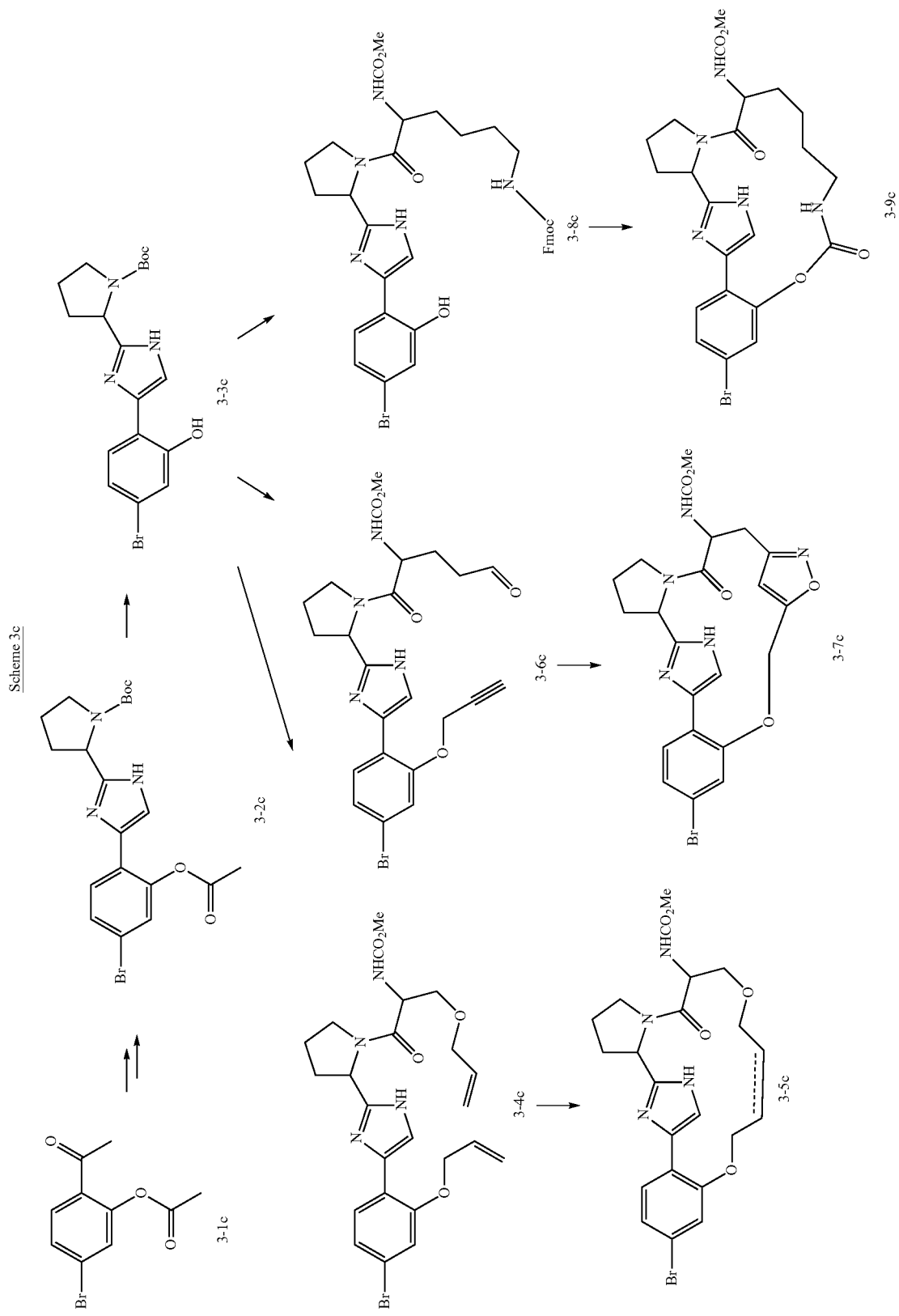
Scheme 3c

Other intermediates with a macrocyclic ring may be prepared by using strategies similar to that described in Scheme 3a and 3b. As exemplified in Scheme 3c, wherein bromophenyl imidazole 3-2c can be obtained from ketone 3-1c using the procedures described above. 3-2c can be reduced by NH₄OAc to alcohol 3-3c, which is then served as an universal intermediate to give the macrocyclic structures 3-5c, 3-7c and 3-9c.

With a variety of suitably substituted imidazopyridines, benzimidazoles and imidazoles such as those listed in Schemes 1-3, 2a, 3a, 3b and 3c in hand, the compounds of the present invention may be prepared through various coupling strategy or a combination of strategies to connect two fragments, optionally with a suitable cyclic or acyclic linker or formation of a cyclic or acyclic linker. The said strategy may include, but not limited to, Stille coupling, Suzuki coupling, Sonogashira coupling, Heck coupling, Buchwald amidation, Buchwald amination, amide coupling, ester bond formation, William etherification, Buchwald etherification, alkylation, pericyclic reaction with different variations, or the like.

Scheme 4

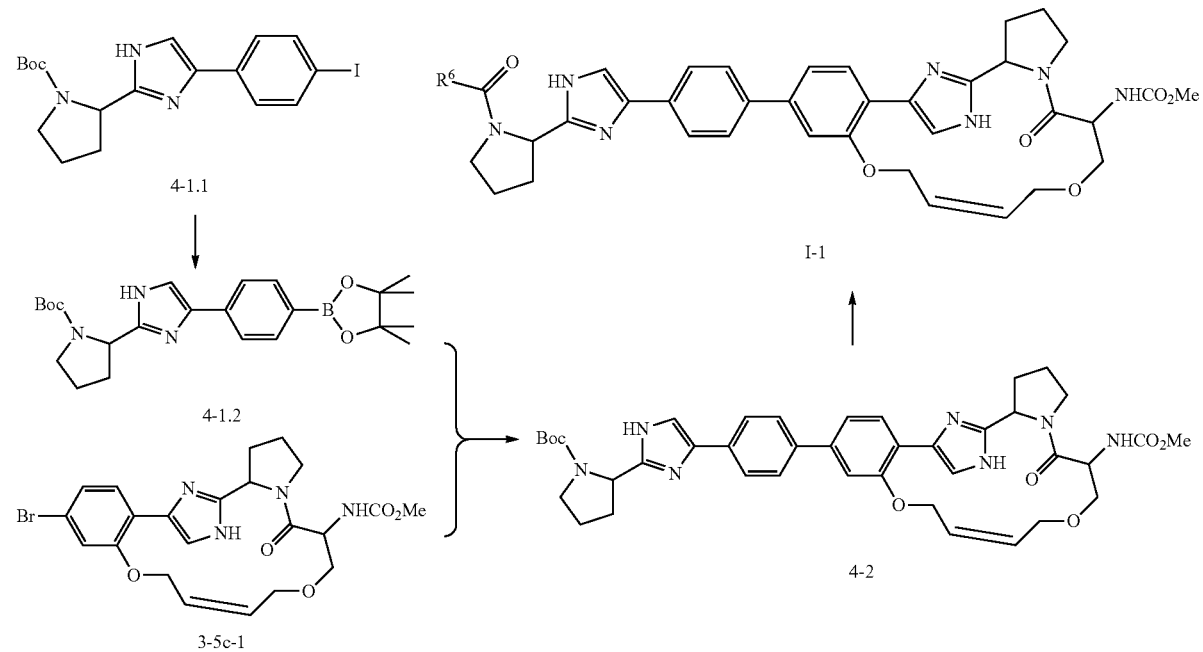

An example of the strategies that may be used to prepare the compounds of the present invention is shown in Scheme 4. Both iodide 4-1.1 and its corresponding boronate derivative 4-1.2 can be prepared using similar procedures described previously. The bromide 3-5c-1 can be coupled with boronate 4-1.2 under Suzuki condition in the presence of a Pd-catalyst to generate a core structure 4-2. Compound 4-2 then may be served as a common intermediate for further derivatizations to the title compounds I-1 using the procedures described in Schemes 3a and 3b.

Scheme 4a

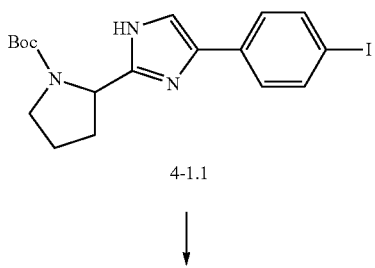

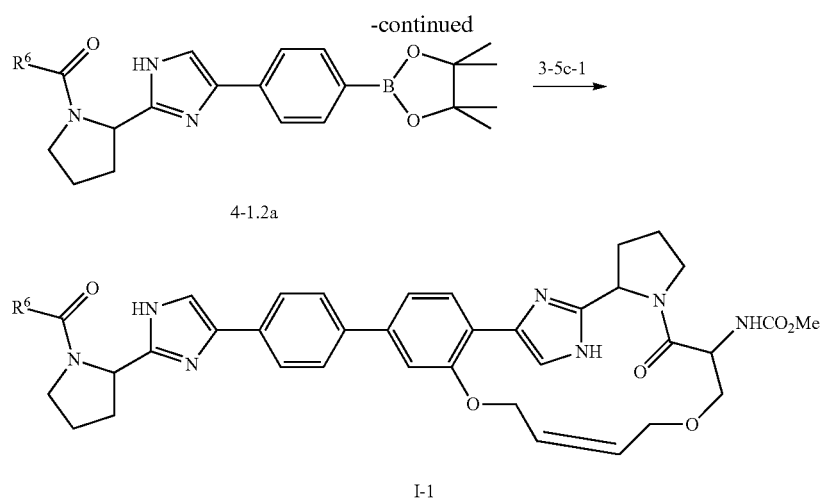
Alternatively, as shown in Scheme 4a, the compounds of the present invention (for example I-1) may also be derived from key intermediates 4-1.2a and 3-5c-1 using the Suzuki coupling procedures described previously. The intermediate 4-1.2a has the desired acyl group already installed from 4-1.1 using similar sequences shown in Scheme 3b.

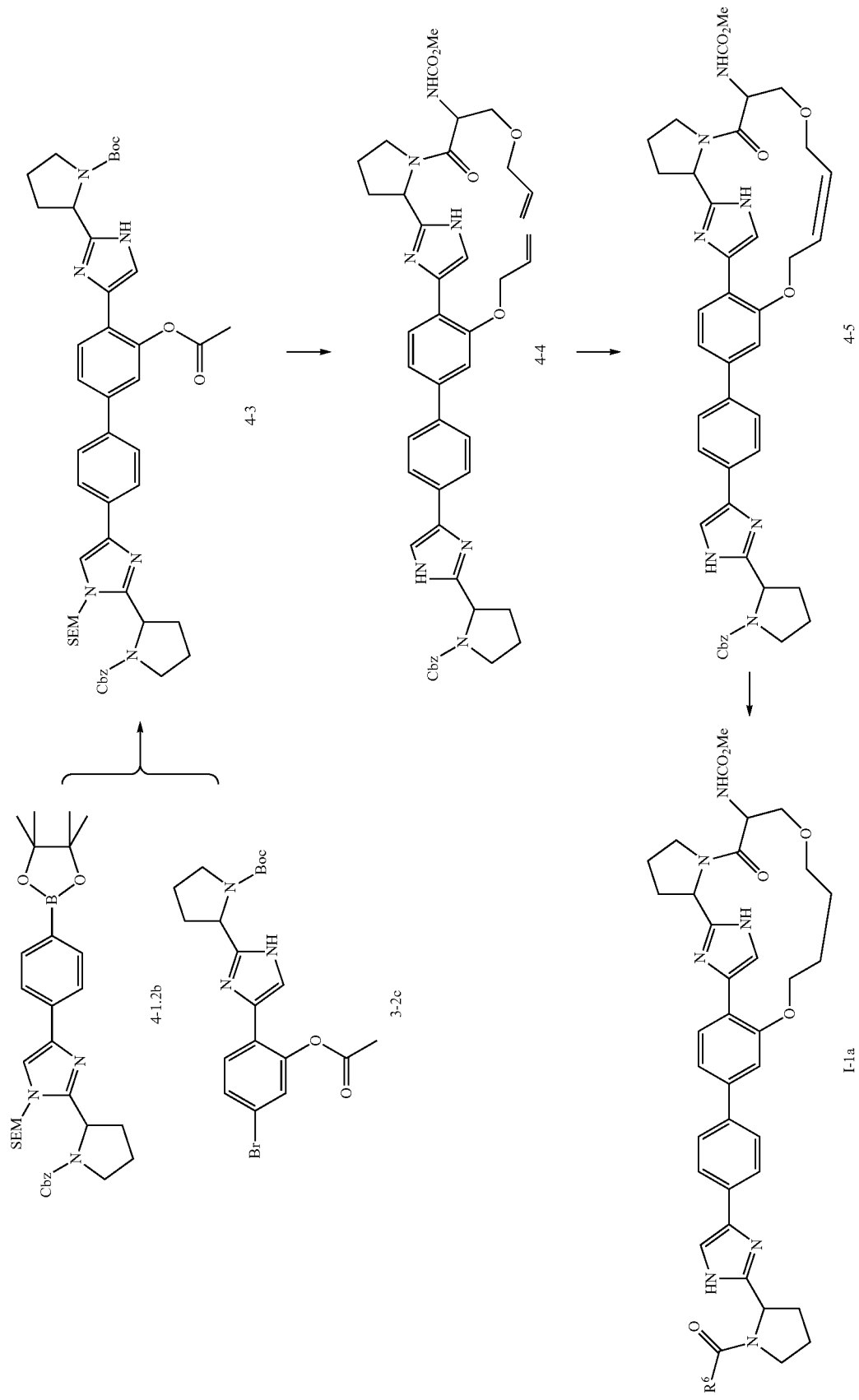
Scheme 4b

Yet alternatively, as shown in Scheme 4b, the compounds of the present invention (for example I-1a) may also be derived from key intermediate 4-3 after Suzuki coupling of 4-1.2b and 3-2c using the procedures described previously. Compound 4-3 can be converted to di-olefin 4-4 in a few steps: a) selectively reduced to alcohol; b) allylated to allylic ether; c) deprotected Boc and SEM; and d) capped with a carbamate-protected allylglycine, using the procedures described previously. As discussed earlier, the di-olefin 4-4 can be converted to the title compound I-1a through RCM to macrocyclic intermediate 4-5 followed by de-Cbz under hydrogenation condition and capping with an acyl derivative (such as $R^6COOH$), all using the procedures described earlier.

The compounds of the present invention containing five-membered heteroaryl other than imidazole may be prepared using similar procedures described above in Schemes 1-4 and 4a. For example, some intermediates containing a desired, suitably substituted five-membered heteroaryl have been published in US 2008/0311075A1 by C. Bachand, et al from BMS, which is incorporated by reference. These intermediates are compiled in the following Table 13.

TABLE 13

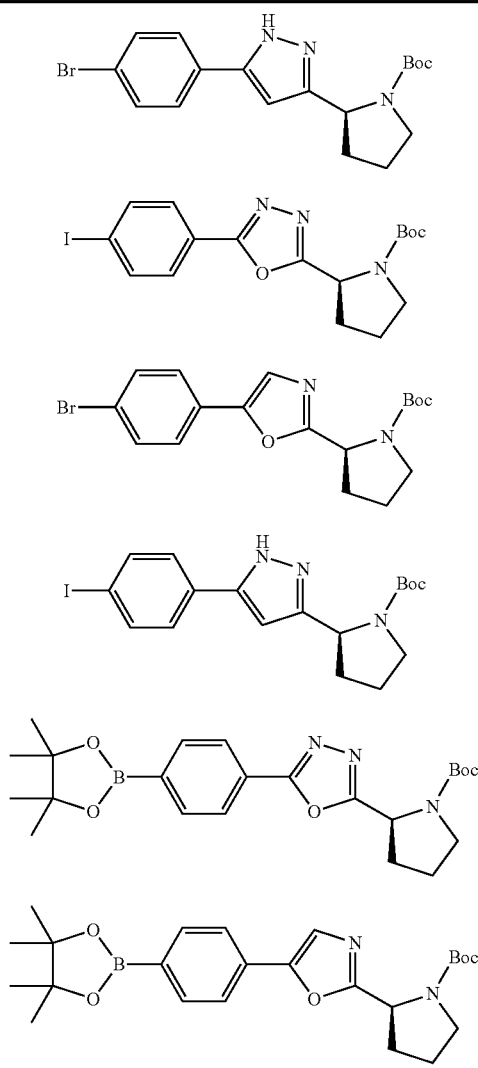

TABLE 13-continued

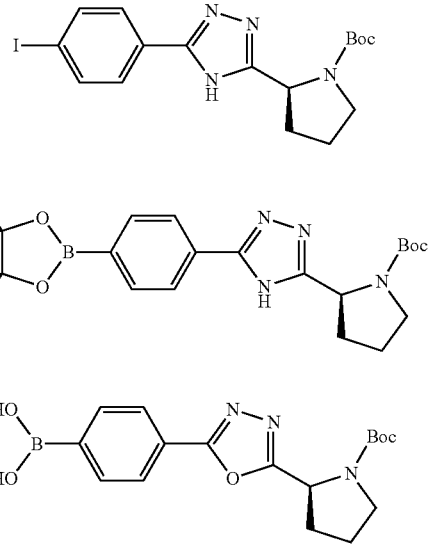

Some intermediates and/or precursors that may be used for the synthesis of the compounds of the present invention have also been disclosed in the following patent publications: WO 2009/102568A1; WO 2009/102633A1; WO 2010/065668A1; WO 2010/065674A1; WO 2010/065681A1; WO 2010/091413A1; WO 2010/096462A1; WO 2010/096777A1; WO 2010/099527A1; US 2010/0233120A1; WO 2010/111483A1; WO 2010/111534A1; WO 2010/111673A1; WO 2010/120935A1; WO 2010/132538A1A1; WO 2010/132601A1; WO 2010/138368A1; WO 2010/138488A1; WO 2010/138790A1; WO 2010/138791A1; WO 2010/144646A2; WO 2010/148006A1; US 2010/0215618A1; WO 2011/004276A1; WO 2011/009084A2; WO 2011/015657A1; WO 2011/015658A1; WO 2011/026920A1; WO 2011/028596A1; WO 2011/031904A1; and WO 2011/031934A1, which are incorporated herein by reference in their entirety.

The synthesis of the compounds of the present invention involves 5/6-membered fused heteroaryl intermediates other than benzimidazoles, various 5/6-membered fused heteroaryl are known in the literature. The synthesis of other 5/6-membered fused heteroaryl intermediates depends on the chemical features of each structure. For example, a typical synthesis of indole intermediate is illustrated in Scheme 5. The commercially available bromoiodoaniline 5-1 may be coupled to the commercially available acetylene 5-1.1 under the Sonogashira conditions to give phenylacetylene 5-2. The latter may be cyclized to indole 5-3 under heat or microwave condition in the presence of a copper catalyst.

Scheme 5

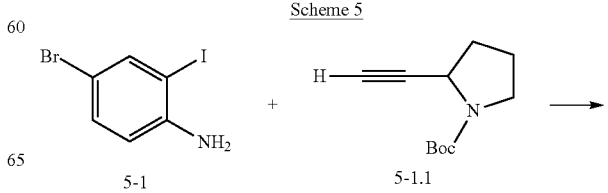

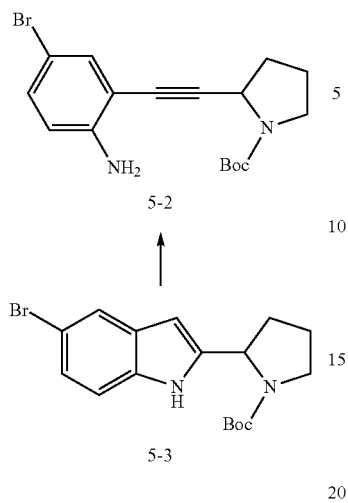

5-2

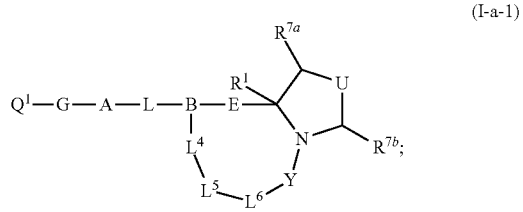

5-3

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis," 3rd Ed (1999), J Wiley and Sons.

In certain aspects, the invention is a process of making a compound of Formula (I) comprising the steps of:

i) preparing a compound of Formula (I-a-1):

(I-a-1)

via a transition-metal catalyzed cross-coupling reaction, ring-closure metathesis or other intramolecular ring-closure reaction such as various type of Diels-Alder reaction, amide (lactam) formation, reductive amination, oximation, ester formation (lactonization), carbamate or urea formation;

wherein E at each occurrence is independently an optionally substituted 5-membered heteroaryl containing one or more nitrogen atom;

$Q^1$ is or hydrogen;

Alternatively, G and $Q^1$ can be taken together to form a group selected from:

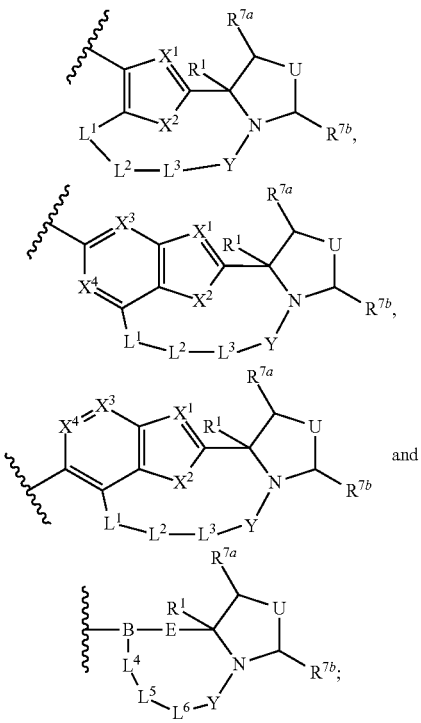

$X^3$ and $X^4$ at each occurrence are each independently N or $C(R^{12})$; and $R^{12}$ at each occurrence is independently hydrogen, halogen, hydroxy, optionally substituted $C_1$-$C_4$ alkyl or $O(C_1$-$C_4$ alkyl); $Z^a$ is independently an amino protecting group or —C(O)—$R^6$; wherein $R^6$ is $C_1$-$C_8$ alkyl optionally substituted with amino, hydroxy, protected amino, or $O(C_1$-$C_4$ alkyl); and A, B, E, G, L, U, $X^1$, $X^2$, Y, $L^1$, $L^2$, $L^3$, $L^4$, $L^5$, $L^6$, $R^1$, $R^{7a}$ and $R^{7b}$ are as defined for Formula I;

ii) when $Q^1$ is

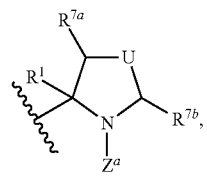

wherein $Z^a$ is an amino protecting group, selectively deprotecting a compound of Formula (I-a-1) to give the corresponding amine of Formula (I-b-1):

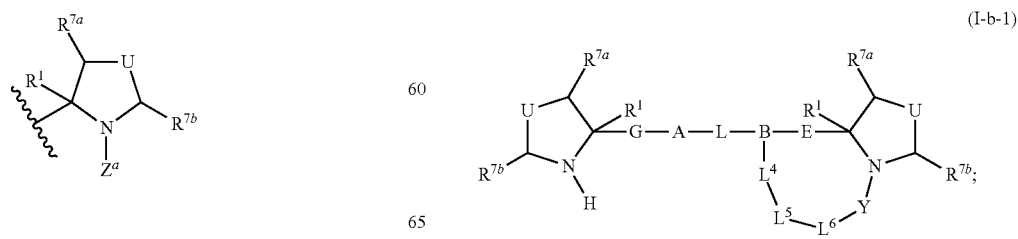

(I-b-1)

and iii) Capping the released amino group of a compound of Formula (I-b-1) with LG-C(O)—R⁶, wherein LG is a leaving group; to give the compound of Formula (I-c-1):

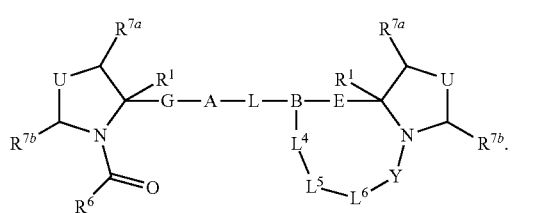
(I-c-1)

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

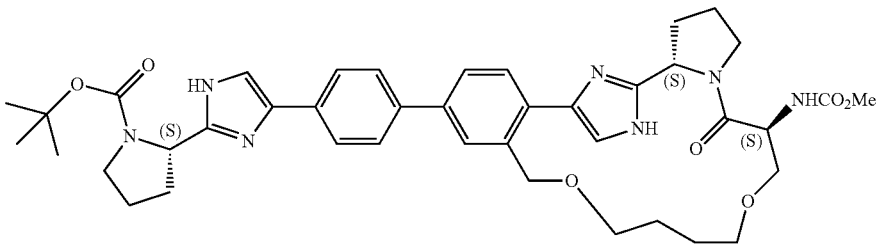

The title compound was prepared from the compound of Example 347 (described below) using procedures similar to that described in Example 345 (described below). ESIMS m/z=740.60 [M+H]⁺.

Example 83

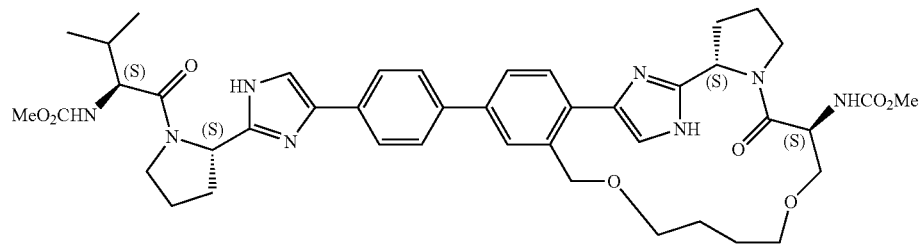

The title compound was prepared from the compound of Example 1 using procedures similar to that described in Example 346 (described below). ESIMS m/z=797.76 [M+H]⁺.

Example 344

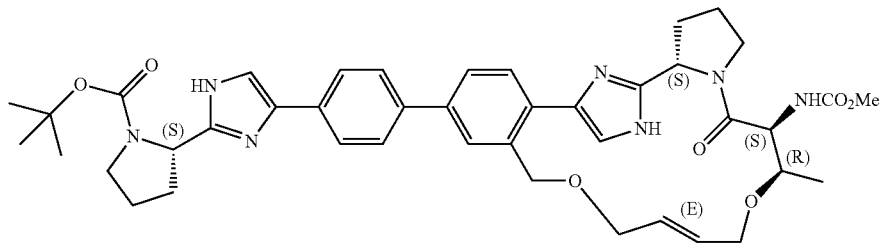

Step 344a. Into a solution of 4'-bromo-2'-hydroxyacetophenone (2.00 g, 9.85 mmol) in pyridine (50 mL) at 0° C. was added acetyl chloride (1.05 mL, 14.8 mmol). The resultant mixture were warmed up to room temperature and stirred for 12 hours before being evaporated to dryness. The residue was partitioned (EtOAc-H$_2$O) and the organics were washed with brine, dried (Na$_2$SO$_4$), filtered and evaporated. The residue was purified by flash column chromatography (silica, EtOAc-hexanes) to give the desired compound as a colorless oil (2.31 g, 96%).

Step 344b. Into a solution of the compound from step 344a (2.31 g, 9.39 mmol) in acetic acid (40 mL) was added bromine (0.48 mL, 9.39 mmol). The resultant mixture were stirred at room temperature for 3 hours before being evaporated to dryness. The residue was partitioned (EtOAc-H$_2$O) and the organics were washed with brine, dried (Na$_2$SO$_4$), filtered and evaporated to give the crude desired compound as a light yellow oil (3.13 g).

Step 344c. Into a solution of the crude compound from step 344b (9.39 mmol at most) in CH$_3$CN (45 mL) were added N-Boc-L-proline (2.63 g, 12.2 mmol) and DIPEA (3.51 mL, 28.2 mmol). The resultant mixture were stirred at room temperature for 30 minutes before being evaporated to dryness. The residue was partitioned (EtOAc-H$_2$O) and the organics were washed with brine, dried (Na$_2$SO$_4$), filtered and evaporated to give the crude desired compound as a red brown foam (3.65 g). ESIMS m/z=492.17, 494.14 [M+Na]$^+$.

Step 344d. Into a solution of the crude compound from step 344c (9.39 mmol at most) in toluene (40 mL) was added NH$_4$OAc (6.90 g, 89.5 mmol). The resultant mixture were heated up to 100° C. for 14 hours before being cooled down and evaporated to dryness. The residue was partitioned (EtOAc-H$_2$O) and the organics were washed with brine, dried (Na$_2$SO$_4$), filtered and evaporated. The residue was purified by flash column chromatography (silica, EtOAc-hexanes) to give the desired compound as a dark brown foam (0.851 g, 3 steps 23%). ESIMS m/z=408.17, 410.17 [M+H]$^+$.

Step 344e. Into a solution of the compound from step 344d (0.300 g, 0.735 mmol) in CH$_2$Cl$_2$ (3.6 mL) and H$_2$O (3.6 mL) were added NaOH (58.8 mg, 1.47 mmol), TBAI (27.1 mg, 73.5 mmol) and allyl bromide (0.19 mL, 2.21 mmol). The resultant mixture were stirred vigorously at room temperature for 3 hours before being partitioned (EtOAc-H$_2$O). The organics were washed with brine, dried (Na$_2$SO$_4$), filtered and evaporated. The residue was purified by flash column chromatography (silica, EtOAc-hexanes) to give the desired compound as a brown oil (0.225 g, 68%). ESIMS m/z=448.21, 450.21 [M+H]$^+$.

Step 344f. A solution of the compound from step 344e (0.225 g, 0.502 mmol) in CH$_2$Cl$_2$ (3 mL) was treated with HCl in 1,4-dioxane (4 M, 6 mL) for 30 min. The volatiles were evaporated off to give the crude desired compound as a yellow solid which was directly used in the next step. ESIMS m/z=348.16, 350.16 [M+H]$^+$.

Step 344g. A mixture of the crude compound from step 344f (0.502 mmol at most) and (2S,3R)-3-(allyloxy)-2-(methoxycarbonylamino)butanoic acid (prepared from O-2-propen-1-yl-L-threonine, according to WO 2008/021927, 0.131 g, 0.603 mmol) in CH$_2$Cl$_2$ (6 mL) was treated with HATU (0.191 g, 0.502 mmol) in the presence of DIPEA (1.25 mL, 10.0 mmol) for 30 minutes at rt. The volatiles were evaporated off to provide a brown sirup, which was purified by flash column chromatography (silica, EtOAc-hexanes) to give the desired compound as a light yellow brown oil (0.224 g, 2 steps 81%). ESIMS m/z=547.27, 549.27 [M+H]$^+$.

Step 344h. Into a solution of compound from step 344g (0.224 g, 0.409 mmol) in toluene (160 mL) was added Zhan-1b catalyst (59.9 mg, 81.7 μmol). The resultant mixture were degassed and heated up to 80° C. under N$_2$ for 6 hours before the addition of another portion of Zhan-1b catalyst (59.9 mg, 81.7 μmol). The mixture were degassed and heated up to 80° C. under N$_2$ for another 6 hours before all volatiles were removed by rotavap. The residue was purified by flash column chromatography (silica, EtOAc-hexanes) to afford the desired compound as a greenish oil (44.5 mg, 21%). ESIMS m/z=519.26, 521.26 [M+H]$^+$.

Step 344i. A mixture of 2,4'-dibromoacetophenone (5.00 g, 18.0 mmol), N-Boc-L-proline (3.87 g, 18.0 mmol) and in CH$_3$CN (60 mL) was treated with TEA (5.40 mL, 37.8 mmol) at room temperature until the disappearance of the starting material. The volatiles were evaporated and the residue was partitioned (EtOAc-water). The organics were washed with brine, dried (Na$_2$SO$_4$), filtered and evaporated. The residue was purified by chromatography (silica, hexanes-ethyl acetate) to give the desired compound as a light yellow foam (6.73 g, 91%). $^1$H NMR (CDCl$_3$) 7.76 (t, J=8.0 Hz, 2H), 7.63 (dd, J=5.0, 8.5 Hz, 2H), 5.51, 5.16 (2d, J=16.0 Hz, 1H), 5.32, 5.28 (2d, J=16.5 Hz, 1H), 4.48, 4.40 (dd, J=5.0, 8.5 Hz, 1H), 3.56 (m, 1H), 3.43 (m, 1H), 2.30 (m, 2H), 2.06 (m, 1H), 1.92 (m, 1H), 1.46, 1.43 (2s, 9H).

Step 344j. A solution of the compound from step 344i (6.73 g, 16.3 mmol) in toluene (100 mL) was treated with ammonium acetate (25.1 g, 0.327 mol) at 100° C. for 14 hours. The volatiles were evaporated and the residue was partitioned (EtOAc-aqueous NaHCO$_3$). The organics were washed with brine, dried (Na$_2$SO$_4$), filtered and evaporated. The residue was purified by chromatography (silica, hexanes-ethyl acetate) to give the desired compound as a yellow foam (6.10 g, 95%). ESIMS m/z=392.24, 394.24 [M+H]$^+$. $^1$H NMR (CDCl$_3$) 7.57 (bs, 1H), 7.48 (m, 3H), 7.23 (s, 1H), 4.97 (m, 1H), 3.42 (m, 2H), 2.99 (m, 1H), 2.16 (m, 2H), 1.97 (m, 1H), 1.46 (s, 9H).

Step 344k. A mixture of the compound from step 344j (1.00 g, 2.55 mmol), bis(pinacolato)diboron (1.35 g, 5.33 mmol), Pd(PPh$_3$)$_4$ (0.147 g, 0.128 mmol) and potassium acetate (0.640 g, 6.53 mmol) in 1,4-dioxane (20 mL) was degassed and heated at 80° C. under N$_2$ for 14 hours. The volatiles were evaporated and the residue was partitioned (EtOAc-water). The organics were washed with brine, dried (Na$_2$SO$_4$), filtered and evaporated. The residue was purified by chromatography (silica, hexanes-ethyl acetate) to give the desired compound as a light yellow solid (0.978 g, 87%). ESIMS m/z=440.39 [M+H]$^+$. $^1$H NMR (CDCl$_3$) 11.03, 10.55 (2s, 1H), 7.79 (m, 3H), 7.45 (m, 1H), 7.26 (m, 1H), 4.97 (m, 1H), 3.41 (m, 2H), 3.06, 2.91 (2m, 1H), 2.17 (m, 2H), 1.97 (m, 1H), 1.49 (s, 9H), 1.35 (s, 12H).

Step 344l. A mixture of the compound from step 344h (44.5 mg, 85.7 µmol), the compound from step 344k (94.0 mg, 0.214 mmol) and NaHCO$_3$ (72.0 mg, 0.857 mmol) in DME (9 mL) and H$_2$O (3 mL) was added Pd(PPh$_3$)$_4$ (4.9 mg, 4.2 µmol). The resultant mixture were degassed and heated to 95° C. under N$_2$ for 1 hour. The volatiles were evaporated and the residue was partitioned (EtOAc-H$_2$O). The organics were washed with brine, dried (Na$_2$SO$_4$), filtered and evaporated. The residue was purified by flash column chromatography (silica, hexanes-ethyl acetate) to give the title compound as a light yellow solid (40.9 mg, 64%). ESIMS m/z=752.59 [M+H]$^+$.

Example 345

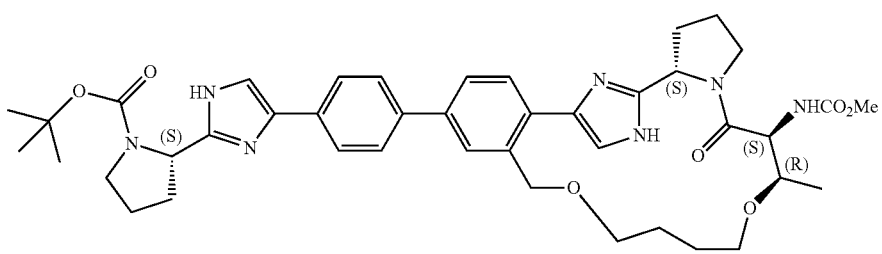

Into a solution of the compound from Example 344 (40.9 mg, 54.4 µmol) in MeOH (10 mL) was added palladium hydroxide (20 wt % on carbon, 20.0 mg). The resulting mixture was hydrogenated with hydrogen balloon at room temperature for 3 days before being filtered through a plug of celite. The filtrate was concentrated and purified by flash column chromatography (silica, CH$_2$Cl$_2$-MeOH) to give the title compound as a yellow white solid (37.8 mg, 92%). ESIMS m/z=754.62 [M+H]$^+$.

Example 346

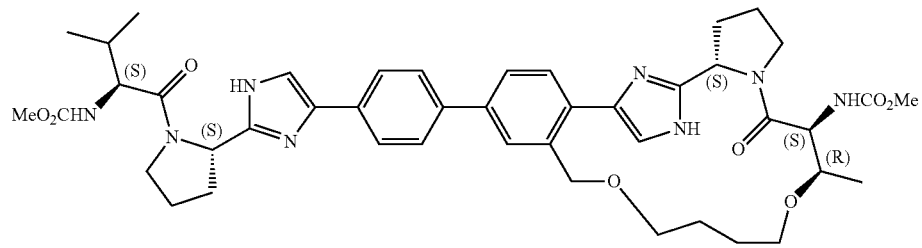

Step 346a. A solution of the compound from Example 345 (37.8 mg, 50.1 µmmol) in CH$_2$Cl$_2$ (3 mL) was treated with HCl in 1,4-dioxane (4 M, 6 mL) for 30 min. The volatiles were evaporated off to give the crude desired compound as a yellow solid which was directly used in the next step. ESIMS m/z=654.54 [M+H]$^+$.

Step 346b. A mixture of the crude compound from step 346a (50.1 µmmol at most) and (S)-(methoxycarbonyl)amino-3-methyl-butyric acid (prepared according to WO 2008/021927, 9.6 mg, 55.1 µmol) in DMF (3 mL) was treated with HATU (19.0 mg, 50.1 µmol) in the presence of DIPEA (0.13 mL, 1.00 mmol) for 2 hours at rt. The volatiles were evaporated off to provide a brown sirup, which was purified by flash column chromatography (silica, CH$_2$Cl$_2$-MeOH) to give the title compound as a very light yellow solid (28.0 mg, 2 steps 69%). ESIMS m/z=811.73 [M+H]$^+$.

Example 347

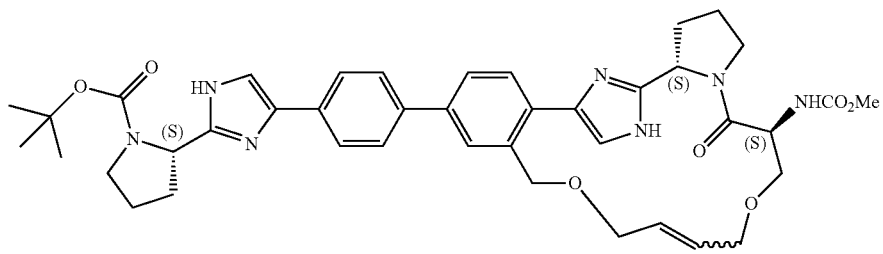

Step 347a. The desired compound was prepared from the crude compound from step 344f and (S)-3-(allyloxy)-2-(methoxycarbonylamino)propanoic acid (prepared from O-2-propen-1-yl-L-serine (*Org. & Biomolecular Chem.* 2005, 3(10), 2016-2025), according to WO 2008/021927) using procedures similar to that described in step 344g. ESIMS m/z=533.38, 535.36 [M+H]$^+$.

Step 347b. The desired compound was prepared from the compound from step 347a using procedures similar to that described in step 344h. ESIMS m/z=505.31, 507.31 [M+H]$^+$.

Step 347c. The title compound was prepared from the compound from step 347b and the compound from step 1k using procedures similar to that described in step 344l. ESIMS m/z=738.64 [M+H]$^+$.

Example 348

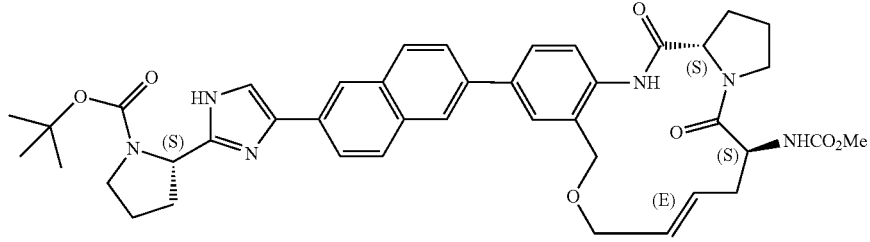

Step 348a. Into a solution of 5-bromo-2-nitro-benzoic acid (1.00 g, 4.06 mmol) in THF (20 mL) at 0° C. was added sequentially Et$_3$N (1.13 mL, 8.13 mmol) and isobutyl chloroformate (0.64 mL, 4.88 mmol). The resultant mixture were kept at 0° C. for 30 minutes before being cooled down to −78° C. NaBH$_4$ (0.615 g, 16.3 mmol) and EtOH (10 mL) were added to the reaction sequentially at −78° C., and the reaction was gradually warmed up to 0° C. and stirred for 1 hour. The reaction was quenched by aqueous NH$_4$Cl and the volatiles were evaporated to dryness. The residue was partitioned (EtOAc-H$_2$O) and the organics were washed with brine, dried (Na$_2$SO$_4$), filtered and evaporated to give the crude desired compound as a light yellow solid (1.06 g).

Step 348b. Into a solution of the crude compound from step 348a (4.06 mmol at most) in CH$_2$Cl$_2$ (12 mL) and H$_2$O (8 mL) were added 50% aqueous NaOH (2 mL), TBAI (0.150 g, 0.406 mmol) and allyl bromide (4 mL). The resultant mixture were stirred vigorously at room temperature for 12 hours before being partitioned (EtOAc-H$_2$O). The organics were washed with brine, dried (Na$_2$SO$_4$), filtered and evaporated. The residue was purified by flash column chromatography (silica, EtOAc-hexanes) to give the desired compound as a light yellow oil (0.935 g, 2 steps 85%). ESIMS m/z=448.21, 450.21 [M+H]$^+$.

Step 348c. Into a solution of the compound from step 348b (0.935 g, 3.44 mmol) in THF (40 mL) at 0° C. were added AcOH (1.6 mL) and Zn dust (2.40 g, 34.4 mmol). The resultant mixture were stirred vigorously at 0° C. for 1 hour and then warmed up to room temperature for 2 hours. The mixture was filtered through celite and the filtrate was evaporated to dryness. The residue was partitioned (EtOAc-H$_2$O) and the organics were washed with brine, dried (Na$_2$SO$_4$), filtered and evaporated. The residue was purified by flash column chromatography (silica, EtOAc-hexanes) to give the desired compound as a red brown oil (0.246 g, 30%). ESIMS m/z=448.21, 450.21 [M+H]$^+$.

Step 348d. Into a solution of N-Boc-L-proline (0.241 g, 1.12 mmol) in THF (10 mL) at 0° C. were added sequentially Et$_3$N (0.17 mL, 1.22 mmol) and isobutyl chloroformate (0.14 mL, 1.12 mmol). The resultant mixture were kept at 0° C. for 30 minutes before the addition of the compound from step 7c (0.246 g, 1.02 mmol) in THF (5 mL). The reaction was gradually warmed up to 35° C. and stirred for 14 hours. The reaction was quenched by aqueous NaHCO$_3$ and the volatiles were evaporated to dryness. The residue was partitioned (EtOAc-H$_2$O) and the organics were washed with brine, dried (Na$_2$SO$_4$), filtered and evaporated. The residue was purified by flash column chromatography (silica, EtOAc-hexanes) to give the desired compound as a yellow brown oil (0.288 g, 65%). ESIMS m/z=461.21, 463.21 [M+Na]$^+$.

Step 348e. The desired compound was prepared from the compound from step 348d using procedures similar to that described in step 344f. ESIMS m/z=339.13, 341.12 [M+H]$^+$.

Step 348f. The desired compound was prepared from the crude compound from step 348e and (S)-2-(methoxycarbonylamino)pent-4-enoic acid (prepared according to WO 2008/021927) using procedures similar to that described in step 344g. ESIMS m/z=494.22, 496.22 [M+H]$^+$.

Step 348g. The desired compound was prepared from the compound from step 348f using procedures similar to that described in step 1h. ESIMS m/z=466.11, 468.11 [M+H]$^+$.

Step 348h. 6-bromo-N-methoxy-N-methyl-2-naphthamide (prepared according to *J. Med. Chem.*, 2006, 49, 4721-4736, 3.57 g, 12.1 mmol) in THF (60 mL) was treated with methyl magnesium bromide (3M in Et$_2$O, 8.09 mL, 24.3 mmol) slowly at 0° C. for 1 hour. The solution was warmed up to rt for 2 hours before being quenched with aqueous NH$_4$Cl. The volatiles were removed and the residue was partitioned (EtOAc-water). The organics were washed with brine, dried (Na$_2$SO$_4$), filtered and evaporated to give the crude desired compound as a white solid (2.89 g, 96%).

Step 348i. The compound from step 348h (2.89 g, 11.6 mmol) in acetic acid (60 mL) was treated with bromine (0.59 mL, 11.6 mmol) dropwise for 1 hour. The volatiles were evaporated and the residue was partitioned (EtOAc-saturated aqueous NaHCO$_3$). The organics were washed with brine, dried (Na$_2$SO$_4$), filtered and evaporated to give the crude desired compound as a light yellow solid (3.898 g).

Step 348j. A mixture of the compound from step 348i (at most 11.6 mmol) and N-Boc-L-proline (3.75 g, 17.4 mmol) in CH$_3$CN (60 mL) was added DIPEA (2.89 mL, 23.2 mmol) slowly. The mixture was stirred at rt until the disappearance of the starting material. The volatiles were evaporated and the residue was partitioned (EtOAc-water). The organics were washed with brine, dried (Na$_2$SO$_4$), filtered and evaporated to give the crude desired compound as a yellow-white foam (4.762 g). ESIMS m/z=462.03, 464.02 [M+H]$^+$.

Step 348k. A solution of the compound from step 348j (at most 11.6 mmol) in toluene (60 mL) was added ammonium acetate (13.4 g, 0.174 mol) and the resultant mixture was heated up at 100° C. for 14 hours. The volatiles were evaporated and the residue was partitioned (EtOAc-aq. NaHCO$_3$). The organics were washed with brine, dried (Na$_2$SO$_4$), filtered and evaporated. The residue was purified by flash column chromatography (silica, hexanes-ethyl acetate) to give the desired compound as a yellow brown powder (3.14 g, 4 steps, 61%). ESIMS m/z=442.02, 444.02 [M+H]$^+$.

Step 348l. A mixture of the compound from step 348k (0.200 g, 0.452 mmol), bis(pinacolato)diboron (0.144 g, 0.565 mmol), PdCl$_2$(dppf) (36.9 mg, 0.0452 mmol) and potassium acetate (88.7 mg, 0.904 mmol) in DMSO (5 mL) was degassed and heated at 80° C. under N$_2$ for 17 hours. The reaction mixture was allowed to cool down and partitioned (EtOAc-water). The organic layer was washed with brine, dried (Na$_2$SO$_4$), filtered and evaporated. The residue was purified by chromatography (silica, hexanes-ethyl acetate) to give the desired compound as a yellow solid (0.188 g, 85%). ESIMS m/z=490.12 [M+H]$^+$.

Step 348m. The title compound was prepared from the compound from step 348g and the compound from step 348l using procedures similar to that described in step 344l. ESIMS m/z=749.60 [M+H]$^+$.

Example 349

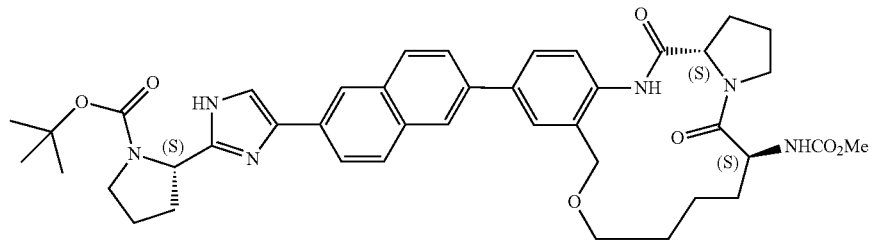

The title compound was prepared from the compound of Example 348 using procedures similar to that described in Example 345. ESIMS m/z=751.40 [M+H]$^+$.

Example 350

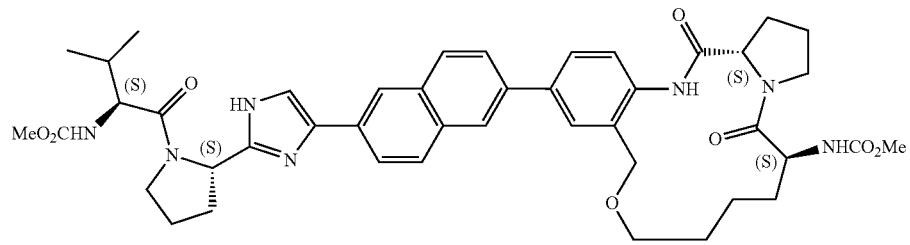

The title compound was prepared from the compound of Example 349 using procedures similar to that described in example 346. ESIMS m/z=808.42 [M+H]$^+$.

The title compounds of examples 2-82, 84-343 (compounds 2-82 and 84-342) may be prepared using the chemistry described above.

TABLE 1
Examples 1-219.
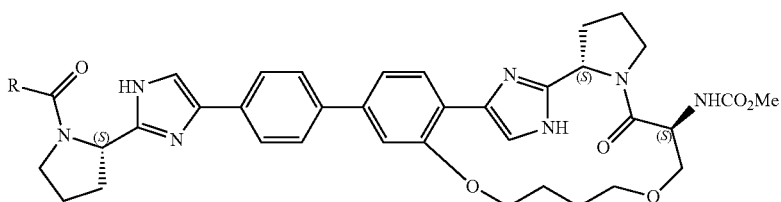
| Entry | |
|---|---|
| 1 | 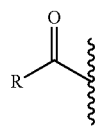 |
| 2 | 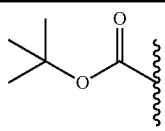 |
| 3 | 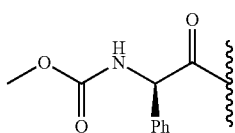 [SMILES: *C(=O)[C@H](NC(=O)OC)c1ccccc1] |
| 4 | 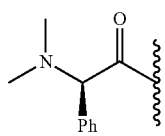 [SMILES: *C(=O)[C@@H](c1ccccc1)N(C)C] |
| 5 | 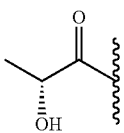 [SMILES: *C(=O)[C@@H](C)O] |
| 6 | 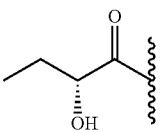 |
| 7 | 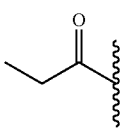 [SMILES: *C(=O)CC] |
| 8 | 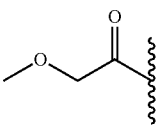 |
| 9 | 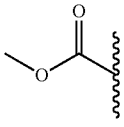 [SMILES: *C(=O)OC] |

TABLE 1-continued
Examples 1-219.
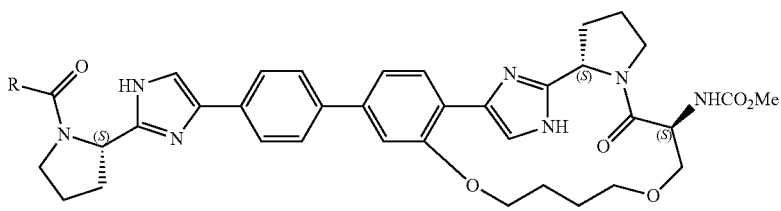
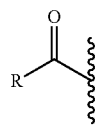
| Entry | |
|---|---|
| 10 | 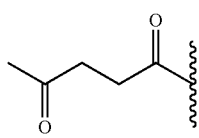 [SMILES: *C(=O)CCC(C)=O] |
| 11 | 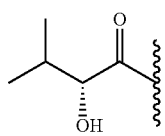 [SMILES: *C(=O)[C@H](O)C(C)C] |
| 12 | 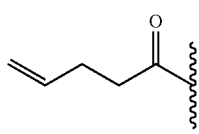 [SMILES: *C(=O)CCC=C] |
| 13 | 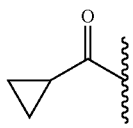 |
| 14 | 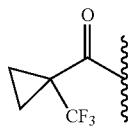 |
| 15 | 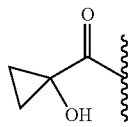 |
| 16 | 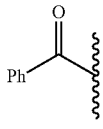 |
| 17 | 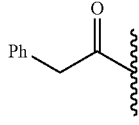 [SMILES: *C(=O)Cc1ccccc1] |

TABLE 1-continued
Examples 1-219.
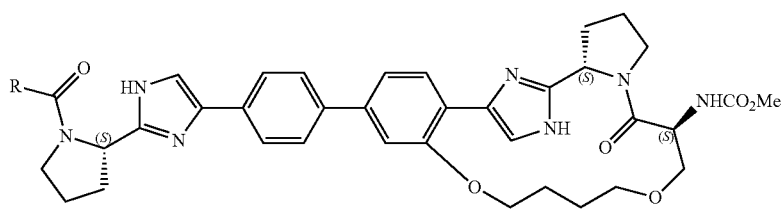
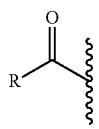
| Entry | |
|---|---|
| 18 | 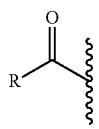 |
| 19 | 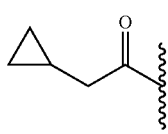 [SMILES: *C(=O)CC1CC1] |
| 20 | 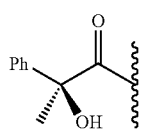 |
| 21 | 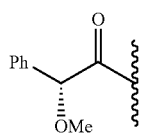 [SMILES: *C(=O)[C@H](OC)c1ccccc1] |
| 22 | 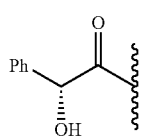 [SMILES: *C(=O)[C@H](O)c1ccccc1] |
| 23 | 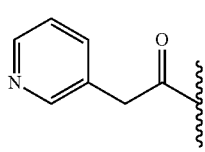 [SMILES: *C(=O)Cc1cccnc1] |
| 24 | 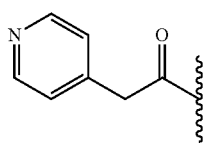 [SMILES: *C(=O)Cc1ccncc1] |
| 25 | 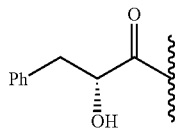 [SMILES: *C(=O)[C@H](O)Cc1ccccc1] |

TABLE 1-continued
Examples 1-219.
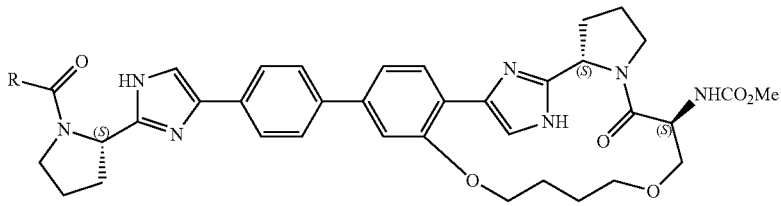
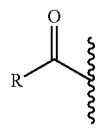
| Entry | |
|---|---|
| 26 | 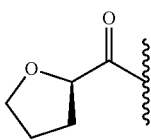 [SMILES: *C(=O)[C@H]1CCCO1] |
| 27 | 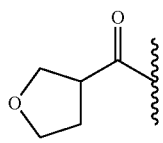 [SMILES: *C(=O)C1CCOC1] |
| 28 | 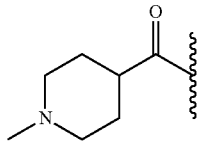 [SMILES: *C(=O)C1CCN(C)CC1] |
| 29 | 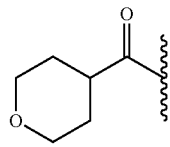 [SMILES: *C(=O)C1CCOCC1] |
| 30 | 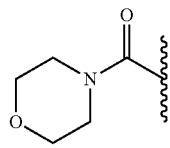 [SMILES: *C(=O)N1CCOCC1] |
| 31 | 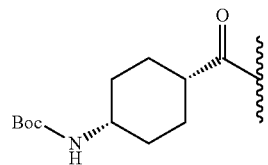 [SMILES: *C(=O)[C@H]1CC[C@@H](NC(=O)OC(C)(C)C)CC1] |
| 32 | 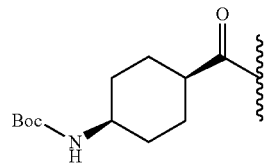 [SMILES: *C(=O)[C@H]1CC[C@@H](NC(=O)OC(C)(C)C)CC1] |

TABLE 1-continued
Examples 1-219.
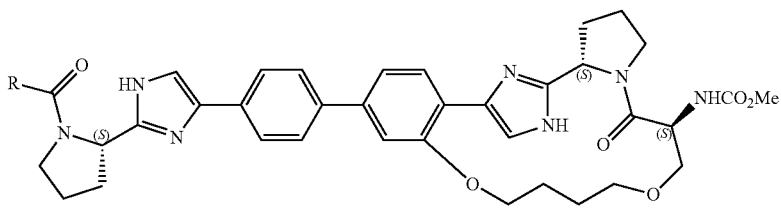
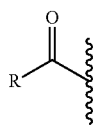
| Entry | |
|---|---|
| 33 | 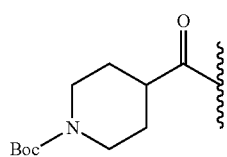 [SMILES: *C(=O)C1CCN(C(=O)OC(C)(C)C)CC1] |
| 34 | 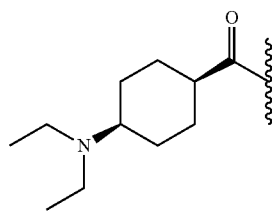 [SMILES: *C(=O)[C@H]1CC[C@@H](N(CC)CC)CC1] |
| 35 | 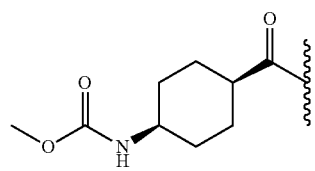 [SMILES: *C(=O)[C@H]1CC[C@@H](NC(=O)OC)CC1] |
| 36 | 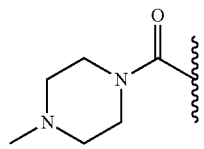 [SMILES: *C(=O)N1CCN(C)CC1] |
| 37 | 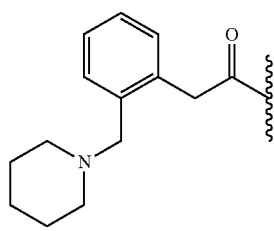 [SMILES: *C(=O)Cc1ccccc1CN1CCCCC1] |
| 38 | 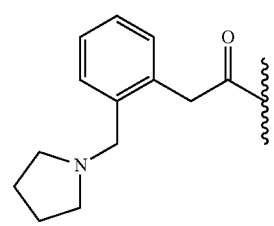 [SMILES: *C(=O)Cc1ccccc1CN1CCCC1] |

TABLE 1-continued
Examples 1-219.
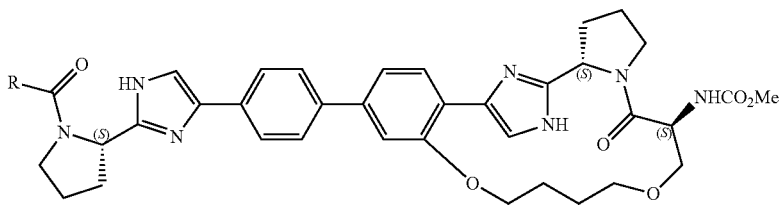
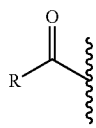
| Entry | |
|---|---|
| 39 | 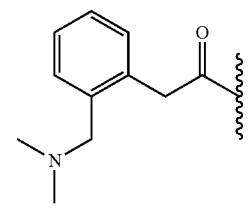 [SMILES: *C(=O)Cc1ccccc1CN(C)C] |
| 40 | 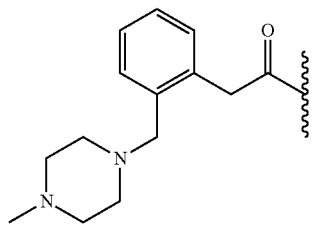 [SMILES: *C(=O)Cc1ccccc1CN1CCN(C)CC1] |
| 41 | 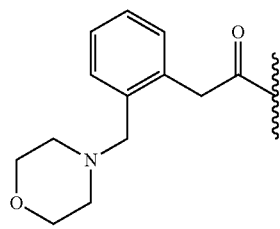 [SMILES: *C(=O)Cc1ccccc1CN1CCOCC1] |
| 42 | 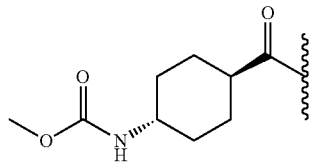 [SMILES: *C(=O)[C@H]1CC[C@H](NC(=O)OC)CC1] |
| 43 | 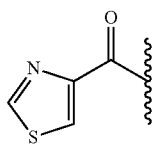 [SMILES: *C(=O)c1cscn1] |
| 44 | 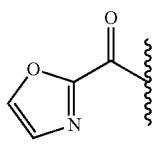 [SMILES: *C(=O)c1ncco1] |

TABLE 1-continued
Examples 1-219.
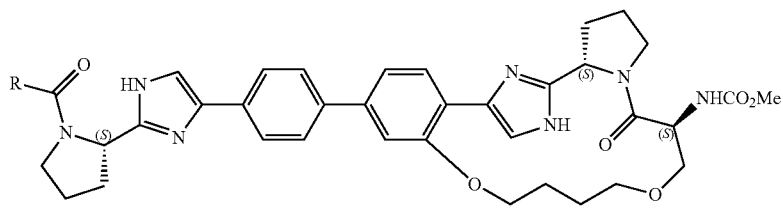
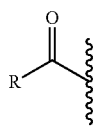
| Entry | |
|---|---|
| 45 | 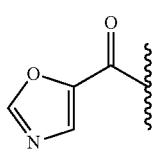 [SMILES: *C(=O)c1cnco1] |
| 46 | 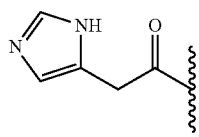 [SMILES: *C(=O)Cc1cnc[nH]1] |
| 47 | 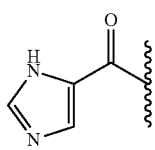 [SMILES: *C(=O)c1cnc[nH]1] |
| 48 | 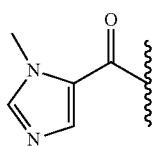 [SMILES: *C(=O)c1cncn1C] |
| 49 | 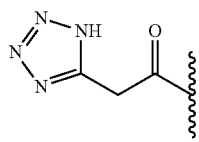 [SMILES: *C(=O)Cc1nnn[nH]1] |
| 50 | 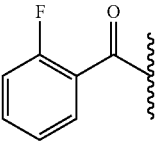 [SMILES: *C(=O)c1ccccc1F] |
| 51 | 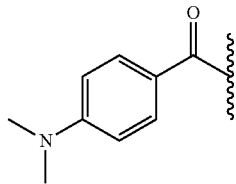 [SMILES: *C(=O)c1ccc(N(C)C)cc1] |

TABLE 1-continued
Examples 1-219.
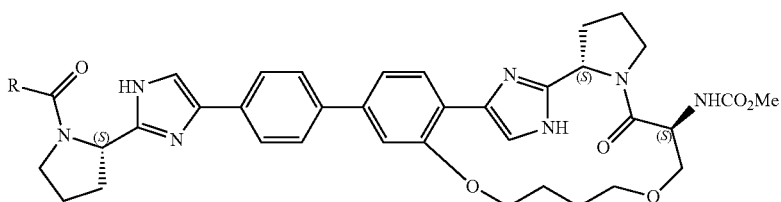
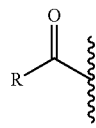
| Entry | |
|---|---|
| 52 | 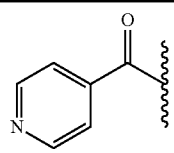 |
| 53 | 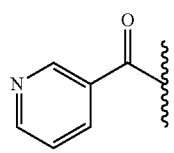 [SMILES: *C(=O)c1cccnc1] |
| 54 | 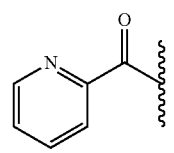 [SMILES: *C(=O)c1ccccn1] |
| 55 | 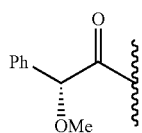 [SMILES: *C(=O)[C@H](OC)c1ccccc1] |
| 56 | 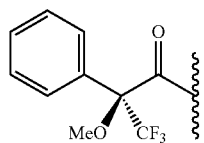 [SMILES: *C(=O)[C@@](OC)(c1ccccc1)C(F)(F)F] |
| 57 | 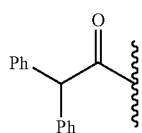 [SMILES: *C(=O)C(c1ccccc1)c1ccccc1] |
| 58 | 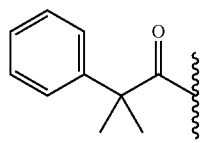 [SMILES: *C(=O)C(C)(C)c1ccccc1] |
| 59 | 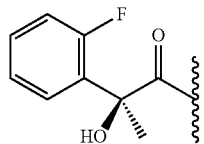 [SMILES: *C(=O)[C@@](C)(O)c1ccccc1F] |

TABLE 1-continued
Examples 1-219.
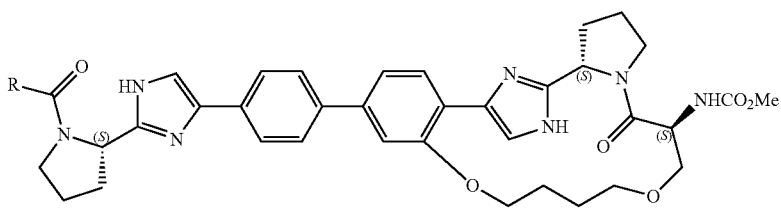
| Entry | R |
|---|---|
| 60 |  |
| 61 | 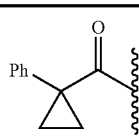 |
| 62 | 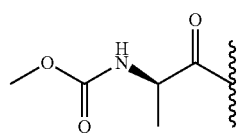 [SMILES: *C(=O)[C@@H](C)NC(=O)OC] |
| 63 | 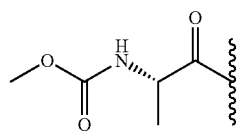 [SMILES: *C(=O)[C@H](C)NC(=O)OC] |
| 64 | 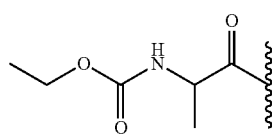 [SMILES: *C(=O)C(C)NC(=O)OCC] |
| 65 | 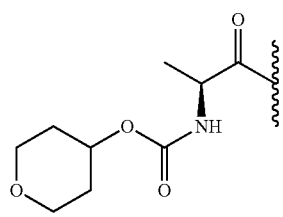 [SMILES: *C(=O)[C@H](C)NC(=O)OC1CCOCC1] |
| 66 | 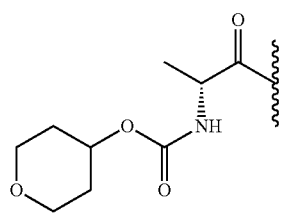 [SMILES: *C(=O)[C@@H](C)NC(=O)OC1CCOCC1] |

173 174
TABLE 1-continued
Examples 1-219.
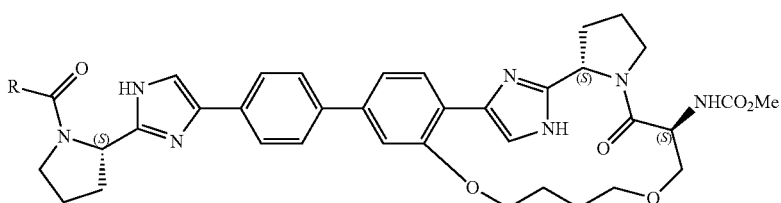
| Entry | |
|---|---|
| 67 | 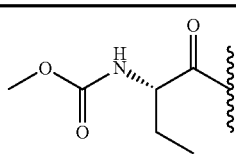 |
| 68 | 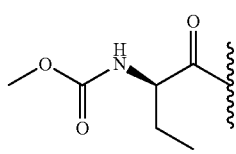 [SMILES: *C(=O)[C@@H](CC)NC(=O)OC] |
| 69 | 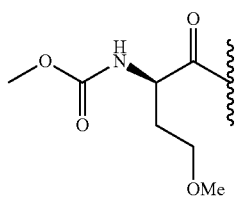 [SMILES: *C(=O)[C@@H](CCOC)NC(=O)OC] |
| 70 | 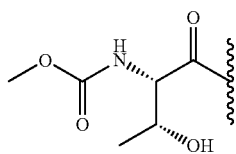 [SMILES: *C(=O)[C@@H](NC(=O)OC)[C@@H](C)O] |
| 71 | 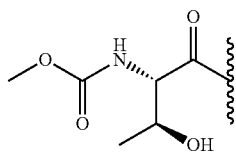 [SMILES: *C(=O)[C@@H](NC(=O)OC)[C@H](C)O] |
| 72 | 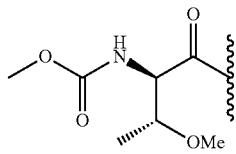 [SMILES: *C(=O)[C@H](NC(=O)OC)[C@@H](C)OC] |
| 73 | 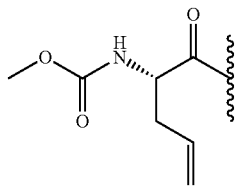 [SMILES: *C(=O)[C@H](CC=C)NC(=O)OC] |

TABLE 1-continued
Examples 1-219.
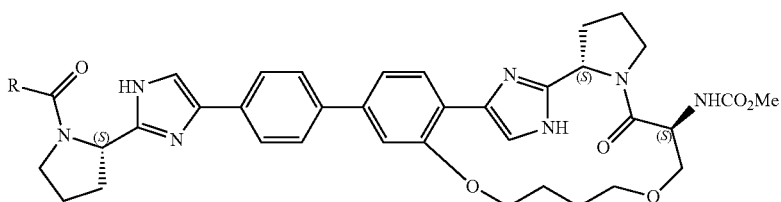
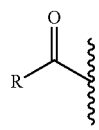
| Entry | |
|---|---|
| 74 | 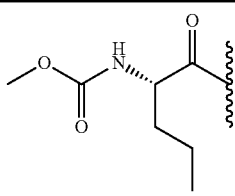 |
| 75 | 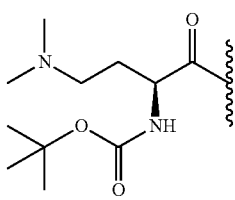 [SMILES: *C(=O)[C@H](CCN(C)C)NC(=O)OC(C)(C)C] |
| 76 | 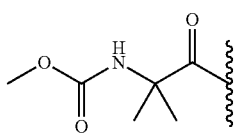 [SMILES: *C(=O)C(C)(C)NC(=O)OC] |
| 77 | 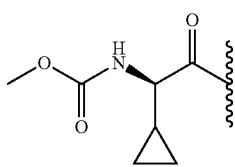 [SMILES: *C(=O)[C@H](NC(=O)OC)C1CC1] |
| 78 | 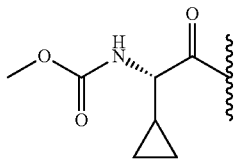 [SMILES: *C(=O)[C@@H](NC(=O)OC)C1CC1] |
| 79 | 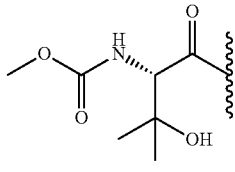 [SMILES: *C(=O)[C@@H](NC(=O)OC)C(C)(C)O] |
| 80 | 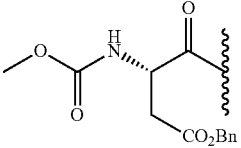 |

TABLE 1-continued
Examples 1-219.
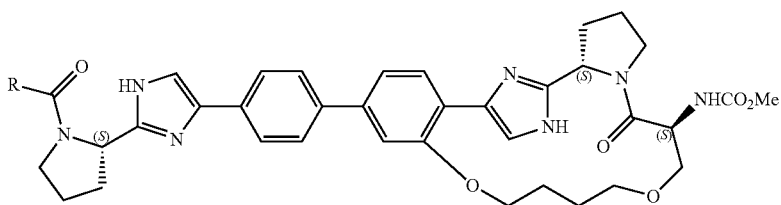
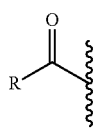
| Entry | |
|---|---|
| 81 | 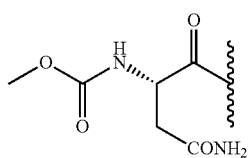 [SMILES: *C(=O)[C@H](CC(N)=O)NC(=O)OC] |
| 82 | 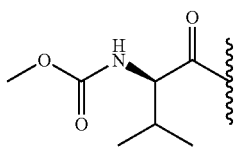 [SMILES: *C(=O)[C@H](NC(=O)OC)C(C)C] |
| 83 | 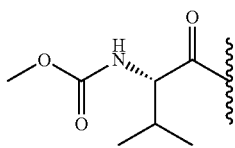 [SMILES: *C(=O)[C@@H](NC(=O)OC)C(C)C] |
| 84 | 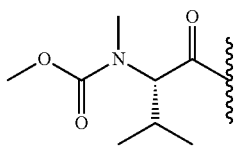 [SMILES: *C(=O)[C@H](C(C)C)N(C)C(=O)OC] |
| 85 | 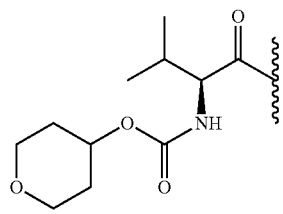 [SMILES: *C(=O)[C@@H](NC(=O)OC1CCOCC1)C(C)C] |
| 86 | 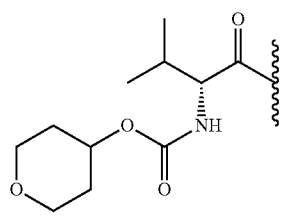 [SMILES: *C(=O)[C@H](NC(=O)OC1CCOCC1)C(C)C] |

TABLE 1-continued
Examples 1-219.
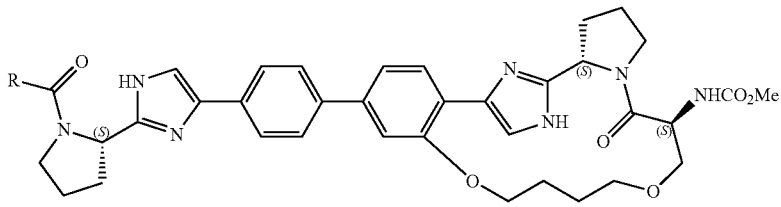
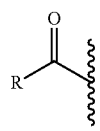
| Entry | |
|---|---|
| 87 | 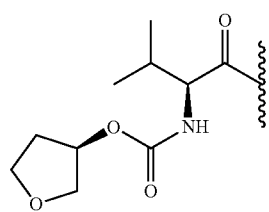 [SMILES: *C(=O)[C@@H](NC(=O)O[C@@H]1CCOC1)C(C)C] |
| 88 | 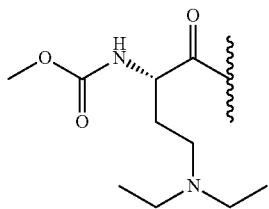 [SMILES: *C(=O)[C@H](CCN(CC)CC)NC(=O)OC] |
| 89 | 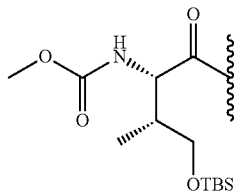 [SMILES: *C(=O)[C@@H](NC(=O)OC)[C@@H](C)CO[Si](C)(C)C(C)(C)C] |
| 90 | 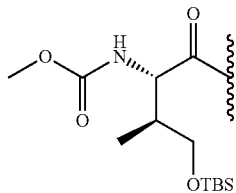 [SMILES: *C(=O)[C@@H](NC(=O)OC)[C@H](C)CO[Si](C)(C)C(C)(C)C] |
| 91 | 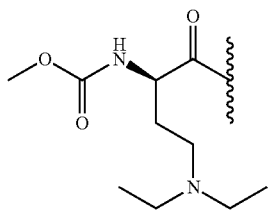 [SMILES: *C(=O)[C@@H](CCN(CC)CC)NC(=O)OC] |

TABLE 1-continued
Examples 1-219.
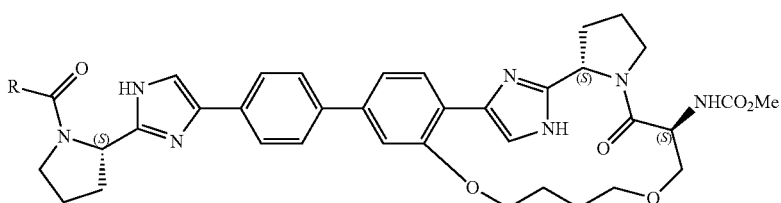
| Entry | |
|---|---|
| 92 | 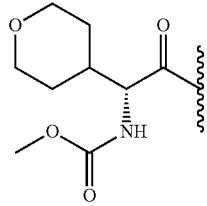 [SMILES: *C(=O)[C@H](NC(=O)OC)C1CCOCC1] |
| 93 | 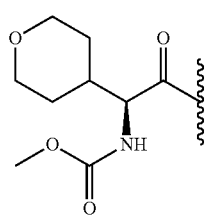 [SMILES: *C(=O)[C@@H](NC(=O)OC)C1CCOCC1] |
| 94 | 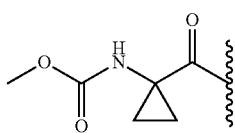 [SMILES: *C(=O)C1(NC(=O)OC)CC1] |
| 95 | 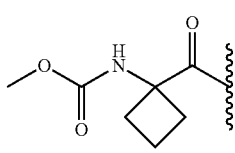 [SMILES: *C(=O)C1(NC(=O)OC)CCC1] |
| 96 | 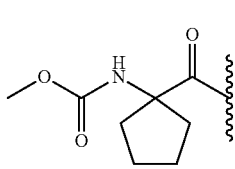 [SMILES: *C(=O)C1(NC(=O)OC)CCCC1] |
| 97 | 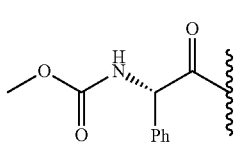 [SMILES: *C(=O)[C@@H](NC(=O)OC)c1ccccc1] |
| 98 | 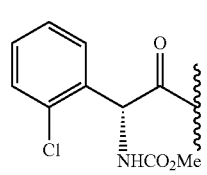 |

TABLE 1-continued
Examples 1-219.
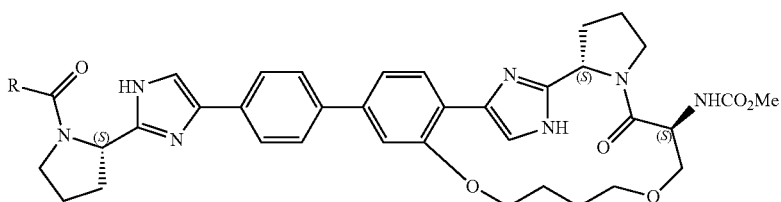
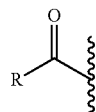
| Entry | |
|---|---|
| 99 | 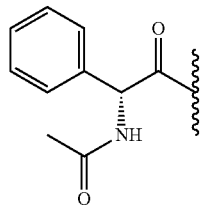 [SMILES: *C(=O)[C@H](NC(C)=O)c1ccccc1] |
| 100 | 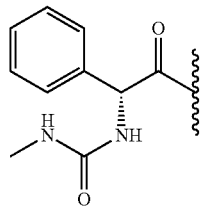 [SMILES: *C(=O)[C@H](NC(=O)NC)c1ccccc1] |
| 101 | 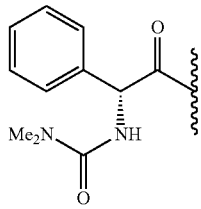 [SMILES: *C(=O)[C@H](NC(=O)N(C)C)c1ccccc1] |
| 102 | 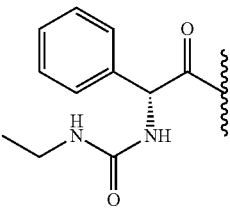 [SMILES: *C(=O)[C@H](NC(=O)NCC)c1ccccc1] |
| 103 | 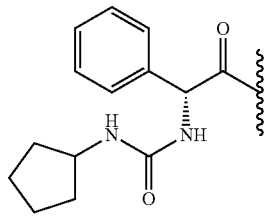 [SMILES: *C(=O)[C@H](NC(=O)NC1CCCC1)c1ccccc1] |
| 104 | 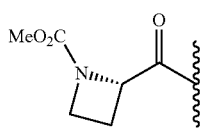 [SMILES: *C(=O)[C@@H]1CCN1C(=O)OC] |

TABLE 1-continued
Examples 1-219.
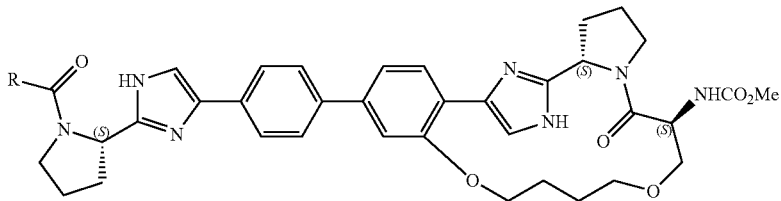
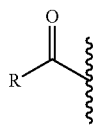
| Entry | |
|---|---|
| 105 | 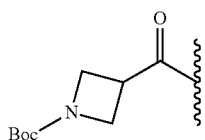 [SMILES: *C(=O)C1CN(C(=O)OC(C)(C)C)C1] |
| 106 | 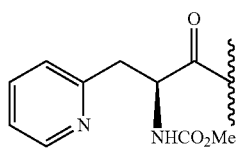 |
| 107 | 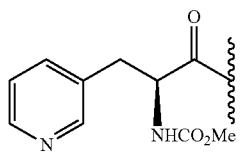 |
| 108 | 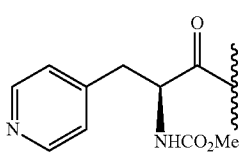 |
| 109 | 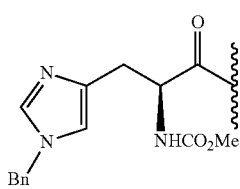 |
| 110 | 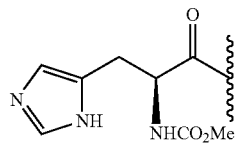 |
| 111 | 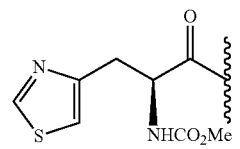 |

TABLE 1-continued
Examples 1-219.
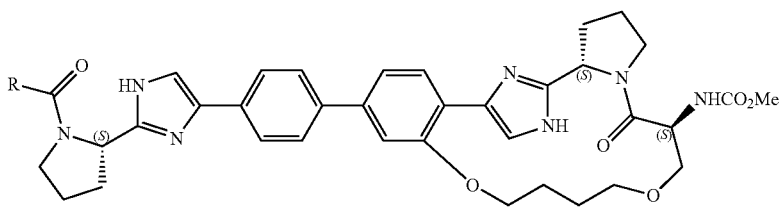
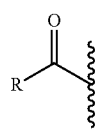
| Entry | |
|---|---|
| 112 | 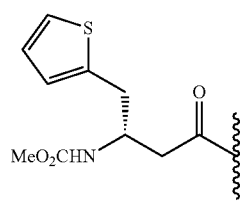 |
| 113 |  |
| 114 | 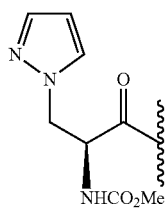 |
| 115 | 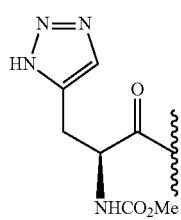 |
| 116 | 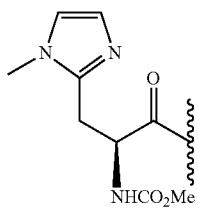 |

TABLE 1-continued
Examples 1-219.
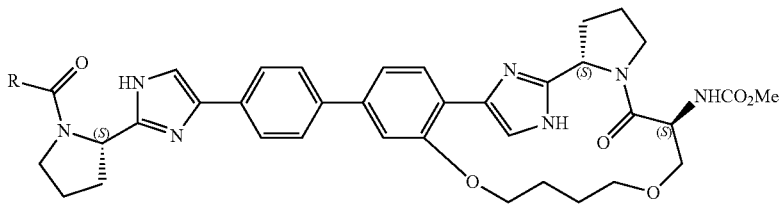
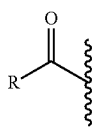
| Entry | |
|---|---|
| 117 | 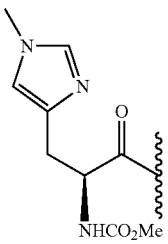 |
| 118 | 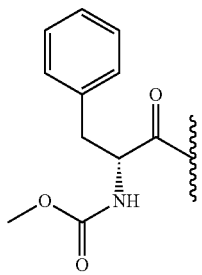 [SMILES: *C(=O)[C@@H](Cc1ccccc1)NC(=O)OC] |
| 119 | 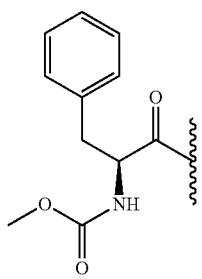 [SMILES: *C(=O)[C@H](Cc1ccccc1)NC(=O)OC] |
| 120 | 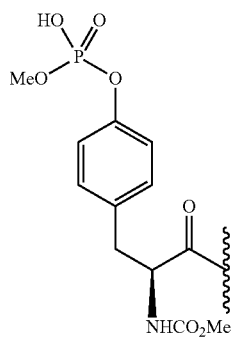 |

TABLE 1-continued
Examples 1-219.
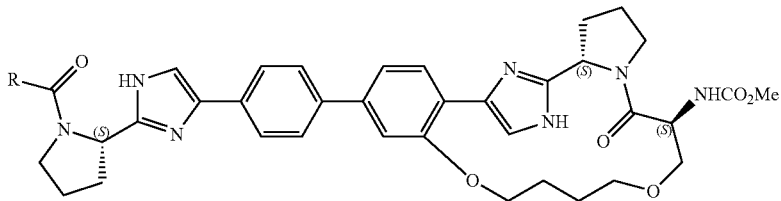
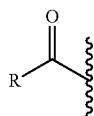
Entry
121
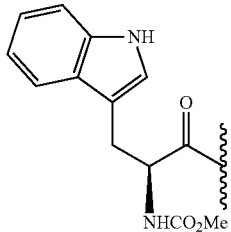
122
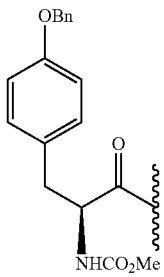
123
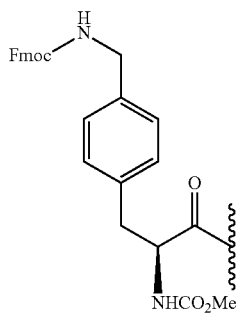
124
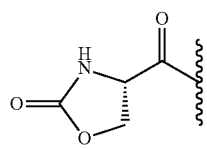 [SMILES: *C(=O)[C@@H]1COC(=O)N1]
125
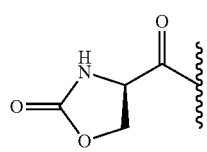 [SMILES: *C(=O)[C@H]1COC(=O)N1]

TABLE 1-continued
Examples 1-219.
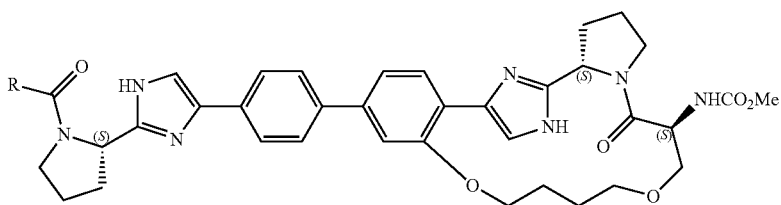
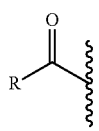
| Entry | |
|---|---|
| 126 | 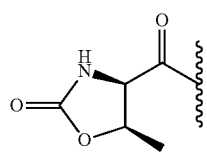 [SMILES: *C(=O)[C@@H]1NC(=O)O[C@@H]1C] |
| 127 | 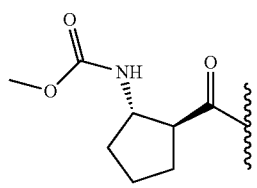 [SMILES: *C(=O)[C@H]1CCC[C@@H]1NC(=O)OC] |
| 128 | 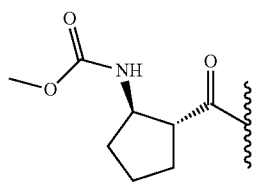 [SMILES: *C(=O)[C@@H]1CCC[C@H]1NC(=O)OC] |
| 129 | 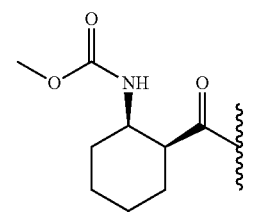 [SMILES: *C(=O)[C@H]1CCCC[C@H]1NC(=O)OC] |
| 130 | 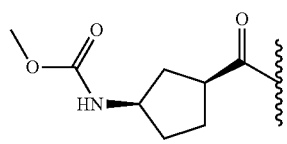 [SMILES: *C(=O)[C@H]1CC[C@@H](NC(=O)OC)C1] |
| 131 | 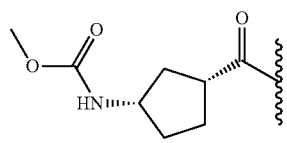 [SMILES: *C(=O)[C@@H]1CC[C@H](NC(=O)OC)C1] |

TABLE 1-continued
Examples 1-219.
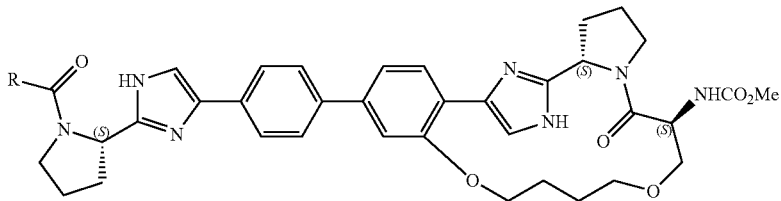
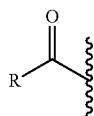
| Entry | |
|---|---|
| 132 | 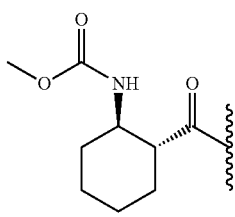 [SMILES: *C(=O)[C@@H]1CCCC[C@H]1NC(=O)OC] |
| 133 | 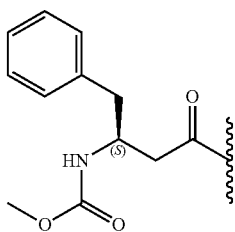 |
| 134 | 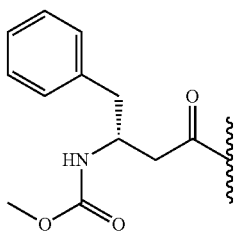 [SMILES: *C(=O)C[C@@H](Cc1ccccc1)NC(=O)OC] |
| 135 | 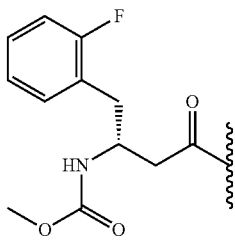 [SMILES: *C(=O)C[C@@H](Cc1ccccc1F)NC(=O)OC] |
| 136 | 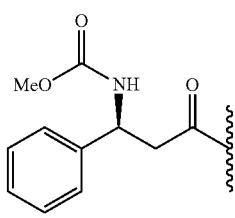 [SMILES: *C(=O)C[C@H](NC(=O)OC)c1ccccc1] |

TABLE 1-continued
Examples 1-219.
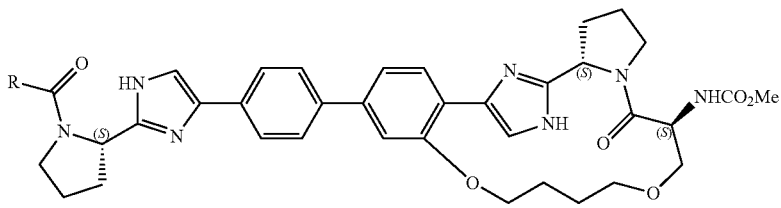
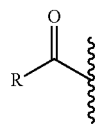
| Entry | |
|---|---|
| 137 | 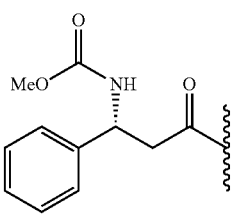 [SMILES: *C(=O)C[C@@H](NC(=O)OC)c1ccccc1] |
| 138 | 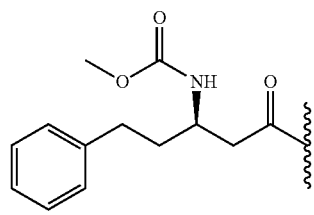 [SMILES: *C(=O)C[C@@H](CCc1ccccc1)NC(=O)OC] |
| 139 | 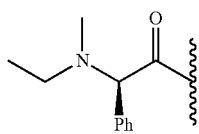 [SMILES: *C(=O)[C@@H](c1ccccc1)N(C)CC] |
| 140 | 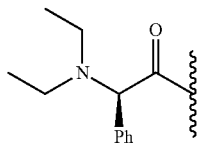 [SMILES: *C(=O)[C@@H](c1ccccc1)N(CC)CC] |
| 141 | 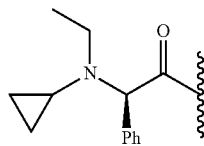 [SMILES: *C(=O)[C@@H](c1ccccc1)N(CC)C1CC1] |
| 142 | 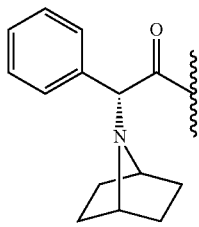 [SMILES: *C(=O)[C@@H](c1ccccc1)N1C2CCC1CC2] |

TABLE 1-continued
Examples 1-219.
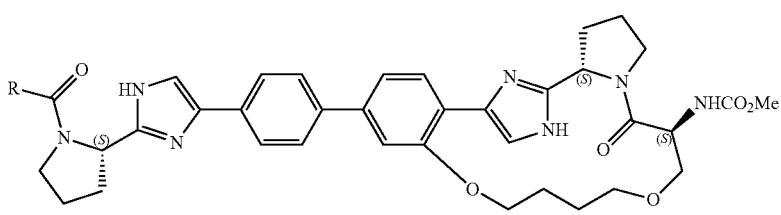
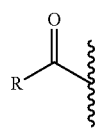
| Entry | |
|---|---|
| 143 | 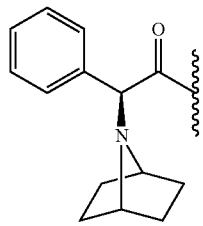 [SMILES: *C(=O)[C@H](c1ccccc1)N1C2CCC1CC2] |
| 144 | 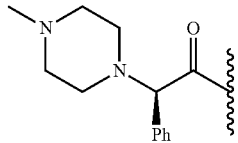 [SMILES: *C(=O)[C@@H](c1ccccc1)N1CCN(C)CC1] |
| 145 | 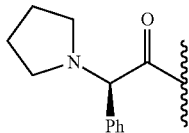 [SMILES: *C(=O)[C@@H](c1ccccc1)N1CCCC1] |
| 146 | 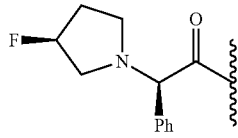 |
| 147 | 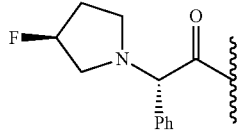 [SMILES: *C(=O)[C@H](c1ccccc1)N1CC[C@H](F)C1] |
| 148 | 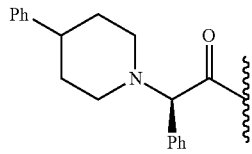 |
| 149 | 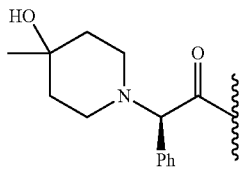 [SMILES: *C(=O)[C@@H](c1ccccc1)N1CCC(C)(O)CC1] |

TABLE 1-continued
Examples 1-219.
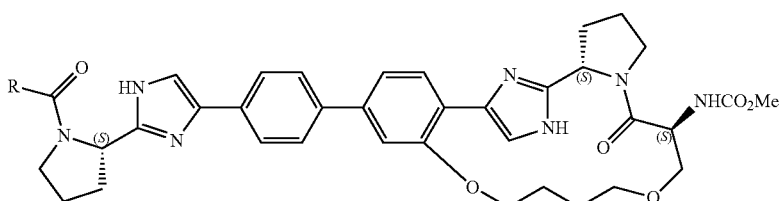
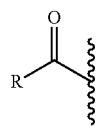
| Entry | |
|---|---|
| 150 | 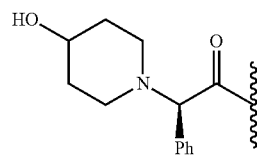 [SMILES: *C(=O)[C@@H](c1ccccc1)N1CCC(O)CC1] |
| 151 | 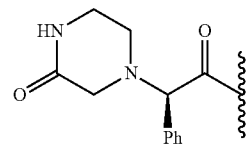 [SMILES: *C(=O)[C@@H](c1ccccc1)N1CCNC(=O)C1] |
| 152 | 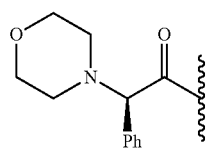 [SMILES: *C(=O)[C@@H](c1ccccc1)N1CCOCC1] |
| 153 | 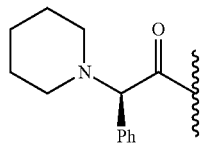 [SMILES: *C(=O)[C@@H](c1ccccc1)N1CCCCC1] |
| 154 | 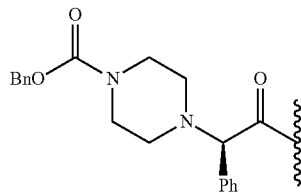 [SMILES: *C(=O)[C@@H](c1ccccc1)N1CCN(C(=O)OCc2ccccc2)CC1] |
| 155 | 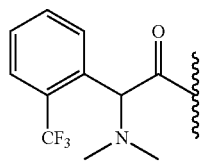 [SMILES: *C(=O)C(c1ccccc1C(F)(F)F)N(C)C] |
| 156 | 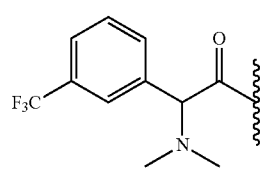 [SMILES: *C(=O)C(c1cccc(C(F)(F)F)c1)N(C)C] |

TABLE 1-continued
Examples 1-219.
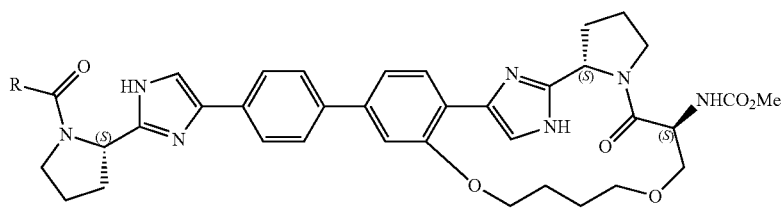
| Entry | |
|---|---|
| 157 | 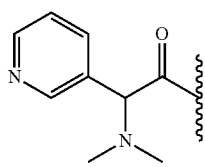 [SMILES: *C(=O)C(c1cccnc1)N(C)C] |
| 158 | 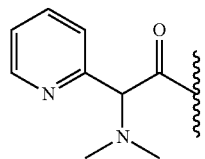 [SMILES: *C(=O)C(c1ccccn1)N(C)C] |
| 159 | 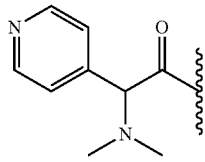 |
| 160 | 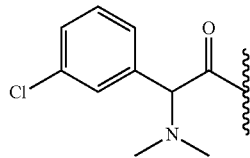 [SMILES: *C(=O)C(c1cccc(Cl)c1)N(C)C] |
| 161 | 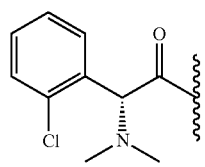 [SMILES: *C(=O)[C@@H](c1ccccc1Cl)N(C)C] |
| 162 | 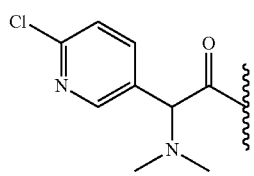 |
| 163 | 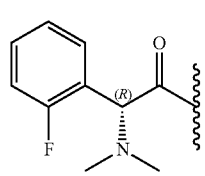 |

TABLE 1-continued
Examples 1-219.
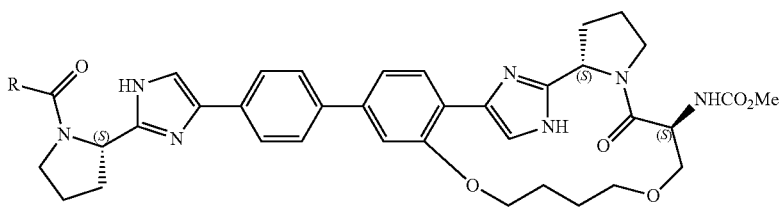
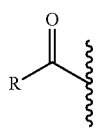
| Entry | |
|---|---|
| 164 | 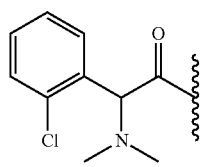 [SMILES: *C(=O)C(c1ccccc1Cl)N(C)C] |
| 165 | 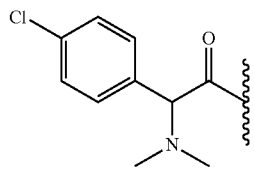 [SMILES: *C(=O)C(c1ccc(Cl)cc1)N(C)C] |
| 166 | 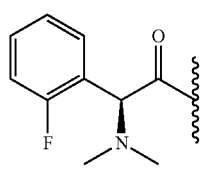 [SMILES: *C(=O)[C@H](c1ccccc1F)N(C)C] |
| 167 | 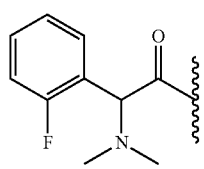 [SMILES: *C(=O)C(c1ccccc1F)N(C)C] |
| 168 | 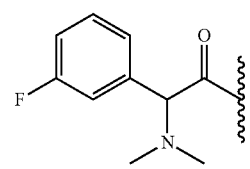 [SMILES: *C(=O)C(c1cccc(F)c1)N(C)C] |
| 169 | 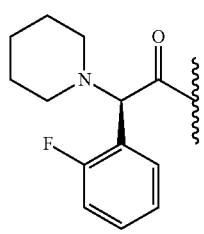 [SMILES: *C(=O)[C@@H](c1ccccc1F)N1CCCCC1] |

TABLE 1-continued
Examples 1-219.
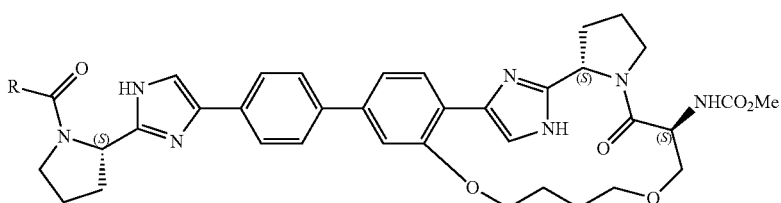
| Entry | |
|---|---|
| 170 | 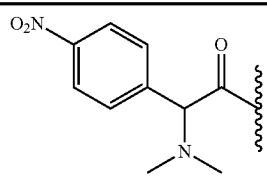 |
| 171 | 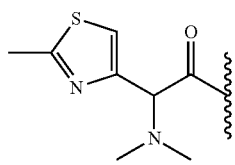 [SMILES: *C(=O)C(c1csc(C)n1)N(C)C] |
| 172 | 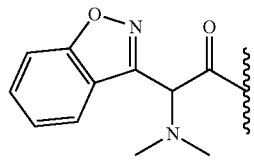 [SMILES: *C(=O)C(c1noc2ccccc12)N(C)C] |
| 173 | 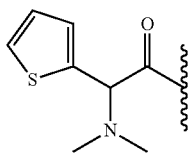 [SMILES: *C(=O)C(c1cccs1)N(C)C] |
| 174 | 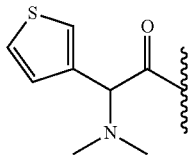 [SMILES: *C(=O)C(c1ccsc1)N(C)C] |
| 175 | 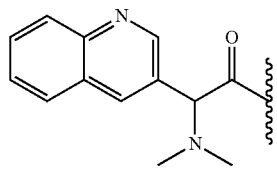 [SMILES: *C(=O)C(c1cnc2ccccc2c1)N(C)C] |
| 176 | 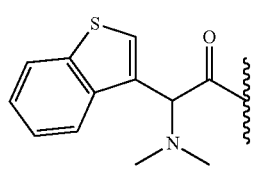 [SMILES: *C(=O)C(c1csc2ccccc12)N(C)C] |

TABLE 1-continued
Examples 1-219.
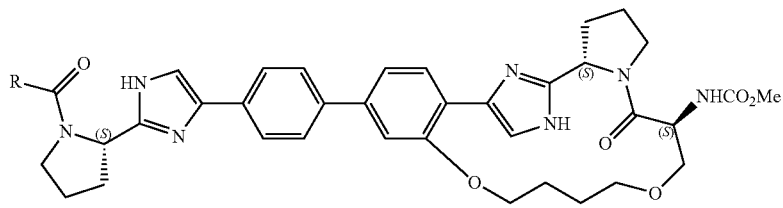
Entry
177
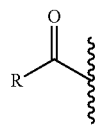
178
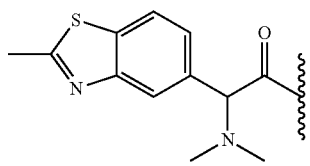 [SMILES: *C(=O)C(c1ccc2sc(C)nc2c1)N(C)C]
179
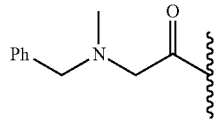
180
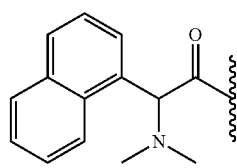 [SMILES: *C(=O)C(c1cccc2ccccc12)N(C)C]
181
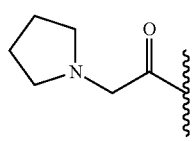 [SMILES: *C(=O)CN1CCCC1]
182
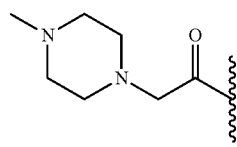 [SMILES: *C(=O)CN1CCN(C)CC1]
183
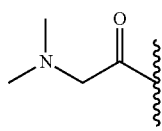

TABLE 1-continued
Examples 1-219.
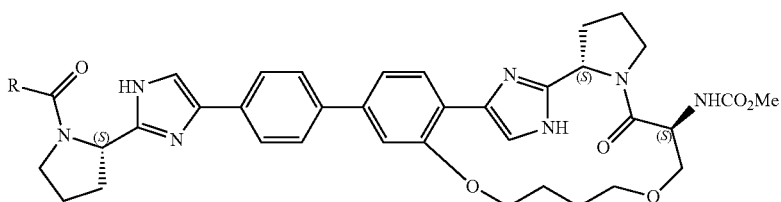
| Entry | |
|---|---|
| 184 | 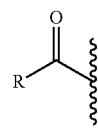 |
| 185 | 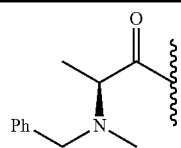 |
| 186 | 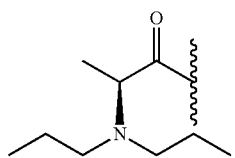 [SMILES: *C(=O)[C@H](C)N(CCC)CCC] |
| 187 | 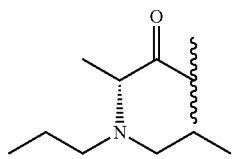 [SMILES: *C(=O)[C@@H](C)N(CCC)CCC] |
| 188 | 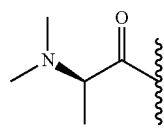 [SMILES: *C(=O)[C@@H](C)N(C)C] |
| 189 | 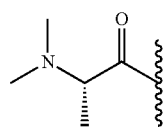 |
| 190 | 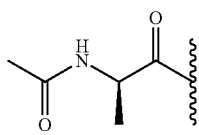 [SMILES: *C(=O)[C@@H](C)NC(C)=O] |
| 191 | 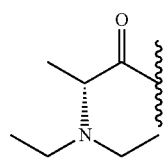 [SMILES: *C(=O)[C@@H](C)N(CC)CC] |

TABLE 1-continued
Examples 1-219.
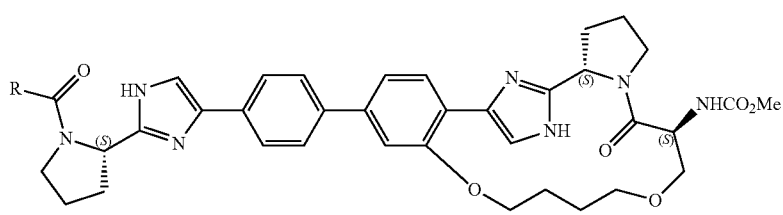
| Entry | |
|---|---|
| 192 | 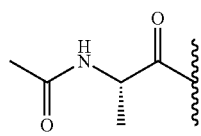 |
| 193 | 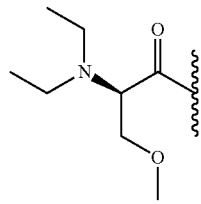 [SMILES: *C(=O)[C@@H](COC)N(CC)CC] |
| 194 | 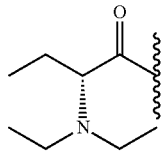 [SMILES: *C(=O)[C@@H](CC)N(CC)CC] |
| 195 | 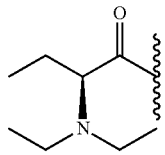 [SMILES: *C(=O)[C@H](CC)N(CC)CC] |
| 196 | 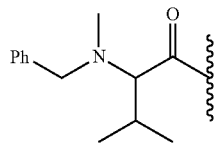 |
| 197 | 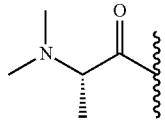 |
| 198 | 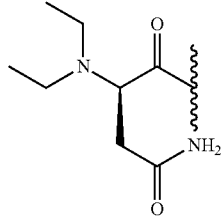 [SMILES: *C(=O)[C@@H](CC(N)=O)N(CC)CC] |

TABLE 1-continued
Examples 1-219.
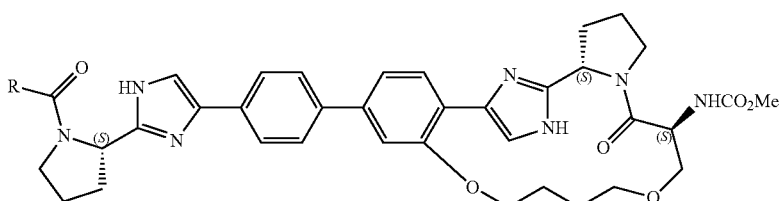
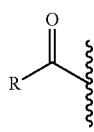
| Entry | |
|---|---|
| 199 | 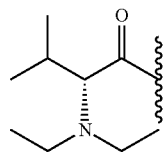 [SMILES: *C(=O)[C@@H](C(C)C)N(CC)CC] |
| 200 | 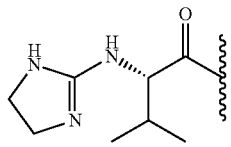 [SMILES: *C(=O)[C@@H](NC1=NCCN1)C(C)C] |
| 201 | 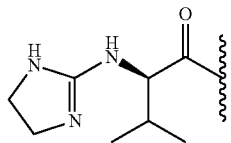 [SMILES: *C(=O)[C@H](NC1=NCCN1)C(C)C] |
| 202 | 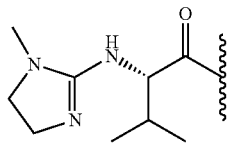 [SMILES: *C(=O)[C@@H](NC1=NCCN1C)C(C)C] |
| 203 | 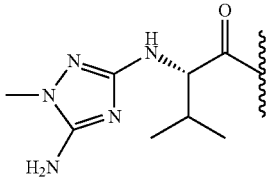 [SMILES: *C(=O)[C@@H](Nc1nc(N)n(C)n1)C(C)C] |
| 204 | 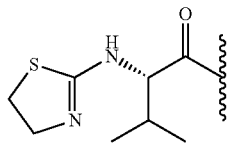 [SMILES: *C(=O)[C@@H](NC1=NCCS1)C(C)C] |
| 205 | 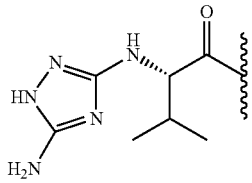 |

TABLE 1-continued
Examples 1-219.
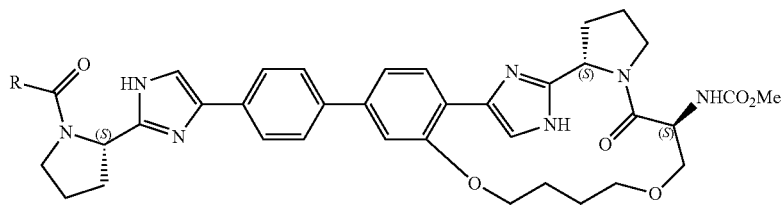
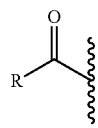
| Entry | |
|---|---|
| 206 | 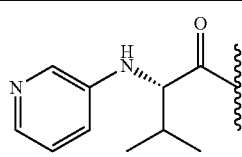 |
| 207 | 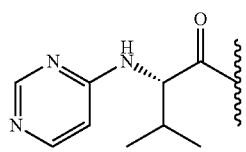 [SMILES: *C(=O)[C@@H](Nc1ccncn1)C(C)C] |
| 208 | 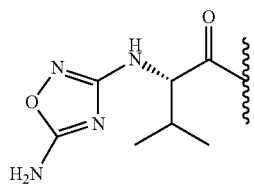 |
| 209 | 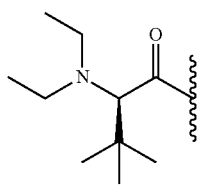 [SMILES: *C(=O)[C@H](N(CC)CC)C(C)(C)C] |
| 210 | 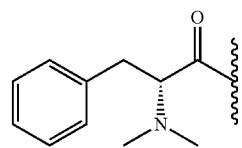 [SMILES: *C(=O)[C@@H](Cc1ccccc1)N(C)C] |
| 211 | 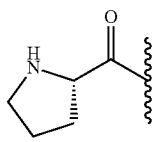 [SMILES: *C(=O)[C@@H]1CCCN1] |
| 212 | 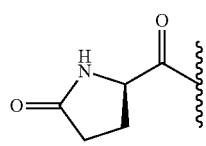 [SMILES: *C(=O)[C@H]1CCC(=O)N1] |

TABLE 1-continued
Examples 1-219.
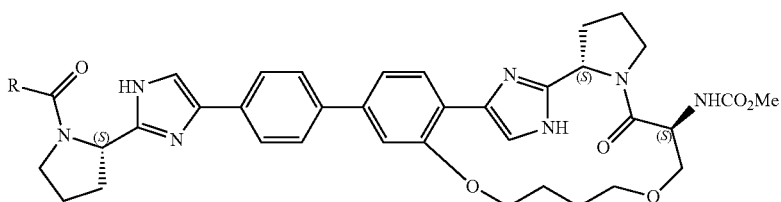
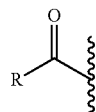
| Entry | |
|---|---|
| 213 | 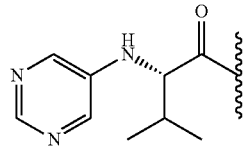 |
| 214 | 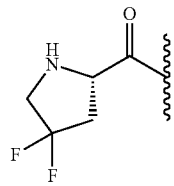 [SMILES: *C(=O)[C@@H]1CC(F)(F)CN1] |
| 215 | 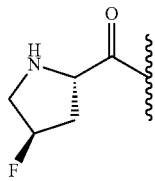 [SMILES: *C(=O)[C@@H]1C[C@@H](F)CN1] |
| 216 | 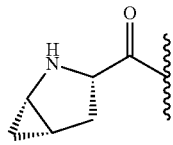 |
| 217 | 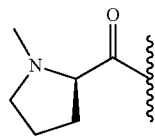 [SMILES: *C(=O)[C@H]1CCCN1C] |
| 218 | 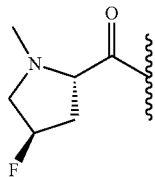 [SMILES: *C(=O)[C@@H]1C[C@@H](F)CN1C] |
| 219 | 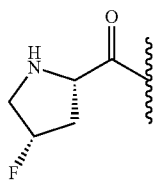 [SMILES: *C(=O)[C@@H]1C[C@H](F)CN1] |

TABLE 2

Examples 220-229.

| Entry | R | R' | R" | U |
|---|---|---|---|---|
| 220 | Me | H | H | CH$_2$ |
| 221 | H | H | H | CF$_2$ |
| 222 | Me | H | H | S |
| 223 | H | H | H | CH(F) (stereo) |
| 224 | H | Me | H | CH$_2$ |
| 225 | H | H | H | CH(F) (stereo) |
| 226 | H | Ph | H | CH$_2$ |
| 227 | H | H | H | C(OH)(Me) (stereo) |
| 228 | H | H | Ph | CH$_2$ |
| 229 | H | H | H | C(OH)(Me) (stereo) |

TABLE 3

Examples 230-239.

| Entry | R | R' | R" |
|---|---|---|---|
| 230 | Me | H | H |
| 231 | H | CO$_2$Me | H |
| 232 | H | F | H |
| 233 | H | H | CO$_2$Me |
| 234 | H | H | F |
| 235 | H | OMe | H |
| 236 | H | Cl | H |

TABLE 3-continued
Examples 230-239.
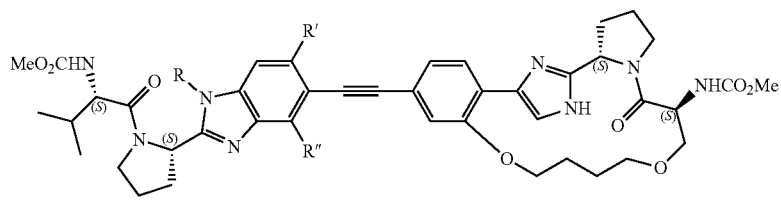
| Entry | R | R' | R'' |
|-------|---|-----|------|
| 237 | H | H | OMe |
| 238 | H | H | Cl |
| 239 | H | CF₃ | H |
TABLE 4
Examples 240-249.
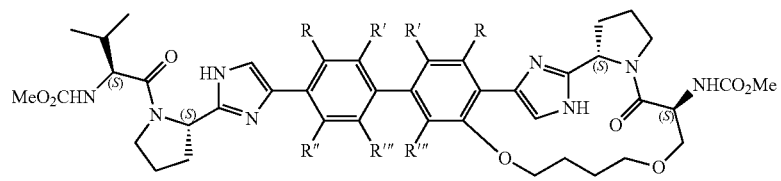
| Entry | R | R' | R'' | R''' |
|-------|---|-----|------|-------|
| 240 | F | H | H | H |
| 241 | F | F | H | H |
| 242 | Me | H | H | H |
| 243 | Me | Me | H | H |
| 244 | H | H | Me | Me |
| 245 | H | H | Et | Et |
| 246 | CF₃ | H | H | H |
| 247 | CF₃ | H | CF₃ | H |
| 248 | Cl | H | H | H |
| 249 | Cl | H | Cl | H |
TABLE 5
Examples 250-264.
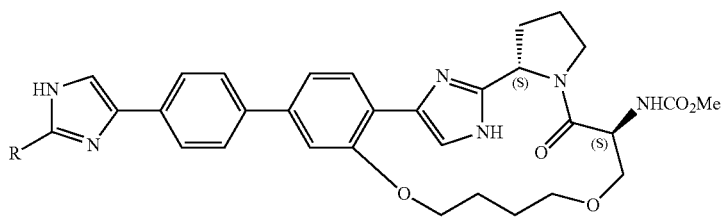
| Entry | R |
|-------|---|
| 250 | 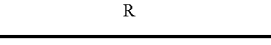 |

TABLE 5-continued
Examples 250-264.
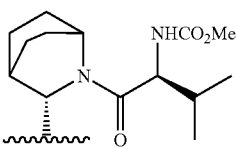
| Entry | R |
|---|---|
| 251 | 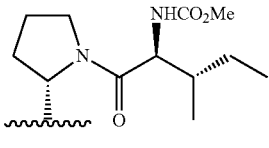 |
| 252 | 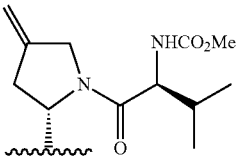 |
| 253 | 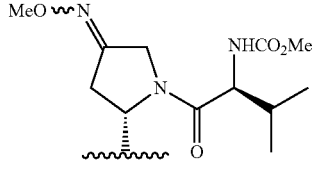 |
| 254 | 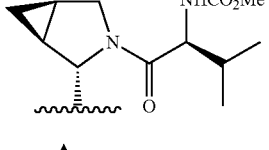 |
| 255 | 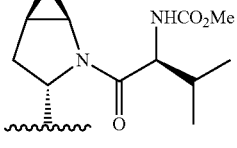 |
| 256 | 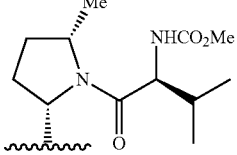 |
| 257 | 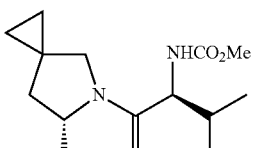 |
| 258 | |

TABLE 5-continued
Examples 250-264.
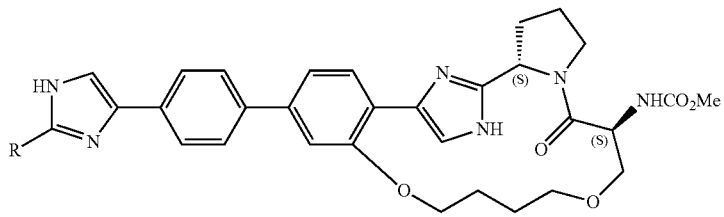
| Entry | R |
|---|---|
| 259 | (2,4-pyrrolidine with Me at 4, N-acyl-Val-NHCO2Me) |
| 260 | (2,4-pyrrolidine with F at 4, N-acyl-Val-NHCO2Me) |
| 261 | (cyclopentane with =CF2 exocyclic, acyl-Val-NHCO2Me) |
| 262 | (N-ethyl, N-(1-methylethyl) amide of Val-NHCO2Me) |
| 263 | (N-methyl, N-(cyclopropyl-CH) amide of Val-NHCO2Me) |
| 264 | (allyl-CH-NH-C(O)-Val-NHCO2Me) |

TABLE 6
Examples 265-282.
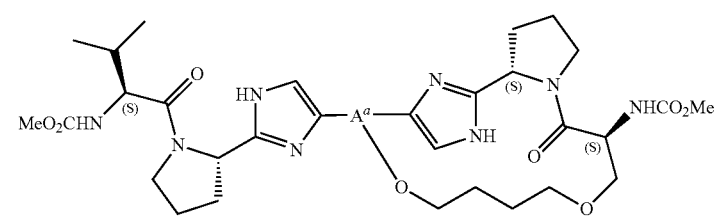
| Entry | $A^a$ |
|---|---|
| 265 | 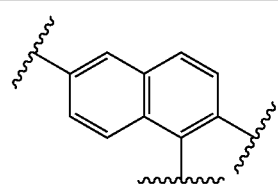 [SMILES: *c1ccc2c(*)c(*)ccc2c1] |
| 266 | 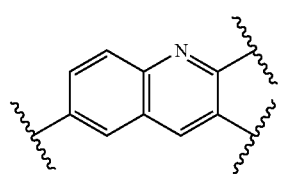 [SMILES: *c1ccc2nc(*)c(*)cc2c1] |
| 267 | 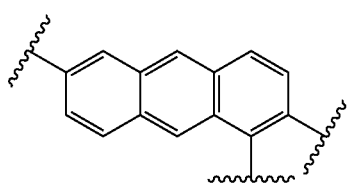 [SMILES: *c1ccc2cc3c(*)c(*)ccc3cc2c1] |
| 268 | 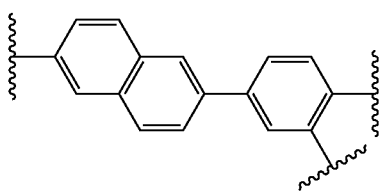 [SMILES: *c1ccc2cc(-c3ccc(*)c(*)c3)ccc2c1] |
| 269 | 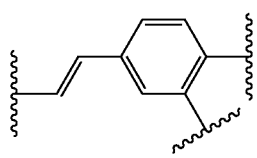 [SMILES: */C=C/c1ccc(*)c(*)c1] |
| 270 | 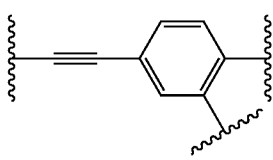 [SMILES: *C#Cc1ccc(*)c(*)c1] |
| 271 | 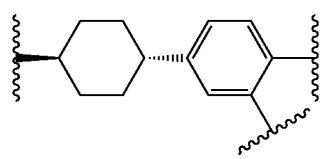 [SMILES: *c1ccc([C@H]2CC[C@H](*)CC2)cc1*] |

TABLE 6-continued

Examples 265-282.

| Entry | $A^a$ |
|---|---|
| 272 | piperazine-pyrimidine |
| 273 | pyrazole-pyridine |
| 274 | phenyl-pyridine |
| 275 | thiophene-phenyl |
| 276 | phenyl-CH=CH-phenyl |
| 277 | phenyl-C≡C-thiazole |
| 278 | thiazole-thiophene |

TABLE 6-continued
Examples 265-282.
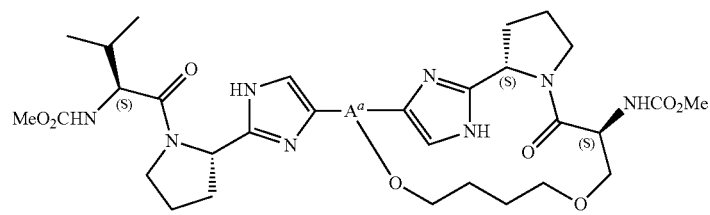
| Entry | $A^a$ |
|---|---|
| 279 | |
| 280 | |
| 281 | |
| 282 | |

TABLE 7
Compounds 283-303.
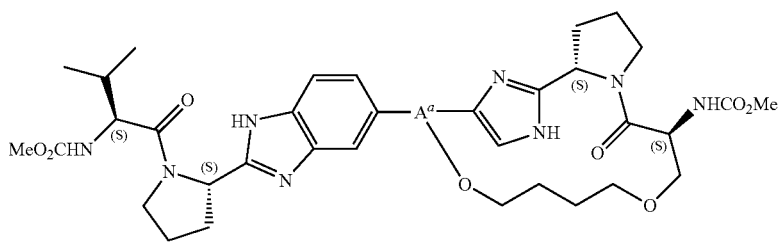
| Entry | A^a |
|---|---|
| 283 | 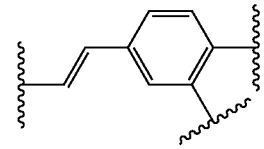 [SMILES: */C=C/c1ccc(*)c(*)c1] |
| 284 | 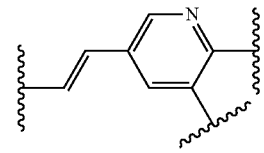 [SMILES: */C=C/c1cnc(*)c(*)c1] |
| 285 | 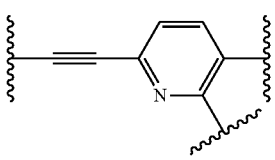 |
| 286 | 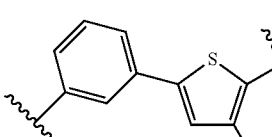 |
| 287 | 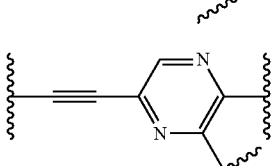 |
| 288 | 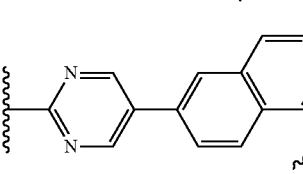 |
| 289 | 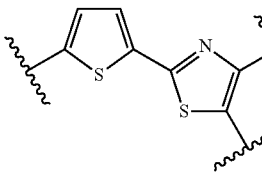 |
| 290 | 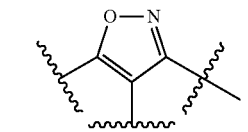 [SMILES: *c1noc(*)c1*] |

TABLE 7-continued
Compounds 283-303.
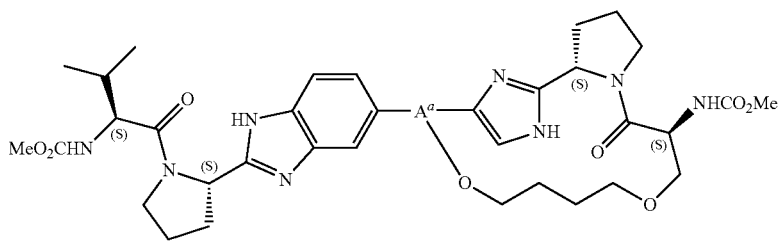
| Entry | $A^a$ |
|---|---|
| 291 | 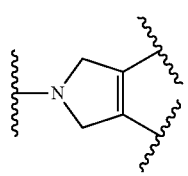 [SMILES: *C1=C(*)CN(*)C1] |
| 292 | 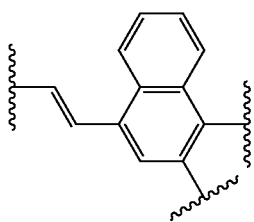 [SMILES: */C=C/c1cc(*)c(*)c2ccccc12] |
| 293 | 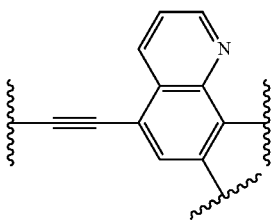 [SMILES: *C#Cc1cc(*)c(*)c2ncccc12] |
| 294 | 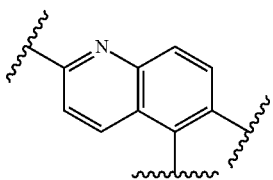 [SMILES: *c1ccc2c(*)c(*)ccc2n1] |
| 295 | 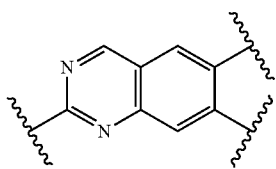 [SMILES: *c1ncc2cc(*)c(*)cc2n1] |
| 296 | 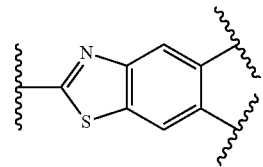 [SMILES: *c1nc2cc(*)c(*)cc2s1] |

TABLE 7-continued
Compounds 283-303.
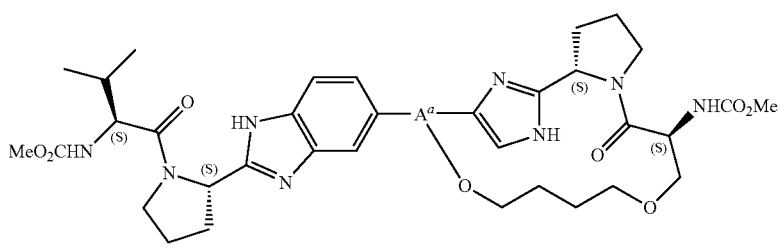
| Entry | $A^a$ |
|---|---|
| 297 | 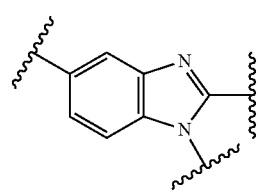 [SMILES: *c1ccc2c(c1)nc(*)n2*] |
| 298 | 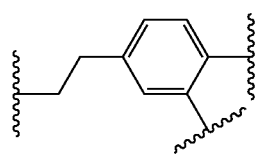 [SMILES: *CCc1ccc(*)c(*)c1] |
| 299 | 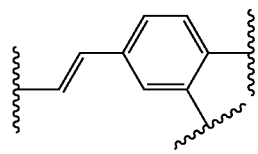 [SMILES: */C=C/c1ccc(*)c(*)c1] |
| 300 | 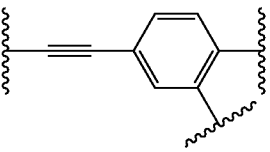 |
| 301 | 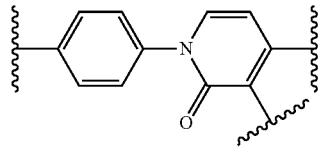 [SMILES: *c1ccc(-n2ccc(*)c(*)c2=O)cc1] |
| 302 | 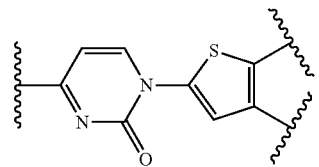 [SMILES: *c1ccn(-c2cc(*)c(*)s2)c(=O)n1] |
| 303 | 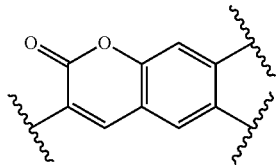 [SMILES: *c1cc2cc(*)c(=O)oc2cc1*] |

TABLE 8
Examples 304-315.
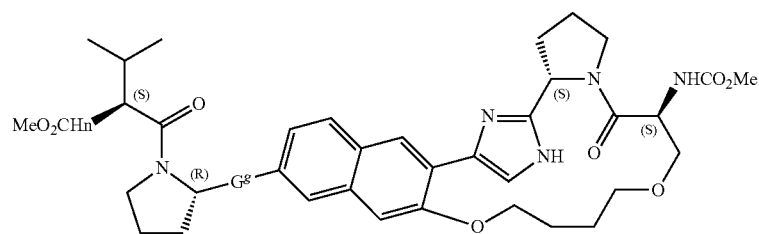
| Entry | G^g |
|---|---|
| 304 | 3,5-pyrazolediyl (1H-pyrazole-3,5-diyl) |
| 305 | 4H-1,2,4-triazole-3,5-diyl |
| 306 | oxazole-2,5-diyl |
| 307 | 1H-benzimidazole-2,5-diyl |
| 308 | 1H-indole-2,6-diyl |
| 309 | 1H-pyrrolo[3,2-b]pyridine-2,6-diyl |
| 310 | 5H-pyrrolo[3,2-d]pyrimidine-2,6-diyl |
| 311 | 3H-imidazo[4,5-b]pyridine-2,5-diyl |
| 312 | 3H-imidazo[4,5-c]pyridine-2,6-diyl |

TABLE 8-continued
Examples 304-315.
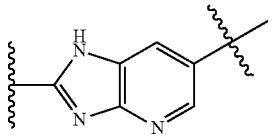 [SMILES: *c1cnc2nc(*)[nH]c2c1]
| Entry | $G^g$ |
|---|---|
| 313 | 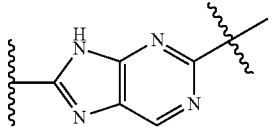 [SMILES: *c1ncc2nc(*)[nH]c2n1] |
| 314 | 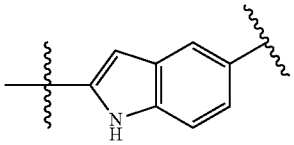 [SMILES: *c1ccc2[nH]c(*)cc2c1] |
| 315 | 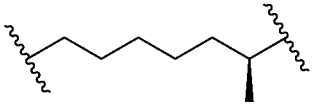 [SMILES: *CCCCC[C@@H](*)C] |
TABLE 9
Examples 316-333.
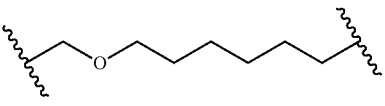 [SMILES: *CCCCCCOC*]
| Entry | $L^a$—$L^b$—$L^c$ |
|---|---|
| 316 | 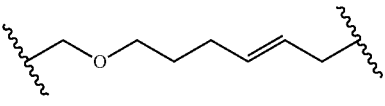 [SMILES: *C/C=C/CCCOC*] |
| 317 |  |
| 318 |  |

TABLE 9-continued
Examples 316-333.
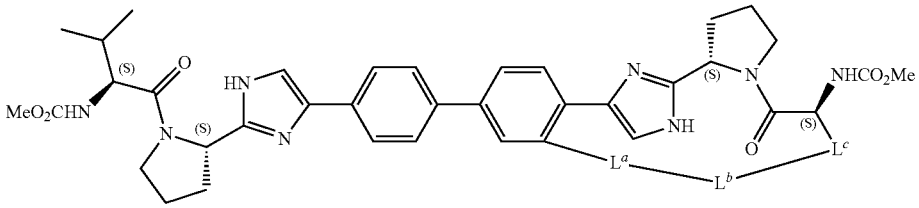
| Entry | $L^a$—$L^b$—$L^c$ |
|---|---|
| 319 | 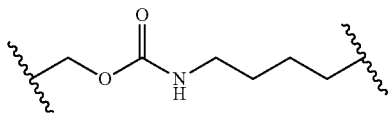 [SMILES: *CCCCNC(=O)OC*] |
| 320 | 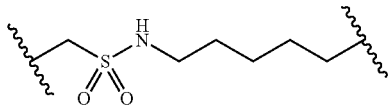 [SMILES: *CCCCCNS(=O)(=O)C*] |
| 321 | 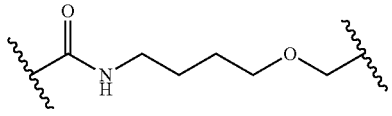 [SMILES: *COCCCCNC(*)=O] |
| 322 | 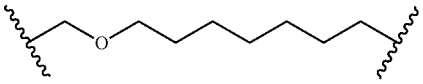 [SMILES: *CCCCCCCOC*] |
| 323 | 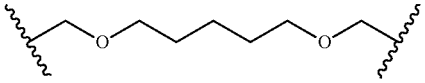 [SMILES: *COCCCCCOC*] |
| 324 | 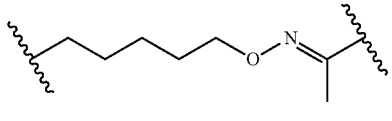 [SMILES: *CCCCCO/N=C(/*)C] |
| 325 | 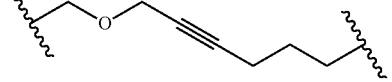 |
| 326 | 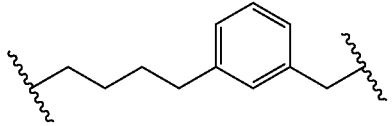 [SMILES: *CCCCc1cccc(C*)c1] |
| 327 | 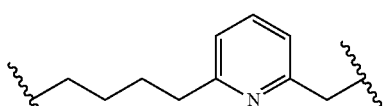 |
| 328 | 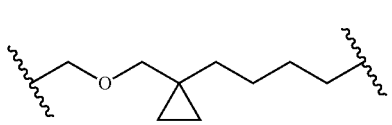 [SMILES: *CCCCC1(COC*)CC1] |

TABLE 9-continued
Examples 316-333.
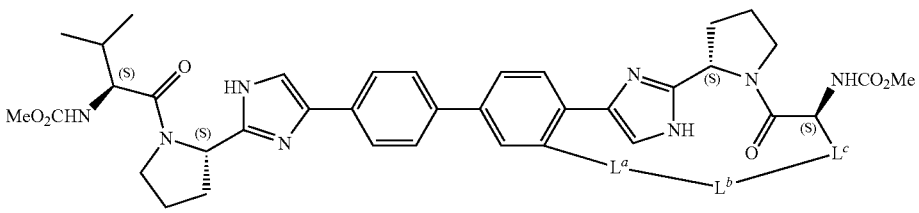
| Entry | $L^a$—$L^b$—$L^c$ |
|---|---|
| 329 |  |
| 330 | 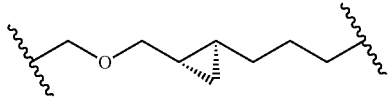 [SMILES: *CCC[C@H]1C[C@@H]1COC*] |
| 331 | 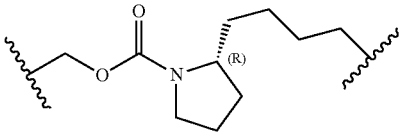 |
| 332 | 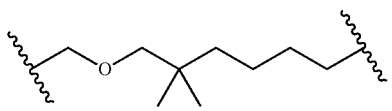 [SMILES: *CCCCC(C)(C)COC*] |
| 333 | 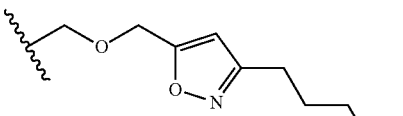 |
TABLE 10
Compounds 334-343.
Compound 334
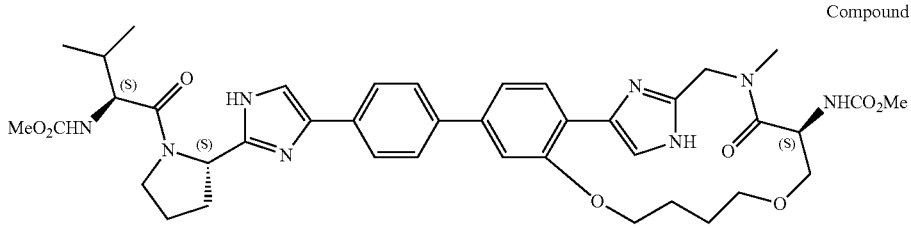
Compound 335
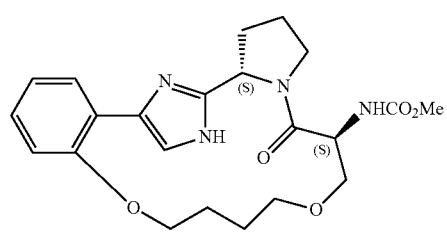

TABLE 10-continued
Compounds 334-343.
Compound 336
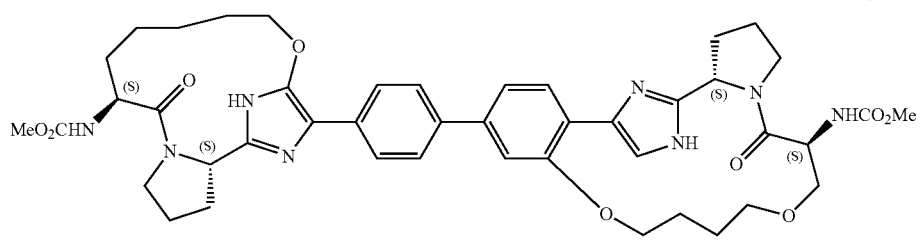
Compound 337
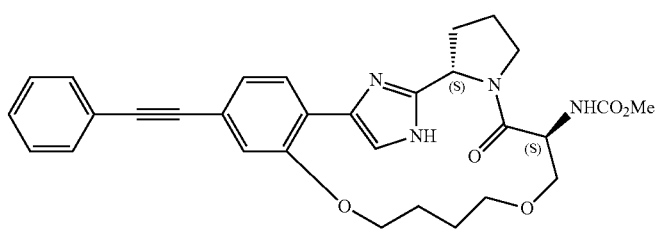
Compound 338
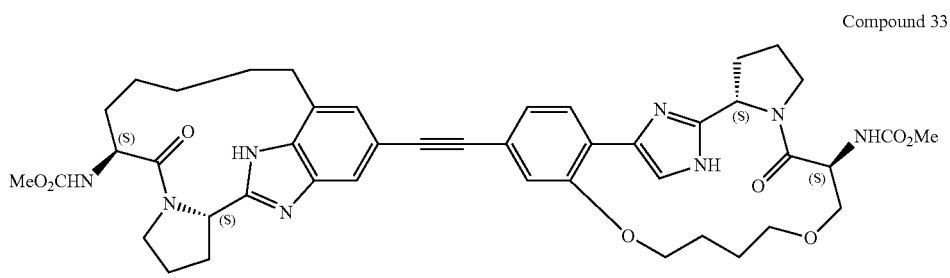
Compound 339
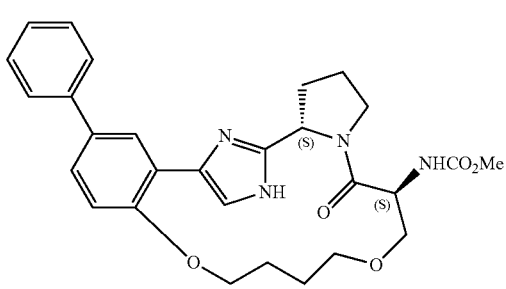
Compound 340
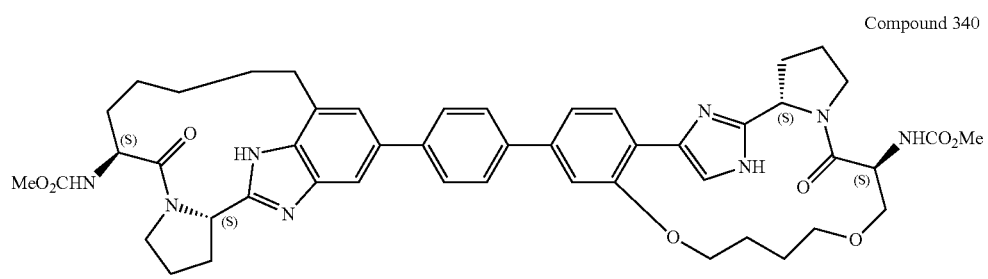

TABLE 10-continued

Compounds 334-343.

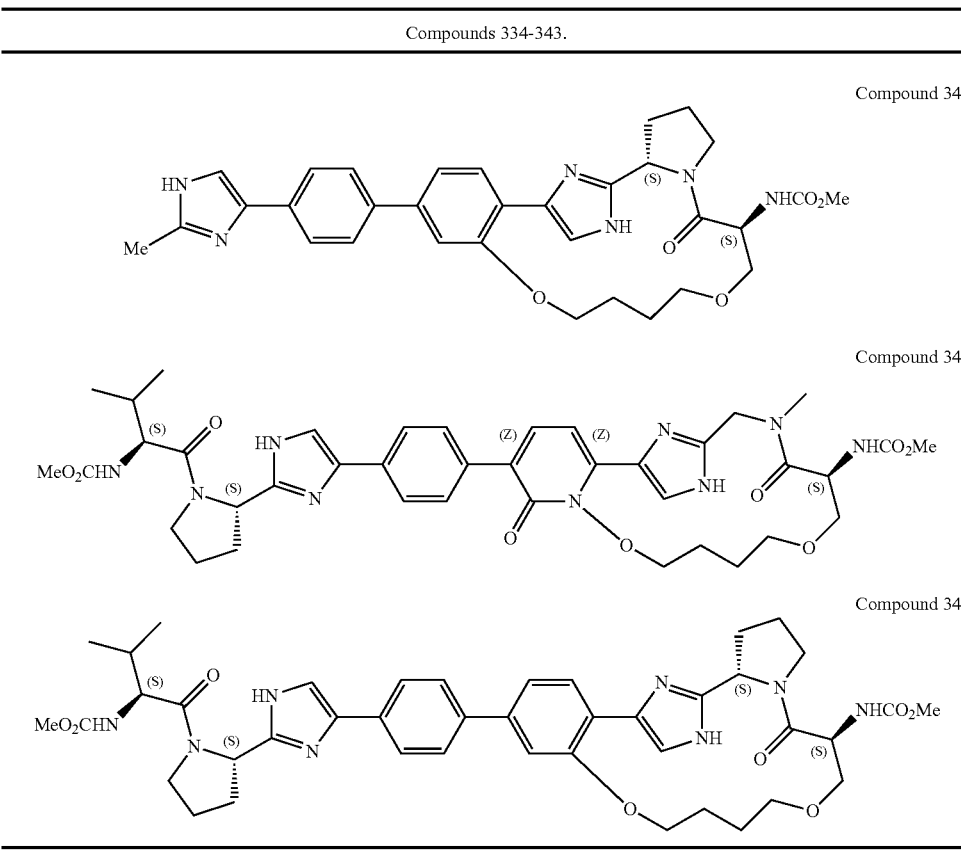

Compound 341

Compound 342

Compound 343

Biological Activity

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV) and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV) and (vi) HCV NS3 to NS5B genes that harbor cell culture adaptive mutations (E1202G, T1280I, K1846T) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/ml or 0.5 mg/ml for 11-7 and Huh-luc/neo-ET cells, respectively.

2. HCV Replicon Assay-qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat#AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat#AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We use the HCV replicon system to assess the potential use of the compounds of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat. #31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat. #31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention may inhibit HCV by mechanisms in addition to or other than NS5A inhibition. In one embodiment the compounds of the present invention inhibit HCV replicon and in another embodiment the compounds of the present invention inhibit NS5A.

The compounds of the present invention can be effective against the HCV 1b genotype. It should also be understood that the compounds of the present invention can inhibit multiple genotypes of HCV. In one embodiment compound of the present invention are active against the 1a, 1b, 2a, 2b, 3a, 4a, and 5a genotypes. Table 13 shows the $EC_{50}$ values of representative compounds of the present invention against the HCV 1a or 1b genotype from the above described qRT-PCR or luciferase assay. $EC_{50}$ ranges against HCV 1a or 1b are as follows: A >1 nM; B 100-1000 pM; C<100 pM.

TABLE 13

| Genotype-1a or 1b replicon $EC_{50}$ | | | | | | | | |
|---|---|---|---|---|---|---|---|---|
| Example | Range | 1b $EC_{50}$ | Example | Range | 1a $EC_{50}$ | Example | Range | 1b $EC_{50}$ |
| 83 | A | >10 nM* | 346 | A | 2.4 nM | 350 | C | 50 pM |

*35% inhibition at 10 nM

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (Vd), or (Ve):

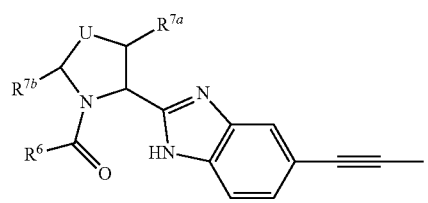

(Vd)

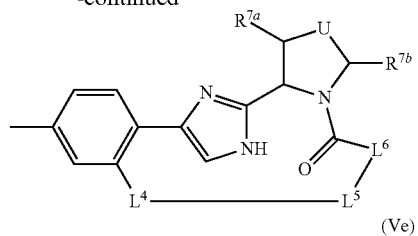

(Ve)

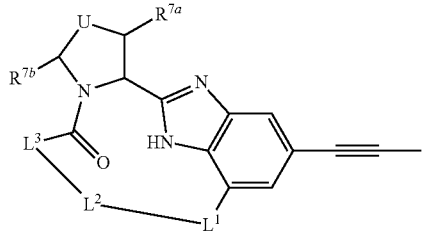

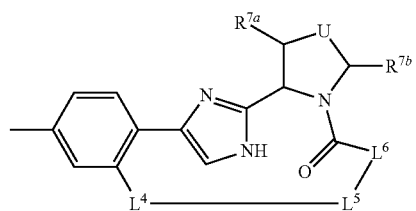

wherein:
$L^1$, $L^3$, $L^4$ and $L^6$ at each occurrence are each independently absent or a linear aliphatic group wherein at least one of $L^1$ and $L^3$ is present and wherein at least one of $L^4$ and $L^6$ is present; $L^2$ is selected from absent, aryl, heteroaryl, heterocyclic, $C_3$-$C_8$ cycloalkyl, and $C_3$-$C_8$ cycloalkenyl, each optionally substituted;

$R^6$ is $C_1$-$C_8$ alkyl optionally substituted with amino, halogen, hydroxy, protected amino, or $O(C_1$-$C_4$ alkyl);

U at each occurrence is independently $CH_2$, CHF, CHMe, $CF_2$, C=$CH_2$, C=$CF_2$, or $C(R^7)_2$, wherein $R^7$ is hydrogen, halogen, optionally substituted $C_1$-$C_4$ cycloalkyl, or optionally substituted $C_3$-$C_8$ cycloalkyl; alternatively, the two geminal $R^7$ groups are taken together with the carbon to which they are attached to form a spiro, optionally substituted $C_3$-$C_7$ cycloalkyl or optionally substituted 3- to 7-membered heterocyclic;

$R^{7a}$ is hydrogen; and $R^{7b}$ is hydrogen, methyl or optionally substituted $C_3$-$C_8$ cycloalkyl; or alternatively $R^{7a}$ and U or U and $R^{7b}$ are taken together with the carbon atoms to which they are attached to form a fused, optionally substituted $C_3$-$C_8$ cycloalkyl, and the other of $R^{7b}$ or $R^{7a}$ is hydrogen; or yet alternatively, U, $R^{7a}$ and $R^{7b}$ are taken together with the carbon atoms to which they are attached to form a bridged, optionally substituted $C_4$-$C_7$ cycloalkyl; or a pharmaceutically acceptable salt thereof.

2. The compound of claim 1, wherein

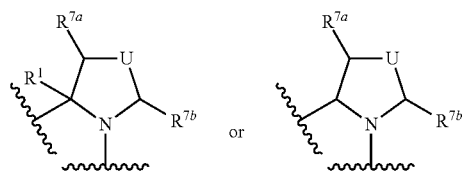

is selected from:

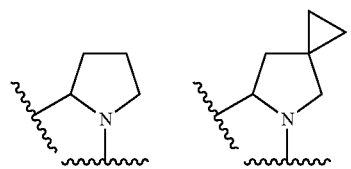 [SMILES: *C1CCCN1* ; *C1CC2(CC2)CN1*]

and the linker -L⁴-L⁵-L⁶- is selected from:

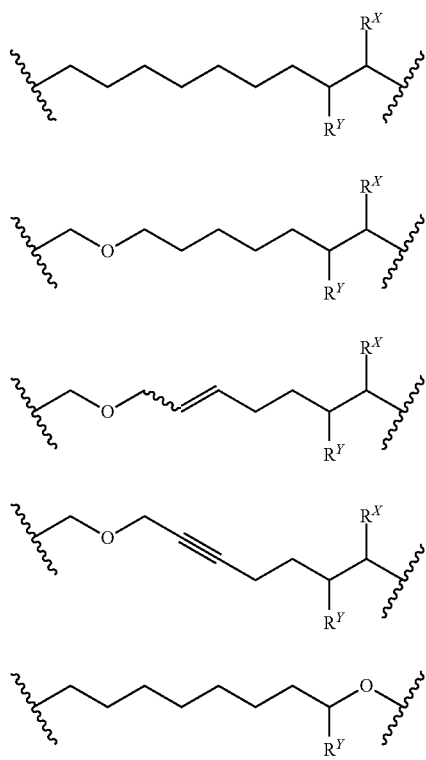

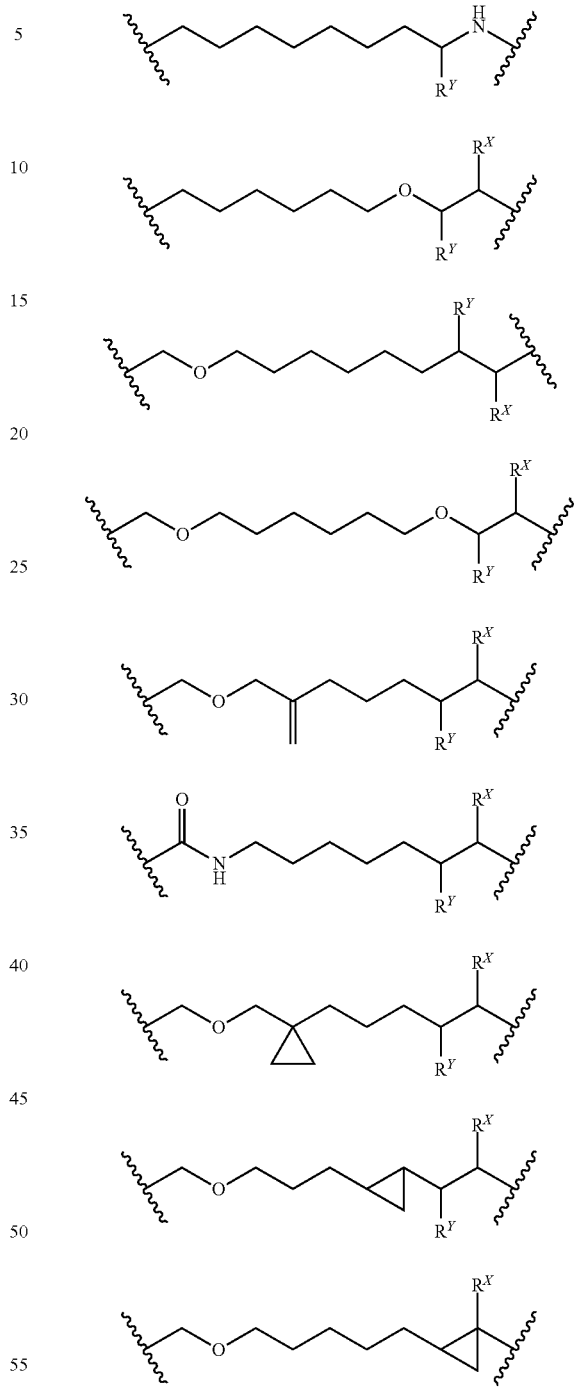

wherein $R^X$ at each occurrence is independently hydrogen, amino, hydroxy, protected amino or $O(C_1-C_4$ alkyl); and $R^Y$ at each occurrence is independently hydrogen or optionally substituted $C_1-C_8$ alkyl; wherein each of the above shown groups is further optionally substituted; or a pharmaceutically acceptable salt thereof.

3. A compound selected from the group of compounds 1-219 compiled in the following tables:

| Compounds 1-219 |
|---|
| 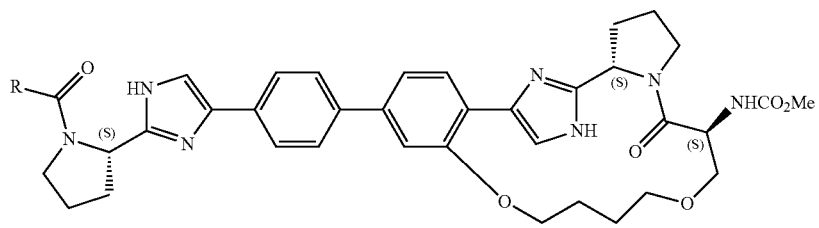 |
| 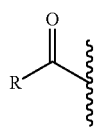 |
| Entry | |
|---|---|
| 1 | 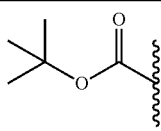 |
| 2 | 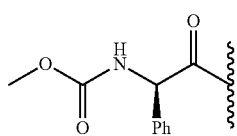 [SMILES: *C(=O)[C@H](NC(=O)OC)c1ccccc1] |
| 3 | 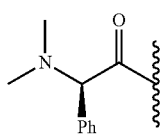 [SMILES: *C(=O)[C@@H](c1ccccc1)N(C)C] |
| 4 | 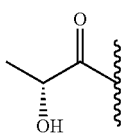 [SMILES: *C(=O)[C@@H](C)O] |
| 5 | 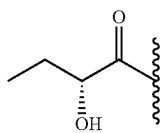 [SMILES: *C(=O)[C@H](O)CC] |
| 6 | 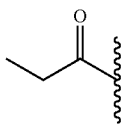 [SMILES: *C(=O)CC] |
| 7 | 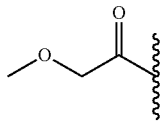 [SMILES: *C(=O)COC] |
| 8 | 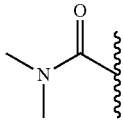 [SMILES: *C(=O)N(C)C] |
| 9 | 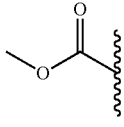 [SMILES: *C(=O)OC] |

Compounds 1-219
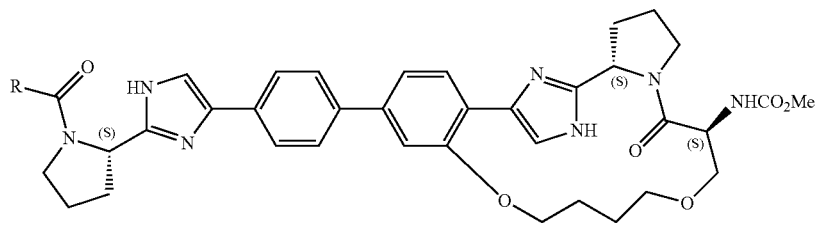
| Entry | |
|---|---|
| 10 | 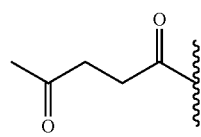 [SMILES: *C(=O)CCC(C)=O] |
| 11 | 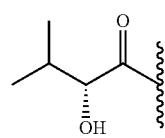 [SMILES: *C(=O)[C@H](O)C(C)C] |
| 12 | 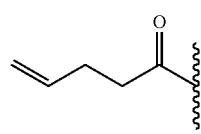 [SMILES: *C(=O)CCC=C] |
| 13 | 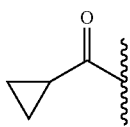 [SMILES: *C(=O)C1CC1] |
| 14 | 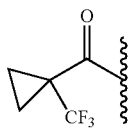 |
| 15 | 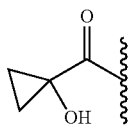 |
| 16 | 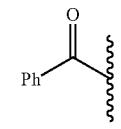 |
| 17 | 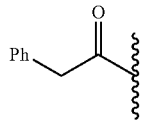 |

-continued
Compounds 1-219
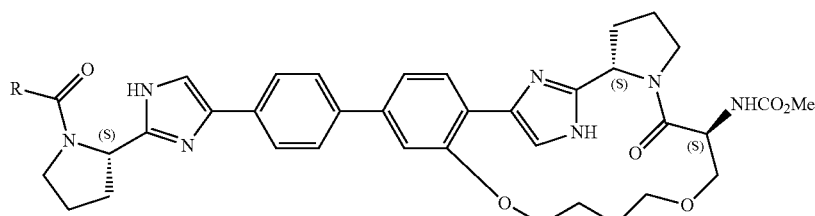
R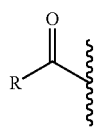
| Entry | |
|---|---|
| 18 | 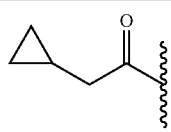 [SMILES: *C(=O)CC1CC1] |
| 19 | 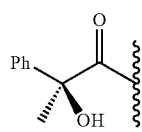 [SMILES: *C(=O)[C@@](C)(O)c1ccccc1] |
| 20 | 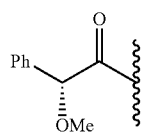 [SMILES: *C(=O)[C@H](OC)c1ccccc1] |
| 21 | 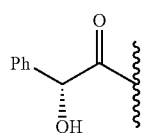 |
| 22 | 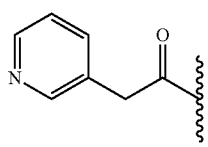 |
| 23 | 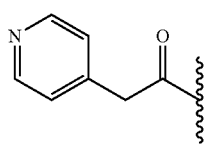 |
| 24 | 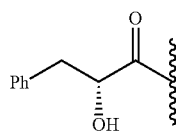 [SMILES: *C(=O)[C@H](O)Cc1ccccc1] |
| 25 | 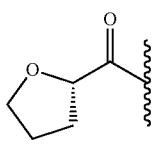 [SMILES: *C(=O)[C@@H]1CCCO1] |

-continued
Compounds 1-219
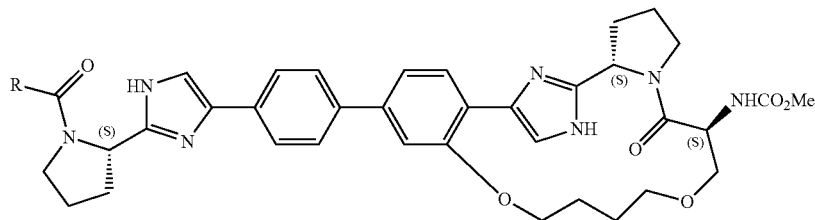
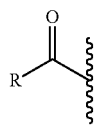
| Entry | |
|---|---|
| 26 | 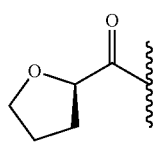 [SMILES: *C(=O)[C@H]1CCCO1] |
| 27 | 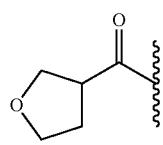 [SMILES: *C(=O)C1CCOC1] |
| 28 | 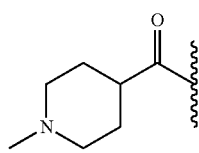 [SMILES: *C(=O)C1CCN(C)CC1] |
| 29 | 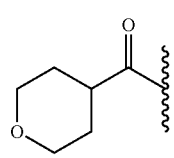 [SMILES: *C(=O)C1CCOCC1] |
| 30 | 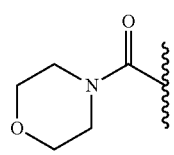 [SMILES: *C(=O)N1CCOCC1] |
| 31 | 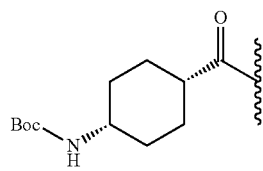 [SMILES: *C(=O)[C@H]1CC[C@@H](NC(=O)OC(C)(C)C)CC1] |
| 32 | 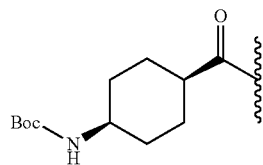 [SMILES: *C(=O)[C@H]1CC[C@@H](NC(=O)OC(C)(C)C)CC1] |

-continued
Compounds 1-219
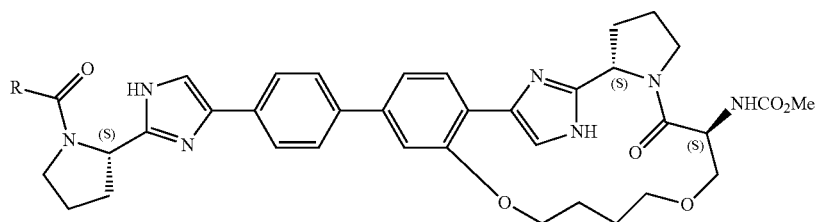
| Entry | 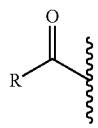 |
|---|---|
| 33 | 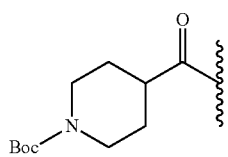 |
| 34 | 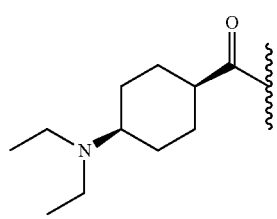 [SMILES: *C(=O)[C@H]1CC[C@@H](N(CC)CC)CC1] |
| 35 | 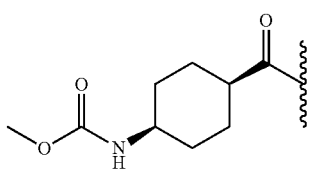 [SMILES: *C(=O)[C@H]1CC[C@@H](NC(=O)OC)CC1] |
| 36 | 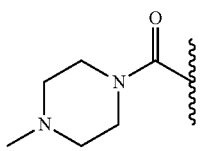 [SMILES: *C(=O)N1CCN(C)CC1] |
| 37 | 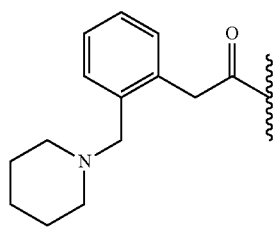 [SMILES: *C(=O)Cc1ccccc1CN1CCCCC1] |
| 38 | 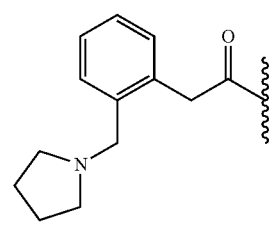 [SMILES: *C(=O)Cc1ccccc1CN1CCCC1] |

-continued
Compounds 1-219
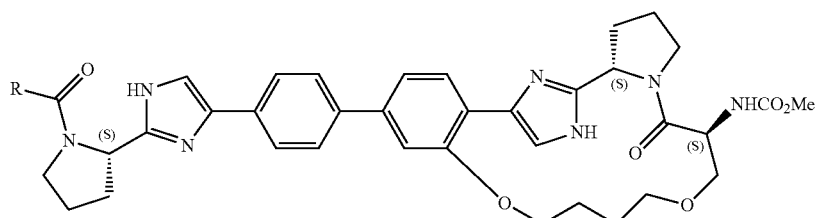
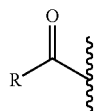
| Entry | |
|---|---|
| 39 | 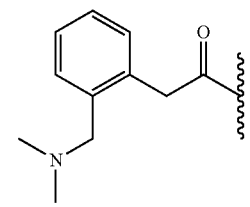 [SMILES: *C(=O)Cc1ccccc1CN(C)C] |
| 40 | 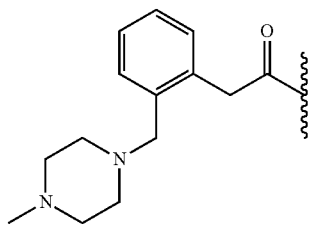 [SMILES: *C(=O)Cc1ccccc1CN1CCN(C)CC1] |
| 41 | 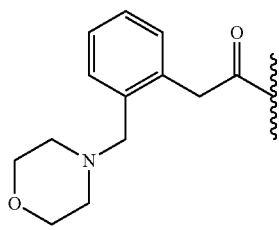 [SMILES: *C(=O)Cc1ccccc1CN1CCOCC1] |
| 42 | 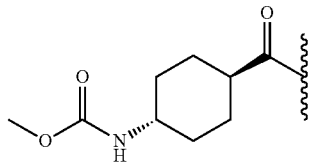 [SMILES: *C(=O)[C@H]1CC[C@H](NC(=O)OC)CC1] |
| 43 | 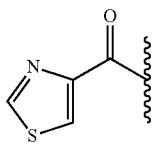 [SMILES: *C(=O)c1cscn1] |
| 44 | 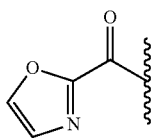 [SMILES: *C(=O)c1ncco1] |

| Compounds 1-219 |
|---|
| 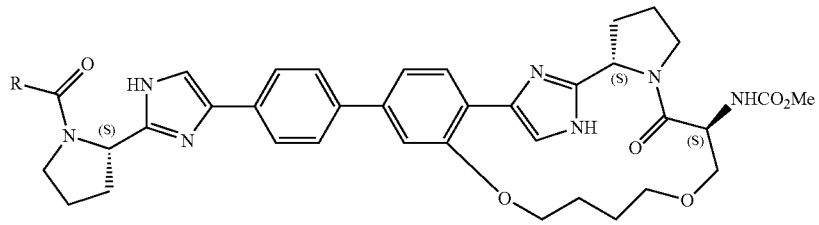 |
| 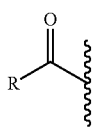 |
| Entry | |
|---|---|
| 45 | 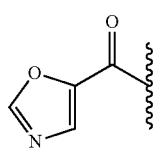 [SMILES: *C(=O)c1cnco1] |
| 46 | 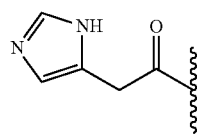 [SMILES: *C(=O)Cc1cnc[nH]1] |
| 47 | 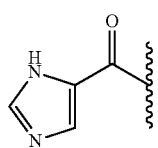 [SMILES: *C(=O)c1cnc[nH]1] |
| 48 | 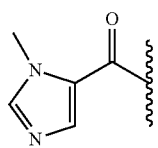 [SMILES: *C(=O)c1cncn1C] |
| 49 | 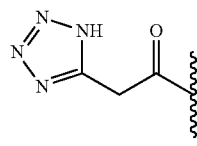 [SMILES: *C(=O)Cc1nnn[nH]1] |
| 50 | 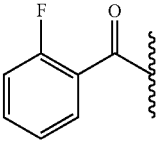 [SMILES: *C(=O)c1ccccc1F] |
| 51 | 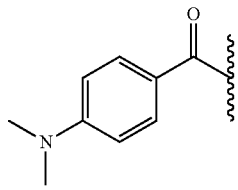 [SMILES: *C(=O)c1ccc(N(C)C)cc1] |

-continued
Compounds 1-219
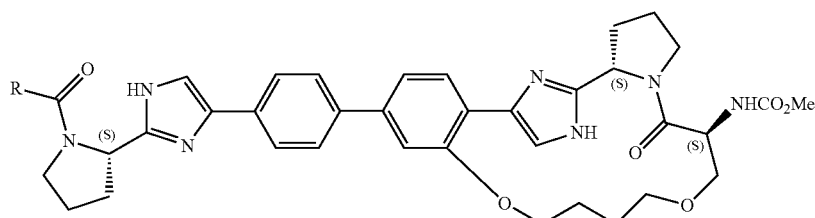
| Entry | R |
|---|---|
| 52 | 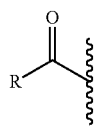 |
| 53 | 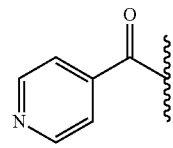 [SMILES: *C(=O)c1ccncc1] |
| 54 | 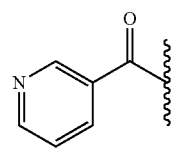 [SMILES: *C(=O)c1cccnc1] |
| 55 | 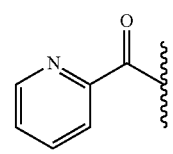 [SMILES: *C(=O)c1ccccn1] |
| 56 | 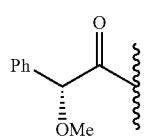 [SMILES: *C(=O)[C@H](OC)c1ccccc1] |
| 57 | 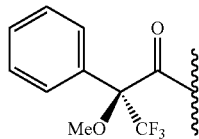 [SMILES: *C(=O)[C@@](OC)(c1ccccc1)C(F)(F)F] |
| 58 | 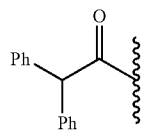 |
| 59 | 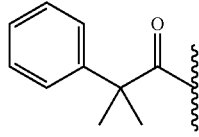 [SMILES: *C(=O)C(C)(C)c1ccccc1] |

-continued
Compounds 1-219
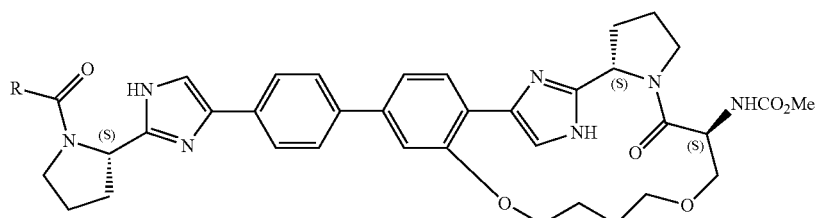
| Entry | R |
|---|---|
| 60 | 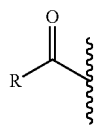 |
| 61 | 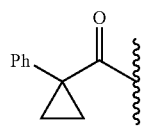 [SMILES: *C(=O)C1(c2ccccc2)CC1] |
| 62 | 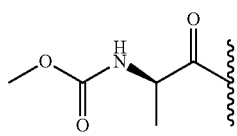 [SMILES: *C(=O)[C@@H](C)NC(=O)OC] |
| 63 | 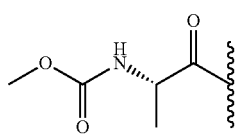 |
| 64 | 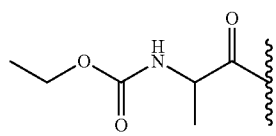 [SMILES: *C(=O)C(C)NC(=O)OCC] |
| 65 | 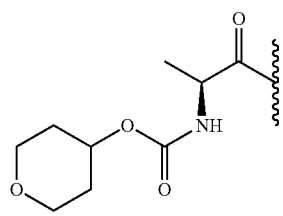 [SMILES: *C(=O)[C@H](C)NC(=O)OC1CCOCC1] |
| 66 | 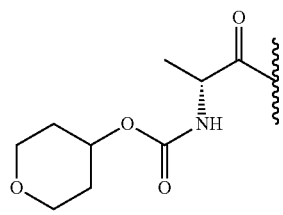 [SMILES: *C(=O)[C@@H](C)NC(=O)OC1CCOCC1] |

-continued

Compounds 1-219

| Entry | |
|---|---|
| 67 | methyl carbamate-NH-CH(Et)-C(O)- |
| 68 | methyl carbamate-NH-CH(Et)-C(O)- |
| 69 | methyl carbamate-NH-CH(CH2CH2OMe)-C(O)- |
| 70 | methyl carbamate-NH-CH(CH(OH)CH3)-C(O)- |
| 71 | methyl carbamate-NH-CH(CH(OH)CH3)-C(O)- |
| 72 | methyl carbamate-NH-CH(CH(OMe)CH3)-C(O)- |
| 73 | methyl carbamate-NH-CH(CH2CH=CH2)-C(O)- |

-continued
Compounds 1-219
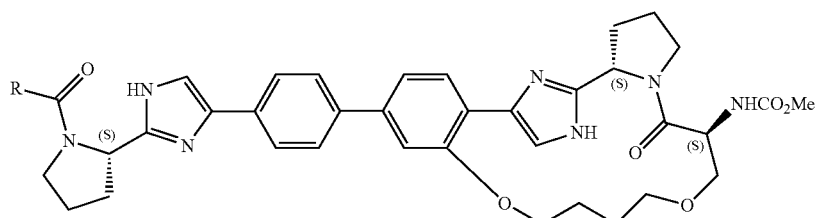
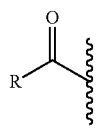
| Entry | |
|---|---|
| 74 | 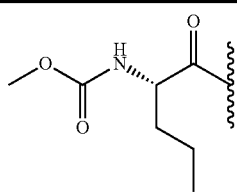 |
| 75 | 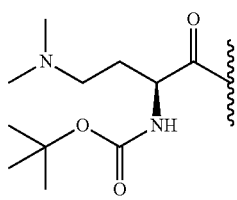 [SMILES: *C(=O)[C@H](CCN(C)C)NC(=O)OC(C)(C)C] |
| 76 | 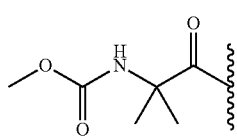 [SMILES: *C(=O)C(C)(C)NC(=O)OC] |
| 77 | 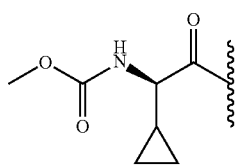 [SMILES: *C(=O)[C@H](NC(=O)OC)C1CC1] |
| 78 | 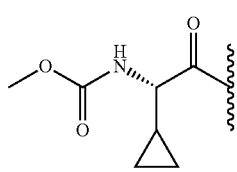 [SMILES: *C(=O)[C@@H](NC(=O)OC)C1CC1] |
| 79 | 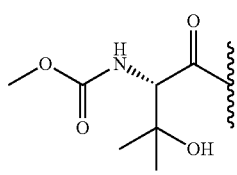 [SMILES: *C(=O)[C@@H](NC(=O)OC)C(C)(C)O] |
| 80 | 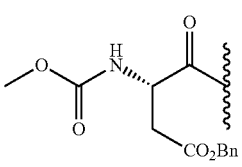 [SMILES: *C(=O)[C@H](CC(=O)OCc1ccccc1)NC(=O)OC] |

Compounds 1-219
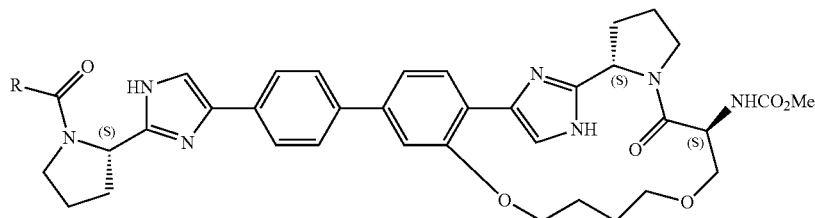
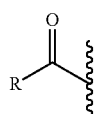
| Entry | |
|---|---|
| 81 | 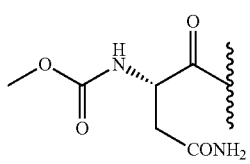 [SMILES: *C(=O)[C@H](CC(N)=O)NC(=O)OC] |
| 82 | 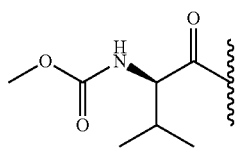 [SMILES: *C(=O)[C@H](NC(=O)OC)C(C)C] |
| 83 | 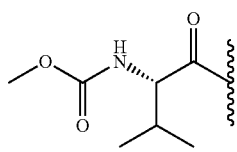 [SMILES: *C(=O)[C@@H](NC(=O)OC)C(C)C] |
| 84 | 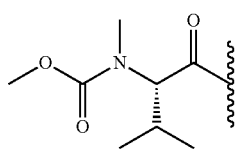 [SMILES: *C(=O)[C@H](C(C)C)N(C)C(=O)OC] |
| 85 | 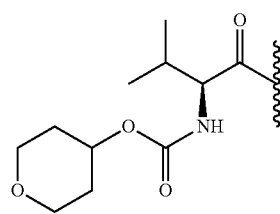 [SMILES: *C(=O)[C@@H](NC(=O)OC1CCOCC1)C(C)C] |
| 86 | 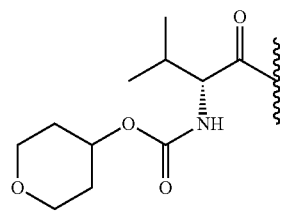 [SMILES: *C(=O)[C@H](NC(=O)OC1CCOCC1)C(C)C] |

-continued
Compounds 1-219
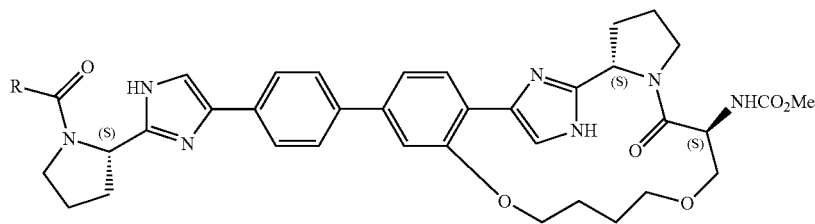
| Entry | 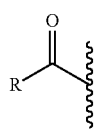 |
|---|---|
| 87 | 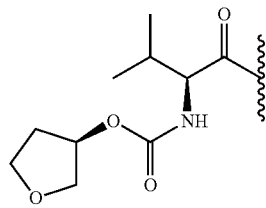 [SMILES: *C(=O)[C@@H](NC(=O)O[C@@H]1CCOC1)C(C)C] |
| 88 | 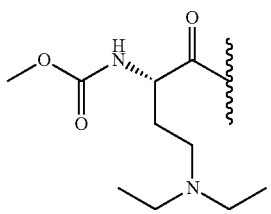 [SMILES: *C(=O)[C@H](CCN(CC)CC)NC(=O)OC] |
| 89 | 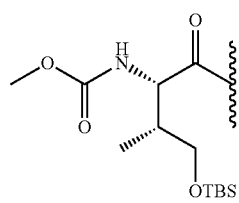 [SMILES: *C(=O)[C@@H](NC(=O)OC)[C@@H](C)CO[Si](C)(C)C(C)(C)C] |
| 90 | 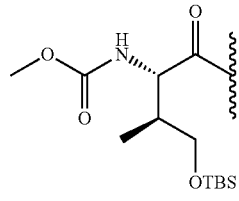 [SMILES: *C(=O)[C@@H](NC(=O)OC)[C@H](C)CO[Si](C)(C)C(C)(C)C] |
| 91 | 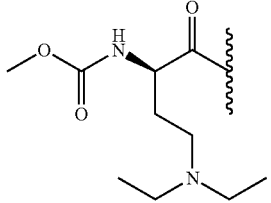 [SMILES: *C(=O)[C@@H](CCN(CC)CC)NC(=O)OC] |

Compounds 1-219
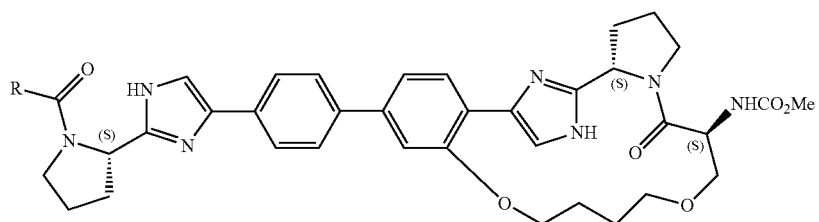
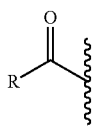
| Entry | |
|---|---|
| 92 | 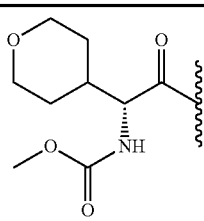 |
| 93 | 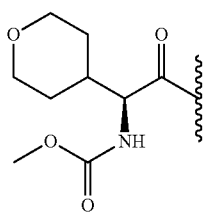 [SMILES: *C(=O)[C@@H](NC(=O)OC)C1CCOCC1] |
| 94 | 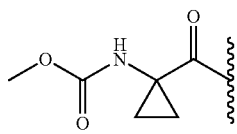 |
| 95 | 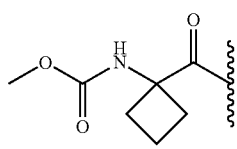 [SMILES: *C(=O)C1(NC(=O)OC)CCC1] |
| 96 | 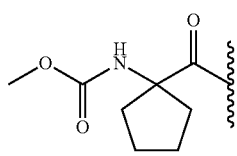 [SMILES: *C(=O)C1(NC(=O)OC)CCCC1] |
| 97 | 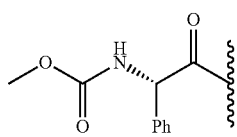 [SMILES: *C(=O)[C@@H](NC(=O)OC)c1ccccc1] |
| 98 | 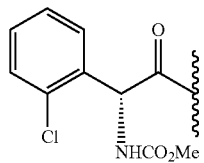 |

Compounds 1-219
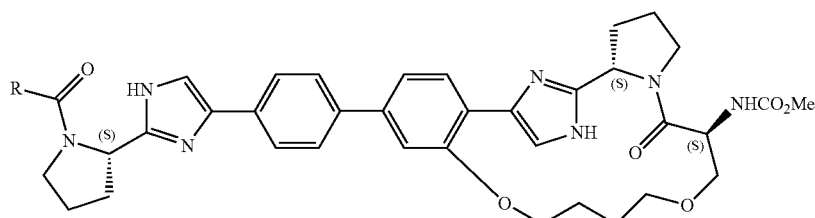
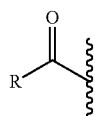
| Entry | |
|---|---|
| 99 | 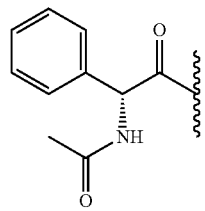 [SMILES: *C(=O)[C@H](NC(C)=O)c1ccccc1] |
| 100 | 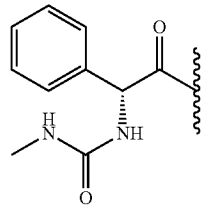 [SMILES: *C(=O)[C@H](NC(=O)NC)c1ccccc1] |
| 101 | 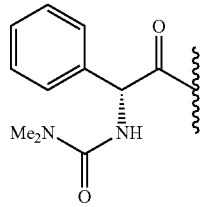 [SMILES: *C(=O)[C@H](NC(=O)N(C)C)c1ccccc1] |
| 102 | 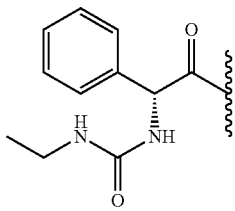 [SMILES: *C(=O)[C@H](NC(=O)NCC)c1ccccc1] |
| 103 | 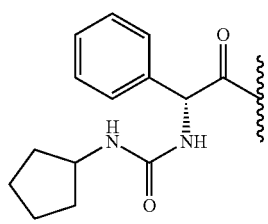 [SMILES: *C(=O)[C@H](NC(=O)NC1CCCC1)c1ccccc1] |
| 104 | 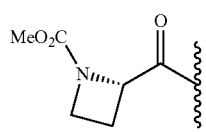 |

Compounds 1-219
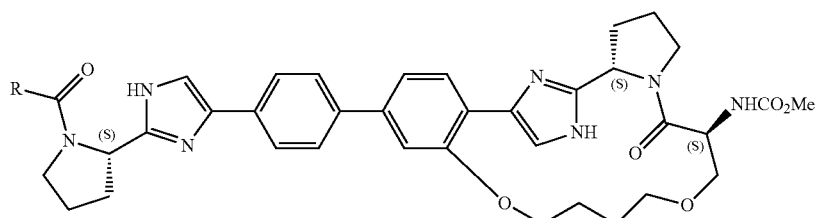
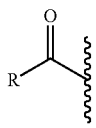
| Entry | |
|---|---|
| 105 | 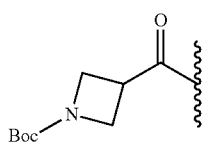 |
| 106 | 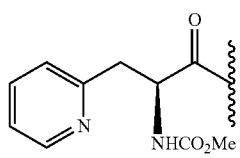 |
| 107 | 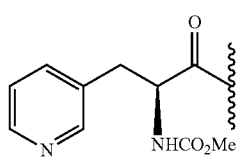 |
| 108 | 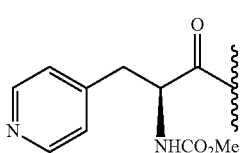 |
| 109 | 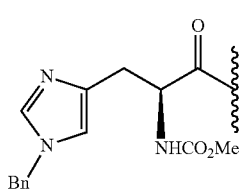 |
| 110 | 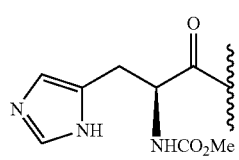 |
| 111 | 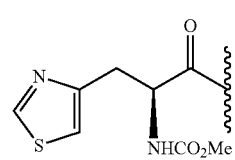 |

Compounds 1-219
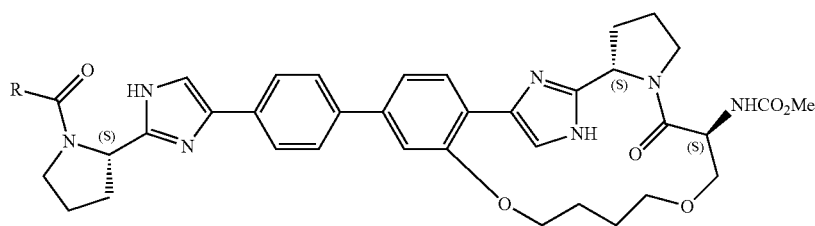
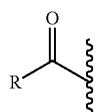
| Entry | |
|---|---|
| 112 | 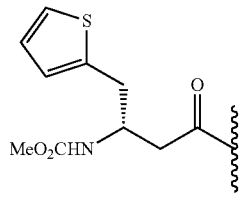 |
| 113 | 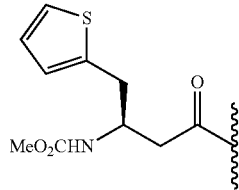 |
| 114 | 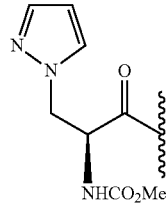 |
| 115 | 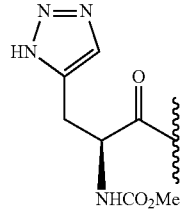 |
| 116 | 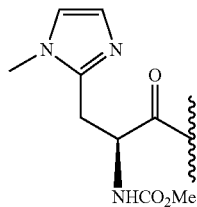 |

Compounds 1-219
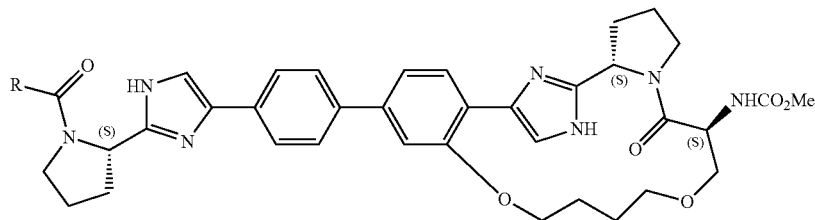
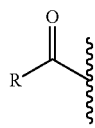
| Entry | |
|---|---|
| 117 | 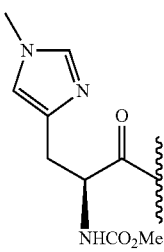 |
| 118 | 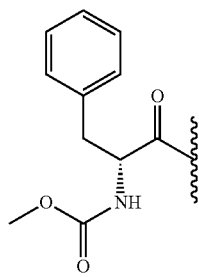 [SMILES: *C(=O)[C@@H](Cc1ccccc1)NC(=O)OC] |
| 119 | 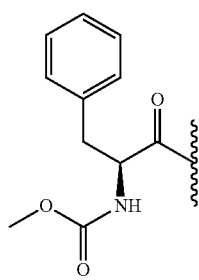 [SMILES: *C(=O)[C@H](Cc1ccccc1)NC(=O)OC] |
| 120 | 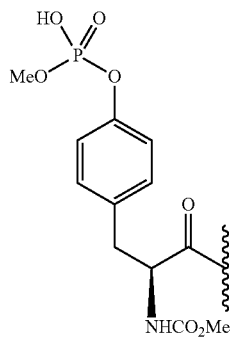 |

Compounds 1-219
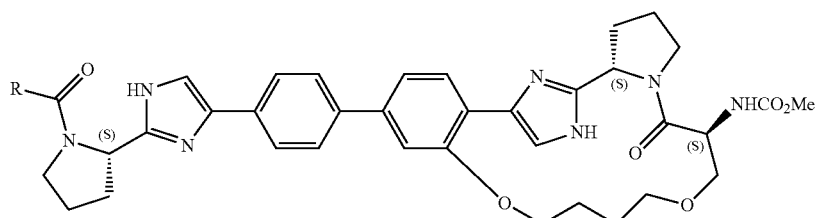
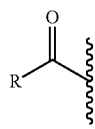
| Entry | |
|---|---|
| 121 | 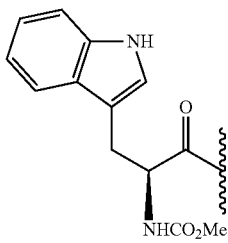 |
| 122 | 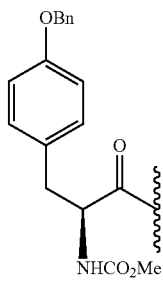 |
| 123 | 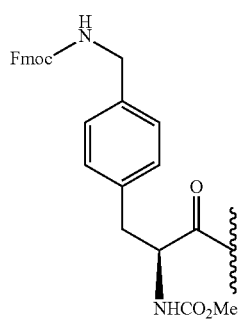 |
| 124 | 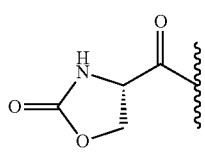 [SMILES: *C(=O)[C@@H]1COC(=O)N1] |
| 125 | 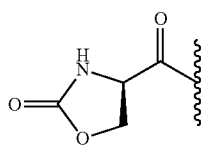 [SMILES: *C(=O)[C@H]1COC(=O)N1] |

-continued
Compounds 1-219
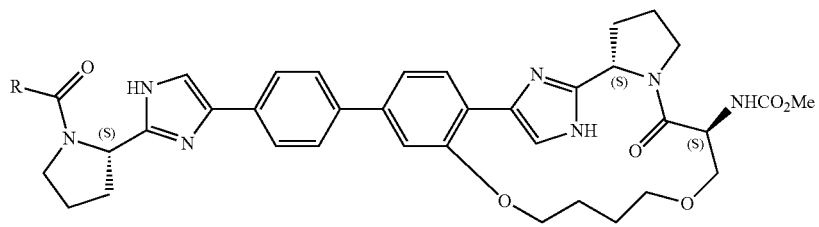
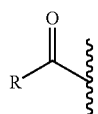
Entry
126
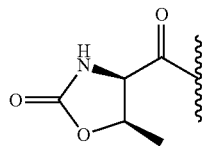 [SMILES: *C(=O)[C@@H]1NC(=O)O[C@@H]1C]
127
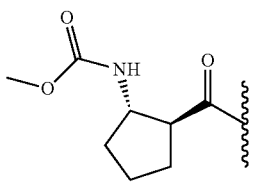 [SMILES: *C(=O)[C@H]1CCC[C@@H]1NC(=O)OC]
128
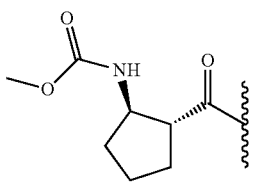 [SMILES: *C(=O)[C@@H]1CCC[C@H]1NC(=O)OC]
129
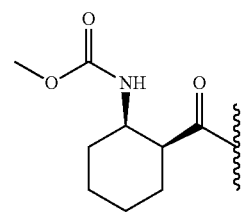 [SMILES: *C(=O)[C@H]1CCCC[C@H]1NC(=O)OC]
130
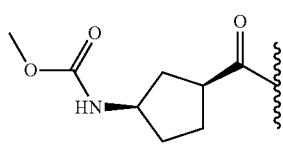 [SMILES: *C(=O)[C@H]1CC[C@@H](NC(=O)OC)C1]
131
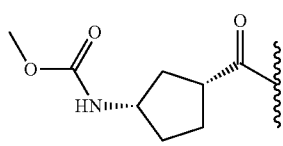 [SMILES: *C(=O)[C@@H]1CC[C@H](NC(=O)OC)C1]

-continued
Compounds 1-219
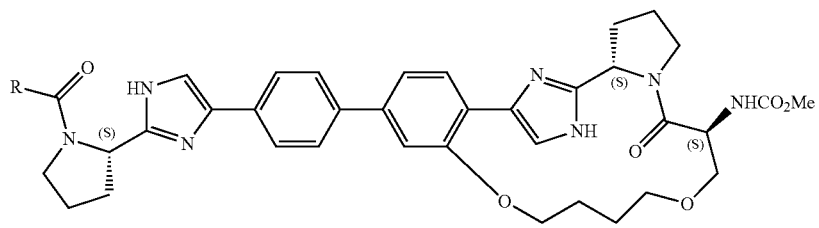
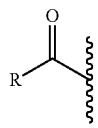
| Entry | |
|---|---|
| 132 | 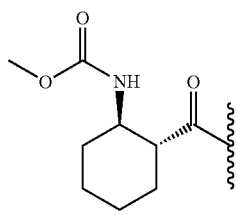 [SMILES: *C(=O)[C@@H]1CCCC[C@H]1NC(=O)OC] |
| 133 | 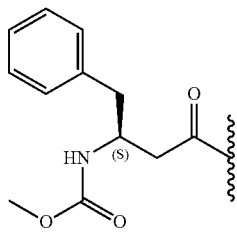 |
| 134 | 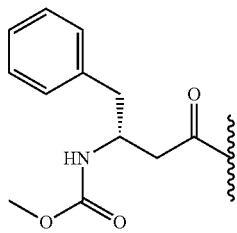 [SMILES: *C(=O)C[C@@H](Cc1ccccc1)NC(=O)OC] |
| 135 | 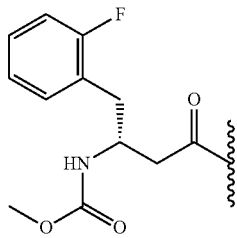 [SMILES: *C(=O)C[C@@H](Cc1ccccc1F)NC(=O)OC] |
| 136 | 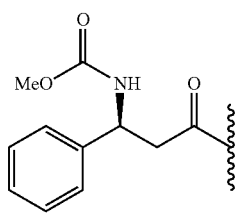 [SMILES: *C(=O)C[C@H](NC(=O)OC)c1ccccc1] |

Compounds 1-219
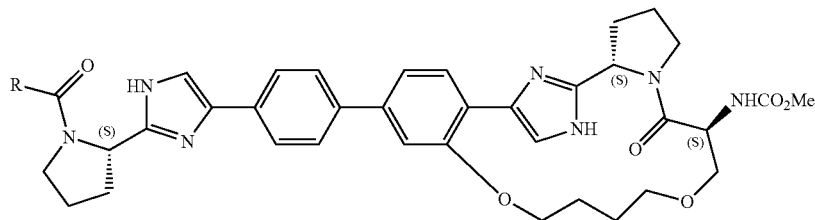
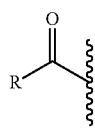
| Entry | |
|---|---|
| 137 | 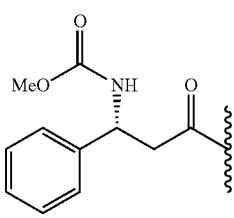 [SMILES: *C(=O)C[C@@H](NC(=O)OC)c1ccccc1] |
| 138 | 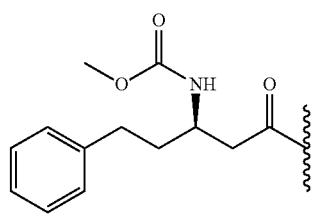 [SMILES: *C(=O)C[C@@H](CCc1ccccc1)NC(=O)OC] |
| 139 | 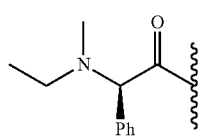 [SMILES: *C(=O)[C@@H](c1ccccc1)N(C)CC] |
| 140 | 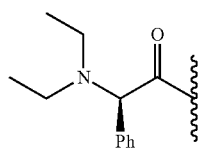 [SMILES: *C(=O)[C@@H](c1ccccc1)N(CC)CC] |
| 141 | 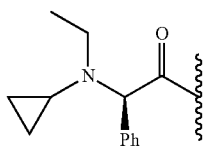 [SMILES: *C(=O)[C@@H](c1ccccc1)N(CC)C1CC1] |
| 142 | 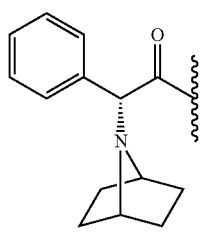 [SMILES: *C(=O)[C@@H](c1ccccc1)N1C2CCC1CC2] |

-continued
Compounds 1-219
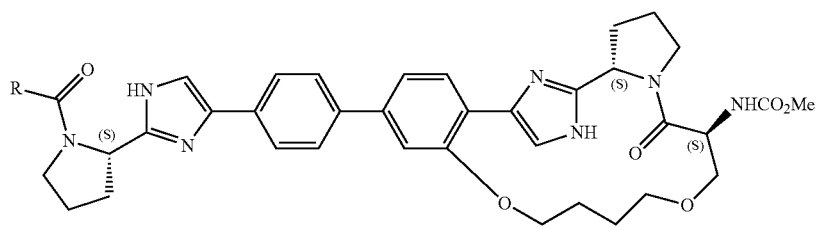
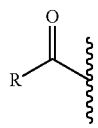
| Entry | |
|---|---|
| 143 | 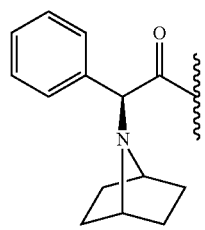 [SMILES: *C(=O)[C@H](c1ccccc1)N1C2CCC1CC2] |
| 144 | 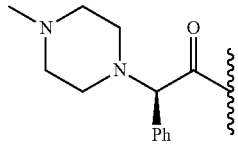 [SMILES: *C(=O)[C@@H](c1ccccc1)N1CCN(C)CC1] |
| 145 | 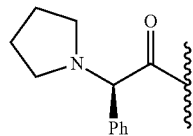 [SMILES: *C(=O)[C@@H](c1ccccc1)N1CCCC1] |
| 146 | 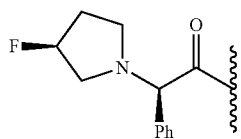 [SMILES: *C(=O)[C@@H](c1ccccc1)N1CC[C@H](F)C1] |
| 147 | 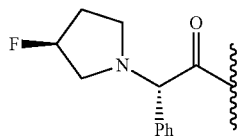 [SMILES: *C(=O)[C@H](c1ccccc1)N1CC[C@H](F)C1] |
| 148 | 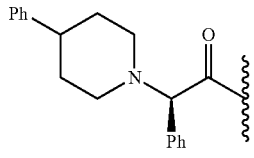 [SMILES: *C(=O)[C@@H](c1ccccc1)N1CCC(c2ccccc2)CC1] |
| 149 | 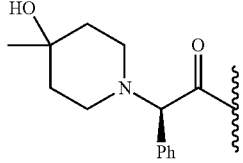 [SMILES: *C(=O)[C@@H](c1ccccc1)N1CCC(C)(O)CC1] |

-continued
Compounds 1-219
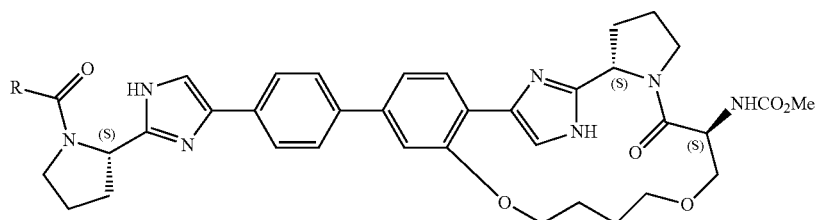
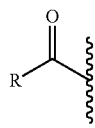
| Entry | |
|---|---|
| 150 | 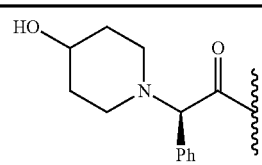 |
| 151 | 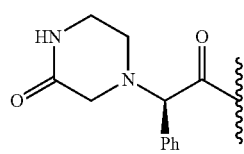 [SMILES: *C(=O)[C@@H](c1ccccc1)N1CCNC(=O)C1] |
| 152 | 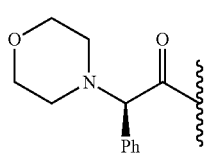 [SMILES: *C(=O)[C@@H](c1ccccc1)N1CCOCC1] |
| 153 | 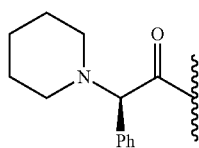 [SMILES: *C(=O)[C@@H](c1ccccc1)N1CCCCC1] |
| 154 | 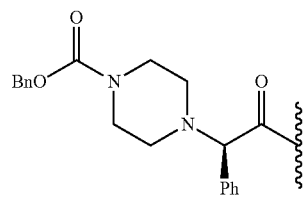 [SMILES: *C(=O)[C@@H](c1ccccc1)N1CCN(C(=O)OCc2ccccc2)CC1] |
| 155 | 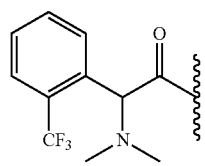 [SMILES: *C(=O)C(c1ccccc1C(F)(F)F)N(C)C] |
| 156 | 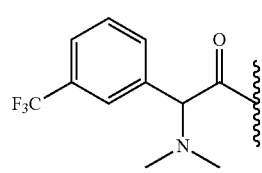 [SMILES: *C(=O)C(c1cccc(C(F)(F)F)c1)N(C)C] |

-continued
Compounds 1-219
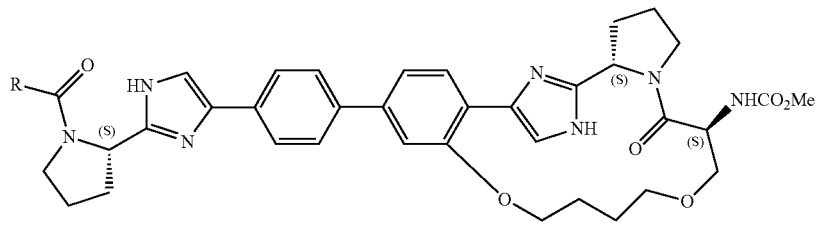
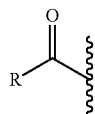
| Entry | |
|---|---|
| 157 | 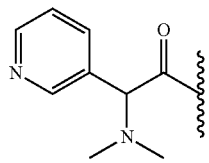 [SMILES: *C(=O)C(c1cccnc1)N(C)C] |
| 158 | 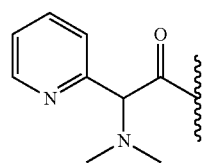 [SMILES: *C(=O)C(c1ccccn1)N(C)C] |
| 159 | 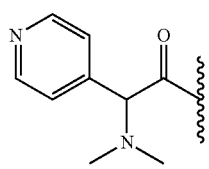 [SMILES: *C(=O)C(c1ccncc1)N(C)C] |
| 160 | 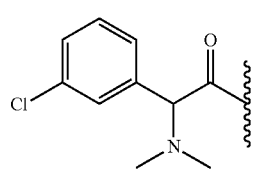 [SMILES: *C(=O)C(c1cccc(Cl)c1)N(C)C] |
| 161 | 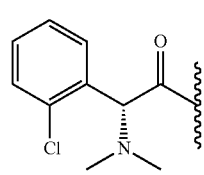 [SMILES: *C(=O)[C@@H](c1ccccc1Cl)N(C)C] |
| 162 | 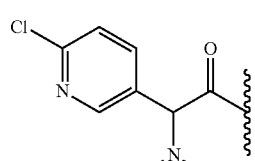 |
| 163 | 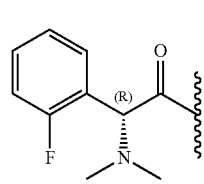 |

-continued
Compounds 1-219
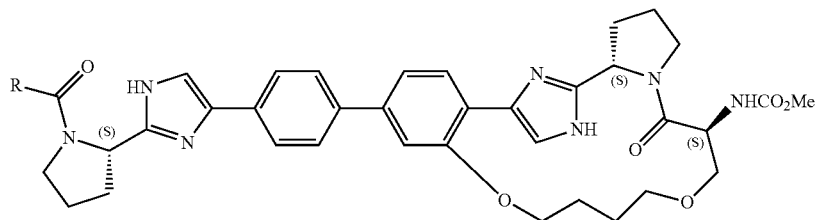
| Entry | 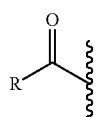 |
|---|---|
| 164 | 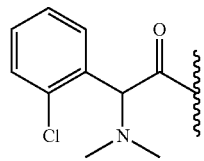 [SMILES: *C(=O)C(c1ccccc1Cl)N(C)C] |
| 165 | 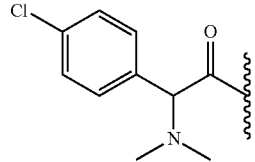 [SMILES: *C(=O)C(c1ccc(Cl)cc1)N(C)C] |
| 166 | 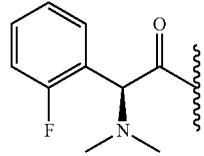 |
| 167 |  |
| 168 | 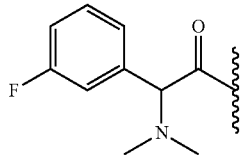 [SMILES: *C(=O)C(c1cccc(F)c1)N(C)C] |
| 169 | 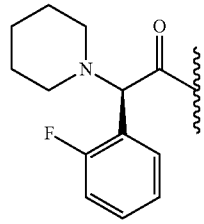 [SMILES: *C(=O)[C@@H](c1ccccc1F)N1CCCCC1] |

-continued
Compounds 1-219
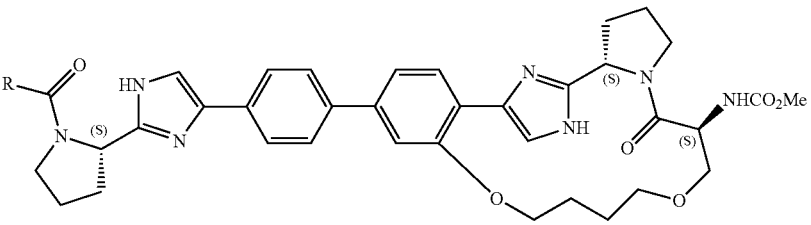
| Entry | |
|---|---|
| 170 | 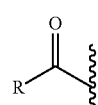 |
| 171 | 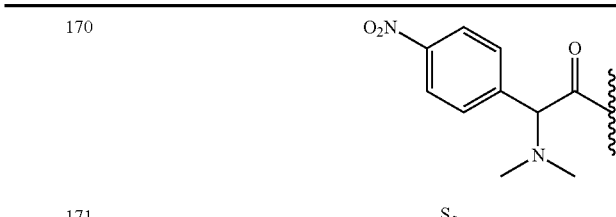 |
| 172 | 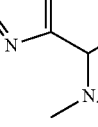 |
| 173 | 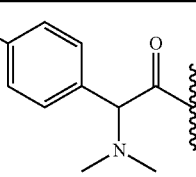 |
| 174 | 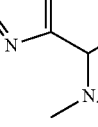 |
| 175 | 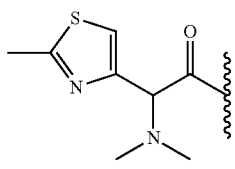 |
| 176 | 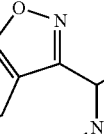 |

-continued
Compounds 1-219
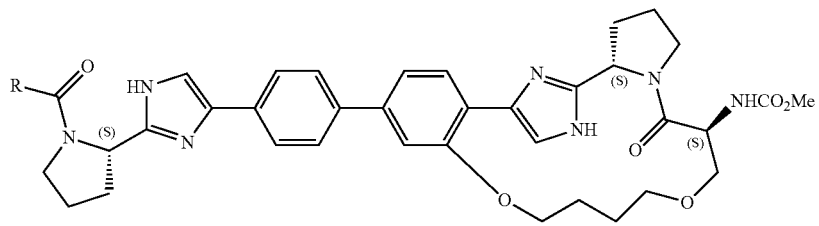
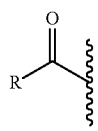
| Entry | |
|---|---|
| 177 | 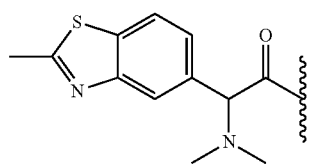 [SMILES: *C(=O)C(c1ccc2sc(C)nc2c1)N(C)C] |
| 178 | 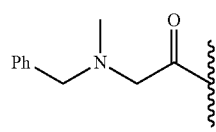 |
| 179 | 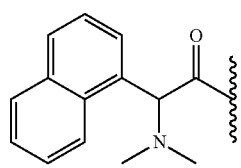 [SMILES: *C(=O)C(c1cccc2ccccc12)N(C)C] |
| 180 | 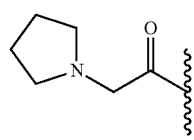 [SMILES: *C(=O)CN1CCCC1] |
| 181 | 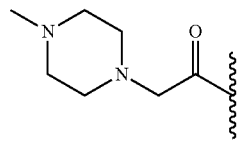 [SMILES: *C(=O)CN1CCN(C)CC1] |
| 182 | 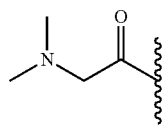 [SMILES: *C(=O)CN(C)C] |
| 183 | 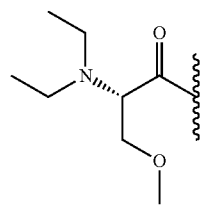 [SMILES: *C(=O)[C@H](COC)N(CC)CC] |

-continued
Compounds 1-219
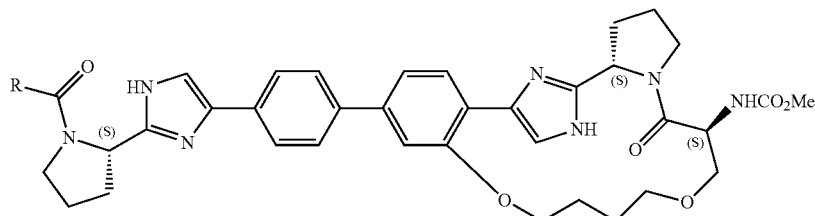
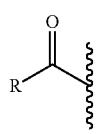
| Entry | |
|---|---|
| 184 | 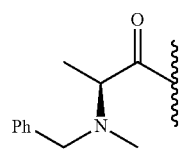 [SMILES: *C(=O)[C@H](C)N(C)Cc1ccccc1] |
| 185 | 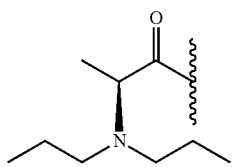 [SMILES: *C(=O)[C@H](C)N(CCC)CCC] |
| 186 | 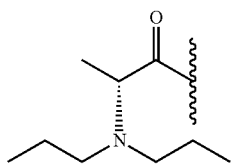 [SMILES: *C(=O)[C@@H](C)N(CCC)CCC] |
| 187 | 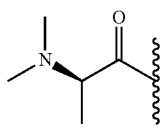 [SMILES: *C(=O)[C@@H](C)N(C)C] |
| 188 | 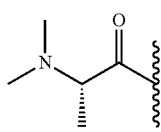 [SMILES: *C(=O)[C@H](C)N(C)C] |
| 189 | 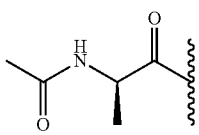 [SMILES: *C(=O)[C@@H](C)NC(C)=O] |
| 190 | 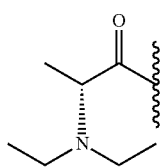 [SMILES: *C(=O)[C@@H](C)N(CC)CC] |

-continued
Compounds 1-219
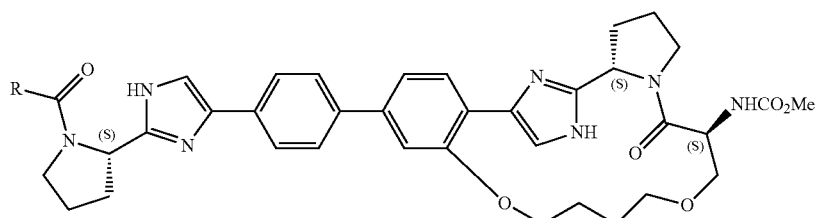
| Entry | |
|---|---|
| 191 | 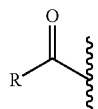 |
| 192 | 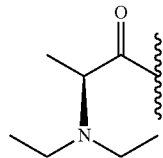 [SMILES: *C(=O)[C@H](C)N(CC)CC] |
| 193 | 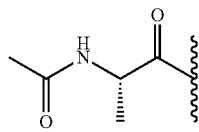 [SMILES: *C(=O)[C@H](C)NC(C)=O] |
| 194 | 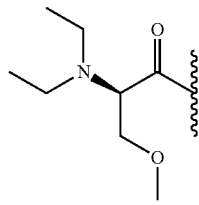 [SMILES: *C(=O)[C@@H](COC)N(CC)CC] |
| 195 | 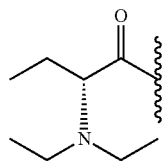 [SMILES: *C(=O)[C@@H](CC)N(CC)CC] |
| 196 | 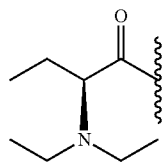 [SMILES: *C(=O)[C@H](CC)N(CC)CC] |
| 197 | 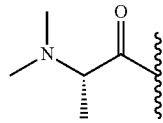 [SMILES: *C(=O)[C@H](C)N(C)C] |

-continued
Compounds 1-219
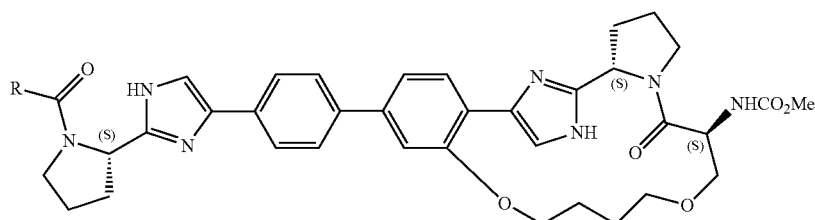
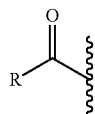
| Entry | |
|---|---|
| 198 | 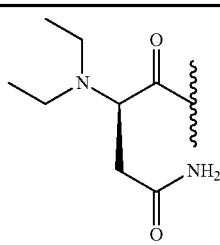 |
| 199 | 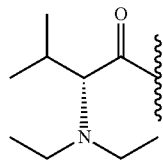 [SMILES: *C(=O)[C@@H](C(C)C)N(CC)CC] |
| 200 | 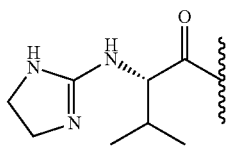 [SMILES: *C(=O)[C@@H](NC1=NCCN1)C(C)C] |
| 201 | 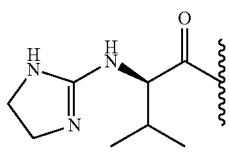 [SMILES: *C(=O)[C@H](NC1=NCCN1)C(C)C] |
| 202 | 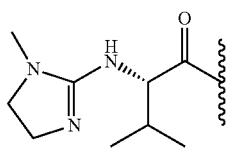 |
| 203 | 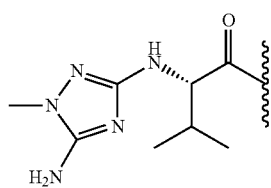 [SMILES: *C(=O)[C@@H](Nc1nc(N)n(C)n1)C(C)C] |
| 204 | 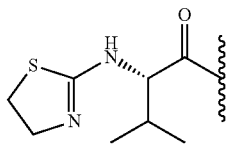 [SMILES: *C(=O)[C@@H](NC1=NCCS1)C(C)C] |

-continued
Compounds 1-219
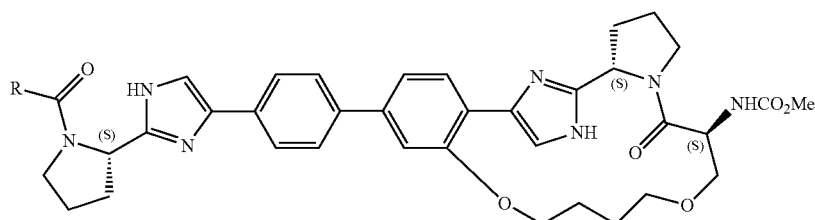
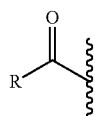
| Entry | |
|---|---|
| 205 | 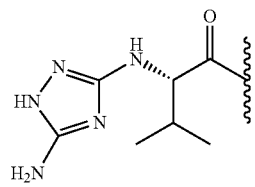 [SMILES: *C(=O)[C@@H](Nc1n[nH]c(N)n1)C(C)C] |
| 206 | 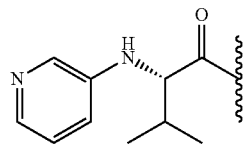 [SMILES: *C(=O)[C@@H](Nc1cccnc1)C(C)C] |
| 207 | 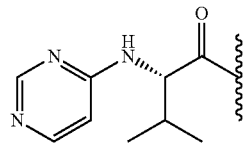 [SMILES: *C(=O)[C@@H](Nc1ccncn1)C(C)C] |
| 208 | 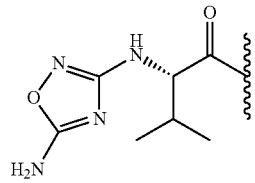 [SMILES: *C(=O)[C@@H](Nc1noc(N)n1)C(C)C] |
| 209 | 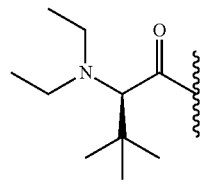 [SMILES: *C(=O)[C@H](N(CC)CC)C(C)(C)C] |
| 210 | 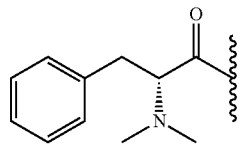 [SMILES: *C(=O)[C@@H](Cc1ccccc1)N(C)C] |
| 211 | 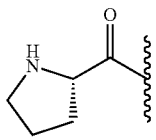 [SMILES: *C(=O)[C@@H]1CCCN1] |

TABLE-continued
Compounds 1-219
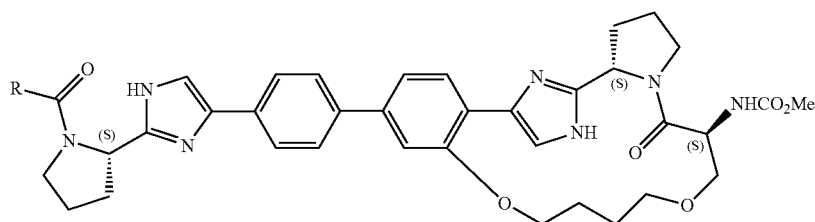
| Entry | |
|---|---|
| 212 | 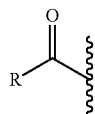 |
| 213 | 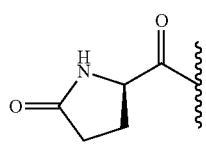 [SMILES: *C(=O)[C@H]1CCC(=O)N1] |
| 214 | 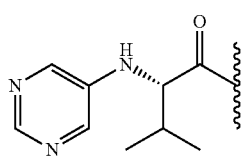 [SMILES: *C(=O)[C@@H](Nc1cncnc1)C(C)C] |
| 215 | 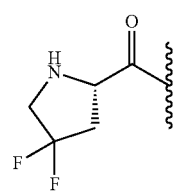 |
| 216 | 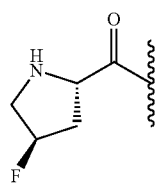 [SMILES: *C(=O)[C@@H]1C[C@@H](F)CN1] |
| 217 | 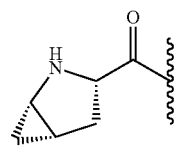 [SMILES: *C(=O)[C@@H]1C[C@@H]2C[C@@H]2N1] |
| 218 | 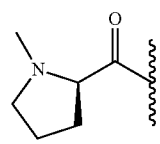 [SMILES: *C(=O)[C@H]1CCCN1C] |

-continued

Compounds 1-219

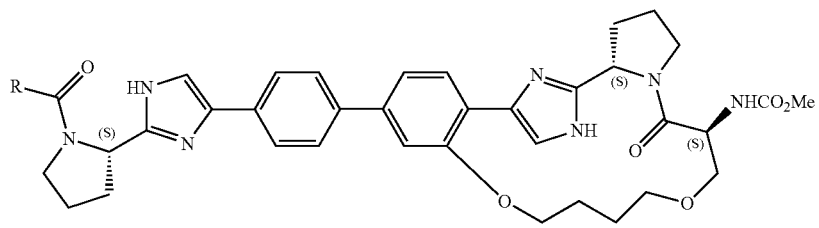

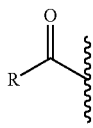

| Entry | |
|---|---|
| 219 | 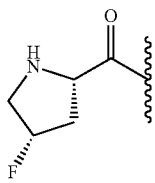 [SMILES: *C(=O)[C@@H]1C[C@H](F)CN1] |

4. A compound represented by Formula (VIb):

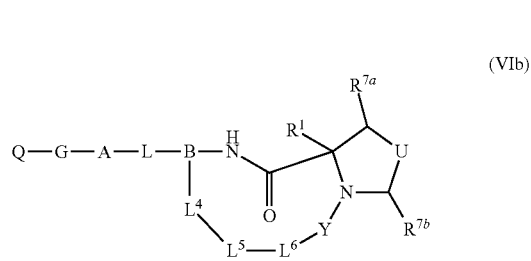
(VIb)

wherein:
A is absent, optionally substituted aryl, or optionally substituted heteroaryl;
L is absent, O, optionally substituted $C_2$-$C_4$ alkenyl, or optionally substituted $C_2$-$C_4$ alkynyl;
Y is C(O);
$R^1$ is hydrogen;
Q is hydrogen or

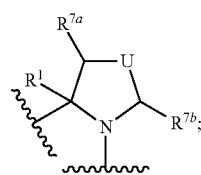

G is absent or selected from

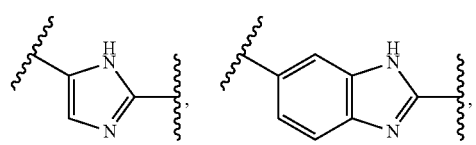

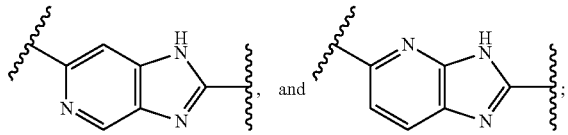

each of which is optionally substituted;
B is optionally substituted phenyl;
each U is $C(R^7)_2$,
each $R^7$ is independently selected from the group consisting of hydrogen, halogen, cyano, hydroxy, $O(C_1$-$C_4$ alkyl), $S(C_1$-$C_4$ alkyl), amino optionally substituted with one or two $C_1$-$C_4$ alkyl, optionally substituted aryl, optionally substituted heteroaryl, optionally substituted $C_1$-$C_4$ alkyl, and optionally substituted $C_3$-$C_8$ alkyl;
alternatively two geminal $R^7$ groups are taken together with the carbon atom to which they are attached to form a spiro, optionally substituted 3- to 7-membered cyclic group selected from the group consisting of cycloalkyl, cycloalkenyl and heterocyclic ring;
$R^{7a}$ and $R^{7b}$ at each occurrence independently selected from the group consisting of hydrogen, optionally substituted aryl, optionally substituted $C_1$-$C_4$ alkyl, and optionally substituted $C_3$-$C_8$ alkyl;
alternatively, $CHR^{7a}$—U or $CHR^{7b}$—U are taken together to form a group selected from CH=CH, fused and optionally substituted $C_3$-$C_8$ cycloalkyl, fused and optionally substituted aryl, or fused and optionally substituted heterocyclic;
yet alternatively, U, $R^{7a}$, and $R^{7b}$ are taken together with the carbon atoms to which they are attached to form a bridged, optionally substituted 4- to 7-membered cyclic group selected from the group consisting of cycloalkyl, cycloalkenyl and heterocyclic;
$R^6$ is selected from the group consisting of $O(C_1$-$C_8$ alkyl), amino, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; and -$L^4$-$L^5$-$L^6$- is

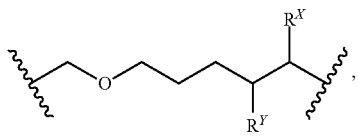

wherein $R^x$ is hydrogen, amino, hydroxy, protected amino or $O(C_1$-$C_4$ alkyl); and $R^Y$ is hydrogen or optionally substituted $C_1$-$C_8$ alkyl; and wherein this group is further optionally substituted;
or a pharmaceutically acceptable salt thereof.

5. A pharmaceutical composition comprising a compound or a combination of compounds according to claim 4 or a pharmaceutically acceptable salt thereof, in combination with a pharmaceutically acceptable carrier or excipient.

6. A method of inhibiting the replication of an RNA-containing virus comprising contacting said virus with a therapeutically effective amount of a compound or combination of compounds of claim 4 or a pharmaceutically acceptable salt thereof; wherein said RNA-containing virus is hepatitis C virus.

7. A method of treating infection caused by an RNA-containing virus comprising administering to a subject in need of such treatment a therapeutically effective amount of a compound or combination of compounds of claim 4 or a pharmaceutically acceptable salt thereof; wherein said RNA-containing virus is hepatitis C virus.

8. The method of claim 7, further comprising the step of co-administering one or more agents selected from the group consisting of a host immune modulator, and an antiviral agent, or a combination thereof.

9. The method of claim 8, wherein the host immune modulator is selected from the group consisting of interferon-alpha, pegylated-interferon-alpha, interferon-beta, interferon-gamma, consensus interferon, a cytokine, and a vaccine.

10. The method of claim 8, wherein the antiviral agent inhibits replication of HCV by inhibiting host cellular functions associated with viral replication.

11. The method of claim 8, wherein the antiviral agent inhibits the replication of HCV by targeting proteins of the viral genome.

12. The method of claim 8, wherein said antiviral agent is an inhibitor of a HCV viral protein, a replication process or a combination thereof, wherein said targeting protein or replication process is selected from the group consisting of helicase, protease, polymerase, metalloprotease, NS4A, NS4B, NS5A, assembly, entry, and IRES.

13. The method of claim 7, further comprising the step of co-administering an agent or combination of agents that treat or alleviate symptoms of HCV infection selected from cirrhosis and inflammation of the liver.

14. The method of claim 7, further comprising the step of co-administering one or more agents that treat patients for disease caused by hepatitis B (HBV) infection.

15. The method of claim 7, further comprising the step of co-administering one or more agents that treat patients for disease caused by human immunodeficiency virus (HIV) infection.

16. The pharmaceutical composition of claim 5, further comprising an agent selected from interferon, pegylated interferon, ribavirin, amantadine, an HCV protease inhibitor, an HCV polymerase inhibitor, an HCV helicase inhibitor, or an internal ribosome entry site inhibitor.

17. The composition of claim 5, further comprising a cytochrome P450 monooxygenase inhibitor or a pharmaceutically acceptable salt thereof.

18. The composition of claim 17, wherein the cytochrome P450 monooxygenase inhibitor is ritonavir.

19. A method of co-administering to a subject in need of anti-hepatitis C viral treatment comprising administering to said subject a cytochrome P450 monooxygenase inhibitor or a pharmaceutically acceptable salt thereof, and a compound of claim 4 or a pharmaceutically acceptable salt thereof.

20. A compound selected from the group of compounds 230-239 and 344-350 compiled in the following tables or a pharmaceutically acceptable salt thereof:

Compounds 230-239

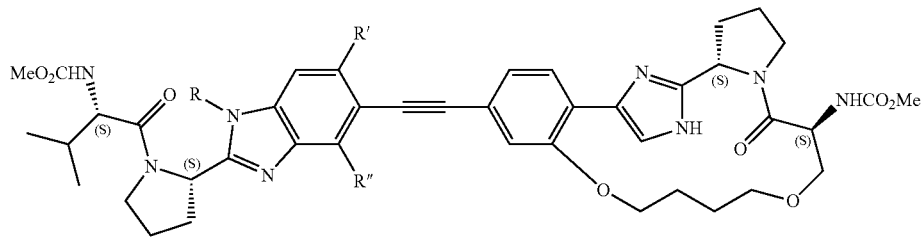

| Entry | R | R' | R'' |
|---|---|---|---|
| 230 | Me | H | H |
| 231 | H | $CO_2Me$ | H |
| 232 | H | F | H |
| 233 | H | H | $CO_2Me$ |
| 234 | H | H | F |
| 235 | H | OMe | H |
| 236 | H | Cl | H |
| 237 | H | H | OMe |
| 238 | H | H | Cl |
| 239 | H | $CF_3$ | H |

Compounds 344-350
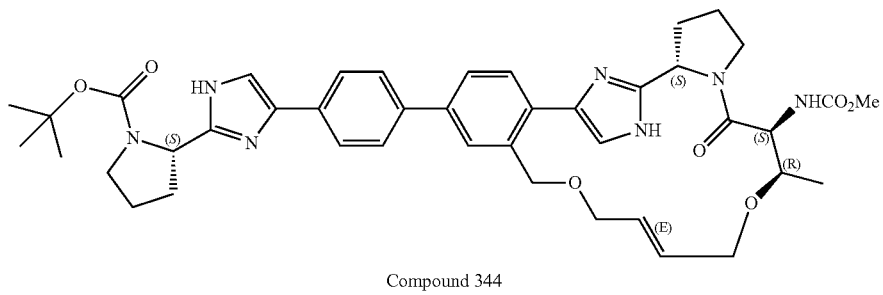
Compound 344
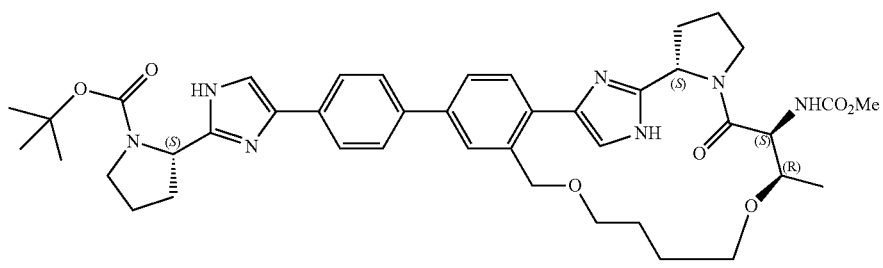
Compound 345
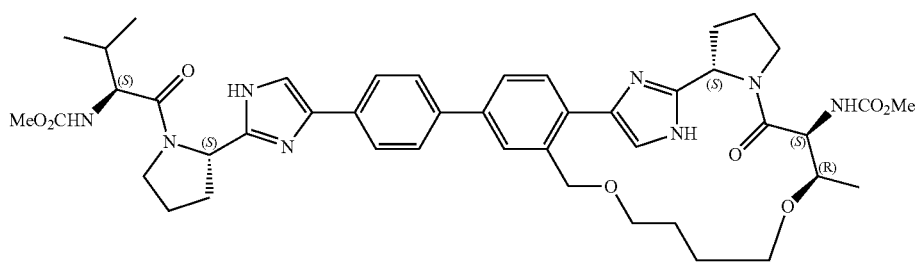
Compound 346
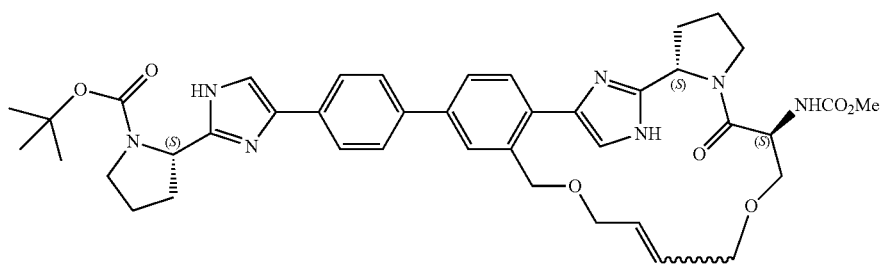
Compound 347
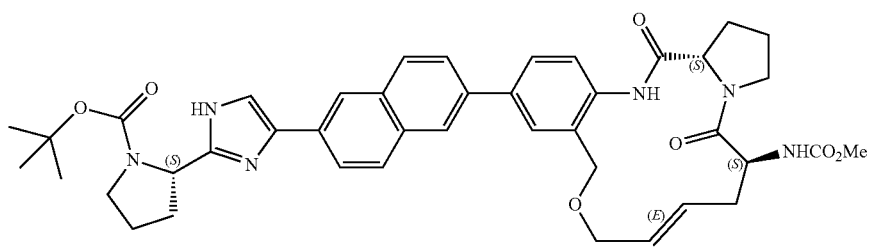
Compound 348

-continued
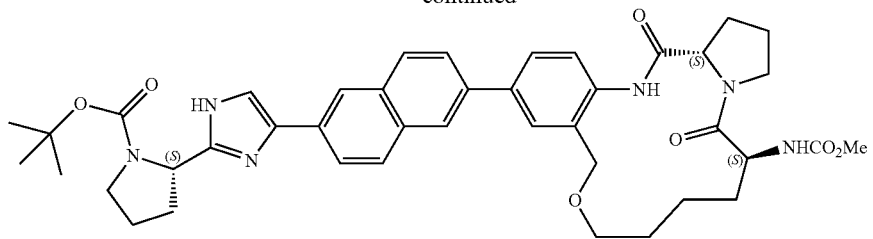
Compound 349
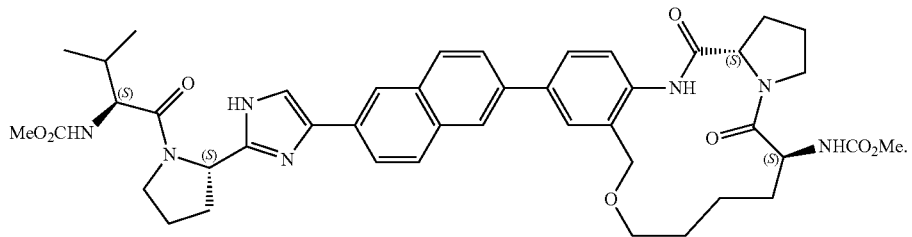
Compound 350
* * * * *

UNITED STATES PATENT AND TRADEMARK OFFICE
CERTIFICATE OF CORRECTION

PATENT NO.        : 9,127,021 B2
APPLICATION NO.   : 13/082621
DATED             : September 8, 2015
INVENTOR(S)       : Qui et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 187 days.

Signed and Sealed this
Twelfth Day of July, 2016

Michelle K. Lee
*Director of the United States Patent and Trademark Office*